US011543408B2

(12) United States Patent
Chou et al.

(10) Patent No.: US 11,543,408 B2
(45) Date of Patent: Jan. 3, 2023

(54) DEVICE AND SYSTEM FOR ANALYZING A SAMPLE, PARTICULARLY BLOOD, AS WELL AS METHODS OF USING THE SAME

(71) Applicant: Essenlix Corporation, Monmouth Junction, NJ (US)

(72) Inventors: Stephen Y. Chou, Princeton, NJ (US); Wei Ding, Princeton, NJ (US)

(73) Assignee: Essenlix Corporation, Monmouth Junction, NJ (US)

( * ) Notice: Subject to any disclaimer, the term of this patent is extended or adjusted under 35 U.S.C. 154(b) by 103 days.

(21) Appl. No.: 16/653,936

(22) Filed: Oct. 15, 2019

(65) Prior Publication Data
US 2020/0049701 A1 Feb. 13, 2020

Related U.S. Application Data

(63) Continuation of application No. 15/742,744, filed as application No. PCT/US2016/051775 on Sep. 14, 2016, now Pat. No. 10,605,805.
(Continued)

(51) Int. Cl.
*G01N 1/00* (2006.01)
*G01N 33/543* (2006.01)
*G01N 1/28* (2006.01)
*G16B 25/00* (2019.01)
*G16B 50/00* (2019.01)
(Continued)

(52) U.S. Cl.
CPC ...... *G01N 33/54366* (2013.01); *B01L 3/5055* (2013.01); *G01N 1/2813* (2013.01); *G01N 1/30* (2013.01); *G01N 33/5094* (2013.01); *G16B 25/00* (2019.02); *G16B 50/00* (2019.02); *G16H 80/00* (2018.01); *B01L 2200/021* (2013.01); *B01L 2200/16* (2013.01); *B01L 2300/02* (2013.01); *B01L 2300/0627* (2013.01); *B01L 2300/12* (2013.01)

(58) Field of Classification Search
None
See application file for complete search history.

(56) References Cited

U.S. PATENT DOCUMENTS 3,368,872 A 2/1968 Natelson
3,447,863 A 6/1969 Patterson
(Continued)

FOREIGN PATENT DOCUMENTS

AU 198813789 A 9/1988
AU 619459 B 1/1992
(Continued)

OTHER PUBLICATIONS

Van Vliet, Dillys et al., Prediction of asthma exacerbations in children by innovative exhaled inflammatory markers: Results of a longitudinal study, PLOS ONE, Mar. 23, 2015, vol. 10. No. 3, e0119434.
(Continued)

*Primary Examiner* — Jyoti Nagpaul

(57) ABSTRACT

The present invention is related to the field of bio/chemical sampling, sensing, assays and applications. Particularly, the present invention is related to how to make the sampling/sensing/assay become simple to use, fast to results, highly sensitive, easy to use, using tiny sample volume (e.g. 0.5 uL or less), operated by a person without any professionals, reading by mobile-phone, or low cost, or a combination of them.

46 Claims, 32 Drawing Sheets

Related U.S. Application Data

(60) Provisional application No. 62/369,181, filed on Jul. 31, 2016, provisional application No. 62/305,123, filed on Mar. 8, 2016, provisional application No. 62/293,188, filed on Feb. 9, 2016, provisional application No. 62/218,455, filed on Sep. 14, 2015.

(51) Int. Cl.

| | | |
|---|---|---|
| G16H 80/00 | (2018.01) | |
| B01L 3/00 | (2006.01) | |
| G01N 1/30 | (2006.01) | |
| G01N 33/50 | (2006.01) | |

(56) References Cited

U.S. PATENT DOCUMENTS

| | | |
|---|---|---|
| 3,895,661 A | 7/1975 | Praglin et al. |
| 3,925,166 A | 12/1975 | Blume |
| 3,992,158 A | 11/1976 | Przybylowicz et al. |
| 4,022,521 A | 5/1977 | Hall et al. |
| 4,066,412 A | 1/1978 | Johnson et al. |
| 4,088,448 A | 5/1978 | Lilja et al. |
| 4,171,866 A | 10/1979 | Tolles |
| 4,233,029 A | 11/1980 | Columbus |
| 4,255,384 A | 3/1981 | Kitajima et al. |
| 4,258,001 A | 3/1981 | Pierce et al. |
| 4,329,054 A | 5/1982 | Bachalo |
| 4,402,614 A | 9/1983 | Porath |
| 4,427,294 A | 1/1984 | Pietro |
| 4,430,436 A | 2/1984 | Koyama et al. |
| 4,596,695 A | 6/1986 | Cottingham |
| 4,745,075 A | 5/1988 | Hadfield et al. |
| 4,806,311 A | 2/1989 | Greenquist |
| 4,883,642 A | 11/1989 | Bisconte |
| 4,906,439 A | 3/1990 | Grenner |
| 4,911,782 A | 3/1990 | Brown |
| 4,950,455 A | 8/1990 | Smith |
| 5,002,736 A | 3/1991 | Babbitt et al. |
| 5,039,487 A | 8/1991 | Smith |
| 5,096,836 A | 3/1992 | Macho et al. |
| 5,122,284 A | 6/1992 | Braynin et al. |
| 5,132,097 A | 7/1992 | Van Deusen et al. |
| 5,169,601 A | 12/1992 | Ohta et al. |
| 5,188,968 A | 2/1993 | Kano et al. |
| 5,223,219 A | 6/1993 | Subramanian et al. |
| 5,281,540 A | 1/1994 | Merkh et al. |
| 5,306,467 A | 4/1994 | Douglas-Hamilton et al. |
| 5,321,975 A | 6/1994 | Wardlaw |
| 5,362,648 A | 11/1994 | Koreyasu et al. |
| 5,413,732 A | 5/1995 | Buhl et al. |
| 5,427,959 A | 6/1995 | Nishimura et al. |
| 5,431,880 A | 7/1995 | Kramer |
| 5,591,403 A | 1/1997 | Gavin et al. |
| 5,623,415 A | 4/1997 | O'Bryan et al. |
| 5,753,456 A | 5/1998 | Naqui et al. |
| 5,768,407 A | 6/1998 | Shen et al. |
| 5,858,648 A | 1/1999 | Steel et al. |
| 5,879,628 A | 3/1999 | Ridgeway et al. |
| 5,888,834 A | 3/1999 | Ishikawa et al. |
| 5,939,326 A | 8/1999 | Chupp et al. |
| 5,948,686 A | 9/1999 | Wardlaw |
| 6,004,821 A | 12/1999 | Levine et al. |
| 6,016,367 A | 1/2000 | Benedetti et al. |
| 6,017,767 A | 1/2000 | Chandler |
| 6,022,734 A | 2/2000 | Wardlaw |
| 6,106,778 A | 8/2000 | Oku et al. |
| 6,180,314 B1 | 1/2001 | Berndt |
| 6,235,536 B1 | 5/2001 | Wardlaw |
| 6,350,613 B1 | 2/2002 | Wardlaw et al. |
| 6,358,475 B1 | 3/2002 | Berndt |
| 6,429,027 B1 | 8/2002 | Chee et al. |
| 6,503,760 B2 | 1/2003 | Malmqvist et al. |
| 6,551,554 B1 | 4/2003 | Vermeiden et al. |
| 6,623,701 B1 | 9/2003 | Eichele et al. |
| 6,632,652 B1 | 10/2003 | Austin et al. |
| 6,714,287 B2 | 3/2004 | Berndt |
| 6,723,290 B1 | 4/2004 | Wardlaw |
| 6,844,201 B2 | 1/2005 | Malmqvist et al. |
| 6,866,823 B2 | 3/2005 | Wardlaw |
| 6,869,570 B2 | 3/2005 | Wardlaw |
| 6,893,850 B2 | 5/2005 | Ostuni et al. |
| 6,921,514 B1 | 7/2005 | Vetter et al. |
| 6,929,953 B1 | 8/2005 | Wardlaw |
| 6,939,032 B2 | 9/2005 | Cosby et al. |
| 7,101,341 B2 | 9/2006 | Tsukashima et al. |
| 7,179,423 B2 | 2/2007 | Bohm et al. |
| 7,282,367 B2 | 10/2007 | Kawamura |
| 7,393,658 B2 | 7/2008 | Carbonell et al. |
| 7,410,617 B2 | 8/2008 | Sakamoto |
| 7,410,807 B2 | 8/2008 | D'Aurora |
| 7,468,160 B2 | 12/2008 | Thompson et al. |
| 7,510,841 B2 | 3/2009 | Stuelpnagel et al. |
| 7,510,848 B2 | 3/2009 | Hammond et al. |
| 7,547,424 B2 | 6/2009 | Haab et al. |
| 7,731,901 B2 | 6/2010 | Wardlaw |
| 7,738,094 B2 | 6/2010 | Goldberg |
| 7,850,916 B2 | 12/2010 | Wardlaw |
| 7,862,773 B2 | 1/2011 | Ibrahim |
| 7,863,411 B2 | 1/2011 | Hammond et al. |
| 7,897,376 B2 | 3/2011 | Porter et al. |
| 7,901,897 B2 | 3/2011 | Stuelpnagel et al. |
| 7,903,241 B2 | 3/2011 | Wardlaw et al. |
| 7,929,121 B2 | 4/2011 | Wardlaw et al. |
| 7,929,122 B2 | 4/2011 | Wardlaw et al. |
| 7,943,093 B2 | 5/2011 | Adrien et al. |
| 7,951,599 B2 | 5/2011 | Levine et al. |
| 7,995,194 B2 | 8/2011 | Wardlaw et al. |
| 8,045,165 B2 | 10/2011 | Wardlaw et al. |
| 8,058,073 B2 | 11/2011 | Chiapperi et al. |
| 8,077,296 B2 | 12/2011 | Wardlaw et al. |
| 8,081,303 B2 | 12/2011 | Levine et al. |
| 8,133,738 B2 | 3/2012 | Levine et al. |
| 8,158,434 B2 | 4/2012 | Wardlaw |
| 8,221,985 B2 | 7/2012 | Wardlaw et al. |
| 8,241,572 B2 | 8/2012 | Wardlaw |
| 8,269,954 B2 | 9/2012 | Levine et al. |
| 8,284,384 B2 | 10/2012 | Levine et al. |
| 8,287,820 B2 | 10/2012 | Williams et al. |
| 8,310,658 B2 | 11/2012 | Wardlaw et al. |
| 8,310,659 B2 | 11/2012 | Wardlaw et al. |
| 8,319,954 B2 | 11/2012 | Wardlaw et al. |
| 8,326,008 B2 | 12/2012 | Lalpuria et al. |
| 8,338,579 B2 | 12/2012 | Adams et al. |
| 8,361,799 B2 | 1/2013 | Levine et al. |
| 8,367,012 B2 | 2/2013 | Wardlaw |
| 8,462,332 B2 | 6/2013 | Pugia et al. |
| 8,467,063 B2 | 6/2013 | Wardlaw et al. |
| 8,472,693 B2 | 6/2013 | Davis et al. |
| 8,481,282 B2 | 7/2013 | Levine et al. |
| 8,502,963 B2 | 8/2013 | Levine et al. |
| 8,513,032 B2 | 8/2013 | Jablonski et al. |
| 8,569,076 B2 | 10/2013 | Wardlaw et al. |
| 8,594,768 B2 | 11/2013 | Phillips et al. |
| 8,604,161 B2 | 12/2013 | Hammond et al. |
| 8,628,952 B2 | 1/2014 | Stuelpnagel et al. |
| 8,633,013 B2 | 1/2014 | Kaiser et al. |
| 8,638,427 B2 | 1/2014 | Wardlaw et al. |
| 8,717,673 B2 | 5/2014 | Selvin et al. |
| 8,741,630 B2 | 6/2014 | Dickinson et al. |
| 8,750,966 B2 | 6/2014 | Phillips et al. |
| 8,778,687 B2 | 7/2014 | Levine et al. |
| 8,781,203 B2 | 7/2014 | Davis et al. |
| 8,796,186 B2 | 8/2014 | Shirazi |
| 8,797,527 B2 | 8/2014 | Hukari et al. |
| 8,835,186 B2 | 9/2014 | Jablonski et al. |
| 8,837,803 B2 | 9/2014 | Wang et al. |
| 8,842,264 B2 | 9/2014 | Wardlaw et al. |
| 8,885,154 B2 | 11/2014 | Wardlaw et al. |
| 8,906,700 B2 | 12/2014 | Lim et al. |
| 8,911,815 B2 | 12/2014 | Kram et al. |
| 8,974,732 B2 | 3/2015 | Lalpuria et al. |
| 8,994,930 B2 | 3/2015 | Levine et al. |
| 9,023,641 B2 | 5/2015 | Rodriguez et al. |
| 9,044,268 B2 | 6/2015 | Phillips et al. |

(56) References Cited

U.S. PATENT DOCUMENTS

| | | |
|---|---|---|
| 9,046,473 B2 | 6/2015 | Levine et al. |
| 9,084,995 B2 | 7/2015 | Wardlaw |
| 9,086,408 B2 | 7/2015 | Egan et al. |
| 9,097,640 B2 | 8/2015 | Goldberg et al. |
| 9,199,233 B2 | 12/2015 | Wardlaw |
| 9,274,094 B2 | 3/2016 | Wardlaw et al. |
| 9,291,617 B2 | 3/2016 | Levine et al. |
| 9,322,835 B2 | 4/2016 | Wardlaw |
| 9,347,962 B2 | 5/2016 | Salsman |
| 9,354,159 B2 | 5/2016 | Vaartstra |
| 9,395,365 B2 | 7/2016 | Levine et al. |
| 9,469,871 B2 | 10/2016 | Bearinger et al. |
| 9,523,670 B2 | 12/2016 | Mueller et al. |
| 9,696,252 B2 | 7/2017 | Wardlaw |
| 2001/0055882 A1 | 12/2001 | Ostuni |
| 2003/0068614 A1 | 4/2003 | Cima et al. |
| 2003/0107946 A1 | 6/2003 | Cosby et al. |
| 2003/0109059 A1 | 6/2003 | Adrien et al. |
| 2004/0131345 A1 | 7/2004 | Kylberg et al. |
| 2004/0156755 A1 | 8/2004 | Levine |
| 2004/0214310 A1 | 10/2004 | Parker et al. |
| 2004/0259162 A1 | 12/2004 | Kappel et al. |
| 2005/0026161 A1 | 2/2005 | Jablonski et al. |
| 2005/0032138 A1 | 2/2005 | Lathrop et al. |
| 2005/0158880 A1 | 7/2005 | Ostuni et al. |
| 2005/0254995 A1 | 11/2005 | Sostek et al. |
| 2006/0015157 A1 | 1/2006 | Leong |
| 2006/0051253 A1 | 3/2006 | Gousepohl |
| 2006/0062440 A1 | 3/2006 | Hollars et al. |
| 2006/0062695 A1 | 3/2006 | Haab et al. |
| 2006/0090658 A1 | 5/2006 | Phillips |
| 2006/0160134 A1 | 7/2006 | Melker et al. |
| 2007/0087442 A1 | 4/2007 | Wardlaw |
| 2007/0128071 A1 | 6/2007 | Shea et al. |
| 2007/0243117 A1 | 10/2007 | Wardlaw |
| 2008/0028962 A1 | 2/2008 | Phillips et al. |
| 2008/0214947 A1 | 9/2008 | Hunt et al. |
| 2008/0274564 A1 | 11/2008 | D'Aurora |
| 2008/0286152 A1 | 11/2008 | Schmidt et al. |
| 2009/0211344 A1 | 8/2009 | Wang |
| 2009/0227472 A1 | 9/2009 | Stuelpnagel et al. |
| 2009/0233329 A1 | 9/2009 | Rodriguez et al. |
| 2009/0246781 A1 | 10/2009 | Klem et al. |
| 2009/0258371 A1 | 10/2009 | Wardlaw et al. |
| 2009/0298716 A1 | 12/2009 | Stuelpnagel et al. |
| 2010/0081583 A1 | 4/2010 | Shirazi |
| 2010/0085067 A1 | 4/2010 | Gabriel et al. |
| 2010/0151593 A1 | 6/2010 | D'Aurora |
| 2010/0216248 A1 | 8/2010 | Wardlaw |
| 2010/0255605 A1 | 10/2010 | Wardlaw |
| 2010/0272345 A1 | 10/2010 | Wardlaw |
| 2010/0273244 A1 | 10/2010 | Wardlaw |
| 2010/0291562 A1 | 11/2010 | Adler |
| 2011/0009297 A1 | 1/2011 | Jones et al. |
| 2011/0206557 A1 | 8/2011 | Phan et al. |
| 2011/0294198 A1 | 12/2011 | Wardlaw |
| 2012/0034647 A1 | 2/2012 | Herzog et al. |
| 2012/0107799 A1 | 5/2012 | Daum |
| 2012/0108787 A1 | 5/2012 | Lue |
| 2012/0157332 A1 | 6/2012 | Kumar et al. |
| 2012/0300293 A1 | 11/2012 | Selvin et al. |
| 2013/0065788 A1 | 3/2013 | Glezer et al. |
| 2013/0102018 A1 | 4/2013 | Schentag et al. |
| 2013/0157288 A1 | 6/2013 | Kilfeather et al. |
| 2013/0209332 A1 | 8/2013 | Wardlaw |
| 2013/0265054 A1 | 10/2013 | Lowery et al. |
| 2013/0309679 A1 | 11/2013 | Ismagilov et al. |
| 2014/0315242 A1 | 10/2014 | Rodriguez et al. |
| 2014/0368631 A1 | 12/2014 | Wardlaw et al. |
| 2015/0036131 A1 | 2/2015 | Salsman |
| 2015/0253321 A1 | 9/2015 | Chou et al. |
| 2015/0317506 A1 | 11/2015 | Xie et al. |
| 2015/0323519 A1 | 11/2015 | Wardlaw |
| 2016/0025637 A1 | 1/2016 | Halverson et al. |
| 2016/0033496 A1 | 2/2016 | Chou et al. |
| 2016/0245797 A1 | 8/2016 | Ahmad et al. |
| 2016/0266091 A1 | 9/2016 | Levine et al. |
| 2017/0021356 A1 | 1/2017 | Dority et al. |
| 2017/0038401 A1 | 2/2017 | Holmes et al. |
| 2017/0045504 A1 | 2/2017 | Bloom |

FOREIGN PATENT DOCUMENTS

| | | |
|---|---|---|
| CN | 1299466 | 6/2001 |
| CN | 1302229 | 7/2001 |
| CN | 1166950 | 9/2004 |
| CN | 1188217 | 2/2005 |
| CN | 102027369 | 4/2011 |
| EP | 261667 A2 | 3/1988 |
| EP | 291153 A1 | 11/1988 |
| EP | 261667 A3 | 5/1989 |
| EP | 0420765 A2 | 4/1991 |
| EP | 2620217 A1 | 4/1991 |
| EP | 291153 B1 | 6/1992 |
| EP | 261667 B1 | 2/1993 |
| EP | 0961110 | 12/1999 |
| EP | 1949310 A2 | 7/2008 |
| EP | 2290100 | 3/2011 |
| EP | 1949310 A4 | 11/2011 |
| EP | 2439515 | 4/2012 |
| EP | 2554987 | 2/2013 |
| EP | 3026433 | 6/2016 |
| EP | 1949310 B1 | 2/2019 |
| RU | 2147123 C1 | 3/2000 |
| RU | 98113214 A | 4/2000 |
| RU | 2186388 C2 | 7/2002 |
| RU | 2477488 C2 | 3/2013 |
| WO | 1991020009 | 12/1991 |
| WO | 1999044743 | 9/1999 |
| WO | 1999045385 | 9/1999 |
| WO | 2003062920 | 7/2003 |
| WO | 2005114145 | 12/2005 |
| WO | 2005100539 | 1/2006 |
| WO | 2007112332 | 10/2007 |
| WO | 2009117652 | 9/2009 |
| WO | 2009117664 | 9/2009 |
| WO | 2009117678 | 9/2009 |
| WO | 2009117682 | 9/2009 |
| WO | 2009124186 | 10/2009 |
| WO | 2009124190 | 10/2009 |
| WO | 2009126800 | 10/2009 |
| WO | 2010115026 | 10/2010 |
| WO | 2014049116 A1 | 4/2014 |
| WO | 2014055559 | 4/2014 |
| WO | 2014089468 | 6/2014 |
| WO | 2014183049 | 11/2014 |
| WO | 2014205576 | 12/2014 |
| WO | 2017048871 | 3/2017 |

OTHER PUBLICATIONS

Written Opinion for PCT/US2018/017713 established by ISA/KR, dated Jun. 20, 2018.

International Search Report and Written Opinion of the International Searching Authority for PCT/US16/46437 established by the ISA/US completed on Dec. 29, 2016.

Case 1. Multiplexing. One binding site for one or multiple storage sites

Different storage sites can have the same detection agent but different concentration or different detection agents of the same or different concentration.

a b
Cross-section view

Case 2. Multiplexing. One storage site for one or multiple binding sites

Different storage sites can have the same detection agent but different concentration or different detection agents of the same or different concentration.

a b

Cross-section view

Case 3. Multiplexing. Multiple binding sites and multiple corresponding storage sites Different storage sites can have the same detection agent but different concentration or different detection agents of the same or different concentration.

a b

Cross-section view

(a)

(b)

DEVICE AND SYSTEM FOR ANALYZING A SAMPLE, PARTICULARLY BLOOD, AS WELL AS METHODS OF USING THE SAME

CROSS-REFERENCING

This application is a continuation of U.S. patent application Ser. No. 15/742,744, filed on Jan. 8, 2018, which is a 371 National Stage Application of PCT Application Serial No. PCT/US2016/051775, filed on Sep. 14, 2016, which claims the benefit of U.S. Provisional Application Ser. No. 62/218,455, filed on Sep. 14, 2015, 62/293,188, filed on Feb. 9, 2016, 62/305,123, filed on Mar. 8, 2016, 62/369,181, filed on Jul. 31, 2016, and PCT/US2016/046437, filed on Sep. 14, 2016, which PCT claims the benefit of U.S. Provisional Application Serial Nos. 62/202,989, filed on Aug. 10, 2015, 62/218,455, filed on Sep. 14, 2015, 62/293,188, filed on Feb. 9, 2016, 62/305,123, filed on Mar. 8, 2016, 62/369,181, filed on Jul. 31, 2016, the contents of which are relied upon and incorporated herein by reference in their entirety. The entire disclosure of any publication or patent document mentioned herein is entirely incorporated by reference.

FIELD

The present invention is related to the field of bio/chemical sampling, sensing, assays and applications.

BACKGROUND

In bio/chemical sample, particularly blood, analysis, there is a need for the methods and devices that can accelerate the process (e.g. binding, mixing reagents, etc.) and quantify the parameters (e.g. analyte concentration, the sample volume, etc.), that can simplify the sample collection and measurement processes, that can handle samples with small volume, that allow an entire assay performed in less than a minute, that allow an assay performed by a smartphone (e.g. mobile phone), that allow non-professional to perform an assay her/himself, and that allow a test result to be communicated locally, remotely, or wirelessly to different relevant parties. The present invention relates to the methods, devices, and systems that can address these needs.

SUMMARY OF INVENTION

The following brief summary is not intended to include all features and aspects of the present invention. The present invention relates to the methods, devices, and systems that make bio/chemical sensing (including, not limited to, immunoassay, nucleic assay, electrolyte analysis, etc.) faster, more sensitive, less steps, easy to perform, smaller amount of samples required, less or reduced (or no) needs for professional assistance, and/or lower cost, than many current sensing methods and devices.

The goal of many of today's laboratory tests is to accurately determine the absolute concentration of an analyte in a sample. For example, a red blood cell (RBC) test involves counting the number of red blood cells in a defined amount of whole blood, and then calculating the number of red blood cells per microliter of whole blood. However, such measurements can be challenging to perform without using a specialized test center (i.e., in an "at home", "in the pharmacy" or "point of care" environment) because such tests often require specialized instrumentation and/or an accurate measuring device that is capable of accurately measuring a relatively small volume (such as an accurate pipette or the like) of a biological fluid.

Measurement of the Relevant Volume

Many assays provide the absolute concentration of an analyte in a sample. However, the results of such assays become quite inaccurate when only a small volume (e.g., 100 nL to 10 µl, for example) is analyzed. This is because small volumes are difficult to dispense and/or measure accurately.

In some assays, a liquid sample can be placed in between two plates that are separated by spacers and analyzed. In theory, the volume of sample analyzed can be calculated by multiplying the area of the sample that is analyzed by the thickness of the sample that is analyzed. In practice, however, such estimates are not easy to make and are quite inaccurate for a variety of reasons. By way of example, some devices use beads to space the plates apart, and either the beads or one of the plates is deformable. Such devices may be prone to inaccuracy for the following reasons:

Spherical spacers have a much smaller contact area (nearly a point) with the plates. In such devices, because of the much smaller contact area, for each unit of pressing force applied, a much larger pressure is applied onto contact area of both the plate and the spheres. This larger pressure causes the spheres and/or the plates (if they are flexible) to deform, which distorts any measurements.

Spherical spacers usually end up being randomly distributed between two plates. Because the spherical spacers are distributed randomly, the inter-spacer distances will vary greatly, and some of the distances are be quite large. This causes the spacers and/or the plates (if they are flexible) to deform to a much greater extent in some areas relative to other, which also distorts the results.

Randomly placed spacers that are close together may become obstacles that block the movement of analytes (e.g., cells), thereby potentially producing "clumps" of analytes or cells which may cause even more difficulties.

Significant deformation of one of the plates may cause cells to lyse, which may cause errors in cell counting efforts.

Volume calculations are inaccurate because the number of spherical spacers in the area analyzed, as well as the extent to which the spacers and/or one of the plates deforms varies from sample to sample.

Deformation causes variation in the time that it takes for molecules to diffuse to the surface of one of the plates.

In devices that uses spherical spacers, the volume of the part of the sample that has been analyzed can potentially be estimated by a) counting the spheres in the volume of the sample analyzed and b) experimentally estimate the thickness of a layer of sample (e.g., add an internal standard, such as an immiscible liquid that contains a known concentration of calibrant, that can be used to calculate the distance between the plates). However, the extra steps are inconvenient to perform and, because the top plate and/or the spacers are significantly deformed in use, the measurements obtained from such devices are still not very accurate.

In contrast, embodiments of the present method and device rely on spacers that have a substantially uniform height, a nearly uniform cross-section (e.g. a pillar with straight sidewall), and planar (i.e., "flat") tops, that are fixed to one or more of the plates in regular pattern in which the spacers are separated from one another by a consistent, defined, distance (i.e., not at random positions that are governed by Poisson statistics). During use of some implementations of the present method and device, the spacers and plates are not significantly compressed or deformed in any dimension, at least while the plates are in the closed position and being pulled together by capillary force. The present device can have many advantages in that, in use of the present device, the volume of the part of the sample from which data is obtained (i.e., the "relevant volume" or the volume of the part of the sample in the analyzed area) can be readily calculated very accurately and, in some cases, can even be calculated prior to initiating an assay, even if an unknown amount of the sample is deposited onto the device. Because, in the closed position, the plates are substantially flat (which means that the thickness of the sample is uniform) and the number and dimensions of the spacers in the analyzed area are known, the volume of sample in the area can be readily calculated with high accuracy. The relevant volume sample can be determined without having to count the spacers in an area or estimate the thickness of a layer of sample, after the assay has been performed. There is also need to deposit specific amount of sample into the device. Further, at the beginning of an incubation, the analyte molecules should be evenly distributed throughout the relevant volume (to the extent allowed by Poisson statistics), not more concentrated in one area relative to another.

Decreased Reaction Time

It is know that the diffusion constant of many analytes in an aqueous environment is very low and, as such, many assays require a lengthy incubation time (often several hours and in certain cases days), agitation and the use of agents or forces that encourage mixing. Such assays are designed to allow an analyte to diffuse laterally from an initial location to a remote destination on one of the plates (see, e.g., Wei et al, Nucl. Acids Res. 33: e78 and Toegl et al, J. Biomol. Tech. 2003 14: 197-204, for example). Such systems are limited because it may take several hours to get a result. Further, if a result is obtained, it is often difficult to say with any certainty that a reaction has reached equilibrium at the time which the reaction was terminated. This uncertainty, among other things, makes it impossible to estimate the absolute concentration of the analyte in the sample.

As will be explained in greater detail below, in some embodiments of the present method and device the spacer height and assay end point may be chosen to limit the amount of lateral diffusion of analytes during the assay. In these cases, such an assay (typically a binding assay) can be run in a very short time. In addition, the concentration of the analyte in the sample can be estimated very accurately, even though the entire sample may not have been analyzed or may be of an unknown volume.

In these embodiments, an assay may be stopped and/or assay results may be read at a time that is i. equal to or longer to the time that it takes for a target entity to diffuse across the thickness of the uniform thickness layer at the closed configuration (i.e., shorter than the time that it would take for the analyte to vertically diffuse from one plate to the other); and ii. shorter than the time that it takes the target entity to laterally diffuse across the linear dimension of the predetermined area of the binding site (i.e., shorter than the time that it would take for the analyte to laterally diffuse from one side of the binding site to other). In such "local binding" configurations, the volume of the part of the sample from which data is obtained (the "relevant volume") can be estimated reasonably accurately because it is the volume of the sample that is immediately above the analyzed area. Indeed, the volume of the part of the sample from which data is obtained may be known before the assay is initiated. Such "local binding" embodiments have an additional advantage in that the sample and, optionally, any detection reagents are pressed into a thin layer over a binding site and, as such, binding between any analytes and/or detection reagents should reach equilibrium more quickly than in embodiments in which the sample is not pressed into a thin layer, e.g., if a drop of sample is simply placed on top of a plate with the binding site. As such, in many cases, binding equilibrium may be reached in a matter of seconds rather than minutes and, as such, many assays, particularly binding assays, can be done very quickly, e.g., in less than a minute.

Multiplexing

In addition, the "local binding" configuration allows one to perform multiplex assays without fluidically isolating the different reactions from one another. In other words, multiple assays can be done in an open environment, without the assays being walled off from one another (i.e., without fluidic isolation). For example, in local binding embodiments, two different analytes in the same sample can be assayed side-by-side and, because the assay is be stopped and/or the assay results are be read prior to diffusion of the one analyte from one assay area into the other, the absolute concentrations of those analytes in the sample can be determined separately from one another, even though they are not fluidically isolated from one another.

Being able to perform multiple assays on one sample, without fluidic isolation, by simply sandwiching a sample between two plates and performing the assay in a diffusion-limited way has several advantages. For example, the assays can be done by simply dropping a droplet of a sample (e.g., blood) of an unknown volume, spreading out the sample across the plates by pressing the plates together, incubating the sample for a period of time and taking a reading from multiple sites in the device. In practicing this method, one does not need to transfer defined amounts of a sample into several chambers, which is difficult to implement without an accurate fluid transfer and/or measuring device. Moreover, the assay is extremely rapid for the reasons set out above. Further, because the plates do not need to be made with "walls" the manufacture of the device is straightforward. Finally, there is no requirement for ports in any of the plates, i.e., ports that could potentially be used for adding or removing sample or a reagent while the device is in closed position.

Amplification Surface

In addition, in some embodiments of the present device and method, the device may contain an "amplification surface" see, e.g., a surface enhances the signal, e.g., fluorescence or luminescence, that is produced by a detection agent. In some cases, the signal can enhanced by a nanoplasmonic effect (e.g., surface-enhanced Raman scattering). Examples of signal enhancement by an amplification surface are described, e.g., in Li et al, Optics Express 2011 19: 3925-3936 and WO2012/024006, which are incorporated herein by reference. In some cases, the amplification surface may be a disk-coupled dots-on-pillar antenna array (D2PA), which has been described in U.S. Pat. No. 9,013,690. In use, a device containing an amplification surface may a signal by $10^3$ fold or more, compared to a detector that is not configured to enhance the signal, thereby allowing analytes to be detected with an extremely high sensitivity. In some embodiments, the amount of analyte in a relevant volume of a sample, particularly non-cell analytes that are detected using a sandwich assay, can be counted digitally, e.g., using the methods described in WO2014144133. The use of an amplification surface, in some cases, allows the assay to be read using a smartphone or the like.

Other Features

In embodiments of the present device, the spacers are fixed to the one or more the plates are not able to change position or be swept away if the plate is immersed in an aqueous environment. The spacers are not spherical and they are not affixed to the surface of a plate via a weak force, such as an electrostatic force, gravity or the like. In some embodiments, a plate having spacers may be a monolithic. In many embodiments, the spacers are not pre-made and then affixed onto a plate (e.g., glued on or the like). Rather, the spacers may be grown and/or etched on a plate using an embossing and/or microfabrication (e.g., a photolithography) process.

The parameters of the spacers (e.g., their cross-section, spacing and density, etc.) can be optimized so that, in the closed position, the top plate (which may be flexible) does not significantly deform over the part of the sample that is being analyzed (the "relevant volume" of the sample). In some cases, the parameters of the spacers may be adjusted depending on the flexibility of the top plate. For example, if the top plate is more flexible, then the spacers may be closer together. Likewise, if the top plate is less flexible, then the spacers may be further apart.

Moreover, in use of many embodiments of the present device, analytes do not migrate directionally through the device after the device is closed. As such, in the closed configuration there may be no sorting or fractionating of the analytes, no directional, forced, flow of the analytes through the device, (e.g., by gravity or electrophoresis), as described in Austin (U.S. Pat. No. 6,632,652). In many cases there is no need for the device to be coupled to a power supply to generate an electromotive force. In many embodiments, there are no "obstacles" to hinder passage of an analyte (cell) while the sample is being spread, leading to analytes that are evenly distributed throughout the relevant volume (to the extent allowed by Poisson statistics), not more concentrated in one area relative to another. In addition, in other devices, the function of the coverplate is to seal the device to prevent liquid leaking out and, as such, the cover-plate is placed on top of the substrate plate at a time at which there is no sample on either of the plates. Such devices do not push liquid onto an open plate surface to produce a thin layer of sample that can be analyzed. Additionally, in other devices, the key function of the pillars is to "filter" or sort nanoparticles (e.g., cells or alike). Hence the inter-pillar distance is determined by the nanoparticles being sorted, not for the goal of making the spacing between the cover plate and the substrate plate uniform. Finally, in devices such as Austin's device, the accuracy of sorting is primarily controlled by the inter-pillar distances not the spacing between the plates, and controlling of the spacing between the plates is not regarded as significant. Hence, such disclosures would not lead one to modify plating spacing uniformity by changing pillar size, shape, inter-pillar spacing, etc.

In view of the above, the present device and method is believed to provide an easy to use, inexpensive, easy to manufacture, and extremely rapid way to determine the absolute concentration of an analyte (or analytes, if the device and method are implemented in a multiplex way) in a liquid sample.

One aspect of the invention is the means that uses a pair of plates that are movable to each other to manipulate a small volume sample or one or a plurality of reagents or both for a simpler, faster, and/or better assaying. The manipulation includes, but limited to, reshaping a sample, forcing a sample flow, making a contact between the sample and reagent, measuring sample volume, reducing diffusion distance, increasing collision frequency, etc.—all of them have benefit effects to certain assays. In the present invention, the special features and properties on the plates, the special methods to handling the plates, and the special ways to handle the reagents and samples provide advantages in assaying.

One aspect of the invention is the means that make at least a portion of a small droplet of a liquid sample deposited on a plate to become a thin film with a thickness that is controlled, predetermined, and uniform over large area. The uniform thickness can be as thin as less than 1 um. Furthermore, the invention allows the same uniform thickness be maintained for a long time period without suffering evaporation to environment.

Another aspect of the invention is the means that utilizes the predetermined uniform thin sample thickness formed by the invention to determine the volume of a portion or entire of the sample without using any pipette or alike.

Another aspect of the invention is an embodiment for the spacers (for controlling the spacing between two plates), that has a pillar shape with a flat top and nearly uniform lateral cross-section. Such spacers offers many advantages in controlling a sample thickness over the spacers of ball (beads) shape.

Another aspect of the invention is embodiments for the spacers (for controlling the spacing between two plates), that has a pillar shape with a flat top and nearly uniform lateral cross-section. Such spacers offers many advantages in controlling a sample thickness over the spacers of ball (beads) shape.

Another aspect of the invention is the means that make certain chemical reactions (or mixing) occur predominately only in a small portion of the sample, not in the other part of the sample, without using fluidic isolation between the two portion of the sample.

Another aspect of the invention is the means that make multiple chemical reactions (or mixing) occur predominately only in each perspective small portion of the sample, not in the other part of the sample, without using fluidic isolation between the different portion of the sample. Thus the invention allows multiplexed assaying in parallel using one small drop of sample without fluidic isolation between different reaction sites.

Another aspect of the invention is the means that make assay (e.g. immunoassay, nucleic acid assay, etc.) faster. For example, a saturation incubation time (the time for the binding between molecules to reach equilibrium) is reduced from hours to less than 60 seconds.

Another aspect of the invention is the means that significantly increase the detection sensitivity by one or a combination of several methods, which including an amplification surface, large or bright labels, etc.

Another aspect of the invention is the means that perform assaying using very small amount of sample, for example as small as 0.5 uL (microliter) or less.

Another aspect of the invention is the means that simplify an assay by allowing a minute body fluid deposited directly from a subject to the testing or sample area.

Another aspect of the invention is the means that simplify and speed up an assay by pre-coating regents on plates. For example, a capture agent and a detection agent are pre-coated and dried on the plates. Another example is that all required sensing reagents are pre-coated on plates, and a sensing is done by depositing a sample on the pre-coated plates without a need of depositing other reagents.

Another aspect of the invention is the means that make reading an assay performed by a mobile phone.

Another aspect of the invention is the means that allow a person to test his/her own biomarkers on their own within 60 secs by directly deposit a drop of their own body fluid (e.g. saliva) between a pair of plastics and taking a picture with a mobile phone.

BRIEF DESCRIPTION OF THE DRAWINGS

The skilled artisan will understand that the drawings, described below, are for illustration purposes only. The drawings are not intended to limit the scope of the present teachings in any way. The drawings may not be in scale. In the figures that present experimental data points, the lines that connect the data points are for guiding a viewing of the data only and have no other means.

illustrates another embodiment of the first and second plates, wherein the first plate does not have a spacer inside the well.

Figure 10:
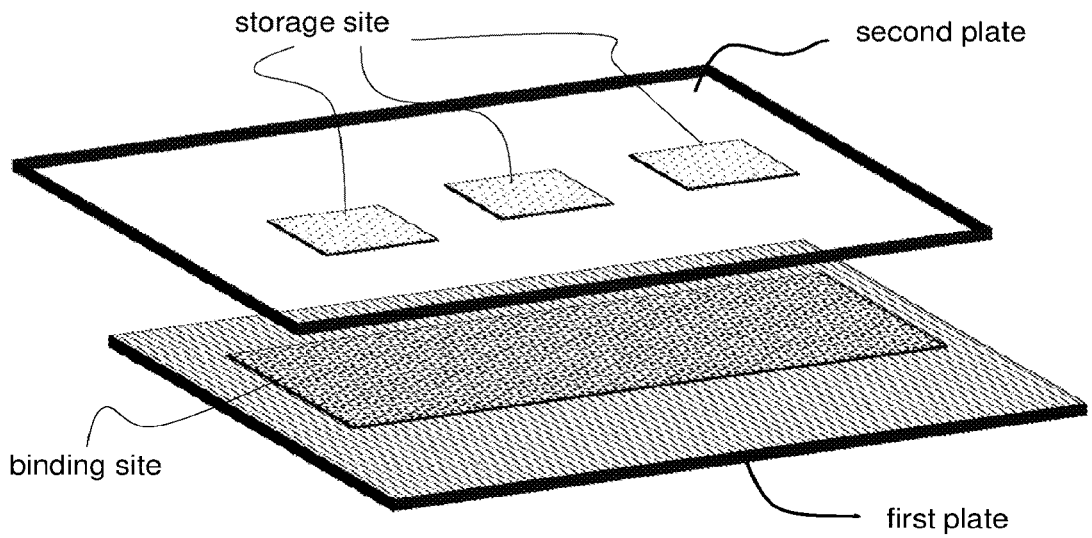
Figure 10:
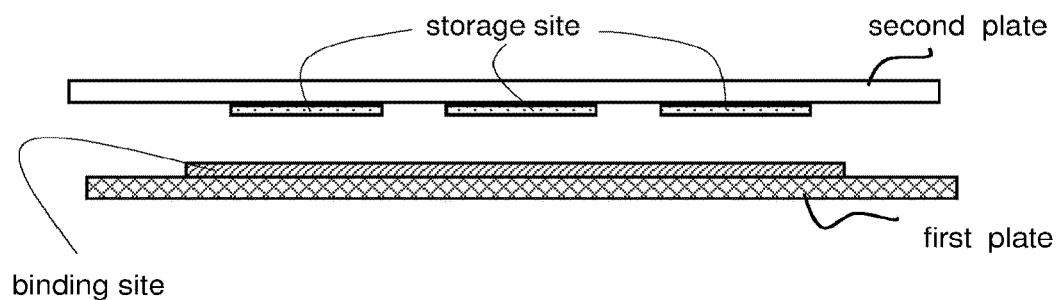

FIG. 10 schematically illustrates an exemplary embodiment of the present invention, a multiplexed detection in a single CROF device using one binding site one plate and a plurality of storage sites on the other plate. Panel (a) and (b) is a perspective and a cross-sectional view of an exemplary device, respectively.

Figure 11:
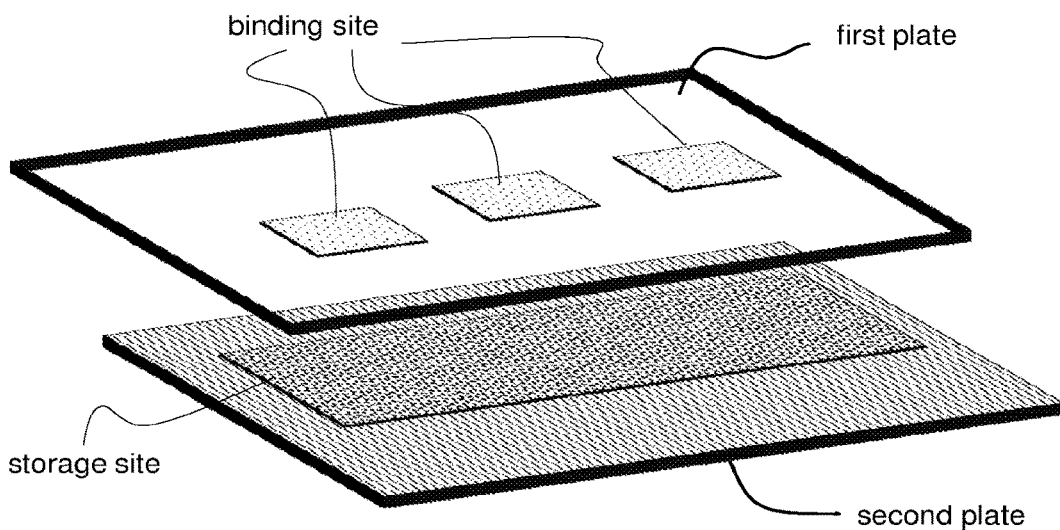
Figure 11:
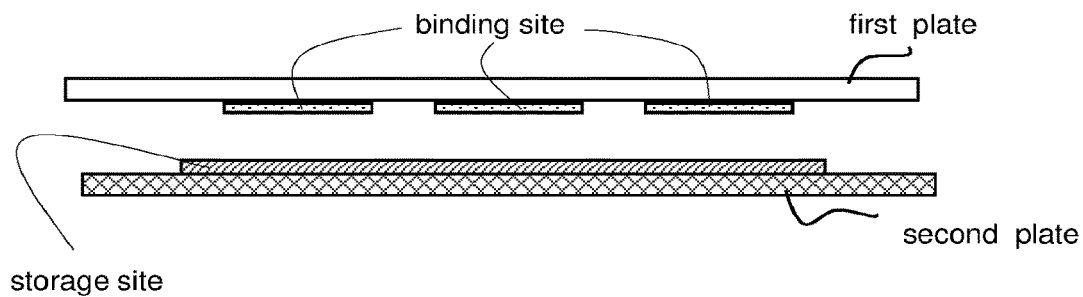

FIG. 11 schematically illustrates a further exemplary embodiment of the present invention, a multiplexed detection in a single CROF device using one storage site on one plate and multiple binding sites on the other plate. Panel (a) and (b) is a perspective and a cross-sectional view of an exemplary device, respectively.

Figure 12:
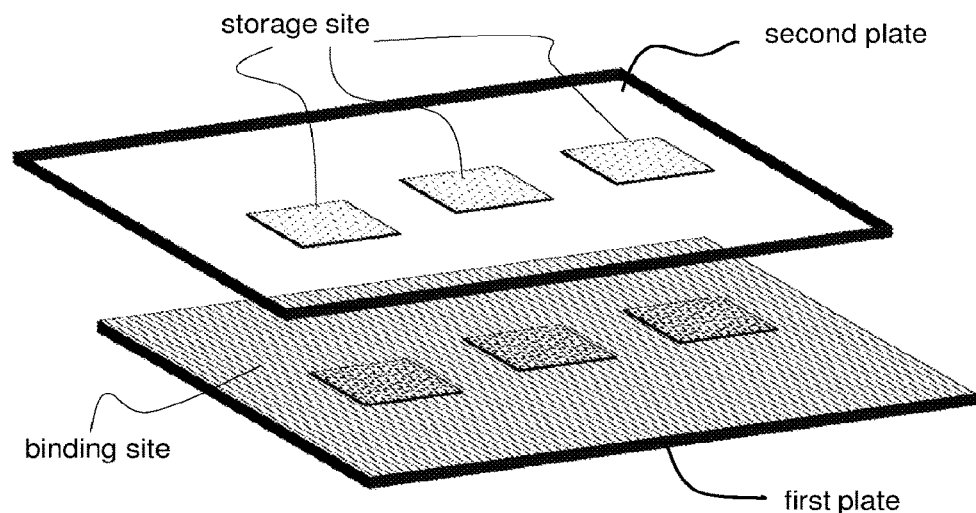
Figure 12:
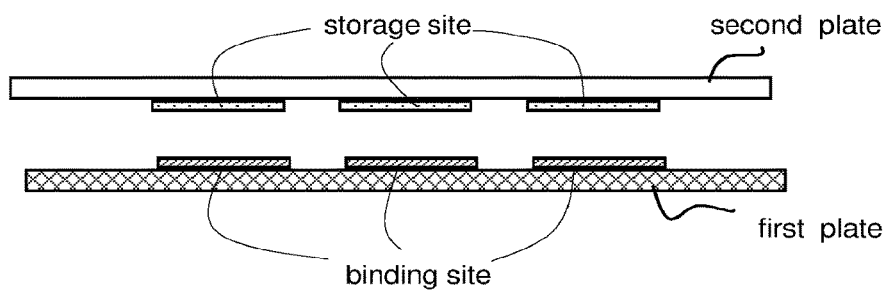

FIG. 12 schematically illustrates a further exemplary embodiment of the present invention, a multiplexed detection in a single CROF device with multiple binding sites on one plate and multiple corresponding storage sites on another plate. Panel (a) and (b) is a perspective and a cross-sectional view of an exemplary device, respectively.

Figure 13A:
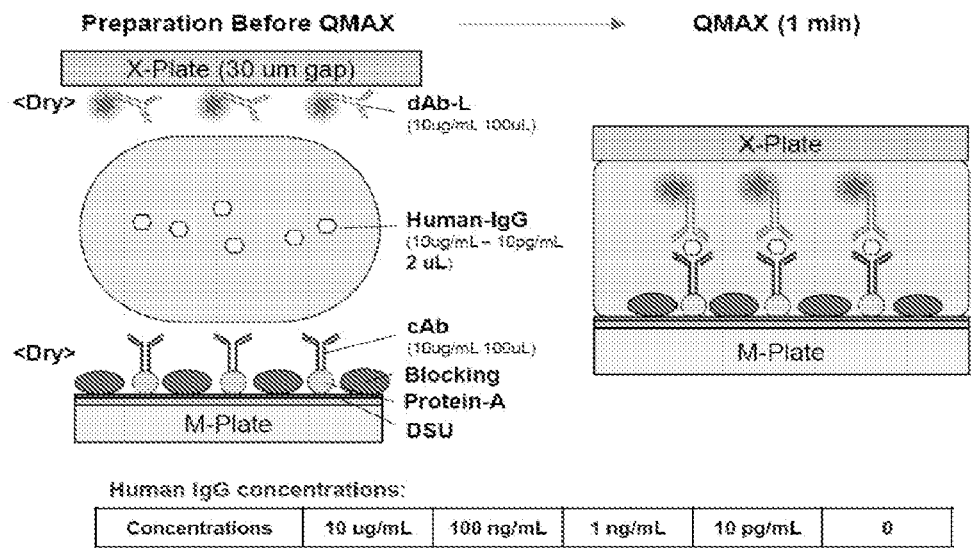

FIG. 13A schematically illustrate a QMAX assay that uses CROF with a spacer array of 30 um spacer height to achieve an assay with an saturation incubation time less than 30 sec.

Figure 13B:
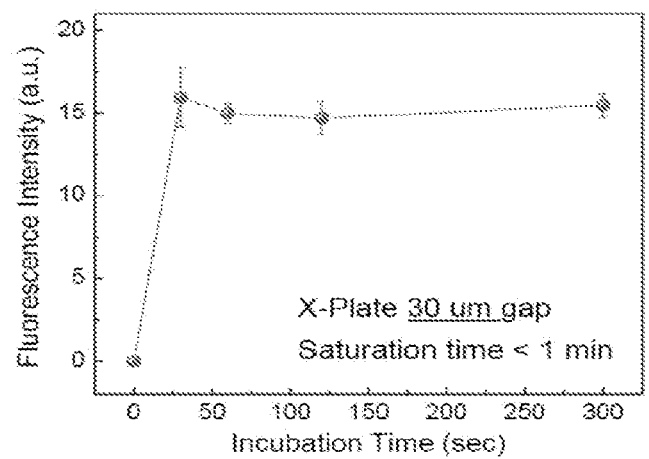

FIG. 13B is the measurement of signal of captured label vs incubation time, demonstrating that the saturation incubation time of less than 30 secs for a QMAX assay described in FIG. 13 a.

Figure 14:
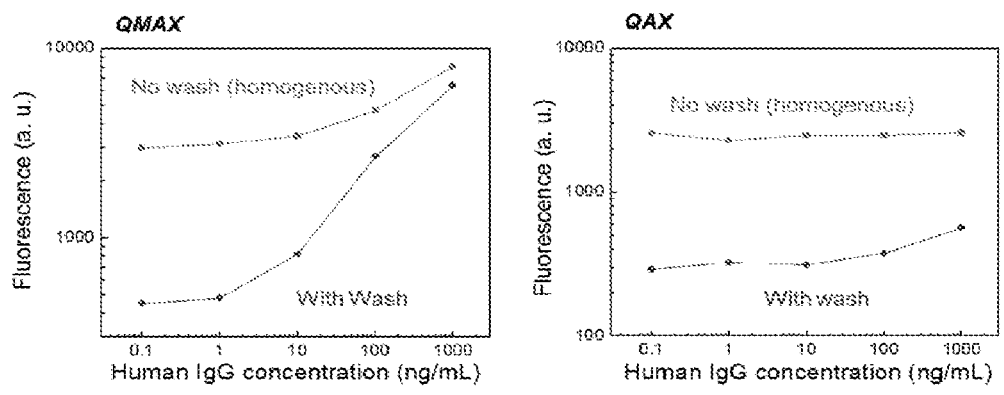

FIG. 14 shows experimentally measured LoD (limit of detection) for QAX & QMAX assay with 30 um gap (for CROF device) with wash (heterogeneous assay) and without wash (homogenous assay).

Figure 15:
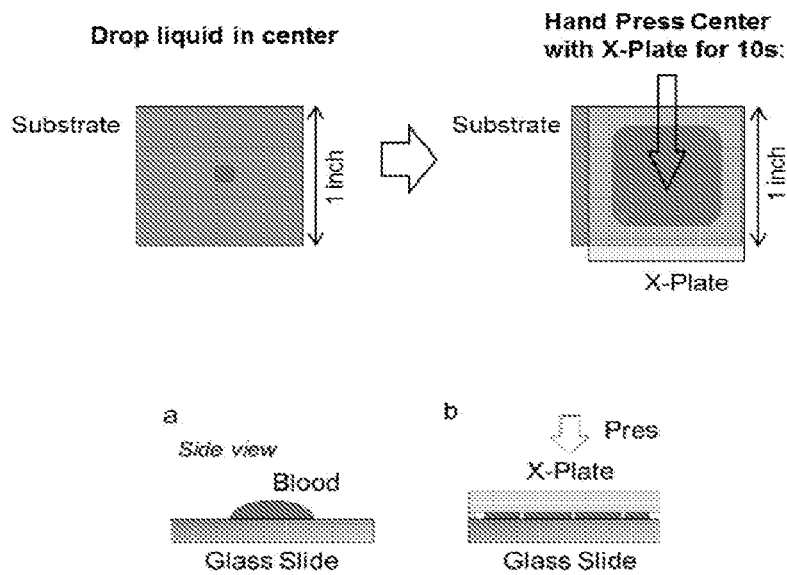

FIG. 15 illustrate a top view and cross-section view of (i) dropping a small volume sample on a glass substrate, (ii) the sample area expanded at the closed configuration of CROF.

Figure 16:
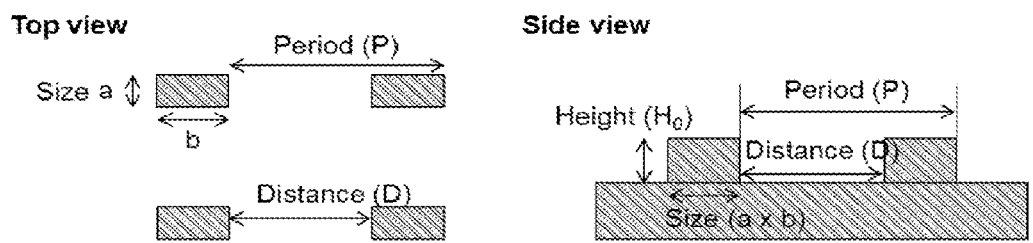

FIG. 16 illustrates the meaning of the some of the terms used herein.

Figure 17:
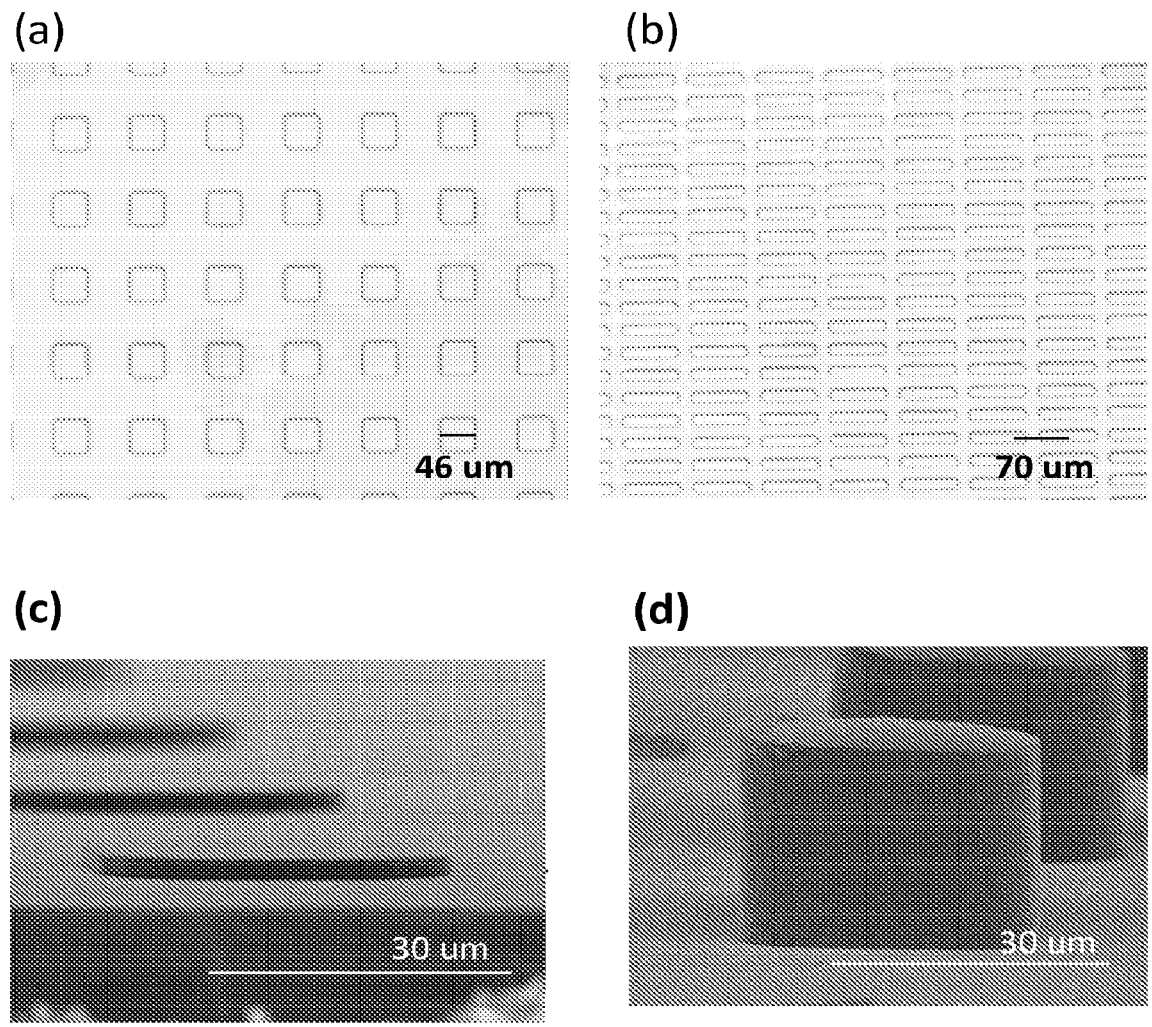

FIG. 17 Spacers on a plate. Top view of photograph of (a) 46 um×46 um pillar spacer size and 54 um inter pillar distance, and (b) 10 um×70 um pillar spacer size and 10 um pillar distance; and prospect view SEM of (c) 30 um×40 um pillar spacer size of 2 um spacer height, and (d) 30 um×40 um pillar spacer size of 30 um spacer height.

Figure 18:
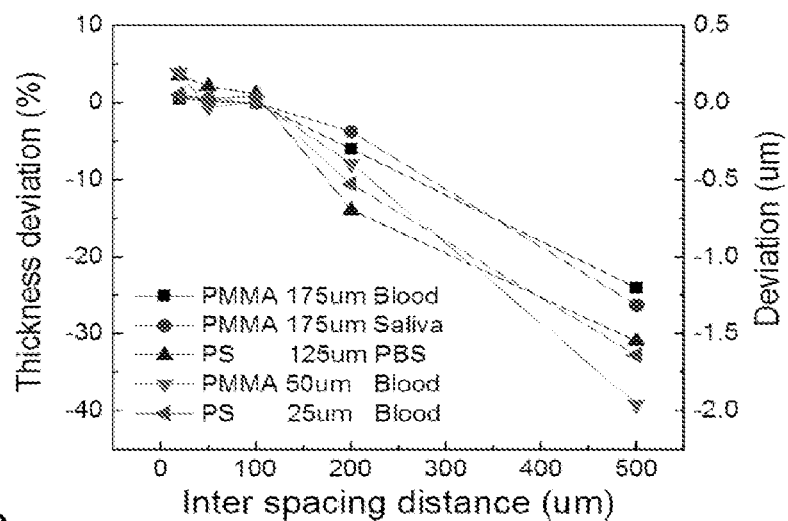
Figure 18:
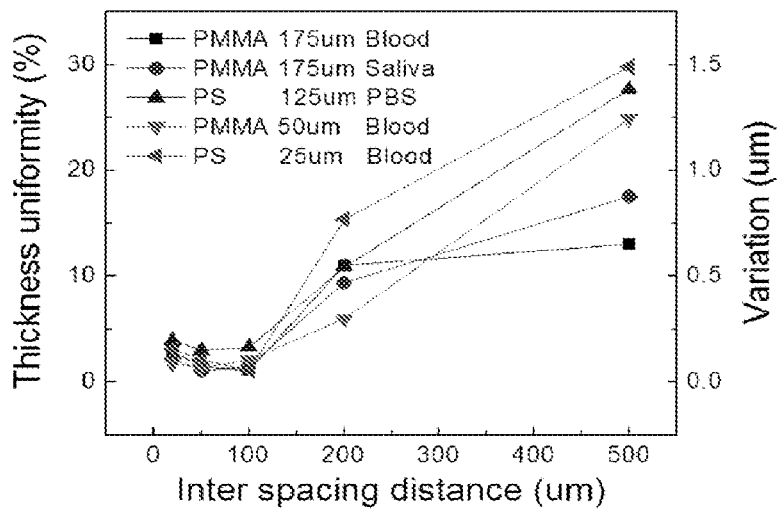

FIG. 18 Effects of IDS and plate thickness and materials on sample thickness. The measured sample thickness deviation and uniformity vs. inter-spacer distance (IDS) for different plate and spacer materials, different plate thickness, and different samples. The substrates of CROF devices are non-treated 250 um thick planar PMMA (25.4 mm×25.4 mm in size. The X-Plates comprises a periodic pillar spacer array of 5 um spacer height, a rectangle shape (10×10 um pillar lateral size, nearly uniform cross-section, and round corners), and 20 um, 50 um, 100 um, 200 um, 500 um inter spacer distance, made of PMMA or PS of 25.4 mm×25.4 mm in size. Sample was 2 uL blood (dropped by direct contact with finger), saliva, or PBS (dropped by pipette), and the CROF devices were hand pressed by hand pressing and rub over 1 in by 1 in area, and were self-hold after the press. In the figure, label ──■── is for 175 um thick PMMA using a blood sample, label ──✦── is for 175 um thick PMMA using a saliva sample, label ──▲── is for 125 um thick PS using PBS sample, label ──▽── is for 50 um thick PMMA using a blood sample, label ──◆── is for 25 um thick PS using a blood sample.

Figure 19:
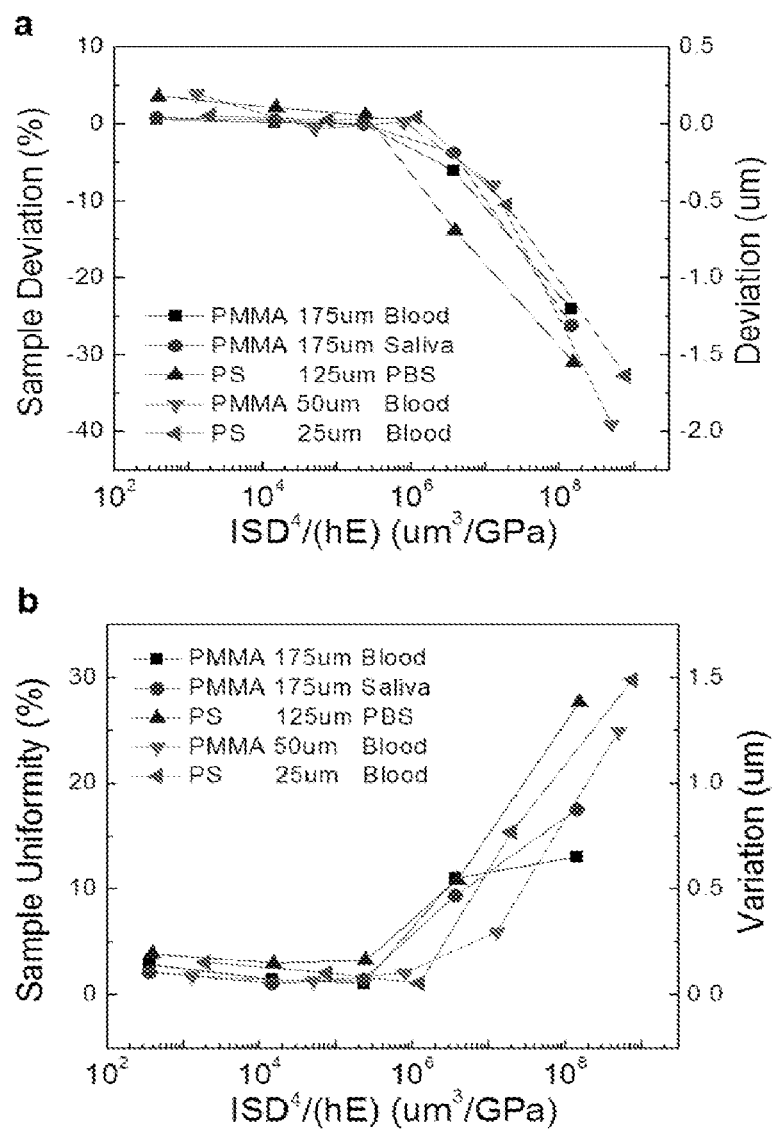

FIG. 19 Measured sample thickness deviation and uniformity vs. $ISD^4/(h \times E)$ (x=1 in the plot) value of X-Plates. ISD is inter spacing distance, h is the height (thickness) of the material, E is the Young's modulus of the material, x is a fitting parameter with a typical range of 1 to 3. In the test, the substrates of CROF devices are non-treated 250 um thick PMMA (25.4 mm×25.4 mm in size), the X-Plates are 175 um thick non-treated PMMA, 125 um thick non-treated PS, 50 um thick non-treated PMMA and 25 um thick non-treated PS (25.4 mm×25.4 mm in size), comprising a periodic pillar spacer array of 5 um spacer height, a rectangle shape (10×10 um pillar lateral size, nearly uniform cross-section, and round corners), and 20 um, 50 um, 100 um, 200 um, 500 um inter spacer distance, the sample was 2 uL blood (dropped by direct contact with finger), saliva, or PBS (dropped by pipette), and the CROF devices were hand pressed by hand pressing and rub over 1 in by 1 in area, and were self-hold after the press. In the calculation of $ISD^4/h^{x=1}/E$, Young's modulus is 2.5 GPa for PMMA, and 3.3 GPa for PS. When $ISD^4/(hE)$'s value is larger than $10^6$ $um^3/Gpa$, the performance of CROF device become worse. In the figure, label ──■── is for 175 um thick PMMA using a blood sample, label ──✦── is for 175 um thick PMMA using a saliva sample, label ──▲── is for 125 um thick PS using PBS sample, label ──▽── is for 50 um thick PMMA using a blood sample, label ──◆── is for 25 um thick PS using a blood sample.

Figure 20:
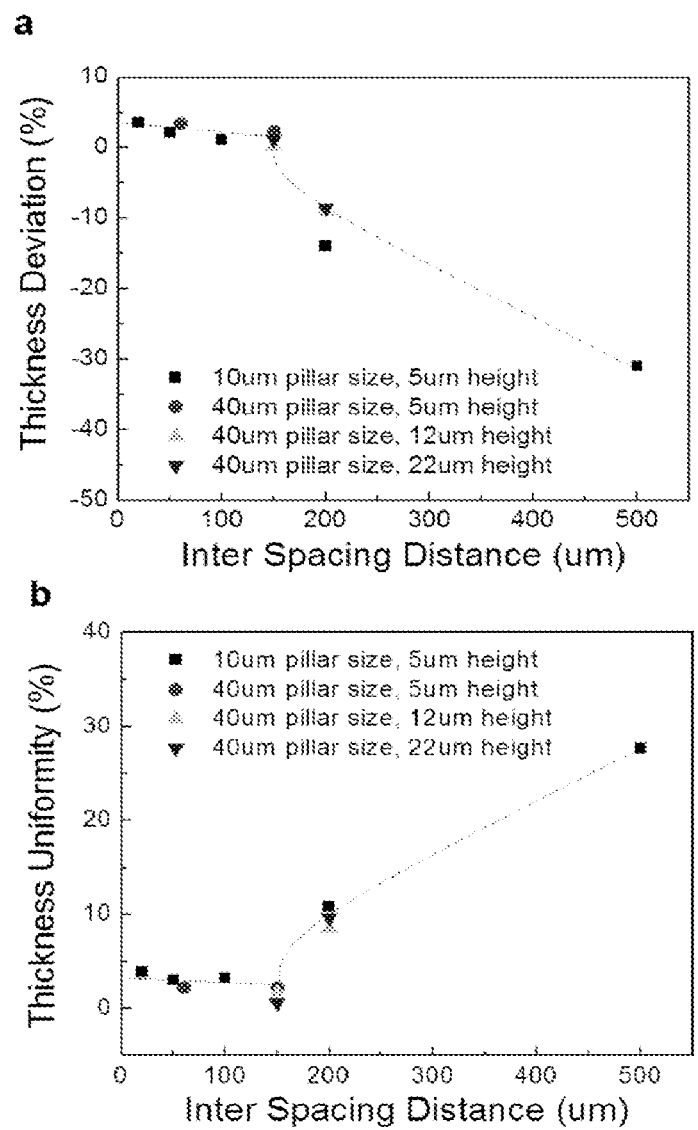

FIG. 20 Measured sample thickness deviation and uniformity vs. inter spacer distance for different pillar spacer's size and height on the X-Plates. The substrate plates of CROF devices are non-treated 1 mm thick Glass (25.4 mm×25.4 mm in size), the X-Plates are 125 um thick non-treated PS (25.4 mm×25.4 mm in size), comprising a periodic pillar spacer array of 5 um spacer height with a rectangle shape of 10×10 um pillar lateral size (nearly uniform cross-section, and round corners) with 20 um, 50 um, 100 um, 200 um, 500 um inter spacer distance (label ──■──), 40×40 um pillar lateral size with 60 um, 150 um and 200 um inter spacer distance (label ──✦──); a periodic pillar spacer array of 12 um spacer height with a rectangle shape of 40×40 um pillar lateral size with 150 um and 200 um inter spacer distance (label ──▲──); a periodic pillar spacer array of 22 um spacer height with a rectangle shape of 40×40 um pillar lateral size with 150 um and 200 um inter spacer distance (label ──▽──); the sample was 2 uL for 5 um thick CROF, 5 uL for 12 um thick CROF and 9 uL for 22 um thick CROF PBS (dropped by pipette), and the CROF devices were hand pressed by hand pressing and rub over 1 in by 1 in area, and were self-hold after the press. (Lines in figures are for eye-guiding purpose.)

Figure 21:
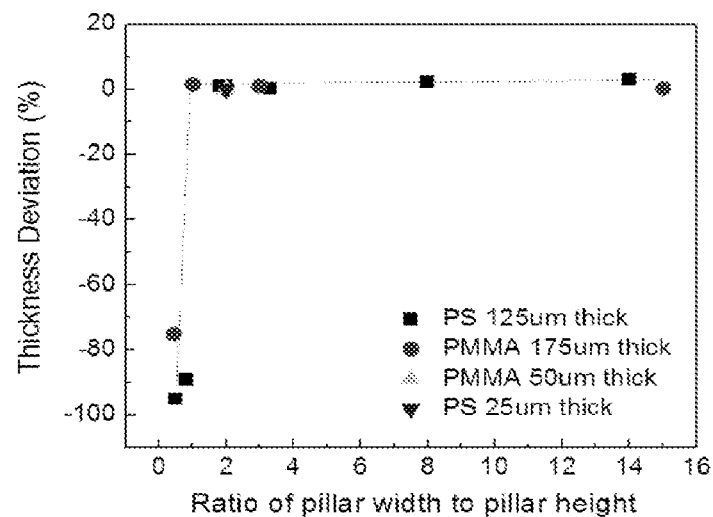
Figure 21:
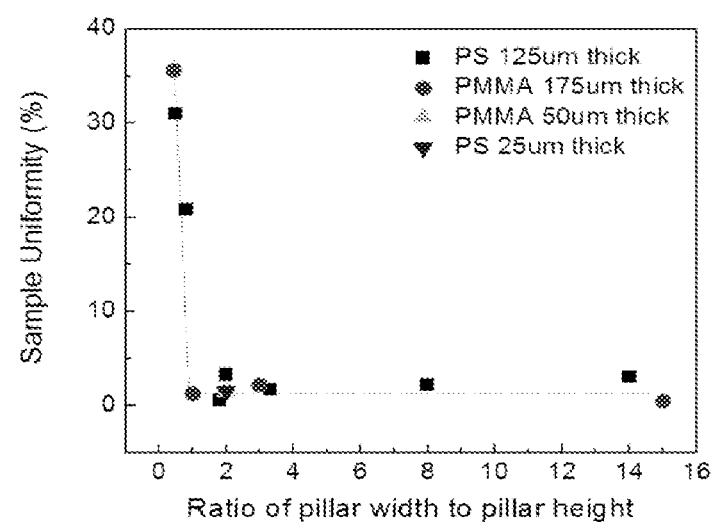

FIG. 21 Measured sample thickness deviation and uniformity vs. different ratio of pillar width to pillar height while keep ISD for all the samples less than 150 um. The substrates of CROF devices are non-treated 1 mm thick Glass (25.4 mm×25.4 mm in size). The CROF devices were hand pressed by hand pressing and rub over 1 in by 1 in area, and were self-hold after the press. Sample in the above figures with label as following:

A. X-Plate made of PS with 125 um thick (with label ──■──), from left to right: 1: X-Plate pillar size 10×10 um, height 22 um, ISD 100 um, 9 uL PBS buffer, Ratio (w/h)=0.45; 2: X-Plate pillar size 10×10 um, height 12 um, ISD 100 um, 5 uL PBS buffer, Ratio (w/h)=0.83; 3: X-Plate pillar size 40×40 um, height 22 um, ISD 150 um, 9 uL PBS buffer, Ratio (w/h)=1.81; 4: X-Plate pillar size 40×40 um, height 5 um, ISD 100 um, 2 uL PBS buffer, Ratio (w/h)=2; 5: X-Plate pillar size 40×40 um, height 12 um, ISD 150 um, 5 uL PBS buffer, Ratio (w/h)=3.33; 6: X-Plate pillar size 40×40 um, height 5 um, ISD 150 um, 2 uL PBS buffer, Ratio (w/h)=8; 7: X-Plate pillar size 70×70 um, height 5 um, ISD 150 um, 2 uL PBS buffer, Ratio (w/h)=14

B. X-Plate made of PMMA with 175 um thick (with label ), from left to right: 1: X-Plate pillar size 10×10 um, height 22 um, ISD 100 um, 5 uL blood, Ratio (w/h)=0.45; 2: X-Plate pillar size 10×10 um, height 5 um, ISD 50 um, 2 uL blood, Ratio (w/h)=2; 3: X-Plate pillar size 30×30 um, height 30 um, ISD 80 um, 12 uL blood, Ratio (w/h)=1; 4: X-Plate pillar size 30×30 um, height 10 um, ISD 80 um, 1 uL blood, Ratio (w/h)=3; 5: X-Plate pillar size 30×30 um, height 2 um, ISD 80 um, 1 uL blood, Ratio (w/h)=15.

C. X-Plate made of PMMA with 50 um thick (with label ), from left to right: 1: X-Plate pillar size 10×10 um, height 5 um, ISD 50 um, 2 uL blood, Ratio (w/h)=2.

D. X-Plate made of PS with 25 um thick (with label ), from left to right: 1: X-Plate pillar size 10×10 um, height 5 um, ISD 50 um, 2 uL blood, Ratio (w/h)=2.

Figure 22:
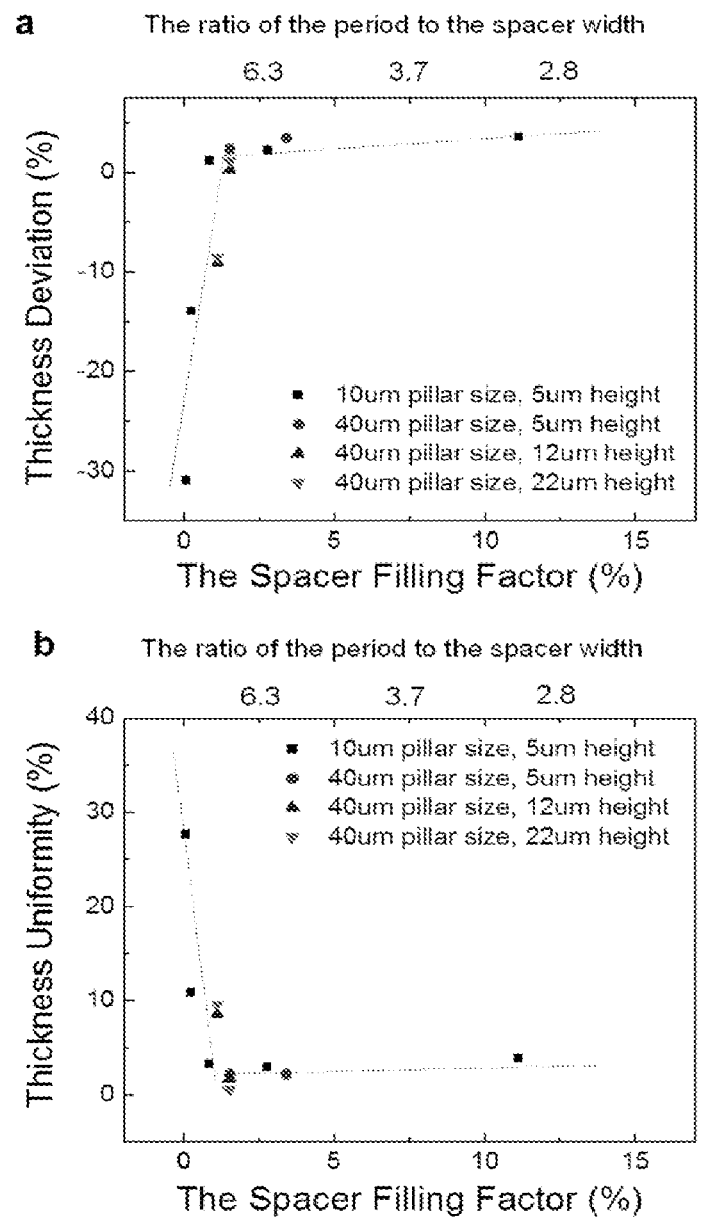

FIG. 22 Measured sample thickness deviation and uniformity vs. inter spacer distance and pillar size/height of X-Plates, with the substrates of CROF devices are non-treated 1 mm thick Glass (25.4 mm×25.4 mm in size), the X-Plates are 125 um thick non-treated PS (25.4 mm×25.4 mm in size), comprising a periodic pillar spacer array of 5 um spacer height with a rectangle shape of 10×10 um pillar lateral size (nearly uniform cross-section, and round corners) with 20 um, 50 um, 100 um, 200 um, 500 um inter spacer distance (label ), 40×40 um pillar lateral size with 60 um, 150 um and 200 um inter spacer distance (label ); a periodic pillar spacer array of 12 um spacer height with a rectangle shape of 40×40 um pillar lateral size with 60 um, 150 um and 200 um inter spacer distance (label ), a periodic pillar spacer array of 22 um spacer height with a rectangle shape of 40×40 um pillar lateral size with 150 um and 200 um inter spacer distance (label ); the sample was 2 uL for 5 um thick CROF, 5 uL for 12 um thick CROF and 9 uL for 22 um thick CROF PBS (dropped by pipette), and the CROF devices were hand pressed by hand pressing and rub over 1 in by 1 in area, and were self-hold after the press. (Lines in figures are for eye-guiding purpose.)

Figure 23:
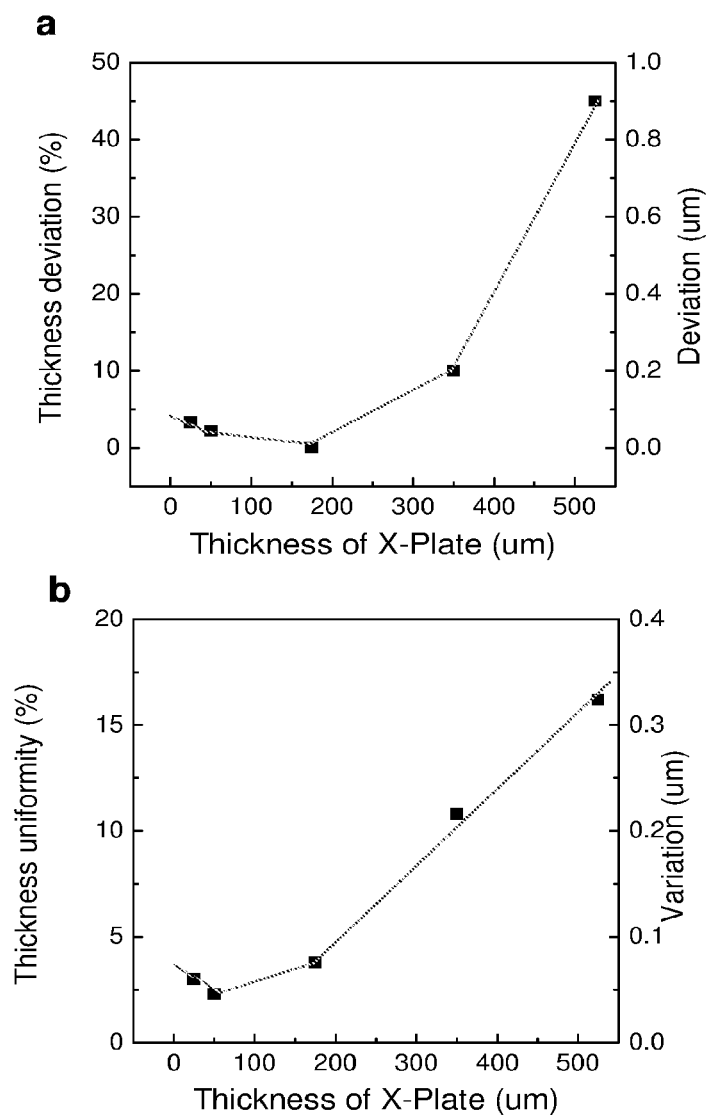

FIG. 23 Measured sample thickness deviation and uniformity vs. different X-Plate thickness (25 um to 525 um) but fixed pillar size (30×38 um), pillar height (2 um) and inter spacing distances (80×82 um) made of non-treated PMMA, where the substrate is a 1 mm thick non-treated Glass (25.4 mm×25.4 mm in size), the sample was 1 uL blood dropped by direct contact with finger, and the CROF devices were hand pressed by hand pressing and rub over 1 in by 1 in area, and were self-hold after the press.

Figure 24:
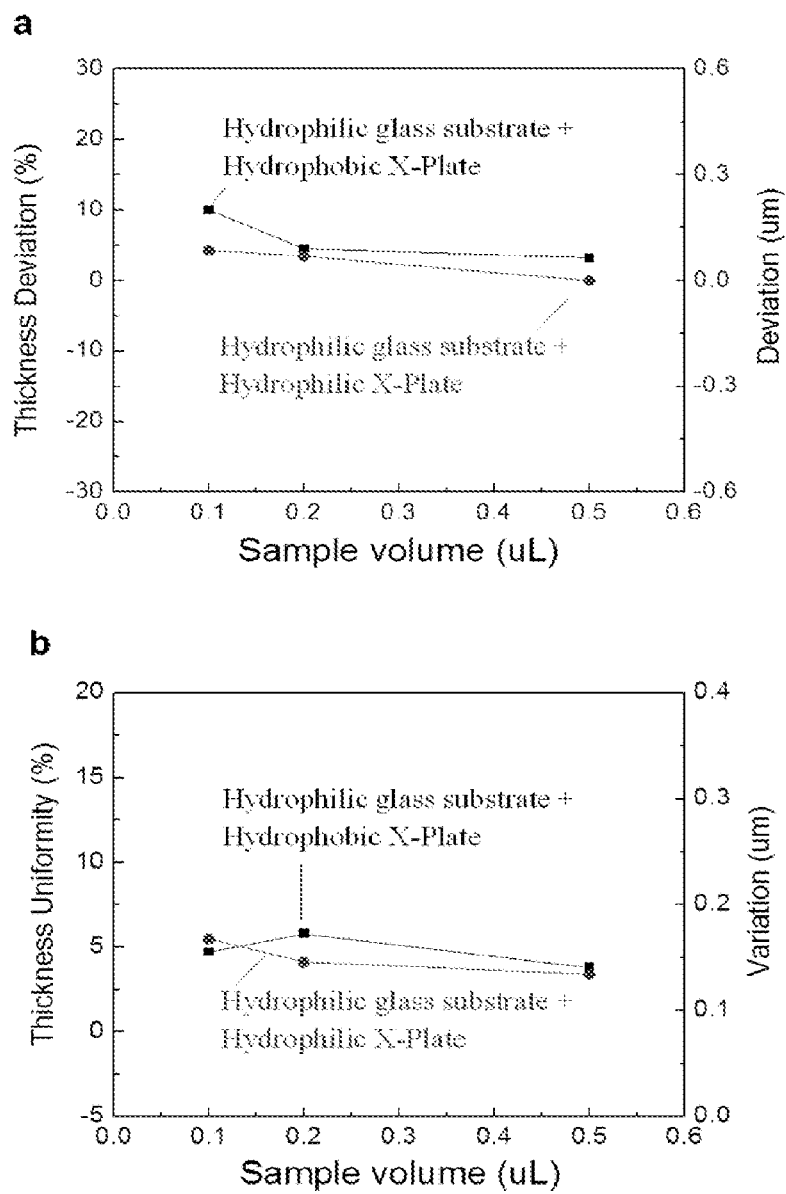

FIG. 24 shows measured spacing size deviation/uniformity of CROF device (different combination pairs of hydrophilic-hydrophilic with label , hydrophilic-hydrophobic with label ) with blood volume from 0.1 uL to 0.5 uL, but same X-Plate pillar size (30×38 um), pillar height (2 um) and inter spacing distances (80×82 um), where the substrate is a 1 mm thick Glass (25.4 mm×25.4 mm in size) and the X-Plate is made of 175 um thick PMMA (25.4 mm×25.4 mm in size). The blood was dropped by direct contact with finger, and the CROF devices were hand pressed by hand pressing and rub over 1 in by 1 in area.

Figure 25:
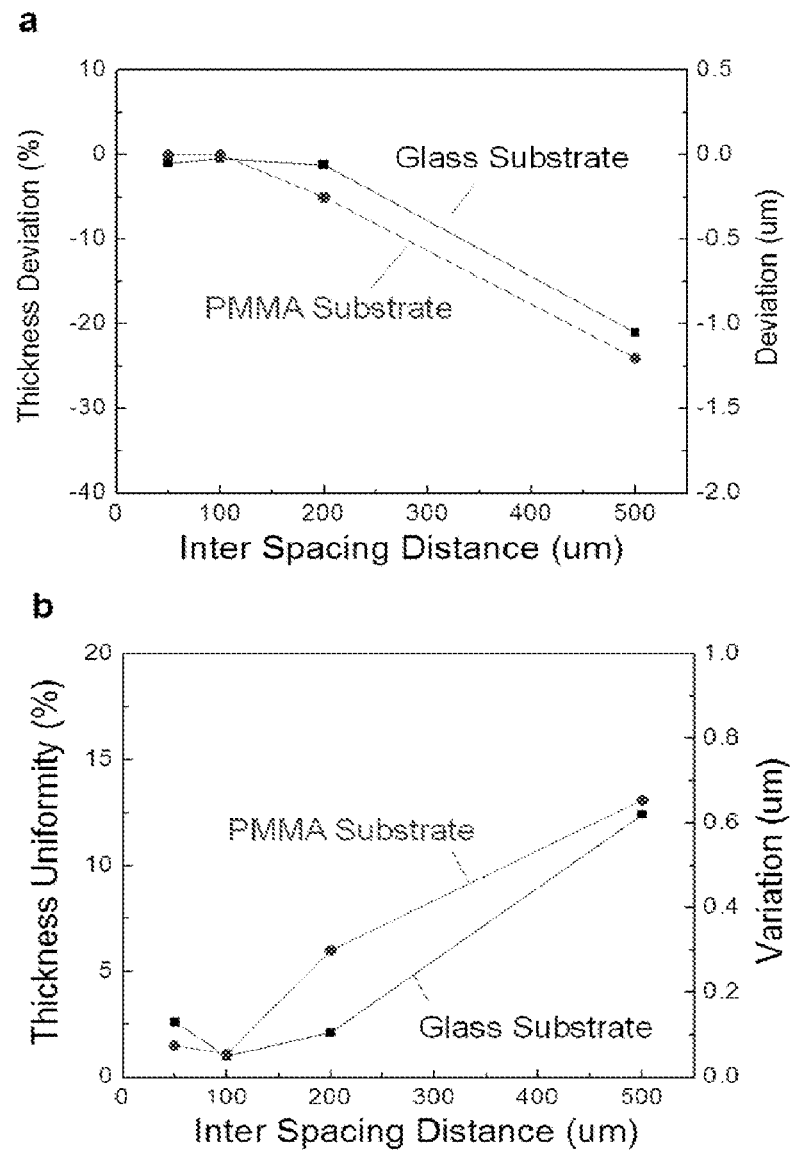

FIG. 25 Measured sample thickness deviation and uniformity vs. substrates of non-treated 1 mm thick Glass with label  or non-treated 250 um thick PMMA with label  (25.4 mm×25.4 mm in size), where the X-Plate is a 175 um thick non-treated PMMA (25.4 mm×25.4 mm in size) comprising a periodic pillar spacer array of 5 um spacer height, a rectangle shape (10×10 um pillar lateral size, nearly uniform cross-section, and round corners), and 50 um, 100 um, 200 um and 500 um inter spacer distance, the sample was 2 uL blood dropped by direct contact with finger, and the CROF devices were hand pressed by hand pressing and rub over 1 in by 1 in area, and were self-hold after the press.

Figure 26:
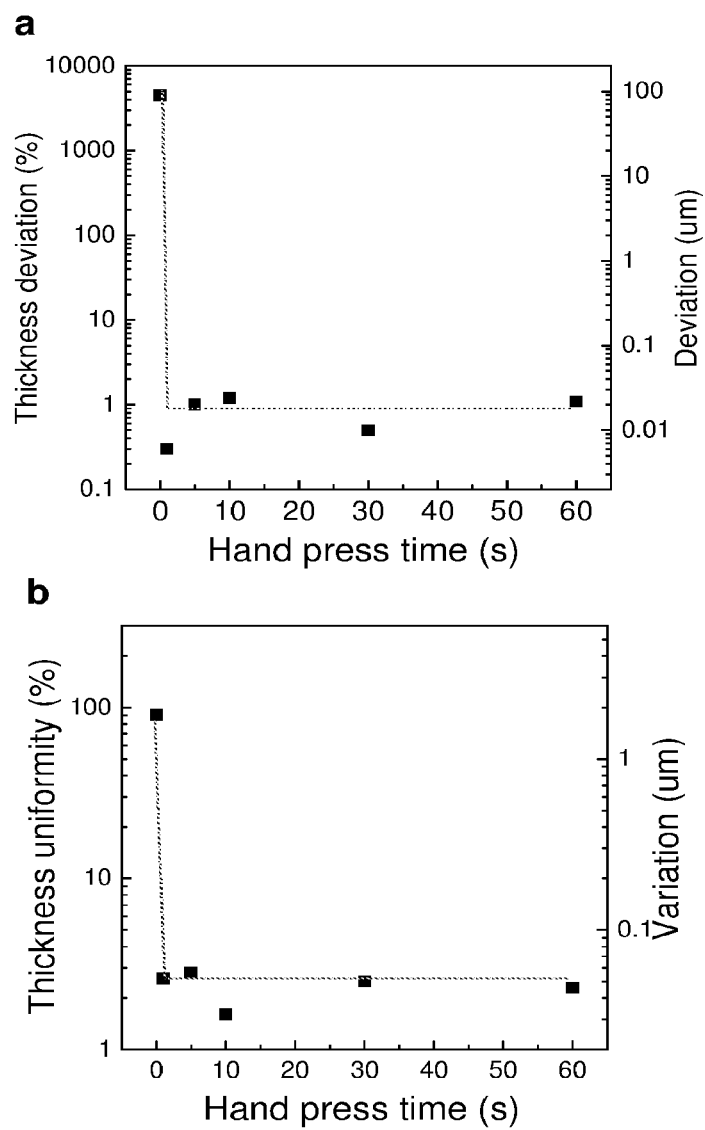

FIG. 26 Measured sample thickness deviation and uniformity vs. tests at different hand pressing time of 0 s to 60 s, where the substrate of CROF devices is non-treated 250 um thick PMMA (25.4 mm×25.4 mm in size), the X-Plate is a 175 um thick non-treated PMMA (25.4 mm×25.4 mm in size) comprising a periodic pillar spacer array of 2 um spacer height, a rectangle shape (30×38 um pillar lateral size, nearly uniform cross-section, and round corners), and 80 um inter spacer distance, the sample was 1 uL blood deposited by direct contact, and the CROF devices were hand pressed by hand pressing and rub over 1 in by 1 in area, and were self-hold after the press.

Figure 27:
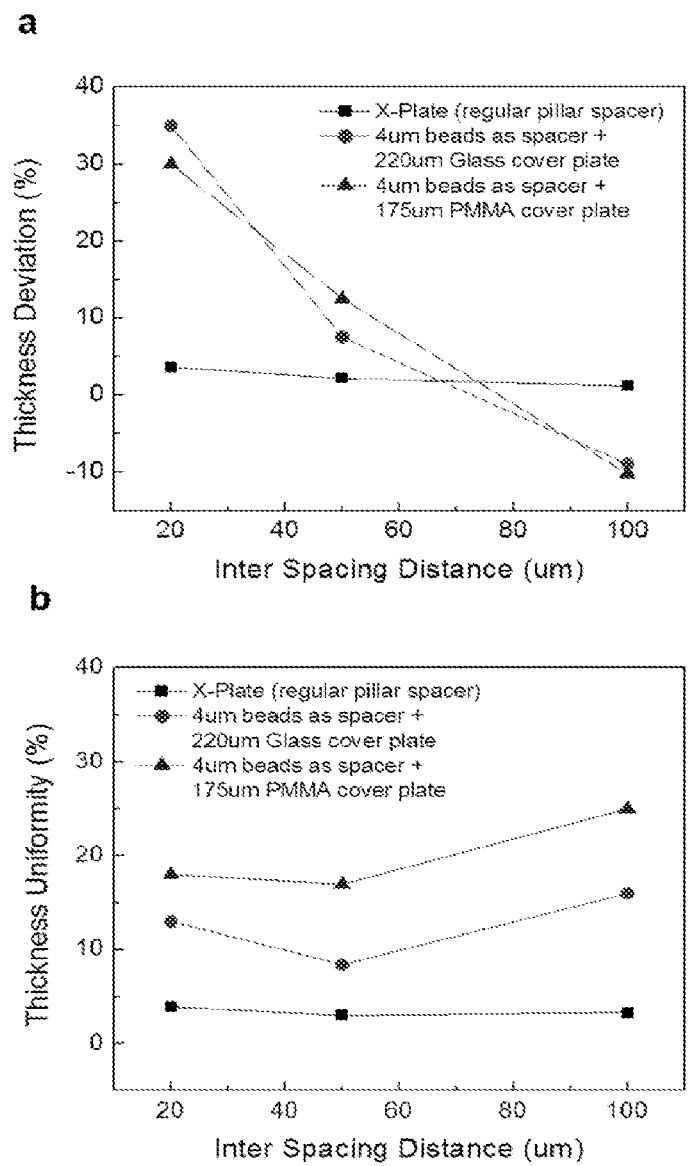

FIG. 27 Measured sample thickness deviation and uniformity vs. the average IDS for using random ball spacer or regular pillar spacer (X-Plate), where the substrate of CROF devices is non-treated 1 mm thick Glass (25.4 mm×25.4 mm in size), the X-Plate is a 175 um thick non-treated PMMA (25.4 mm×25.4 mm in size) comprising a periodic pillar spacer array of 5 um spacer height, a rectangle shape (10×10 um pillar lateral size, nearly uniform cross-section, and round corners), and 20 um, 50 um and 100 um inter spacer distance, the sample was 2 uL PBS, and the CROF devices were hand pressed by hand pressing and rub over 1 in by 1 in area, and were self-hold after the press. The ball is soda lime microspheres with average diameter of 4 um (5% size variation) in PBS. The microspheres are distributed in PBS with concentrations of $4 \times 10^5$/uL, $0.9 \times 10^5$/uL, and $0.2 \times 10^5$/uL, which corresponding to 20 um, 50 um and 100 um average inter spacer distance after press. Two kinds of cover plate are used, non-treated 220 um thick Glass (25.4 mm×25.4 mm in size) and non-treated 175 um thick PMMA (25.4 mm×25.4 mm in size). The all devices were pressed by hand pressing and rub over 1 in by 1 in area, and were self-hold after the press. Label  is for using X-Plate, label  is for using beads as spacer and 220 um thick Glass slide as cover plate, label  is for using beads as spacer and 175 um thick PMMA film as cover plate.

Figure 28:
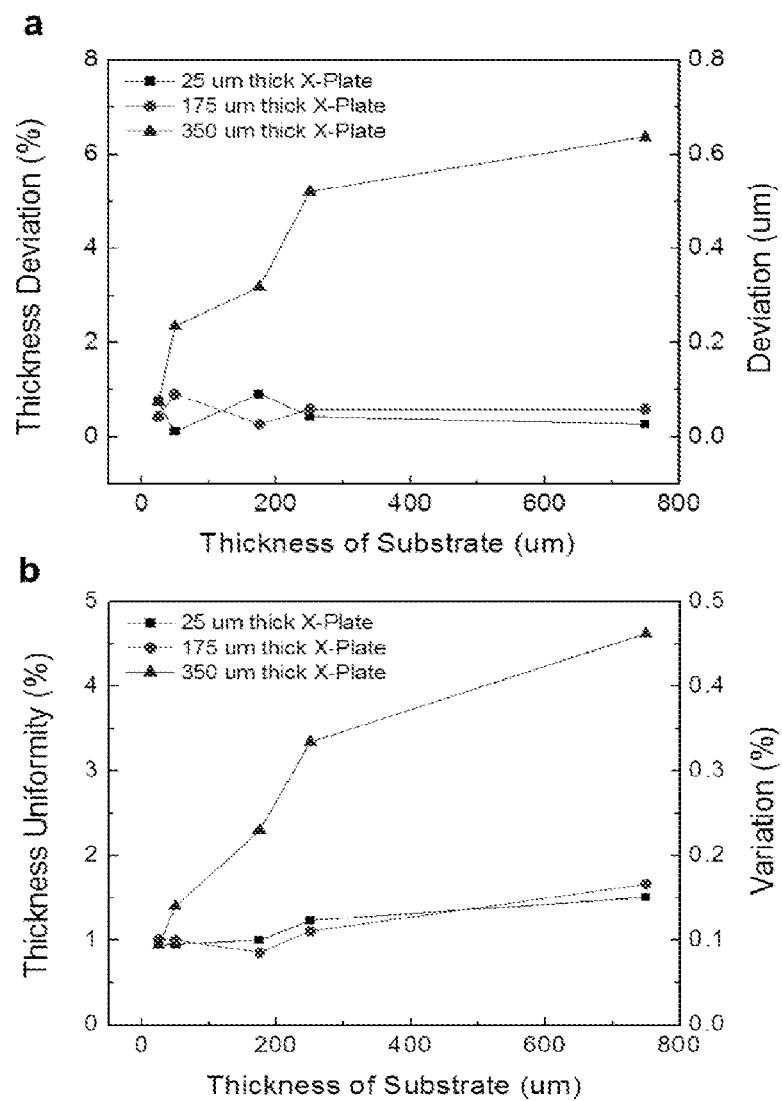

FIG. 28 Measured sample thickness deviation and uniformity vs. different X-Plate thickness (25 um to 350 um) and substrate thickness (25 um to 750 um). X-Plates have fixed pillar size (30×38 um), pillar height (10 um) and inter spacing distances (80×82 um) made of non-treated PMMA with thickness of 25 um, 175 um and 350 um, where the substrate is made of non-treated PMMA (25.4 mm×25.4 mm in size) with thickness of 25 um, 50 um, 175 um, 250 um and 750 um. The sample was 4 uL blood dropped by direct contact with finger, and the CROF devices were hand pressed by hand pressing and rub over 1 in by 1 in area, and were self-hold after the press. In the figure, label ──■── is for using 25 um thick X-Plate, label ──✦── is for using 175 um thick X-Plate, label ──▲── is for 350 um thick X-Plate.

Figure 29:
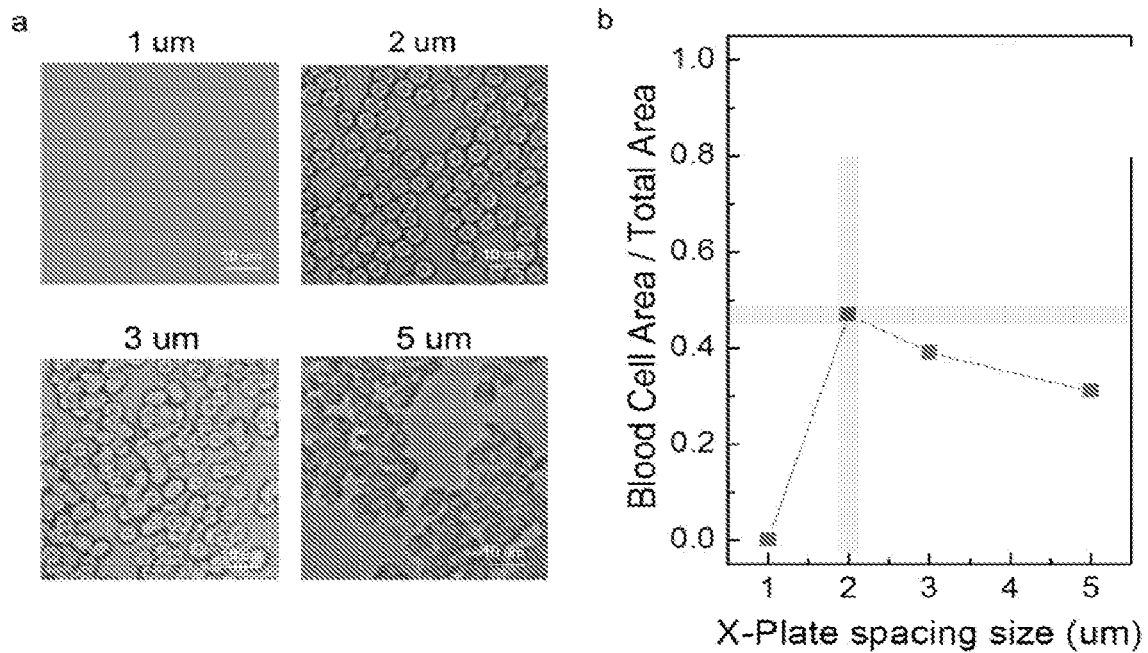

FIG. 29 shows (a) the microscope photo (40×) of blood cells in X-devices with plate spacing (hence a sample thickness) of 1 um, 2 um, 3 um and 5 um. 1 um spacing X-device lyses most (99%) of the RBCs, remains platelets unlysed. 2 um spacing X-device separates each RBC well and makes RBCs single layer. Some stacked RBCs are observed in 3 um spacing X-device, and much more stacked RBCs in 5 um spacing X-device. Single layer cell (2 um X-device) is preferred for counting. And (b) the ratio of the red blood cell area (measured from 2D top view image) to the total lateral area of CROF plate. The maximum at 2 um plate spacing (i.e. sample thickness), because below 2 um some RBC are lysed and higher than 2 um the RBCs are overlapped and rotated, all of them gives smaller RBC area in the 2D image.

Figure 30:
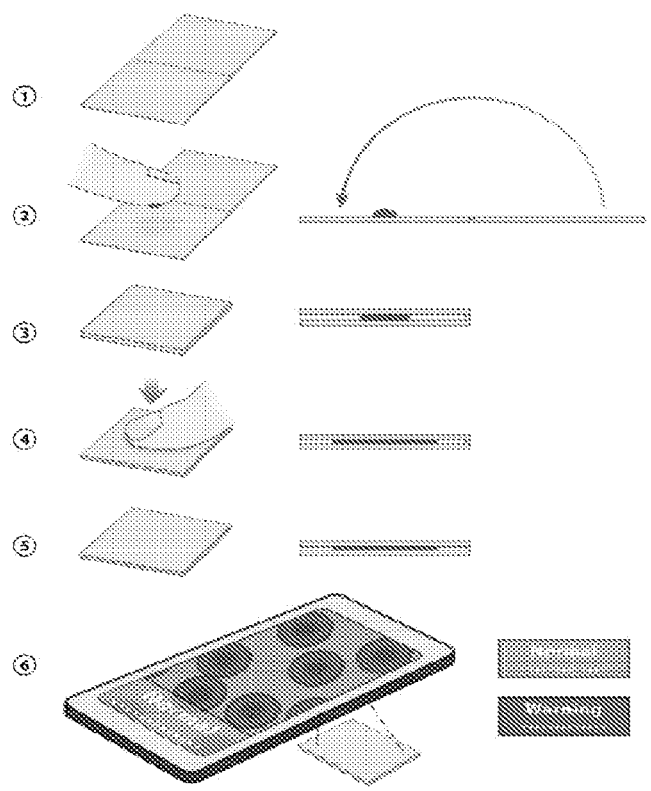
Figure 30:
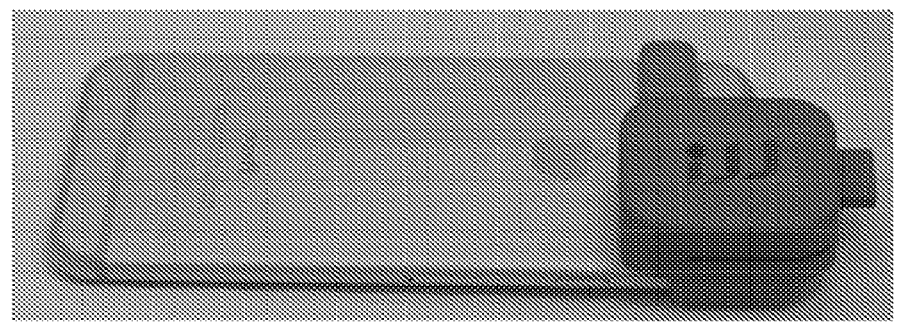

FIG. 30 Schematic of the BCI (Blood-cell-counting by CROF and Imaging) by smartphone (a) and photographs of the device (b). In a blood test using the smartphone-BCI, one person first has a card (1) and pricks her/finger (2), then deposits a small amount of blood directly from the finger onto the CROF-Card by touching the card (2), closes the card (3) and presses by a finger (4) and release it (5), inserts the card into the optical adapter (5), and finally takes a picture of the card using the smartphone (6), and from the pictures taken, the software measures the blood volume and the blood cell counts and other parameters (6). (b) Photo of an actual smartphone and the adapter for the p-BCI.

Figure 31:
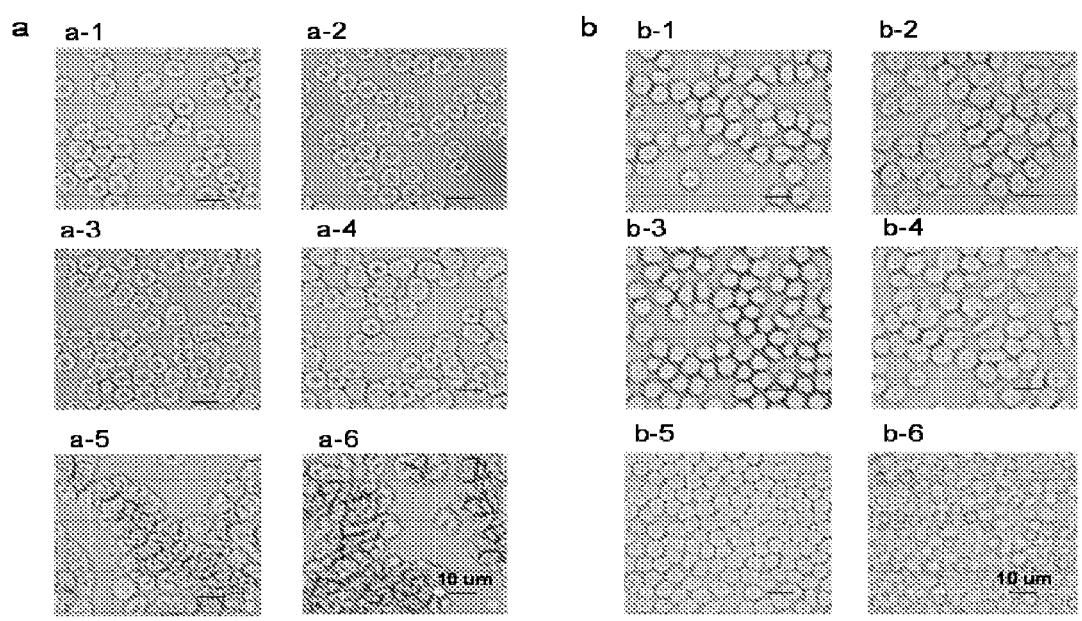

FIG. 31 Bright-field optical microscopy images of fresh (a) and stored (b) undiluted whole blood in the CROF-Card with different final gaps, and illustration of RBCs behavior for different confinement gap. The fresh blood has anticoagulant and was taken from a pricked finger and the stored blood has anticoagulant and was from a commercial vendor. (a-1 to a-6) and (b-1 to b-6): for g=2, 2.2, 2.6, 3, 5, and 10 um, respectively. (c) shows cross-sectional and top-view schematics of (1) RBCs are separated from others, have no observable overlap in CROF with 2 um gap, while (2) RBCs overlap each other in CROF with gap larger than 2 um.

Figure 32:
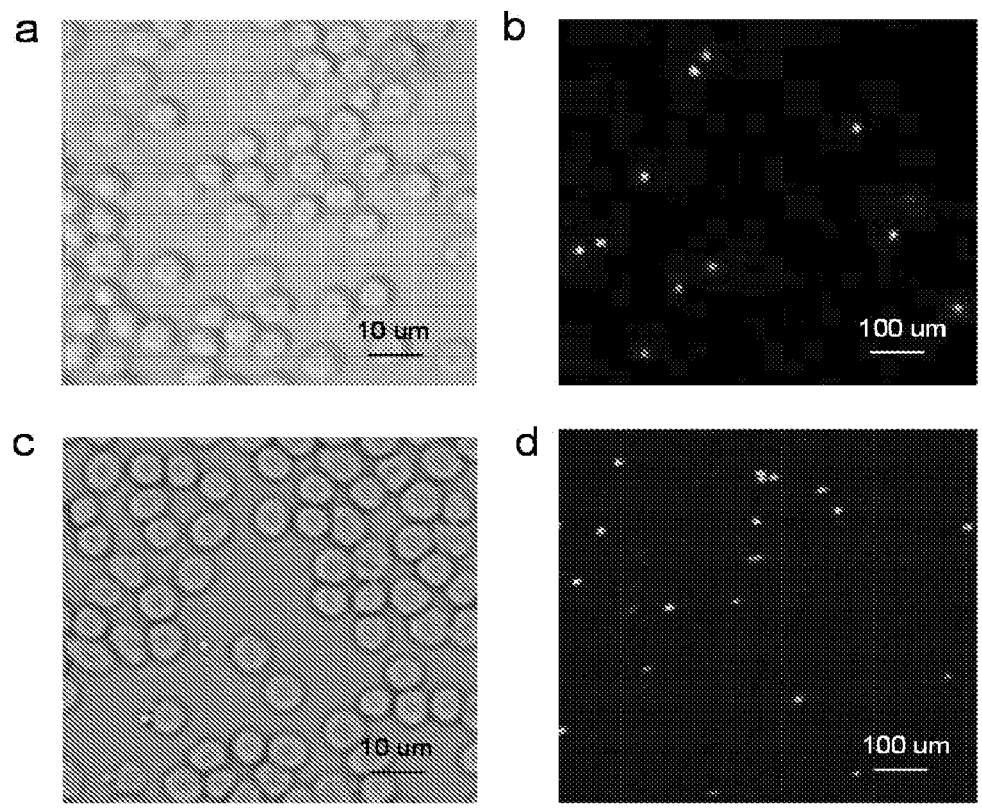

FIG. 32 Bright-field (1) and fluorescence (2) images of the same sample (fresh blood in CROF-Card taken) by smartphone with optical adapter (a) and by a high resolution microscope with DSLR camera (b). The images show that the smartphone with the optical adopter has similar blood cells photo quality as that of the high-resolution microscope and camera.

Figure 33:
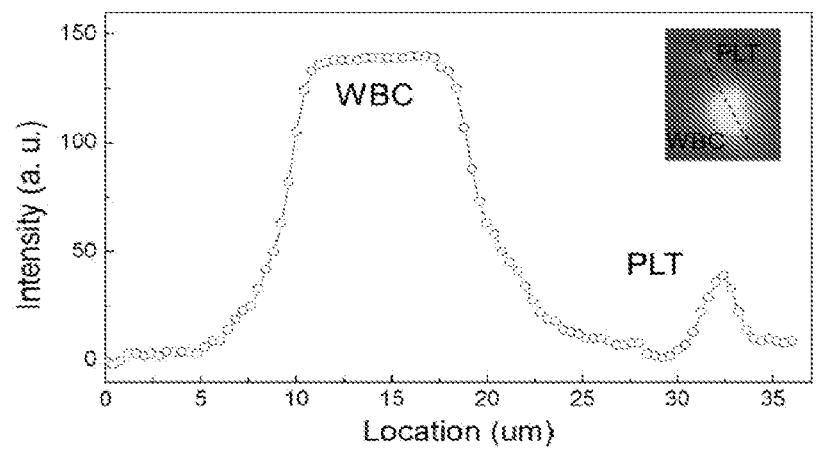

FIG. 33 shows the measured optical intensity of one typical WBC and PLT vs their locations of these separated cells. WBC has a diameter (FWHM) around 12 um, while PLT has a diameter (FWHM) around 2 um. The maximum intensity of WBC is around 3 times larger than PLT. Both the intensity and area give WBC's overall intensity around 108 times larger than PLT's. Thus, if using lower magnification (as 4×), WBC's area become smaller and its overall intensity become lower. PLT's signal will be negligible in that case.

Figure 34:
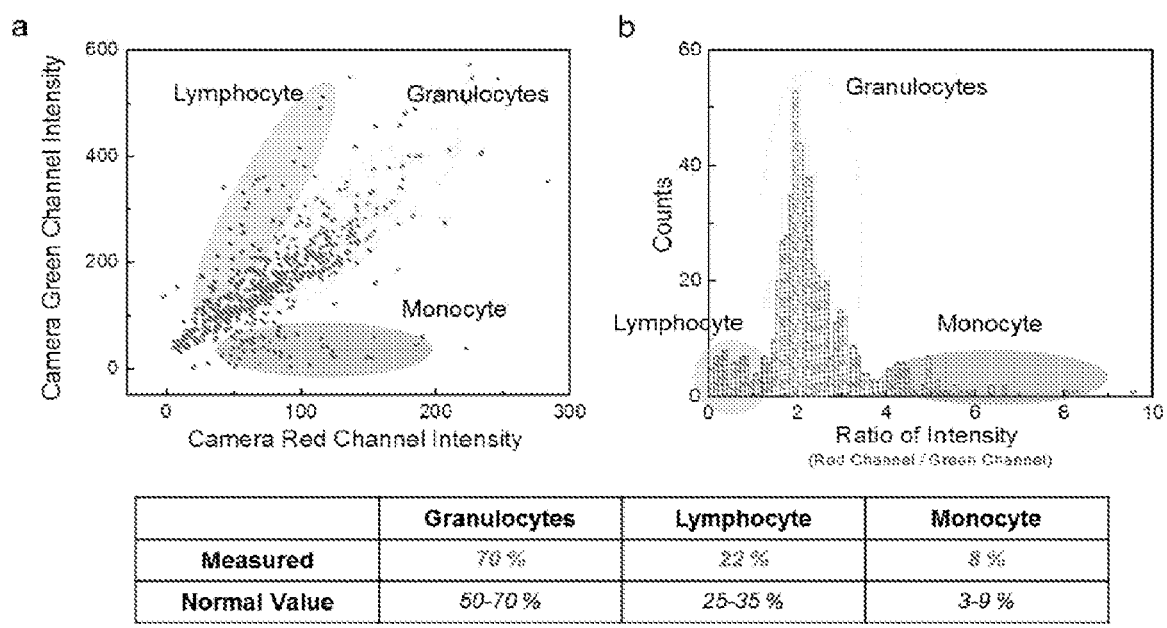

FIG. 34 shows (a) a scatter plot of intensity of the green channel light vs that of the red channel intensities; and (b) histogram of red/green channel intensity ratios for 594 WBCs within the images. From this image we can clearly see that the cells cluster into three distinct regions (shaded areas provided as guides for the eye), corresponding to the three main white cell subpopulations.

DETAILED DESCRIPTION OF EXEMPLARY EMBODIMENTS

The following detailed description illustrates some embodiments of the invention by way of example and not by way of limitation. The section headings and any subtitles used herein are for organizational purposes only and are not to be construed as limiting the subject matter described in any way. The contents under a section heading and/or subtitle are not limited to the section heading and/or subtitle, but apply to the entire description of the present invention.

The citation of any publication is for its disclosure prior to the filing date and should not be construed as an admission that the present claims are not entitled to antedate such publication by virtue of prior invention. Further, the dates of publication provided can be different from the actual publication dates which can need to be independently confirmed.

The present invention is related to, among other things, methods, devices, and systems that can improve and/or speed up the quantification, binding, and/or sensing of an analyte and/or entity in a sample.

Definitions

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present teachings, some exemplary methods and materials are now described.

The terms "polynucleotide", "nucleotide", "nucleotide sequence", "nucleic acid", "nucleic acid molecule", "nucleic acid sequence" and "oligonucleotide" are used interchangeably, and can also include plurals of each respectively depending on the context in which the terms are utilized.

The term "capture agent" as used herein, refers to a binding member, e.g. nucleic acid molecule, polypeptide molecule, or any other molecule or compound, that can specifically bind to its binding partner, e.g., a second nucleic acid molecule containing nucleotide sequences complementary to a first nucleic acid molecule, an antibody that specifically recognizes an antigen, an antigen specifically recognized by an antibody, a nucleic acid aptamer that can specifically bind to a target molecule, etc.

The term "a secondary capture agent" which can also be referred to as a "detection agent" refers a group of biomolecules or chemical compounds that have highly specific affinity to the antigen. The secondary capture agent can be strongly linked to an optical detectable label, e.g., enzyme, fluorescence label, or can itself be detected by another detection agent that is linked to an optical detectable label through bioconjugation (Hermanson, "Bioconjugate Techniques" Academic Press, 2nd Ed., 2008).

The term "capture agent-reactive group" refers to a moiety of chemical function in a molecule that is reactive with capture agents, i.e., can react with a moiety (e.g., a hydroxyl, sulfhydryl, carboxyl or amine group) in a capture agent to produce a stable strong, e.g., covalent bond.

The terms "specific binding" and "selective binding" refer to the ability of a capture agent to preferentially bind to a particular target analyte that is present in a heterogeneous mixture of different target analytes. A specific or selective binding interaction will discriminate between desirable (e.g., active) and undesirable (e.g., inactive) target analytes in a sample, typically more than about 10 to 100-fold or more (e.g., more than about 1000- or 10,000-fold).

The term "sample" as used herein relates to a material or mixture of materials containing one or more analytes or entity of interest. In particular embodiments, the sample may be obtained from a biological sample such as cells, tissues, bodily fluids, and stool. Bodily fluids of interest include but are not limited to, amniotic fluid, aqueous humour, vitreous humour, blood (e.g., whole blood, fractionated blood, plasma, serum, etc.), breast milk, cerebrospinal fluid (CSF), cerumen (earwax), chyle, chime, endolymph, perilymph, feces, gastric acid, gastric juice, lymph, mucus (including nasal drainage and phlegm), pericardial fluid, peritoneal fluid, pleural fluid, pus, rheum, saliva, sebum (skin oil), semen, sputum, sweat, synovial fluid, tears, vomit, urine and exhaled condensate. In particular embodiments, a sample may be obtained from a subject, e.g., a human, and it may be processed prior to use in the subject assay. For example, prior to analysis, the protein/nucleic acid may be extracted from a tissue sample prior to use, methods for which are known. In particular embodiments, the sample may be a clinical sample, e.g., a sample collected from a patient.

The term "analyte" refers to a molecule (e.g., a protein, peptides, DNA, RNA, nucleic acid, or other molecule), cells, tissues, viruses, and nanoparticles with different shapes.

The term "assaying" refers to testing a sample to detect the presence and/or abundance of an analyte.

As used herein, the terms "determining," "measuring," and "assessing," and "assaying" are used interchangeably and include both quantitative and qualitative determinations.

As used herein, the term "light-emitting label" refers to a label that can emit light when under an external excitation. This can be luminescence. Fluorescent labels (which include dye molecules or quantum dots), and luminescent labels (e.g., electro- or chemi-luminescent labels) are types of light-emitting label. The external excitation is light (photons) for fluorescence, electrical current for electroluminescence and chemical reaction for chemi-luminescence. An external excitation can be a combination of the above.

The phrase "labeled analyte" refers to an analyte that is detectably labeled with a light emitting label such that the analyte can be detected by assessing the presence of the label. A labeled analyte may be labeled directly (i.e., the analyte itself may be directly conjugated to a label, e.g., via a strong bond, e.g., a covalent or non-covalent bond), or a labeled analyte may be labeled indirectly (i.e., the analyte is bound by a secondary capture agent that is directly labeled).

The terms "hybridizing" and "binding", with respect to nucleic acids, are used interchangeably.

The term "capture agent/analyte complex" is a complex that results from the specific binding of a capture agent with an analyte. A capture agent and an analyte for the capture agent will usually specifically bind to each other under "specific binding conditions" or "conditions suitable for specific binding", where such conditions are those conditions (in terms of salt concentration, pH, detergent, protein concentration, temperature, etc.) which allow for binding to occur between capture agents and analytes to bind in solution. Such conditions, particularly with respect to antibodies and their antigens and nucleic acid hybridization are well known in the art (see, e.g., Harlow and Lane (Antibodies: A Laboratory Manual Cold Spring Harbor Laboratory, Cold Spring Harbor, N.Y. (1989) and Ausubel, et al, Short Protocols in Molecular Biology, 5th ed., Wley & Sons, 2002).

A subject may be any human or non-human animal. A subject may be a person performing the instant method, a patient, a customer in a testing center, etc.

An "analyte," as used herein is any substance that is suitable for testing in the present method.

As used herein, a "diagnostic sample" refers to any biological sample that is a bodily byproduct, such as bodily fluids, that has been derived from a subject. The diagnostic sample may be obtained directly from the subject in the form of liquid, or may be derived from the subject by first placing the bodily byproduct in a solution, such as a buffer. Exemplary diagnostic samples include, but are not limited to, saliva, serum, blood, sputum, urine, sweat, lacrima, semen, feces, breath, biopsies, mucus, etc.

As used herein, an "environmental sample" refers to any sample that is obtained from the environment. An environmental sample may include liquid samples from a river, lake, pond, ocean, glaciers, icebergs, rain, snow, sewage, reservoirs, tap water, drinking water, etc.; solid samples from soil, compost, sand, rocks, concrete, wood, brick, sewage, etc.; and gaseous samples from the air, underwater heat vents, industrial exhaust, vehicular exhaust, etc. Typically, samples that are not in liquid form are converted to liquid form before analyzing the sample with the present method.

As used herein, a "foodstuff sample" refers to any sample that is suitable for animal consumption, e.g., human consumption. A foodstuff sample may include raw ingredients, cooked food, plant and animal sources of food, preprocessed food as well as partially or fully processed food, etc. Typically, samples that are not in liquid form are converted to liquid form before analyzing the sample with the present method.

The term "diagnostic," as used herein, refers to the use of a method or an analyte for identifying, predicting the outcome of and/or predicting treatment response of a disease or condition of interest. A diagnosis may include predicting the likelihood of or a predisposition to having a disease or condition, estimating the severity of a disease or condition, determining the risk of progression in a disease or condition, assessing the clinical response to a treatment, and/or predicting the response to treatment.

A "biomarker," as used herein, is any molecule or compound that is found in a sample of interest and that is known to be diagnostic of or associated with the presence of or a predisposition to a disease or condition of interest in the subject from which the sample is derived. Biomarkers include, but are not limited to, polypeptides or a complex thereof (e.g., antigen, antibody), nucleic acids (e.g., DNA, miRNA, mRNA), drug metabolites, lipids, carbohydrates, hormones, vitamins, etc., that are known to be associated with a disease or condition of interest.

A "condition" as used herein with respect to diagnosing a health condition, refers to a physiological state of mind or body that is distinguishable from other physiological states. A health condition may not be diagnosed as a disease in some cases. Exemplary health conditions of interest include, but are not limited to, nutritional health; aging; exposure to environmental toxins, pesticides, herbicides, synthetic hormone analogs; pregnancy; menopause; andropause; sleep; stress; prediabetes; exercise; fatigue; chemical balance; etc.

The term "biotin moiety" refers to an affinity agent that includes biotin or a biotin analogue such as desthiobiotin, oxybiotin, 2'-iminobiotin, diaminobiotin, biotin sulfoxide, biocytin, etc. Biotin moieties bind to streptavidin with an affinity of at least $10^{-8}$M. A biotin affinity agent may also include a linker, e.g., -LC-biotin, -LC-LC-Biotin, -SLC-Biotin or -PEGn-Biotin where n is 3-12.

The term "amplify" refers to an increase in the magnitude of a signal, e.g., at least a 10-fold increase, at least a 100-fold increase at least a 1,000-fold increase, at least a 10,000-fold increase, or at least a 100,000-fold increase in a signal.

The term "entity" refers to, but not limited to proteins, peptides, DNA, RNA, nucleic acid, molecules (small or large), cells, tissues, viruses, nanoparticles with different shapes, that would bind to a "binding site". The entity includes the capture agent, detection agent, and blocking agent. The "entity" includes the "analyte", and the two terms are used interchangeably.

The term "binding site" refers to a location on a solid surface that can immobilize an entity in a sample.

The term "entity partners" refers to, but not limited to proteins, peptides, DNA, RNA, nucleic acid, molecules (small or large), cells, tissues, viruses, nanoparticles with different shapes, that are on a "binding site" and would bind to the entity. The entity, include, but not limited to, capture agents, detection agents, secondary detection agents, or "capture agent/analyte complex".

The term "smart phone" or "mobile phone", which are used interchangeably, refers to the type of phones that has a camera and communication hardware and software that can take an image using the camera, manipulate the image taken by the camera, and communicate data to a remote place. In some embodiments, the Smart Phone has a flash light.

The term "average linear dimension" of an area is defined as a length that equals to the area times 4 then divided by the perimeter of the area. For example, the area is a rectangle, that has width w, and length L, then the average of the linear dimension of the rectangle is 4*W*L/(2*(L+W)) (where "*" means multiply and "I" means divide). By this definition, the average line dimension is, respectively, W for a square of a width W, and d for a circle with a diameter d. The area include, but not limited to, the area of a binding site or a storage site.

The term "period" of periodic structure array refers to the distance from the center of a structure to the center of the nearest neighboring identical structure.

The term "storage site" refers to a site of an area on a plate, wherein the site contains reagents to be added into a sample, and the reagents are capable of being dissolving into the sample that is in contract with the reagents and diffusing in the sample.

The term "relevant" means that it is relevant to detection of analytes, quantification and/or control of analyte or entity in a sample or on a plate, or quantification or control of reagent to be added to a sample or a plate.

The term "hydrophilic", "wetting", or "wet" of a surface means that the contact angle of a sample on the surface is less than 90 degree.

The term "hydrophobic", "non-wetting", or "does not wet" of a surface means that the contact angle of a sample on the surface is equal to or larger than 90 degree.

The term "variation" of a quantity refers to the difference between the actual value and the desired value or the average of the quantity. And the term "relative variation" of a quantity refers to the ratio of the variation to the desired value or the average of the quantity. For example, if the desired value of a quantity is Q and the actual value is (Q+Δ), then the Δ is the variation and the Δ/(Q+Δ) is the relative variation. The term "relative sample thickness variation" refers to the ratio of the sample thickness variation to the average sample thickness.

The term "optical transparent" refers to a material that allows a transmission of an optical signal, wherein the term "optical signal" refers to, unless specified otherwise, the optical signal that is used to probe a property of the sample, the plate, the spacers, the scale-marks, any structures used, or any combinations of thereof.

The term "none-sample-volume" refers to, at a closed configuration of a CROF process, the volume between the plates that is occupied not by the sample but by other objects that are not the sample. The objects include, but not limited to, spacers, air bubbles, dusts, or any combinations of thereof. Often none-sample-volume(s) is mixed inside the sample.

The term "saturation incubation time" refers to the time needed for the binding between two types of molecules (e.g. capture agents and analytes) to reach an equilibrium. For a surface immobilization assay, the "saturation incubation time" refers the time needed for the binding between the target analyte (entity) in the sample and the binding site on plate surface reaches an equilibrium, namely, the time after which the average number of the target molecules (the entity) captured and immobilized by the binding site is statistically nearly constant.

In some cases, the "analyte" and "binding entity" and "entity" are interchangeable.

A "processor," "communication device," "mobile device," refer to computer systems that contain basic electronic elements (including one or more of a memory, input-output interface, central processing unit, instructions, network interface, power source, etc.) to perform computational tasks. The computer system may be a general purpose computer that contains instructions to perform a specific task, or may be a special-purpose computer.

A "site" or "location" as used in describing signal or data communication refers to the local area in which a device or subject resides. A site may refer to a room within a building structure, such as a hospital, or a smaller geographically defined area within a larger geographically defined area. A remote site or remote location, with reference to a first site that is remote from a second site, is a first site that is physically separated from the second site by distance and/or by physical obstruction. The remote site may be a first site that is in a separate room from the second site in a building structure, a first site that is in a different building structure from the second site, a first site that is in a different city from the second site, etc.

As used herein, the term "sample collection site" refers to a location at which a sample may be obtained from a subject. A sample collection site may be, for example, a retailer location (e.g., a chain store, pharmacy, supermarket, or department store), a provider office, a physician's office, a hospital, the subject's home, a military site, an employer site, or other site or combination of sites. As used herein, the term "sample collection site" may also refer to a proprietor or representative of a business, service, or institution located at, or affiliated with, the site.

As used herein, "raw data" includes signals and direct read-outs from sensors, cameras, and other components and instruments which detect or measure properties or characteristics of a sample.

"Process management," as used herein, refers to any number of methods and systems for planning and/or monitoring the performance of a process, such as a sample analysis process One with skill in the art will appreciate that the present invention is not limited in its application to the details of construction, the arrangements of components, category selections, weightings, pre-determined signal limits, or the steps set forth in the description or drawings herein. The invention is capable of other embodiments and of being practiced or being carried out in many different ways.

It must be noted that as used herein and in the appended claims, the singular forms "a", "an", and "the" include plural referents unless the context clearly dictates otherwise, e.g., when the word "single" is used. For example, reference to "an analyte" includes a single analyte and multiple analytes, reference to "a capture agent" includes a single capture agent and multiple capture agents, reference to "a detection agent" includes a single detection agent and multiple detection agents, and reference to "an agent" includes a single agent and multiple agents.

Device and System for Analyzing a Sample, Particularly Blood, and Methods for Using the Same Provided herein is a device for analyzing an analyte in a sample, particularly blood. In some embodiments, the device comprises: a first plate and a second plate, wherein:

the plates are movable relative to each other into different configurations (e.g., via a hinge);

one or both plates are flexible;

each of the plates has, on its respective surface, a sample contact area for contacting a sample;

one or both of the plates comprise spacers that are fixed with a respective plate, wherein the spacers have a predetermined substantially uniform height and a pre-determined constant inter-spacer distance that is in the range of 7 um to 200 um (e.g., 7 um to 50 um (microns), 50 um to 120 um or 120 um to 200 um) and wherein at least one of the spacers is inside the sample contact area;

a detector that detects the analyte in the sample;

wherein one of the configurations is an open configuration, in which: the two plates are separated apart, the spacing between the plates is not regulated by the spacers, and the sample is deposited on one or both of the plates; and wherein another of the configurations is a closed configuration which is configured after the sample deposition in the open configuration; and in the closed configuration: at least part of the sample is compressed by the two plates into a layer of highly uniform thickness and is substantially stagnant (i.e., having substantially no current or directional flow) relative to the plates, wherein the uniform thickness of the layer (which may have a lateral area of at least 0.1 mm$^2$, at least 0.5 mm$^2$ or at least 1 mm$^2$) is confined by the inner surfaces of the two plates and is regulated by the plates and the spacers, and has an average thickness equal to or less than 5 um (e.g., 1.8 um to 2 um, 2 um to 2.2 um, 2.2 um to 2.6 um, or 2.6 um to 3.8 um) with a small variation (e.g., a variation of less than 10%, less than 5% or less than 1%); and wherein at the closed configuration, the detector detects the analyte in the at least part of the sample.

As described below, the device may be used for analyzing the analyte which comprises a molecule (e.g., a protein, peptides, DNA, RNA, nucleic acid, or other molecule), cells, tissues, viruses, and nanoparticles with different shapes; and for example, for counting cells (e.g., red blood cells and white blood cells) in a blood sample that is placed in the device.

In some embodiments, the device may comprise a dry reagent coated on one or both plates. In some embodiments, the dry reagent may bind to an analyte in the sample and immobilize the analyte on a surface on one or both of the plates. In these embodiments, the reagent may be an antibody or other specific binding agent, for example. This dry reagent may have a pre-determined area. In other embodiments, the device may comprise a releasable dry reagent on one or more of the plates, e.g., a labeled reagent such as a cell stain or a labeled detection agent such as an antibody or the like. In some cases, there may be a release time control material on the plate that contains the releasable dry reagent, wherein the release time control material delays the time that the releasable dry regent is released into the sample. In some cases, the release time control material delays the time that the dry regent starts is released into the sample by at least 3 seconds, e.g., at least 5 seconds or at least 10 seconds. Some embodiments, the drive may contain multiple dry binding sites and/or multiple reagent sites, thereby allowing multiplex assays to be performed. In some cases, the areas occupied by the drying binding sites may oppose the areas occupied by the reagent sites when the plates are in the closed position.

In some embodiments, the regent comprises anticoagulant and/or staining reagent(s).

In some embodiments, the analyte may be a molecule (e.g., a protein, peptides, DNA, RNA, nucleic acid, or other molecule), cell, tissue, virus, or nanoparticles with different shapes. In some embodiments, the analytes may be white blood cell, red blood cells and platelets. In some embodiments, the analyte is stained.

In some embodiments, the spacers regulating the layer of uniform thickness (i.e., the spacers that are spacing the plates away from each other in the layer) have a "filling factor" of at least 1%, e.g., at least 2% or at least 5%, wherein the filling factor is the ratio of the spacer area that is in contact with the layer of uniform thickness to the total plate area that is in contact with the layer of uniform thickness. In some embodiments, for spacers regulating the layer of uniform thickness, the Young's modulus of the spacers times the filling factor of the spacers is equal or larger than 10 MPa, e.g., at least 15 MPa or at least 20 MPa, where the filling factor is the ratio of the spacer area that is in contact with the layer of uniform thickness to the total plate area that is in contact with the layer of uniform thickness. In some embodiments, the thickness of the flexible plate times the Young's modulus of the flexible plate is in the range 60 to 750 GPa-um, e.g., 100 to 300 GPa-um, 300 to 550 GPa-um, or 550 to 750 GPa-um. In some embodiments, for a flexible plate, the fourth power of the inter-spacer-distance (ISD) divided by the thickness of the flexible plate (h) and the Young's modulus (E) of the flexible plate, ISD$^4$/(hE), is equal to or less than $10^6$ um$^3$/GPa, e.g., less than $10^5$ um$^3$/GPa, less then $10^4$ um$^3$/GPa or less than $10^3$ um$^3$/GPa.

In some embodiments, one or both plates comprises a location marker either on a surface of or inside the plate, that provide information of a location of the plate, e.g., a location that is going to be analyzed or a location onto which the sample should be deposited. In some cases, one or both plates may comprise a scale marker, either on a surface of or inside the plate, that provides information of a lateral dimension of a structure of the sample and/or the plate. In some embodiments, one or both plates comprises an imaging marker, either on surface of or inside the plate that assists an imaging of the sample. For example, the imaging marker could help focus the imaging device or direct the imaging device to a location on the device. In some embodiments, the spacers can function as a location marker, a scale marker, an imaging marker, or any combination of thereof.

In some embodiments, the average thickness of the layer of uniform thickness is in the range of 2 um to 2.2 um and the sample is blood. In some embodiments, the average thickness of the layer of uniform thickness is in the range of 2.2 um to 2.6 um and the sample is blood. In some embodiments, the average thickness of the layer of uniform thickness is in the range of 1.8 um to 2 um and the sample is blood. In some embodiments, the average thickness of the layer of uniform thickness is in the range of 2.6 um to 3.8 um and the sample is blood. In some embodiments, the average thickness of the layer of uniform thickness is in the range of 1.8 um to 3.8 um and the sample is whole blood without a dilution by another liquid.

In some cases, the average thickness of the layer of uniform thickness is about equal to a minimum dimension of an analyte in the sample, e.g., a red blood cell or another cell.

In some embodiments, the inter-spacer distance may substantially periodic. In some cases, the spacers may be in a regular pattern and the spacing between adjacent spacers may be approximately the same. The spacers may pillars with a cross-sectional shape selected from round, polygonal, circular, square, rectangular, oval, elliptical, or any combination of the same and, in some embodiments, the spacers may have a substantially flat top surface, wherein, for each spacer, the ratio of the lateral dimension of the spacer to its height is at least 1. In some cases, the minimum lateral dimension of spacer is less than or substantially equal to the minimum dimension of an analyte in the sample. The minimum lateral dimension of spacer is in the range of 0.5 um to 100 um, e.g., in the range of 2 um to 50 um or 0.5 um to 10 um.

In some embodiments, the sample may be whole blood, e.g., blood from a clinical sample. In some cases, the blood may be obtained by drawing blood from an individual, e.g., by pricking the skin of the individual, and touching the drawn blood (without the aid of a blood transfer device) to one of the plates. In some embodiments, the sample is undiluted whole blood.

In some embodiments, the spacers have a pillar shape and the sidewall corners of the spacers have a round shape with a radius of curverture at least 1 um, e.g., at least 1.2 um, at least 1.5 um or at least 2.0 um. The spacers may have any convenient density, e.g., a density of at least $1000/mm^2$, e.g., a density of at least $1000/mm^2$, a density of at least $2000/mm^2$, a density of at least $5,000/mm^2$ or a density of at least $10,000/mm^2$.

In this device, at least one of the plates may be transparent, thereby allowing the assay to be read optically. Likewise, in this device, at least one of the plates may be made of a flexible polymer, thereby allowing the sample to be efficiently spread by compressing the plates together. In some embodiments, the pressure that compresses the plates, the spacers are not compressible and/or, independently, only one of the plates is flexible. The flexible plate may have a thickness in the range of 10 um to 200 um, e.g., 10 um to 50 um, 50 um to 150 um or 150 um to 200 um. As noted above, in the closed position, the thickness of the layer of uniform thickness may have a small variation. In some embodiments, the variation may be less than 30%, less than 20%, less than 10%, less than 5% or less than 2%, meaning that the thickness of the area does not exceed +/−30%, +/−20%, +/−10%, +/−5% or +/−2% of the average thickness.

In some embodiments, the first and second plates are connected and are configured to be changed from the open configuration to the closed configuration by folding the plates. In some embodiments, the first and second plates can be connected by a hinge and are configured to be changed from the open configuration to the closed configuration by folding the plates such that the device bends along the hinge. The hinge may be a separate material that is attached to the plates or, in some cases, the plates may be integral with the plates. In some cases, the first and second plates are made in a single piece of material and are configured to be changed from the open configuration to the closed configuration by folding the plates, e.g., along a hinge.

In some embodiments, the device is configured to analyze the sample very rapidly. In some cases, the analysis may be done in 60 seconds or less, in 30 seconds, in 20 seconds or less or in 10 seconds or less.

In any embodiments, the dry binding site may comprise a capture agent such as an antibody or nucleic acid. In some embodiments, the releasable dry reagent may be a labeled reagent such as a fluorescently-labeled reagent, e.g., a fluorescently-labeled antibody or a cell stain such Romanowsky's stain, Leishman stain, May-Grunwald stain, Giemsa stain, Jenner's stain, Wright's stain, or any combination of the same (e.g., Wright-Giemsa stain). Such a stan may comprise eosin Y or eosin B with methylene blue. In certain embodiments, the stain may be an alkaline stain such as haematoxylin.

In some embodiments, the detector may be is an optical detector that detects an optical signal. In some embodiments, the detector may be an electric detector that detects an electrical signal In some embodiments, the spacing is fixed on a plate by directly embossing the plate or injection molding of the plate.

In some embodiments, the plate and the spacers are composted of polystyrene, PMMA, PC, COC, COP, or another plastic.

Also provided is a system for rapidly analyzing a sample using a mobile phone. In certain embodiments, this system may comprise: (a) a device as described above; (b) a mobile communication device (e.g., a mobile phone such as an iphone or the like) comprising: i. one or a plurality of cameras for the detecting and/or imaging the sample; ii. electronics, signal processors, hardware and software for receiving and/or processing the detected signal and/or the image of the sample and for remote communication; and (c) a light source from either the mobile communication device or an external source. In some cases, the detector in the device may be provided by the mobile communication device, and detects an analyte in the sample at the closed configuration.

In this system, one of the plates may have a binding site that binds an analyte, wherein at least part of the uniform sample thickness layer is over the binding site, and is substantially less than the average lateral linear dimension of the binding site.

In some embodiments, the system may additionally comprise (d) a housing configured to hold the sample and to be mounted to the mobile communication device. The housing may comprise optics for facilitating the imaging and/or signal processing of the sample by the mobile communication device, and a mount configured to hold the optics on the mobile communication device. In some cases, an element of the optics of the device (e.g., a lens, filter, mirror, prism or a beamsplitter) in the housing may be movable relative to the housing such that the sample may be imaged in at least two channels.

In some embodiments, the mobile communication device may configured to communicate test results to a medical professional (e.g., an MD), a medical facility (e.g., a hospital or testing lab) or an insurance company. In addition, the mobile communication device may be configured to communicate information on the subject (e.g., the subject's age, gender, weight, address, name, prior test results, prior medical history, etc.) with the medical professional, medical facility or insurance company. In certain embodiments, the mobile communication device may configured to receive a prescription, diagnosis or a recommendation from a medical professional. For example, in some embodiments the mobile communication device may send assay results to a remove location where a medical professional gives a diagnosis. The diagnosis may be communicated to the subject via the mobile communication device. In some embodiments, the mobile communication device may be configured to communicate information of the test to a cloud network, and the cloud network process the information to refine the test results. In some embodiments, the mobile communication device may be configured to communicate information of the test and the subject to a cloud network, the cloud network process the information to refine the test results, and the refined test results will send back the subject.

In some embodiments, the mobile communication device may contain hardware and software that allows it to (a) capture an image of the sample; (b) analyze a test location and a control location in image; and (c) compare a value obtained from analysis of the test location to a threshold value that characterizes the rapid diagnostic test. In some cases, the mobile communication device communicates with the remote location via a wireless or cellular network. In any embodiment, the mobile communication device may be a mobile phone.

The system may be used in a method that comprises (a) depositing a sample on the device of the system; (b) assaying an analyte in the sample deposited on the device to generate a result; and (c) communicating the result from the mobile communication device to a location remote from the mobile communication device. The method may comprise analyzing the results at the remote location to provide an analyzed result; and communicating the analyzed result from the remote location to the mobile communication device. As noted above, the analysis may be done by a medical professional at a remote location. And, in some embodiments, the mobile communication device may receive a prescription, diagnosis or a recommendation from a medical professional at a remote location.

In this method, the analyte may be a molecule (e.g., a protein, peptides, DNA, RNA, nucleic acid, or other molecule), a cell, tissue, virus, or nanoparticle nanoparticles with different shapes, for example. In some embodiments, the analytes may be white blood cells, red blood cells and/or platelets.

In this method, the sample may be undiluted whole blood that can be transferred directly onto the device from the site of blood draw. In some embodiments, the blood sample is a clinical sample.

In some embodiments, the assaying step may comprise detecting an analyte in the sample, e.g., a biomarker such as a protein, nucleic acid, cell, or metabolite that is in the blood. This assay may be a binding assay or a biochemical assay, for example.

In some embodiments, the method comprises counting the number of red blood cells and/or counting the number of white blood cells. In some cases, the method may comprise staining the cells in the sample and counting the number of one or more of the neutrophils, lymphocytes, monocytes, eosoniphils and basophils in the sample.

In some embodiments, the method may be used to perform a white blood cell differential (for at least neutrophils, eosinophils and lymphocytes) in order to obtain a potential diagnosis for an infection, inflammation, allergies, asthma, an immune disorders (e.g., an autoimmune disorders or an immune deficiency), leukemia (e.g., chronic myeloid leukemia, chronic lymphocytic leukemia), myelodysplastic syndrome or a cyeloproliferative neoplasms (e.g., myelofibrosis).

Also provided is a method for analyzing a sample. In some embodiments, this method may comprise obtaining a device as described above, depositing the sample onto one or both pates of the device; placing the plates in a closed configuration and applying an external force over at least part of the plates; and analyzing an analyte in the sample in the layer of uniform thickness while the plates are the closed configuration.

In some embodiments, this method may comprise:
(a) obtaining a sample;
(b) obtaining a first and second plates that are movable relative to each other into different configurations, wherein each plate has a sample contact surface that is substantially planar, one or both plates are flexible, and one or both of the plates comprise spacers that are fixed with a respective sample contacting surface, and wherein the spacers have:
 i. a predetermined substantially uniform height,
 ii. a shape of pillar with substantially uniform cross-section and a flat top surface;
 iii. a ratio of the width to the height equal or larger than one;
 iv. a predetermined constant inter-spacer distance that is in the range of 10 µm to 200 µm;
 v. a filling factor of equal to 1% or larger; and
(c) depositing the sample on one or both of the plates when the plates are configured in an open configuration, wherein the open configuration is a configuration in which the two plates are either partially or completely separated apart and the spacing between the plates is not regulated by the spacers;
(d), after (c), using the two plates to compress at least part of the sample into a layer of substantially uniform thickness that is confined by the sample contact surfaces of the plates, wherein the uniform thickness of the layer is regulated by the spacers and the plates, and has an average value in the range of 1.8 µm to 3 µm with a variation of less than 10%, wherein the compressing comprises:
 bringing the two plates together; and
 conformable pressing, either in parallel or sequentially, an area of at least one of the plates to press the plates together to a closed configuration, wherein the conformable pressing generates a substantially uniform pressure on the plates over the at least part of the sample, and the pressing spreads the at least part of the sample laterally between the sample contact surfaces of the plates, and wherein the closed configuration is a configuration in which the spacing between the plates in the layer of uniform thickness region is regulated by the spacers; and
(e) analyzing the blood in the layer of uniform thickness while the plates are the closed configuration;
wherein the filling factor is the ratio of the spacer contact area to the total plate area;
wherein a conformable pressing is a method that makes the pressure applied over an area is substantially constant regardless the shape variation of the outer surfaces of the plates; and
wherein the parallel pressing applies the pressures on the intended area at the same time, and a sequential pressing applies the pressure on a part of the intended area and gradually move to other area.

In some embodiments, this method may comprise: removing the external force after the plates are in the closed configuration; imaging the layer of uniform thickness while the plates are the closed configuration; and counting a number of analytes, e.g., cells in an area of the image. As noted above, in these embodiments, the inter-spacer distance may in the range of 20 um to 200 um or 5 um to 20 um. In these embodiments, the product of the filling factor and the Young's modulus of the spacer is 2 MPa or larger. In some embodiments, the surface variation is less than 30 nm.

In some embodiments, the sample may be an undiluted whole blood into which no anticoagulant has been added. In these embodiments, the depositing step (b) may be done by: i. pricking the skin of a human release a droplet of blood onto the skin and ii. contacting the droplet of blood with one or both of the plates without use of a blood transfer tool.

The analyzing step may be done by, e.g., counting the number of red blood cells and/or counting the number of white blood cells. In some embodiments, the method may comprise staining the cells in the sample and counting the number of neutrophils, lymphocytes, monocytes, eosoniphils and basophils, or any combination thereof.

In any of these embodiments, the imaging and counting may be done by: i. illuminating the cells in the layer of uniform thickness; ii. taking one or more images of the cells using a CCD or CMOS sensor; iii. identifying cells in the image using a computer; and iv. counting a number of cells in an area of the image.

In some embodiments, the external force may be provided by human hand, e.g., by pressing down using a digit such as a thumb, or pinching between a thumb and another digit such as a forefinger on the same hand.

In some embodiments, the method may comprise measuring sodium, potassium, chloride, bicarbonate, blood urea, nitrogen, magnesium, creatinine, glucose, calcium, HDL cholesterol LDL cholesterol levels and/or triglyceride levels in the layer of uniform thickness. The details of how to perform such assays may be adapted from known methods.

In some embodiments, one or more of the plates may comprises a dry reagent coated on one or both plates (e.g., a binding agent, a staining agent, a detection agent or an assay reactant).

In some embodiments, the layer of uniform thickness sample may a thickness uniformity of up to +/−5%, e.g., up to +/−2% or up to +/−1%.

In some embodiments, the spacers are pillars with a cross-sectional shape selected from round, polygonal, circular, square, rectangular, oval, elliptical, or any combination of the same. In some embodiments, the spacing between the spacers is approximately the average thickness of red blood cells.

The sample may be analyzed in a variety of different ways. For example, in some embodiments, the analyzing step comprises imaging cells, e.g., red blood cells, while blood cells, or platelets, in the blood. The analysis may include imaging cancer cells, viruses, or bacterias in the blood. In some embodiments, the method may comprise analyzing the blood comprises detecting of proteins or nucleic acids.

In some embodiments, the analysis may comprise measuring hemocytes, which may comprise determining of the sample thickness using the spacer, determining the lateral area by imaging, and calculating the area of red blood cells using the 2D image. The method may comprise measuring red cell concentration in the blood, white blood cell concentration in the blood, and/or platelet concentration in the blood.

In any of the embodiments described above, the sample may be whole blood.

Immunohistochemistry

In immunohistochemical (IHC) staining methods, a tissue sample is fixed (e.g., in paraformaldehyde), optionally embedding in wax, sliced into thin sections that are less then 100 um thick (e.g., 2 um to 6 um thick), and then mounted onto a support such as a glass slide. Once mounted, the tissue sections may be dehydrated using alcohol washes of increasing concentrations and cleared using a detergent such as xylene.

In most IHC methods, a primary and a secondary antibody may be used. In such methods, the primary antibody binds to antigen of interest (e.g., a biomarker) and is unlabeled. The secondary antibody binds to the primary antibody and directly conjugated either to a reporter molecule or to a linker molecule (e.g., biotin) that can recruit reporter molecule that is in solution. Alternatively, the primary antibody itself may be directly conjugated either to a reporter molecule or to a linker molecule (e.g., biotin) that can recruit reporter molecule that is in solution. Reporter molecules include fluorophores (e.g., FITC, TRITC, AMCA, fluorescein and rhodamine) and enzymes such as alkaline phosphatase (AP) and horseradish peroxidase (HRP), for which there are a variety of fluorogenic, chromogenic and chemiluminescent substrates such as DAB or BCIP/NBT.

In direct methods, the tissue section is incubated with a labeled primary antibody (e.g. an FITC-conjugated antibody) in binding buffer. The primary antibody binds directly with the antigen in the tissue section and, after the tissue section has been washed to remove any unbound primary antibody, the section is be analyzed by microscopy.

In indirect methods, the tissue section is incubated with an unlabeled primary antibody that binds to the target antigen in the tissue. After the tissue section is washed to remove unbound primary antibody, the tissue section is incubated with a labeled secondary antibody that binds to the primary antibody.

After immunohistochemical staining of the antigen, the tissue sample may be stained with another dye, e.g., hematoxylin, Hoechst stain and DAPI, to provide contrast and/or identify other features.

The present device may be used for immunohistochemical (IHC) staining a tissue sample. In these embodiments, the device may comprise
a first plate and a second plate, wherein:
the plates are movable relative to each other into different configurations;
one or both plates are flexible;
each of the plates has, on its respective surface, a sample contact area for contacting a tissue sample or a IHC staining liquid;
the sample contact area in the first plate is smooth and planner;
the sample contact area in the second plate comprise spacers that are fixed on the surface and have a predetermined substantially uniform height and a predetermined constant inter-spacer distance that is in the range of 7 μm to 200 μm;
wherein one of the configurations is an open configuration, in which: the two plates are completely or partially separated apart, the spacing between the plates is not regulated by the spacers; and
wherein another of the configurations is a closed configuration which is configured after a deposition of the sample and the IHC staining liquid in the open configuration; and in the closed configuration: at least part of the sample is between the two plates and a layer of at least part of staining liquid is between the at least part of the sample and the second plate, wherein the thickness of the at least part of staining liquid layer is regulated by the plates, the sample, and the spacers, and has an average distance between the sample surface and the second plate surface is equal or less than 250 μm with a small variation.

In some embodiments, the device may comprise a dry IHC staining agent coated on the sample contact area of one or both plates.

In some embodiments, the device may comprise a dry IHC staining agent coated on the sample contact area of the second plate, and the IHC staining liquid comprise a liquid that dissolve the dry IHC staining agent. The device of claim 1, wherein the thickness of the sample is 2 um to 6 um.

Also provided is a system for rapidly staining and analyzing a tissue sample using a mobile phone comprising:
(a) sample, staining liquid, and device as described above,
(b) a mobile communication device comprising:
  i. one or a plurality of cameras for the detecting and/or imaging the sample;
  ii. electronics, signal processors, hardware and software for receiving and/or processing the detected signal and/or the image of the sample and for remote communication; and
(c) a light source from either the mobile communication device or an external source.

Also provided is a method for rapidly staining and analyzing a tissue sample using a mobile phone, comprising:
(a) depositing a tissue sample and a staining liquid on the device of the system described above, and placing the two plate into a closed configuration;
(b) obtaining a mobile phone that has hardware and software of imaging, data processing, and communication;
(c) assaying by the tissue sample deposited on the CROF device by the mobile phone to generate a result; and
(c) communicating the result from the mobile phone to a location remote from the mobile phone.

Also provided is a method for staining a tissue sample, comprising:
(a) obtaining a tissue sample;
(b) obtaining a stain liquid;
(b) obtaining a first plate and a second plate, wherein:
  the plates are movable relative to each other into different configurations;
  one or both plates are flexible;
  each of the plates has, on its respective surface, a sample contact area for contacting a tissue sample or a IHC staining liquid;
  the sample contact area in the first plate is smooth and planner;
  the sample contact area in the second plate comprise spacers that are fixed on the surface and have a predetermined substantially uniform height and a predetermined constant inter-spacer distance that is in the range of 7 μm to 200 μm;
(c) depositing the tissue sample and the stain liquid on the plates when the plates are configured in an open configuration, wherein the open configuration is a configuration in which the two plates are either partially or completely separated apart and the spacing between the plates is not regulated by the spacers;
(d), after (c), using the two plates to compress at least part of the tissue sample and at least part of the staining liquid into a closed configuration;
  wherein in the closed configuration: at least part of the sample is between the two plates and a layer of at least part of staining liquid is between the at least part of the sample and the second plate, wherein the thickness of the at least part of staining liquid layer is regulated by the plates, the sample, and the spacers, and has an average distance between the sample surface and the second plate surface is equal or less than 250 μm with a small variation.

All of the benefits and advantages (e.g., an accelerated reaction, faster results, etc.) of other embodiments may be applied to this device, system and method.

Further, all parameters described above in the context of other embodiments (e.g., the size, spacing and shape of the spacers, the flexibility of the spacers and plates, and how the device and system can be used, etc.) can be incorporated into IHC embodiments described in this section.

For example, in some embodiments, the spacers regulating the layer of uniform thickness (i.e., the spacers that are spacing the plates away from each other in the layer) have a "filling factor" of at least 1%, e.g., at least 2% or at least 5%, wherein the filling factor is the ratio of the spacer area that is in contact with the layer of uniform thickness to the total plate area that is in contact with the layer of uniform thickness. In some embodiments, for spacers regulating the layer of uniform thickness, the Young's modulus of the spacers times the filling factor of the spacers is equal or larger than 10 MPa, e.g., at least 15 MPa or at least 20 MPa, where the filling factor is the ratio of the spacer area that is in contact with the layer of uniform thickness to the total plate area that is in contact with the layer of uniform thickness. In some embodiments, the thickness of the flexible plate times the Young's modulus of the flexible plate is in the range 60 to 550 GPa-um, e.g., 100 to 300 GPa-um. In some embodiments, for a flexible plate, the fourth power of the inter-spacer-distance (ISD) divided by the thickness of the flexible plate (h) and the Young's modulus (E) of the flexible plate, $ISD^4/(hE)$, is equal to or less than $10^6$ $um^3$/GPa, e.g., less than $10^5$ $um^3$/GPa, less then $10^4$ $um^3$/GPa or less than $10^3$ $um^3$/GPa.

In some embodiments, one or both plates comprises a location marker either on a surface of or inside the plate, that provide information of a location of the plate, e.g., a location that is going to be analyzed or a location onto which the section should be deposited. In some cases, one or both plates may comprise a scale marker, either on a surface of or inside the plate, that provides information of a lateral dimension of a structure of the section and/or the plate. In some embodiments, one or both plates comprises an imaging marker, either on surface of or inside the plate, that assists an imaging of the sample. For example, the imaging marker could help focus the imaging device or direct the imaging device to a location on the device. In some embodiments, the spacers can function as a location marker, a scale marker, an imaging marker, or any combination of thereof.

In some embodiments, the inter-spacer distance may substantially periodic. In some cases, the spacers may be in a regular pattern and the spacing between adjacent spacers may be approximately the same. The spacers may pillars with a cross-sectional shape selected from round, polygonal, circular, square, rectangular, oval, elliptical, or any combination of the same and, in some embodiments, the spacers may have a substantially flat top surface, wherein, for each spacer, the ratio of the lateral dimension of the spacer to its height is at least 1. In some cases, the minimum lateral dimension of spacer is less than or substantially equal to the minimum dimension of an analyte in the sample. The minimum lateral dimension of spacer is in the range of 0.5 um to 100 um, e.g., in the range of 2 um to 50 um or 0.5 um to 10 um.

In some embodiments, the spacers have a pillar shape and the sidewall corners of the spacers have a round shape with a radius of curverture at least 1 um, e.g., at least 1.2 um, at least 1.5 um or at least 2.0 um. The spacers may have any convenient density, e.g., a density of at least 1000/mm$^2$, e.g., a density of at least 1000/mm$^2$, a density of at least 2000/mm$^2$, a density of at least 5,000/mm$^2$ or a density of at least 10,000/mm$^2$.

In this device, at least one of the plates may be transparent, thereby allowing the assay to be read optically. Likewise, in this device, at least one of the plates may be made of a flexible polymer, thereby allowing the sample to be efficiently spread by compressing the plates together. In some embodiments, the pressure that compresses the plates, the spacers are not compressible and/or, independently, only one of the plates is flexible. The flexible plate may have a thickness in the range of 20 um to 200 um, e.g., 50 um to 150 um. As noted above, in the closed position, the thickness of the layer of uniform thickness may have a small variation. In some embodiments, the variation may be less than 10%, less than 5% or less than 2%, meaning that the thickness of the area does not exceed +/−10%, +/−5% or +/−2% of the average thickness.

In some embodiments, the first and second plates are connected and the device can be changed from the open configuration to the closed configuration by folding the plates. In some embodiments, the first and second plates can be connected by a hinge and the device can be changed from the open configuration to the closed configuration by folding the plates such that the device bends along the hinge. The hinge may be a separate material that is attached to the plates or, in some cases, the plates may be integral with the plates.

In some embodiments, the device may be capable analyzing the section very rapidly. In some cases, the analysis may be done in 60 seconds or less, in 30 seconds, in 20 seconds or less or in 10 seconds or less.

In any embodiments, the dry binding site may comprise a capture agent such as an antibody or nucleic acid. In some embodiments, the releasable dry reagent may be a labeled reagent such as a fluorescently-labeled reagent, e.g., a fluorescently-labeled antibody or a cell stain such Romanowsky's stain, Leishman stain, May-Grunwald stain, Giemsa stain, Jenner's stain, Wright's stain, or any combination of the same (e.g., Wright-Giemsa stain). Such a stain may comprise eosin Y or eosin B with methylene blue. In certain embodiments, the stain may be an alkaline stain such as haematoxylin.

In some embodiments, the system may additionally comprise (d) a housing configured to hold the sample and to be mounted to the mobile communication device. The housing may comprise optics for facilitating the imaging and/or signal processing of the sample by the mobile communication device, and a mount configured to hold the optics on the mobile communication device. In some cases, an element of the optics of the device (e.g., a lens, filter, mirror, prism or a beamsplitter, may be movable) such that the sample may be imaged in at least two channels.

In some embodiments, the mobile communication device may configured to communicate test results to a medical professional (e.g., an MD), a medical facility (e.g., a hospital or testing lab) or an insurance company. In addition, the mobile communication device may be configured to communicate information on the subject (e.g., the subject's age, gender, weight, address, name, prior test results, prior medical history, etc.) with the medical professional, medical facility or insurance company. In certain embodiments, the mobile communication device may configured to receive a prescription, diagnosis or a recommendation from a medical professional. For example, in some embodiments the mobile communication device may send assay results to a remove location where a medical professional gives a diagnosis. The diagnosis may be communicated to the subject via the mobile communication device.

In some embodiments, the mobile communication device may contain hardware and software that allows it to (a) capture an image of the sample; (b) analyze a test location and a control location in image; and (c) compare a value obtained from analysis of the test location to a threshold value that characterizes the rapid diagnostic test. In some cases, the mobile communication device communicates with the remote location via a wireless or cellular network. In any embodiment, the mobile communication device may be a mobile phone.

The system may be used in a method that comprises (a) sample on the device of the system; (b) assaying the sample deposited on the device to generate a result; and (c) communicating the result from the mobile communication device to a location remote from the mobile communication device. The method may comprise analyzing the results at the remote location to provide an analyzed result; and communicating the analyzed result from the remote location to the mobile communication device. As noted above, the analysis may be done by a medical professional at a remote location. And, in some embodiments, the mobile communication device may receive a prescription, diagnosis or a recommendation from a medical professional at a remote location.

Also provided is a method for analyzing a tissue section. In some embodiments, this method may comprise obtaining a device as described above, depositing the section onto one or both pates of the device; placing the plates in a closed configuration and applying an external force over at least part of the plates; and analyzing the sample in the layer of uniform thickness while the plates are the closed configuration.

In some embodiments, this method may comprise:
(a) obtaining a tissue section;
(b) obtaining a first and second plates that are movable relative to each other into different configurations, wherein each plate has a sample contact surface that is substantially planar, one or both plates are flexible, and one or both of the plates comprise spacers that are fixed with a respective sample contacting surface, and wherein the spacers have:
  i. a predetermined substantially uniform height,
  ii. a shape of pillar with substantially uniform cross-section and a flat top surface;
  iii. a ratio of the width to the height equal or larger than one;
  iv. a predetermined constant inter-spacer distance that is in the range of 10 μm to 200 μm;
  v. a filling factor of equal to 1% or larger; and
(c) depositing the section on one or both of the plates when the plates are configured in an open configuration, wherein the open configuration is a configuration in which the two plates are either partially or completely separated apart and the spacing between the plates is not regulated by the spacers;
(d), after (c), using the two plates to compress at least part of the section into a layer of substantially uniform thickness that is confined by the sample contact surfaces of the plates, wherein the uniform thickness of the layer is regulated by the spacers and the plates, and has an average value in the range of 1.8 μm to 3 μm with a variation of less than 10%, wherein the compressing comprises:
  bringing the two plates together; and
  conformable pressing, either in parallel or sequentially, an area of at least one of the plates to press the plates together to a closed configuration, wherein the conformable pressing generates a substantially uniform pressure on the plates over the at least part of the sample, and the pressing spreads the at least part of the sample laterally between the sample contact surfaces of the plates, and wherein the closed configuration is a configuration in which the spacing between the plates in the layer of uniform thickness region is regulated by the spacers; and (e) analyzing the section in the layer of uniform thickness while the plates are the closed configuration;

wherein the filling factor is the ratio of the spacer contact area to the total plate area;

wherein a conformable pressing is a method that makes the pressure applied over an area is substantially constant regardless the shape variation of the outer surfaces of the plates; and wherein the parallel pressing applies the pressures on the intended area at the same time, and a sequential pressing applies the pressure on a part of the intended area and gradually move to other area.

In some embodiments, this method may comprise: removing the external force after the plates are in the closed configuration; imaging the section in the layer of uniform thickness while the plates are the closed configuration. As noted above, in these embodiments, the inter-spacer distance may in the range of 20 um to 200 um or 5 um to 20 um. In these embodiments, the product of the filling factor and the Young's modulus of the spacer is 2 MPa or larger. In some embodiments, the surface variation is less than 30 nm.

In any of these embodiments, the imaging and counting may be done by: i. illuminating the section in the layer of uniform thickness; ii. taking one or more images of the section using a CCD or CMOS sensor.

In some embodiments, the external force may be provided by human hand, e.g., by pressing down using a digit such as a thumb, or pinching between a thumb and another digit such as a forefinger on the same hand.

In some embodiments, one or more of the plates may comprises a dry reagent coated on one or both plates (e.g., a binding agent, a staining agent, a detection agent or an assay reactant).

In some embodiments, the layer of uniform thickness sample may a thickness uniformity of up to +/−5%, e.g., up to +/−2% or up to +/−1%.

In some embodiments, the spacers are pillars with a cross-sectional shape selected from round, polygonal, circular, square, rectangular, oval, elliptical, or any combination of the same.

Compressed Regulated Open Flow" (CROF)

Many embodiments of the present invention manipulate the geometric size, location, contact areas, and mixing of a sample and/or a reagent using a method, termed "compressed regulated open flow (CROF)", and a device that performs CROF.

The term "compressed open flow (COF)" refers to a method that changes the shape of a flowable sample deposited on a plate by (i) placing other plate on top of at least a part of the sample and (ii) then compressing the sample between two plates by pushing the two plates towards each other; wherein the compression reduces a thickness of at least a part of the sample and makes the sample flow into open spaces between the plates.

The term "compressed regulated open flow" or "CROF" (or "self-calibrated compressed open flow" or "SCOF" or "SCCOF") refers to a particular type of COF, wherein the final thickness of a part or entire sample after the compression is "regulated" by spacers, wherein the spacers, that are placed between the two plates.

The term "the final thickness of a part or entire sample is regulated by spacers" in a CROF means that during a CROF, once a specific sample thickness is reached, the relative movement of the two plates and hence the change of sample thickness stop, wherein the specific thickness is determined by the spacer.

Figure 1:
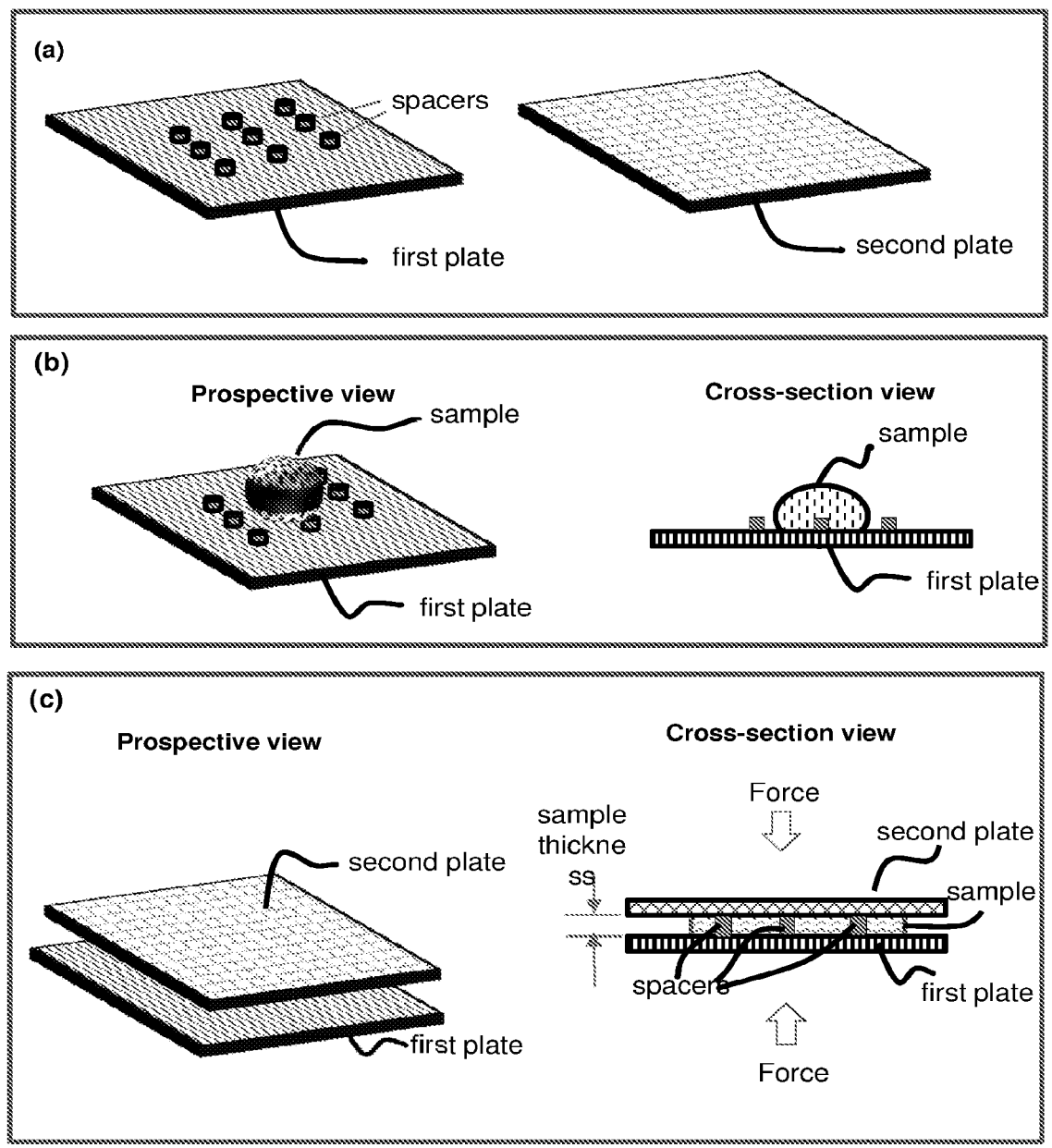
FIG. 1 is an illustration of a CROF (Compressed Regulated Open Flow) embodiment. Panel (a) illustrates a first plate and a second plate wherein the first plate has spacers. Panel (b) illustrates depositing a sample on the first plate (shown), or the second plate (not shown), or both (not shown) at an open configuration. Panel (c) illustrates (i) using the two plates to spread the sample (the sample flow between the plates) and reduce the sample thickness, and (ii) using the spacers and the plate to regulate the sample thickness at the closed configuration. The inner surface of each plate may have one or a plurality of binding sites and or storage sites (not shown).
Figure 2:
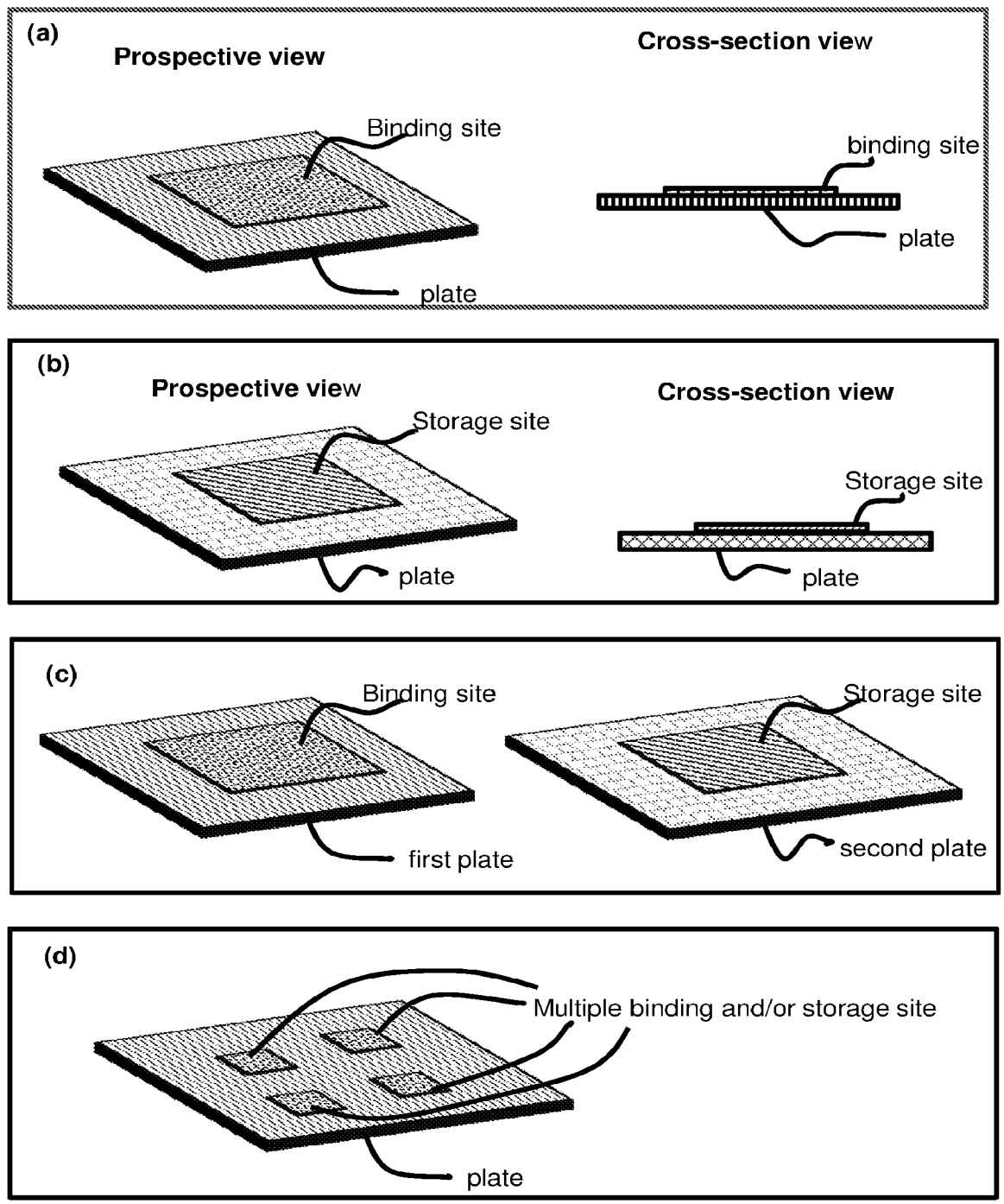
FIG. 2 illustrates plates with a binding site or a storage site. Panel (a) illustrates a plate having a binding site. Panel (b) illustrates a plate having a reagent storage site. Panel (c) illustrates a first plate having a binding site and a second plate having a reagent storage site. Panel (d) illustrates a plate having multiple sites (binding sites and/or storage site).
Figure 3:
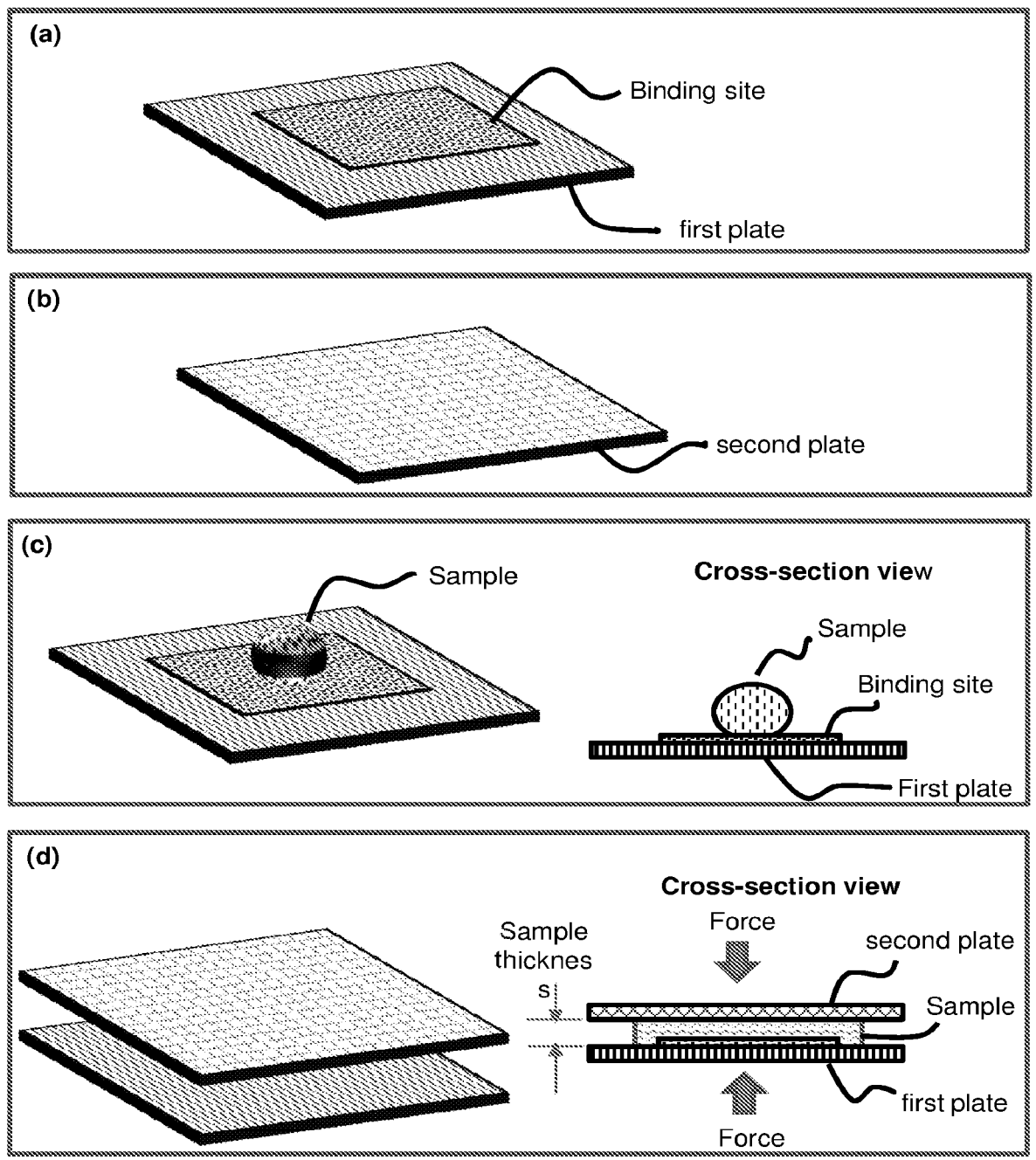
FIG. 3 is a flow-chart and schematic of a method for reducing assay incubation time by reducing sample thickness. Panel (a) illustrates a first plate that has at least one binding site on a substrate surface. Panel (b) illustrates a second plate (which may have a different size from the first plate). Panel (c) illustrates depositing a sample (containing target binding entity) on the substrate surface (shown) or the cover plate (not shown), or both (not shown). Panel (d) illustrates moving the first and second plates so that they are facing each other, and reducing the sample thickness by reducing the spacing of the inner space between the plates. The reduced thickness sample is incubated. The reduced sample thickness speeds up the incubation time. Some embodiment of the method uses spacers to regulate the spacing, which (spacers) are not shown in the illustration.
Figure 4:
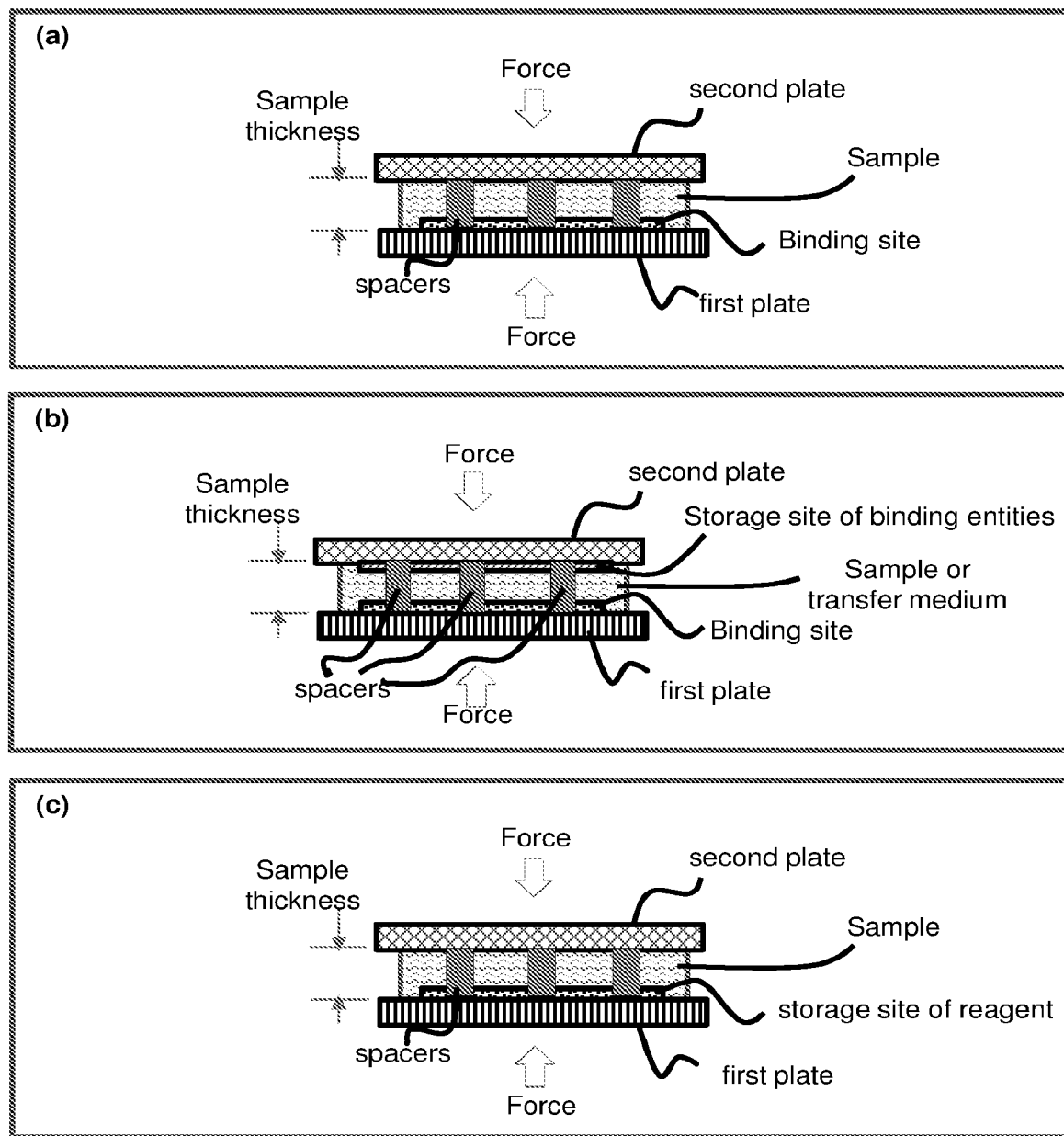
FIG. 4 shows reducing binding or mixing time by reducing the sample thickness using two pates, spacers, and compression (shown in cross-section). Panel (a) illustrates reducing the time for binding entities in a sample to a binding site on a solid surface (X-(Volume to Surface)). Panel (b) illustrates reducing the time for binding entities (e.g. reagent) stored on a surface of plate to a binding site on a surface of another surface (X-(Surface to Surface)). Panel (c) illustrates reducing the time for adding reagents stored on a surface of a plate into a sample that is sandwiched between the plate and other plate (X-(Surface to Volume)).

One embodiment of the method of CROF, as illustrated in FIG. 1, comprises:

(a) obtaining a sample, that is flowable;

(b) obtaining a first plate and a second plate that are movable relative to each other into different configurations, wherein each plate has a sample contact surface that is substantially planar, wherein one or both of the plates comprise spacers and the spacers have a predetermined height, and the spacers are on a respective sample contacting surface;

(c) depositing, when the plates are configured in an open configuration, the sample on one or both of the plates; wherein the open configuration is a configuration in which the two plates are either partially or completely separated apart and the spacing between the plates is not regulated by the spacers; and (d) after (c), spreading the sample by bringing the plates into a closed configuration, wherein, in the closed configuration: the plates are facing each other, the spacers and a relevant volume of the sample are between the plates, the thickness of the relevant volume of the sample is regulated by the plates and the spacers, wherein the relevant volume is at least a portion of an entire volume of the sample, and wherein during the sample spreading, the sample flows laterally between the two plates.

The term "plate" refers to, unless being specified otherwise, the plate used in a CROF process, which a solid that has a surface that can be used, together with another plate, to compress a sample placed between the two plate to reduce a thickness of the sample.

The term "the plates" or "the pair of the plates" refers to the two plates in a CROF process.

The term "first plate" or "second plate" refers to the plate use in a CROF process.

The term "the plates are facing each other" refers to the cases where a pair of plates are at least partially facing each other.

The term "spacers" or "stoppers" refers to, unless stated otherwise, the mechanical objects that set, when being placed between two plates, a limit on the minimum spacing between the two plates that can be reached when compressing the two plates together.

Namely, in the compressing, the spacers will stop the relative movement of the two plates to prevent the plate spacing becoming less than a preset (i.e. predetermined) value. There are two types of the spacers: "open-spacers" and "enclosed-spacers".

The term "open-spacer" means the spacer have a shape that allows a liquid to flow around the entire perimeter of the spacer and flow pass the spacer. For example, a pillar is an open spacer.

The term of "enclosed spacer" means the spacer of having a shape that a liquid cannot flow abound the entire perimeter of the spacer and cannot flow pass the spacer. For example, a ring shape spacer is an enclosed spacer for a liquid inside the ring, where the liquid inside the ring spacer remains inside the ring and cannot go to outside (outside perimeter).

The term "a spacer has a predetermined height" and "spacers have predetermined inter-spacer distance" means, respectively, that the value of the spacer height and the inter spacer distance is known prior to a CROF process. It is not predetermined, if the value of the spacer height and the inter-spacer distance is not known prior to a CROF process. For example, in the case that beads are sprayed on a plate as spacers, where beads are landed on random locations of the plate, the inter-spacer distance is not predetermined. Another example of not predetermined inter spacer distance is that the spacers moves during a CROF processes.

The term "a spacer is fixed on its respective plate" in a CROF process means that the spacer is attached to a location of a plate and the attachment to that location is maintained during a CROF (i.e. the location of the spacer on respective plate does not change). An example of "a spacer is fixed with its respective plate" is that a spacer is monolithically made of one piece of material of the plate, and the location of the spacer relative to the plate surface does not change during CROF. An example of "a spacer is not fixed with its respective plate" is that a spacer is glued to a plate by an adhesive, but during a use of the plate, during CROF, the adhesive cannot hold the spacer at its original location on the plate surface and the spacer moves away from its original location on the plate surface.

The term "a spacer is fixed to a plate monolithically" means the spacer and the plate behavior like a single piece of an object where, during a use, the spacer does not move or separated from its original location on the plate.

The term "open configuration" of the two plates in a CROF process means a configuration in which the two plates are either partially or completely separated apart and the spacing between the plates is not regulated by the spacers The term "closed configuration" of the two plates in a CROF process means a configuration in which the plates are facing each other, the spacers and a relevant volume of the sample are between the plates, the thickness of the relevant volume of the sample is regulated by the plates and the spacers, wherein the relevant volume is at least a portion of an entire volume of the sample.

The term "a sample thickness is regulated by the plate and the spacers" in a CROF process means that for a give condition of the plates, the sample, the spacer, and the plate compressing method, the thickness of at least a port of the sample at the closed configuration of the plates can be predetermined from the properties of the spacers and the plate.

The term "inner surface" or "sample surface" of a plate in a CROF device refers to the surface of the plate that touches the sample, while the other surface (that does not touch the sample) of the plate is termed "outer surface".

The term "X-Plate" of a CROF device refers to a plate that comprises spaces that are on the sample surface of the plate, wherein the spacers have a predetermined inter-spacer distance and spacer height, and wherein at least one of the spacers is inside the sample contact area.

The term "CROF device" refers to a device that performs a CROF process. The term "CROFed" means that a CROF process is used. For example, the term "a sample was CROFed" means that the sample was put inside a CROF device, a CROF process was performed, and the sample was hold, unless stated otherwise, at a final configuration of the CROF.

The term "CROF plates" refers to the two plates used in performing a CROF process.

The term "surface smoothness" or "surface smoothness variation" of a planar surface refers to the average deviation of a planar surface from a perfect flat plane over a short distance that is about or smaller than a few micrometers. The surface smoothness is different from the surface flatness variation. A planar surface can have a good surface flatness, but poor surface smoothness.

The term "surface flatness" or "surface flatness variation" of a planar surface refers to the average deviation of a planar surface from a perfect flat plane over a long distance that is about or larger than 10 um. The surface flatness variation is different from the surface smoothness. A planar surface can have a good surface smoothness, but poor surface flatness (i.e. large surface flatness variation).

The term "relative surface flatness" of a plate or a sample is the ratio of the plate surface flatness variation to the final sample thickness.

The term "final sample thickness" in a CROF process refers to, unless specified otherwise, the thickness of the sample at the closed configuration of the plates in a CORF process.

The term "compression method" in CROF refers to a method that brings two plates from an open configuration to a closed configuration.

The term of "interested area" or "area of interest" of a plate refers to the area of the plate that is relevant to the function that the plates perform.

The term "at most" means "equal to or less than". For example, a spacer height is at most 1 um, it means that the spacer height is equal to or less than 1 um.

The term "sample area" means the area of the sample in the direction approximately parallel to the space between the plates and perpendicular to the sample thickness.

The term "sample thickness" refers to the sample dimension in the direction normal to the surface of the plates that face each other (e.g., the direction of the spacing between the plates).

The term "plate-spacing" refers to the distance between the inner surfaces of the two plates.

The term "deviation of the final sample thickness" in a CROF means the difference between the predetermined spacer height (determined from fabrication of the spacer) and the average of the final sample thickness, wherein the average final sample thickness is averaged over a given area (e.g. an average of 25 different points (4 mm apart) over 1.6 cm by 1.6 cm area).

The term "uniformity of the measured final sample thickness" in a CROF process means the standard deviation of the measured final sample thickness over a given sample area (e.g. the standard deviation relative to the average).

The term "relevant volume of a sample" and "relevant area of a sample" in a CROF process refers to, respectively, the volume and the area of a portion or entire volume of the sample deposited on the plates during a CROF process, that is relevant to a function to be performed by a respective method or device, wherein the function includes, but not limited to, reduction in binding time of analyte or entity, detection of analytes, quantify of a volume, quantify of a concentration, mixing of reagents, or control of a concentration (analytes, entity or reagents).

The term "some embodiments", "in some embodiments" "in the present invention, in some embodiments", "embodiment", "one embodiment", "another embodiment", "certain embodiments", "many embodiments", or alike refers, unless specifically stated otherwise, to an embodiment(s) that is (are) applied to the entire disclosure (i.e. the entire invention).

The term "height" or "thickness" of an object in a CROF process refers to, unless specifically stated, the dimension of the object that is in the direction normal to a surface of the plate. For example, spacer height is the dimension of the spacer in the direction normal to a surface of the plate, and the spacer height and the spacer thickness means the same thing.

The term "area" of an object in a CROF process refers to, unless specifically stated, the area of the object that is parallel to a surface of the plate. For example, spacer area is the area of the spacer that is parallel to a surface of the plate.

The term "lateral" or "laterally" in a CROF process refers to, unless specifically stated, the direction that is parallel to a surface of the plate.

The term "width" of a spacer in a CROF process refers to, unless specifically stated, a lateral dimension of the spacer.

The term "a spacer inside a sample" means that the spacer is surrounded by the sample (e.g. a pillar spacer inside a sample).

The term "critical bending span" of a plate in a CROF process refers the span (i.e. distance) of the plate between two supports, at which the bending of the plate, for a given flexible plate, sample, and compression force, is equal to an allowed bending. For example, if an allowed bending is 50 nm and the critical bending span is 40 um for a given flexible plate, sample, and compression force, the bending of the plate between two neighboring spacers 40 um apart will be 50 nm, and the bending will be less than 50 nm if the two neighboring spacers is less than 40 um.

The term "flowable" for a sample means that when the thickness of the sample is reduced, the lateral dimension increases. For an example, a stool sample is regarded flowable.

In some embodiments of the present invention, a sample under a CROF process do not to be flowable to benefit from the process, as long as the sample thickness can be reduced under a CROF process. For an example, to stain a tissue by put a dye on a surface of the CROF plate, a CROF process can reduce the tissue thickness and hence speed up the saturation incubation time for staining by the dye.

Reducing (Shortening) Binding or Mixing Time

It is desirable to reduce the incubation/reaction time in performing assays or other chemical reactions. For example, in the surface immobilization assays where a target analyte in a sample is detected by being captured by capture agents immobilized on a plate surface (i.e. a solid phase), it is often desirable to have a short saturation incubation time for capturing target analytes in the sample, or immobilizing of the capture agents and detection agents in a solution on a plate surface, or both. Another example is the need to shorten the time of coating a capture agent to a plate surface. And another example is the need to shorten the time of mixing a reagent into a sample.

The present invention provides the methods and devise that reduce (i.e. shorten) the saturation incubation time needed for binding an entity in sample to a binding site on a solid surface (i.e. the time for an entity from a volume to a surface). Another aspect of the present invention is to reduce the time needed for a binding of an entity stored on a plate surface to a binding site on another plate surface (i.e. the time for an entity from one surface to another surface). Another aspect of the present invention is to reduce the time needed for adding/mixing of a reagent stored on a surface into a volume of a sample (i.e. a time for adding/mixing a reagent from a surface into a volume of a sample).

The present invention reduces the saturation incubation time of binding and/or mixing in an assay by using the devices and methods that spread a sample (or a liquid) to a thinner thickness, thereby reducing the time for an entity diffusing across the sample's thickness. A diffusion time of an entity in a material (e.g. liquid or solid or semi-solid) is proportional to the square to the diffusion distance, hence a reduction of the sample thickness can reduce the diffusion distance, leading to drastically reduction of diffusion time and the saturation incubation time. A thinner thickness (e.g. a tight confined space) also increases the frequency of collisions of an entity with other entities in a material, further enhancing a binding and a mixing. The means in the present invention also make the reduction of the sample's thickness precise, uniform, fast, simple (less operation steps) and applicable to reduce the sample thickness to micrometer or nanometer thick. The inventions have great utilities in fast, low-cost, PoC, diagnostics and chemical/bio analysis. Several embodiments of the present invention are illustrated in FIG. 1-4.

1.1 Reducing the Saturation Incubation Time of Binding an Entity in a Sample to a Binding Site on a Solid Surface by Reducing the Sample Thickness.

X1. A method for reducing the saturation incubation time of binding a target entity in a sample to a binding site of a plate surface, as illustrated in FIGS. 1-2, 3a, and 4a, comprising:

(a) obtaining a sample that is flowable and contains a target entity which is capable of diffusing in the sample;

(b) obtaining a first plate and a second plate that are movable relative to each other into different configurations, wherein the first plate has, on its surface, a binding site that is configured to bind the target entity, wherein one or both of the plates comprise spacers, and each of the spacers is fixed with its respective plate and has a predetermined height;

(c) depositing, when the plates are configured in an open configuration, the sample on one or both of the plates; wherein the open configuration is a configuration in which the two plates are either partially or completely separated apart and the spacing between the plates is not regulated by the spacers;

(d) after (c), spreading the sample by bringing the plates into a closed configuration, wherein, in the closed configuration: the plates are facing each other, the spacers and a relevant volume of the sample are between the plates, the binding site is in contact with the relevant volume, and the thickness of the relevant volume of the sample is regulated by the plates and the spacers, is thinner than the maximum thickness of the sample when the plates are in the open configuration;

wherein the relevant volume is a portion or an entire volume of the sample; and wherein the reduced thickness of the sample reduces the saturation incubation time for binding of the target entity in the relevant volume to the binding site.

For a given sample volume, a CROF reduces sample thickness but increase the sample lateral dimension. The present invention utilize the fact to perform (a) local binding or mixing in portion of the sample, and (b) multiplexing of multiple binding or mixing sites, without a fluidic barrier to fluidically separate a sample into different isolation liquid pockets.

X2. A device for reducing the saturation incubation time to bind target entity in a relevant volume of a sample to a surface, as illustrated in FIGS. 1-2, 3a, and 4a, comprising:

a first plate and a second plate that (a) are movable relative to each other into different configurations, (b) each plate has a sample contact area for contacting a sample that has a target entity in a relevant volume of the sample, (c) one of the plate has binding site that binds the target entity, and (d) at least one of the plates comprises spacers that have a predetermined inter-spacer distance and height and are fixed on its respective surface, wherein at least one of the spacers is inside the sample contact area;

wherein one of the configurations is an open configuration, in which: the two plates are either partially or completely separated apart, and the spacing between the plates is not regulated by the spacers, wherein another of the configuration is a closed configuration, which is configured after the sample deposition in an open configuration; and in the closed configuration: the plates are facing each other, the spacers and the relevant volume of the sample are between the plates, the binding site is in contact with the relevant volume, and the thickness of the relevant volume of the sample is regulated by the plates and the spacers, is thinner than the maximum thickness of the sample when the plates are in the open configuration; wherein the relevant volume is a portion or an entire volume of the sample; and wherein the reduced thickness of the sample reduces the saturation incubation time for a binding of the target entity in the relevant volume to the binding site.

1.2 Reducing Saturation Incubation Time for a Binding of an Entity Stored on One Plate Surface to a Binding Site on Another Plate Surface X3. A method for reducing the saturation incubation time to bind an entity stored on a storage site of one plate to a relevant binding site on another plate, as illustrated in FIGS. 1, 3*c*, and 4*b*, comprising:

(a) obtaining a first plate and a second plate that are movable relative to each other into different configurations, wherein a surface of first plate has a binding site, and a surface of the second plate has a storage site that contains an entity to be bound to the binding site; wherein the area of the binding site and the area of the storage site is less than that of respective plates; and wherein one or both of the plates comprise spacers and each of the spacers is fixed with its respective plate and has a predetermined height;

(b) obtaining a transfer medium, wherein the entity on the storage site are capable of being dissolving into the transfer medium and diffusing in the transfer medium;

(c) depositing, when the plates are configured in an open configuration, the transfer medium on one or both of the plates; wherein the open configuration is a configuration in which the two plates are partially or completely separated apart and the spacing between the plates is not regulated by the spacers;

(d) after (c), spreading the transfer medium by bringing the plates into a closed configuration, wherein, in the closed configuration: the plates are facing each other, the spacers, the binding site, the storage site and at least a portion of the transfer medium are between the plates, the binding site and the storage site are at least partially on top of each other, the transfer medium contacts at least a part of the binding site and the storage site, the thickness of the transfer medium is regulated by the plates and the spacers, is thinner than the maximum thickness of the transfer medium when the plates are in the open configuration;

wherein the reduced thickness of the transfer medium reduces the time for the binging of the entity stored on the second plate to the binding site on the first plate.

X4. A device for reducing the saturation incubation time for binding an entity stored on a storage site of one plate to a binding site on another plate, as illustrated in FIGS. 1, 3*c*, and 4*b*, comprising:

a first plate and a second plate that are movable relative to each other into different configurations, wherein a surface of first plate has a binding site; and a surface of the second plate has a storage site that contains an entity to be bound to the binding site; wherein the area of the binding site and the area of the storage site is less than that of respective plates; and wherein one or both of the plates comprise spacers and each of the spacers is fixed with its respective plate and has a predetermined height;

wherein one of the configurations is an open configuration, in which: the two plates are either partially or completely separated apart, the spacing between the plates is not regulated by the spacers, and a transfer medium can be deposited on one or both of the plates, wherein the entity on the storage site are capable of being dissolving into the transfer medium and diffusing in the transfer medium, wherein another of the configuration is a closed configuration, which is configured after the transfer medium deposition in an open configuration; and in the closed configuration: the plates are facing each other, the spacers, the binding site, the storage site and at least a portion of the transfer medium are between the plates, the binding site and the storage site are at least partially on top of each other, the transfer medium contacts at least a part of the binding site and the storage site, the thickness of the transfer medium is regulated by the plates and the spacers, is thinner than the maximum thickness of the transfer medium when the plates are in the open configuration;

wherein the reduced thickness of the transfer medium reduces the saturation incubation time for a binging of entity on the storage site of the second plate to the binding site of the first plate.

In the method of paragraph X3 and the device of paragraph X4, in some embodiments, the transfer medium comprises a liquid that allows a diffusion of the entity or a reagent or both.

In the method of paragraph X3 and the device of paragraph X4, in some embodiments, the transfer medium is a sample, where the sample contains an analyte (also termed target analyte) that binds the binding site.

In the method of paragraph X3 and the device of paragraph X4, in some embodiments, the transfer medium is a sample, where the sample contains an analyte (also termed target analyte) that binds the binding site and the reagent is a detection agent that binds to the analytes.

1.3 Reducing the Time for Adding (Mixing) Reagent Stored on Surface into a Liquid Sample Many assays need to have reagents added into a sample (including a liquid). Often the concentration of the added reagents in the sample or the liquid need to be controlled. There are needs for new methods that are simple and/or low cost to perform such reagents addition and concentration control. Two examples where reagents additions are needed are (a) blood cell counting where anticoagulant and/or staining reagent(s) may be added into a blood sample, and (b) immunoassays where detection agents are added to bind a target analyte in solution.

One aspect of the present invention is the methods, devices, and systems that make the reagent addition and the reagent concentration control simple and/or low cost. In one embodiment of the current invention, a reagent layer (e.g. dried reagent layer) is first put on a plate surface of a CROF device, then a sample is deposited into the CROF device, and a CROF process makes the sample in contact with the reagent and the sample thickness thinner than the thickness when the sample at the open configuration of the CROF plates. By reducing the sample thickness, it would reduce the diffusion time of the reagent diffuses from the surface into the entire sample, and hence it reduces the time for mixing the reagent with the sample.

X5. A method for reducing the time for mixing a reagent stored on a plate surface into a sample, as illustrated in FIGS. 1, 3*b*, and 4*c*, comprising:
  (a) obtaining a first plate and a second plate that are movable relative to each other into different configurations, wherein the first plate has, on its surface, a storage site that contains reagents to be added into a sample, and the reagents are capable of being dissolving into the sample and diffusing in the sample; and wherein one or both of the plates comprise spacers and each of the spacers is fixed with its respective plate and has a predetermined height;
  (b) obtaining the sample;
  (c) depositing, when the plates are configured in an open configuration, the sample on one or both of the plates; wherein the open configuration is a configuration in which the two plates are partially or completely separated apart and the spacing between the plates is not regulated by the spacers;
  (d) after (c), spreading the sample by bringing the plates into a closed configuration, wherein, in the closed configuration: the plates are facing each other, the spacers, the storage site, and at least a portion of the sample are between the plates, the sample contacts at least a portion of the storage site, the thickness of the sample on the storage site is regulated by the plates and the spacers, is thinner than the maximum thickness of the sample when the plates are in the open configuration;
  wherein the reduced thickness of the sample reduces the time for mixing the reagents on the storage site with the sample.

In the method of paragraph X5, it further comprises a step of incubation while the plates are in the closed configuration, wherein the incubation time is selected in such that results in a significant number of the reagents dissolved in the sample are contained in the relevant volume of the sample, wherein the relevant volume is the volume of the sample that sits on the storage site and the incubation is a process to allow the reagent to dissolve and diffuse in the sample.

In the method of paragraph X5, it further comprises a step that, after (d) and while the plates are in the closed configuration, incubating for a time equal or less than a factor times the diffusion time of the reagent in the sample across the sample thickness regulated by the plates at the closed configuration, and then stopping the incubation; wherein the incubation allows the reagent to diffuse into the sample; and wherein the factor is 0.0001, 0.001, 0.01, 0.1, 1, 1.1, 1.2, 1.3, 1.5, 2, 3, 4, 5, 10, 100, 1000, 10,000, or a range between any to the values. For example, if the factor is 1.1 and the diffusion time is 20 seconds, then the incubation time is equal to or less than 22 second. In one preferred embodiment, the factor is 0.1, 1, 1.5 or a range between any to the values.

X6. A device for reducing the time to add a reagent stored on a plate surface into a sample, as illustrated in FIGS. 1, 3*b*, and 4*c*, comprising:
  a first plate and a second plate that are movable relative to each other into different configurations, wherein the first plate has, on its surface, a storage site that contains reagents to be added into a sample, the reagents are capable of being dissolving into the sample and diffusing in the sample; and wherein one or both of the plates comprise spacers and each of the spacers is fixed with its respective plate and has a predetermined height;
  wherein one of the configurations is an open configuration, in which: the two plates are either partially or completely separated apart, the spacing between the plates is not regulated by the spacers, and the sample is deposited on one or both of the plates;
  wherein another of the configuration is a closed configuration, which is configured after the transfer medium deposition in the open configuration; and in the closed configuration: the plates are facing each other, the spacers, the storage site, and at least a portion of the sample are between the plates, the sample contacts at least a portion of the storage site, the thickness of the sample on the storage site is regulated by the plates and the spacers, is thinner than the maximum thickness of the sample when the plates are in the open configuration;
  wherein the reduced thickness of the sample reduces the time for mixing the reagents on the storage site with the sample.

In the method or the devices of any of paragraphs X1-6, in some embodiments, the relevant volume of the sample is the volume of the sample that sits on (i.e. on top of) the binding site or the storage site.

In the method or the devices of any of paragraphs X1-6, in some embodiments, the relevant volume of the sample is the volume of the sample that sits on (i.e. on top of) the entire area or a partial area of the binding site or the storage site.

In the method or the devices of any of paragraphs X1-6, in some embodiments, the ratio of the lateral dimension of the binding site or the storage site to the sample thickness at the closed configuration is 1.5 3 or larger, 3 or larger, 5 or larger, 10 or larger, 20 or larger, 30 or larger, 50 or larger, 100 or larger, 200 or larger, 1000 or larger, 10,000 or larger, or a range between any two of the values.

In the method or the devices of any of paragraphs X1-6, the ratio of the lateral dimension of the binding site or the storage site to the sample thickness at the closed configuration is between 3 and 20 in a preferred embodiment, 20 and 100 in another preferred embodiment, and 100 and 1000 in another preferred embodiment, and 1000 and 10,000 in another preferred embodiment.

In the method of any of paragraphs X1 and X3, in some embodiments, the final reduced sample thickness is significantly smaller than that of the area of the binding site, so that the entity in the sample area that is outside of the binding site will take longer time to bind to the binding site. With a proper selection of the incubation time, the entity that bind to the binding sites will be primarily the entity in the sample volume that sites on the binding site (i.e. the sample volume that is just above the binding area). Then the calculation of the concentration of the entity in the sample would be based on the sample thickness and the binding site area.

In the method of paragraph X5, in some embodiments, the final reduced sample thickness is significantly smaller than that of the area of the storage site, so that the entity In the sample area that is outside of the binding site will take longer time to bind to the binding site. With a proper selection of the incubation time, the entity that bind to the binding sites will be primarily the entity in the sample volume that sites on the binding site (i.e. the sample volume that is just above the binding area). Then the calculation of the concentration of the entity in the sample would be based on the sample thickness and the binding site area.

In the method of any of paragraphs X2, X4, X6, it further comprises a compressing device that bring the plates from an open configurations to a closed configurations. In some embodiments, the compressing device is one or any combination of the embodiments described in the disclosures In the method of any of paragraphs X2, X4, X6, it further comprises a compressing device that bring the plates from an open configurations to a closed configurations, and a holding device that is configured to hold the plates are in the closed configuration. In some embodiments, the holding device is one or any combination of the embodiments described in the disclosures.

In the method of any of paragraphs X2, X4, X6, it further comprises a compressing device that bring the plates from an open configurations to a closed configurations, and a holding device that is configured to hold the plates are in the closed configuration for a time of 0.001 sec or less, 0.01 sec or less, 0.1 sec or less, 1 sec or less, 5 sec or less, 10 sec or less, 20 sec or less, 30 sec or less, 40 sec or less, 1 min or less, 2 min or less, 3 min or less, 5 min or less, 10 min or less, 20 min or less, 30 min or less, 60 min or less, 90 min or less, 120 min or less, 180 min or less, 250 min or less, or a range between any two of these values.

In the method of any of paragraphs X2, X4, X6, it further comprises a compressing device that bring the plates from an open configurations to a closed configurations, and a holding device that is configured to hold the plates are in the closed configuration for a time of, in a preferred embodiment, 0.001 sec or less, 0.01 sec or less, 0.1 sec or less, 1 sec or less, 5 sec or less, 10 sec or less, 20 sec or less, 30 sec or less, 40 sec or less, 1 min or less, 2 min or less, 3 min or less, or a range between any two of these values.

Final Sample Thickness.

The final sample thickness at the closed configuration of the plates may be a significant factor in reducing the saturation incubation time. The final sample thickness after the sample thickness reduction/deformation, depending upon the properties of entity and samples as well as the applications, as discussed with respect to the regulated spacing of the plates.

In some embodiments, The final sample thickness is less than about 0.5 um (micrometer), less than about 1 um, less than about 1.5 um, less than about 2 um, less than about 4 um, less than about 6 um, less than about 8 um, less than about 10 um, less than about 12 um, less than about 14 um, less than about 16 um, less than about 18 um, less than about 20 um, less than about 25 um, less than about 30 um, less than about 35 um, less than about 40 um, less than about 45 um, less than about 50 um, less than about 55 um, less than about 60 um, less than about 70 um, less than about 80 um, less than about 90 um, less than about 100 um, less than about 110 um, less than about 120 um, less than about 140 um, less than about 160 um, less than about 180 um, less than about 200 um, less than about 250 um, less than about 300 um, less than about 350 um, less than about 400 um, less than about 450 um, less than about 500 um, less than about 550 um, less than about 600 um, less than about 650 um, less than about 700 um, less than about 800 um, less than about 900 um, less than about 1000 um (1 mm), less than about 1.5 mm, less than about 2 mm, less than about 2.5 mm, less than about 3 mm, less than about 3.5 mm, less than about 4 mm, less than about 5 mm, less than about 6 mm, less than about 7 mm, less than about 8 mm, less than about 9 mm, less than about 10 mm, or a range between any two of the values.

In certain embodiments, the final sample thickness at the closed configuration is less than 0.5 um (micron), less than 1 um, less than 5 um, less than 10 um, less than 20 um, less than 30 um, less than 50 um, less than 100 um, less than 200 um, less than 300 um, less than 500 um, less than 800 um, less than 200 um, less than 1 mm (millimeter), less than 2 mm (millimeter), less than 4 mm (millimeter), less than 8 mm (millimeter), or a range between any two of the values.

In certain embodiments, the Q-methods make the final sample thickness uniform and flat surfaces of the first plate and the second plate are used.

In the present invention, the sample incubation are done in various temperatures, humidity, gas environment, and different time durations, with or without shaking.

Incubation Time.

In the method of any of paragraphs X1 and X3, it further comprises a step that, after (d) and while the plates are in the closed configuration, incubating for a time equal or less than a factor times the diffusion time of the entity in the sample diffusing across the sample thickness regulated by the plates at the closed configuration, and then stopping the incubation; wherein the incubation allows binding of the entity to the binding site; and wherein the factor is 0.0001, 0.001, 0.01, 0.1, 1, 1.1, 1.2, 1.3, 1.5, 2, 3, 4, 5, 10, 100, 1000, 10,000, or a range between any to the values. For example, if the factor is 1.1 and the diffusion time is 20 seconds, then the incubation time is equal to or less than 22 second. In one preferred embodiment, the factor is 0.1, 1, 1.5 or a range between any to the values.

In the method of paragraphs X5, it further comprises a step that, after (d) and while the plates are in the closed configuration, incubating for a time equal or less than a factor times the diffusion time of the reagents diffusing across the sample thickness regulated by the plates at the closed configuration, and then stopping the incubation; wherein the incubation allows binding of the entity to the binding site; and wherein the factor is 0.0001, 0.001, 0.01, 0.1, 1, 1.1, 1.2, 1.3, 1.5, 2, 3, 4, 5, 10, 100, 1000, 10,000, or a range between any to the values. For example, if the factor is 1.1 and the diffusion time is 20 seconds, then the incubation time is equal to or less than 22 second. In one preferred embodiment, the factor is 0.1, 1, 1.5 or a range between any to the values.

The method of any of paragraphs of X1, X3 and X5, or the device of any of paragraph of X2, X4, and X6, wherein at least one of the spacers is inside the sample contact area.

The method of any of paragraphs of X1, X3 and X5, or the device of any of paragraph of X2, X4, and X6, wherein spacers that have a predetermined inter-spacer distance.

In the method of any of paragraphs X1, X3, X5, it further comprises a step of incubation while the plates are in the closed configuration, the saturation incubation time is 0.001 sec or less, 0.01 sec or less, 0.1 sec or less, 1 sec or less, 5 sec or less, 10 sec or less, 20 sec or less, 30 sec or less, 40 sec or less, 1 min or less, 2 min or less, 3 min or less, 5 min or less, 10 min or less, 20 min or less, 30 min or less, 60 min or less, 90 min or less, 120 min or less, 180 min or less, 250 min or less, or a range between any two of these values.

In the method of any of paragraphs X1, X3, X5, the saturation incubation time at the reduced sample thickness at the closed configuration is 0.001 sec or less, 0.01 sec or less, 0.1 sec or less, 1 sec or less, 5 sec or less, 10 sec or less, 20 sec or less, 30 sec or less, 40 sec or less, 1 min or less, 2 min or less, 3 min or less, 5 min or less, 10 min or less, 20 min or less, 30 min or less, 60 min or less, 90 min or less, 120 min or less, 180 min or less, 250 min or less, or a range between any two of these values.

In some embodiments, capture agents are first immobilized at the binding site, then the sample are in contact with the binding site and the entity in the sample are captured by the capture agents, and finally detection agents are added to be bound with the captured entity and the a signal from the detection agents will be read (e.g. by optical methods or electrical methods or a combination). In some embodiments, other reagents besides of capture agents and detection agents are added (e.g. blocking agent).

In many applications such as PoC, it is desirable to have simple and/or low-cost devices and methods to add additional reagents into a sample. One aspect of the present invention is related to simple and/or low-cost devices and methods to add additional reagents into a sample. The added additional reagents include detection agents, blocking agents, light signal enhancers, light signal quenchers, or others. In some embodiments of the present invention, it controls the assay processes by using different release time of the reagents stored on the same location. The different release time can be attached by adding other materials that have different dissolve rate.

In certain embodiments, the reagent concentration mixed in the sample can be controlled by controlling the sample thickness (e.g. control the ratio of the sample thickness to the storage site area and/or the mixing time).

1. Plates, Spacers, Scale-Marks, Sample Thickness Regulation 2.1 Plate Configurations and Sample Thickness Regulation Open Configuration.

In some embodiments, in the open configuration, the two plates (i.e. the first plate and the second plate) are separated from each other. In certain embodiments, the two plates have one side connected together during all operations of the plates (including the open and closed configuration), the two plates open and close similar to a book. In some embodiments, the two plates have rectangle (or square) shape and have two sides of the rectangle connected together during all operations of the plates.

In some embodiments, the open configuration comprises a configuration that the plates are far away from each other, so that the sample is deposited onto one plate of the pair without a hindrance of the other plate of the pair.

In some embodiments, the open configuration comprises a configuration that the plates are far way, so that the sample is directly deposited onto one plate, as if the other plate does not exist.

In some embodiments, the open configuration comprises a configuration that the pair of the plates are spaced apart by a distance at least 10 nm, at least 100 nm, at least 1000 nm, at least 0.01 cm, at least 0.1 cm, at least 0.5 cm, at least 1 cm, at least 2 cm, or at least 5 cm, or a range of any two of the values.

In some embodiments, the open configuration comprises a configuration that the pair of plates are oriented in different orientations. In some embodiments, the open configuration comprises a configuration that defines an access gap between the pair of plates that is configured to permit sample addition.

In some embodiments, the open configuration comprises a configuration, wherein each plate has a sample contact surface and wherein at least one of the contact surfaces of the plates is exposed when the plates are in the one open configuration.

Closed Configuration and Sample Thickness Regulation.

In present invention, a closed configuration of the two plates is the configuration that a spacing (i.e. the distance) between the inner surfaces of the two plates is regulated by the spacers between the two plates. Since the inner surfaces (also termed "sample surface") of the plates are in contact with the sample during the compression step of a CROF process, hence at the closed configuration, the sample thickness is regulated by the spacers.

During the process of bring the plates from an open configuration to a closed configuration, the plates are facing each other (at least a part of the plates are facing each other) and a force is used to bring the two plates together. When the two plates are brought from an open configuration to a closed configuration, the inner surfaces of the two plate compress the sample deposited on the plate(s) to reduce the sample thickness (while the sample has an open flow laterally between the plates), and the thickness of a relevant volume of the sample is determined by the spacers, the plates, and the method being used and by the sample mechanical/fluidic property. The thickness at a closed configuration can be predetermined for a given sample and given spacers, plates and plate pressing method.

The term "regulation of the spacing between the inner surfaces of the plates by the spacers" or "the regulation of the sample thickness by the plates and the spacer", or a thickness of the sample is regulated by the spacers and the plates" means that the thickness of the sample in a CROF process is determined by a given plates, spacers, sample, and pressing method.

In some embodiments, the regulated sample thickness at the closed configuration is the same as the height of a spacer; in this case, at the closed configuration, the spacers directly contact both plates (wherein one plate is the one that the spacer is fixed on, and the other plate is the plate that is brought to contact with the spacer).

In certain embodiments, the regulated sample thickness at the closed configuration is larger than the height of a spacer; in this case, at the closed configuration, the spacers directly contacts only the plate that has the spacers fixed or attached on its surface, and indirectly contact the other plate (i.e. indirect contact). The term "indirect contact" with a plate means that the spacer and the plate is separated by a thin sample layer, which is termed "residual sample layer" and its thickness is termed "the residue thickness". For given spacers and plates, a given plate pressing method, and a given sample, the residual thickness can be predetermined (predetermined means prior to reach the closed configuration), leading to a predetermination of the sample thickness at the closed configuration. This is because the residue layer thickness is the same for the given conditions (the sample, spacers, plates, and pressing force) and can be pre-calibrated and/or calculated. The regulated sample thickness is approximately equal to the spacer height plus the sample residue thickness.

In many embodiments, the size and shape of the pillars are pre-characterized (i.e. pre-determined) before their use. And the pre-determined information are used to for later assaying, such as determination of the sample volume (or relevant volume) and others.

In some embodiments, the regulating of the sample thickness includes applying a closing (compression) force to the plates to maintain the spacing between the plates.

In some embodiments, the regulating of the sample thickness includes establishing the spacing between the plates with the spacers, a closing force applied to the plates, and physical properties of the sample, and optionally wherein the physical properties of the sample include at least one of viscosity and compressibility.

2.2 Plates

In present invention, generally, the plates of CROF are made of any material that (i) is capable of being used to regulate, together with the spacers, the thickness of a portion or entire volume of the sample, and (ii) has no significant adverse effects to a sample, an assay, or a goal that the plates intend to accomplish. However, in certain embodiments, particular materials (hence their properties) are used for the plate to achieve certain objectives.

In some embodiments, the two plates have the same or different parameters for each of the following parameters: plate material, plate thickness, plate shape, plate area, plate flexibility, plate surface property, and plate optical transparency.

Plate Materials.

The plates are made a single material, composite materials, multiple materials, multilayer of materials, alloys, or a combination thereof. Each of the materials for the plate is an inorganic material, am organic material, or a mix, wherein examples of the materials are given in paragraphs of Mat-1 and Mat-2.

Mat-1. The inorganic materials for the plates include, not limited to, glass, quartz, oxides, silicon-dioxide, silicon-nitride, hafnium oxide (HfO), aluminum oxide (AlO), semi-conductors: (silicon, GaAs, GaN, etc.), metals (e.g. gold, silver, copper, aluminum, Ti, Ni, etc.), ceramics, or any combinations of thereof.

Mat-2 The organic materials for the spacers include, not limited to, polymers (e.g. plastics) or amorphous organic materials. The polymer materials for the spacers include, not limited to, acrylate polymers, vinyl polymers, olefin polymers, cellulosic polymers, noncellulosic polymers, polyester polymers, Nylon, cyclic olefin copolymer (COC), poly (methyl methacrylate) (PMMA), polycarbonate (PC), cyclic olefin polymer (COP), liquid crystalline polymer (LCP), polyimide (PA), polyethylene (PE), polyimide (PI), polypropylene (PP), poly(phenylene ether) (PPE), polystyrene (PS), polyoxymethylene (POM), polyether ether ketone (PEEK), polyether sulfone (PES), poly(ethylene phthalate) (PET), polytetrafluoroethylene (PTFE), polyvinyl chloride (PVC), polyvinylidene fluoride (PVDF), polybutylene terephthalate (PBT), fluorinated ethylene propylene (FEP), perfluoroalkoxyalkane (PFA), polydimethylsiloxane (PDMS), rubbers, or any combinations of thereof.

In some embodiments, the plates are each independently made of at least one of glass, plastic, ceramic, and metal. In some embodiments, each plate independently includes at least one of glass, plastic, ceramic, and metal.

In some embodiments, one plate is different from the other plate in lateral area, thickness, shape, materials, or surface treatment. In some embodiments, one plate is the same as the other plate in lateral area, thickness, shape, materials, or surface treatment.

The materials for the plates are rigid, flexible or any flexibility between the two. The rigid (i.e. stiff) or flexibility is relative to a give pressing forces used in bringing the plates into the closed configuration.

In some embodiments, a selection of rigid or flexible plate are determined from the requirements of controlling a uniformity of the sample thickness at the closed configuration.

In some embodiments, at least one of the two plates are transparent (to a light). In some embodiments at least a part or several parts of one plate or both plates are transparent. In some embodiments, the plates are non-transparent.

Plate Thickness.

In some embodiments, the average thicknesses for at least one of the pates are 2 nm or less, 10 nm or less, 100 nm or less, 500 nm or less, 1000 nm or less, 2 um (micron) or less, 5 um or less, 10 um or less, 20 um or less, 50 um or less, 100 um or less, 150 um or less, 200 um or less, 300 um or less, 500 um or less, 800 um or less, 1 mm (millimeter) or less, 2 mm or less, 3 mm or less, or a range between any two of the values.

In some embodiments, the average thicknesses for at least one of the plates are at most 3 mm (millimeter), at most 5 mm, at most 10 mm, at most 20 mm, at most 50 mm, at most 100 mm, at most 500 mm, or a range between any two of the values.

In some embodiments, the thickness of a plate is not uniform across the plate. Using a different plate thickness at different location can be used to control the plate bending, folding, sample thickness regulation, and others.

Plate Shape and Area.

Generally, the plates can have any shapes, as long as the shape allows a compress open flow of the sample and the regulation of the sample thickness. However, in certain embodiments, a particular shape may be advantageous. The shape of the plate can be round, elliptical, rectangles, triangles, polygons, ring-shaped, or any superpositions of these shapes.

In some embodiments, the two plates can have the same size or shape, or different. The area of the plates depend on the application. The area of the plate is at most 1 mm2 (millimeter square), at most 10 mm2, at most 100 mm2, at most 1 cm2 (centimeter square), at most 5 cm2, at most 10 cm2, at most 100 cm2, at most 500 cm2, at most 1000 cm2, at most 5000 cm2, at most 10,000 cm2, or over 10,000 cm2, or any arrange between any of the two values. The shape of the plate can be rectangle, square, round, or others.

In certain embodiments, at least one of the plate is in the form of a belt (or strip) that has a width, thickness, and length. The width is at most 0.1 cm (centimeter), at most 0.5 cm, at most 1 cm, at most 5 cm, at most 10 cm, at most 50 cm, at most 100 cm, at most 500 cm, at most 1000 cm, or a range between any two of the values. The length can be as long as it needed. The belt can be rolled into a roll.

Plate Surface Flatness.

In many embodiments, an inner surface of the plates are flat or significantly flat, planar. In certain embodiments, the two inner surfaces are, at the closed configuration, parallel with each other. Flat inner surfaces facilitates a quantification and/or controlling of the sample thickness by simply using the predetermined spacer height at the closed configuration. For non-flat inner surfaces of the plate, one need to know not only the spacer height, but also the exact the topology of the inner surface to quantify and/or control the sample thickness at the closed configuration. To know the surface topology needs additional measurements and/or corrections, which can be complex, time consuming, and costly.

A flatness of the plate surface is relative to the final sample thickness (the final thickness is the thickness at the closed configuration), and is often characterized by the term of "relative surface flatness" is the ratio of the plate surface flatness variation to the final sample thickness.

In some embodiments, the relative surface is less than 0.01%, 0.1%, less than 0.5%, less than 1%, less than 2%, less than 5%, less than 10%, less than 20%, less than 30%, less than 50%, less than 70%, less than 80%, less than 100%, or a range between any two of these values.

Plate Surface Parallelness.

In some embodiments, the two surfaces of the plate is significantly parallel with each other. In certain embodiments, the two surfaces of the plate is not parallel with each other.

Plate Flexibility.

In some embodiments, a plate is flexible under the compressing of a CROF process. In some embodiments, both plates are flexible under the compressing of a CROF process. In some embodiments, a plate is rigid and another plate is flexible under the compressing of a CROF process. In some embodiments, both plates are rigid. In some embodiments, both plate are flexible but have different flexibility.

Plate Optical Transparency.

In some embodiments, a plate is optical transparent. In some embodiments, both plates are optical transparent. In some embodiments, a plate is optical transparent and another plate is opaque. In some embodiments, both plates are opaque. In some embodiments, both plate are optical transparent but have different optical transparency. The optical transparency of a plate refers a part or the entire area of the plate.

Surface Wetting Properties.

In some embodiments, a plate has an inner surface that wets (i.e. contact angle is less 90 degree) the sample, the transfer liquid, or both. In some embodiments, both plates have an inner surface that wets the sample, the transfer liquid, or both; either with the same or different wettability. In some embodiments, a plate has an inner surface that wets the sample, the transfer liquid, or both; and another plate has an inner surface that does not wet (i.e. the contact angle equal to or larger than 90 degree). The wetting of a plate inner surface refers a part or the entire area of the plate.

In some embodiments, the inner surface of the plate has other nano or microstructures to control a lateral flow of a sample during a CROF. The nano or microstructures include, but not limited to, channels, pumps, and others. Nano and microstructures are also used to control the wetting properties of an inner surface.

2.3 Spacers

Spacers' Function.

In present invention, the spacers are configured to have one or any combinations of the following functions and properties: the spacers are configured to (1) control, together with the plates, the thickness of the sample or a relevant volume of the sample (Preferably, the thickness control is precise, or uniform or both, over a relevant area); (2) allow the sample to have a compressed regulated open flow (CROF) on plate surface; (3) not take significant surface area (volume) in a given sample area (volume); (4) reduce or increase the effect of sedimentation of particles or analytes in the sample; (5) change and/or control the wetting propertied of the inner surface of the plates; (6) identify a location of the plate, a scale of size, and/or the information related to a plate, or (7) do any combination of the above.

Spacer Architectures and Shapes.

To achieve desired sample thickness reduction and control, in certain embodiments, the spacers are fixed its respective plate. In general, the spacer can have any shape, as long as the spacers are capable of regulating the sample thickness during a CROF process, but certain shapes are preferred to achieve certain functions, such as better uniformity, less overshoot in pressing, etc.

The spacer(s) is a single spacer or a plurality of spacers. (e.g. an array). Some embodiments of a plurality of spacers is an array of spacers (e.g. pillars), where the inter-spacer distance is periodic or aperiodic, or is periodic or aperiodic in certain areas of the plates, or has different distances in different areas of the plates.

There are two kinds of the spacers: open-spacers and enclosed-spacers. The open-spacer is the spacer that allows a sample to flow through the spacer (i.e. the sample flows around and pass the spacer. For example, a post as the spacer), and the enclosed spacer is the spacer that stop the sample flow (i.e. the sample cannot flow beyond the spacer. For example, a ring shape spacer and the sample is inside the ring). Both types of spacers use their height to regular the final sample thickness at a closed configuration.

In some embodiments, the spacers are open-spacers only. In some embodiments, the spacers are enclosed-spacers only. In some embodiments, the spacers are a combination of open-spacers and enclosed-spacers.

The term "pillar spacer" means that the spacer has a pillar shape and the pillar shape refers to an object that has height and a lateral shape that allow a sample to flow around it during a compressed open flow.

In some embodiments, the lateral shapes of the pillar spacers are the shape selected from the groups of (i) round, elliptical, rectangles, triangles, polygons, ring-shaped, star-shaped, letter-shaped (e.g. L-shaped, C-shaped, the letters from A to Z), number shaped (e.g. the shapes like 0 1, 2, 3, 4, . . . to 9); (ii) the shapes in group (i) with at least one rounded corners; (iii) the shape from group (i) with zig-zag or rough edges; and (iv) any superposition of (i), (ii) and (iii). For multiple spacers, different spacers can have different lateral shape and size and different distance from the neighboring spacers.

In some embodiments, the spacers may be and/or may include posts, columns, beads, spheres, and/or other suitable geometries. The lateral shape and dimension (i.e., transverse to the respective plate surface) of the spacers can be anything, except, in some embodiments, the following restrictions: (i) the spacer geometry will not cause a significant error in measuring the sample thickness and volume; or (ii) the spacer geometry would not prevent the out-flowing of the sample between the plates (i.e. it is not in enclosed form). But in some embodiments, they require some spacers to be closed spacers to restrict the sample flow.

In some embodiments, the shapes of the spacers have rounded corners. For example, a rectangle shaped spacer has one, several or all corners rounded (like a circle rather 90 degree angle). A round corner often make a fabrication of the spacer easier, and in some cases less damage to a biological material.

The sidewall of the pillars can be straight, curved, sloped, or different shaped in different section of the sidewall. In some embodiments, the spacers are pillars of various lateral shapes, sidewalls, and pillar-height to pillar lateral area ratio.

In a preferred embodiment, the spacers have shapes of pillars for allowing open flow.

Spacers' Materials.

In the present invention, the spacers are generally made of any material that is capable of being used to regulate, together with the two plates, the thickness of a relevant volume of the sample. In some embodiments, the materials for the spacers are different from that for the plates. In some embodiments, the materials for the spaces are at least the same as a part of the materials for at least one plate.

The spacers are made a single material, composite materials, multiple materials, multilayer of materials, alloys, or a combination thereof. Each of the materials for the spacers is an inorganic material, am organic material, or a mix, wherein examples of the materials are given in paragraphs of Mat-1 and Mat-2. In a preferred embodiment, the spacers are made in the same material as a plate used in CROF.

Spacer's Mechanical Strength and Flexibility.

In some embodiments, the mechanical strength of the spacers are strong enough, so that during the compression and at the closed configuration of the plates, the height of the spacers is the same or significantly same as that when the plates are in an open configuration. In some embodiments, the differences of the spacers between the open configuration and the closed configuration can be characterized and predetermined.

The material for the spacers is rigid, flexible or any flexibility between the two. The rigid is relative to a give pressing forces used in bringing the plates into the closed configuration: if the space does not deform greater than 1% in its height under the pressing force, the spacer material is regarded as rigid, otherwise a flexible. When a spacer is made of material flexible, the final sample thickness at a closed configuration still can be predetermined from the pressing force and the mechanical property of the spacer.

Spacer Inside Sample.

To achieve desired sample thickness reduction and control, particularly to achieve a good sample thickness uniformity, in certain embodiments, the spacers are placed inside the sample, or the relevant volume of the sample. In some embodiments, there are one or more spacers inside the sample or the relevant volume of the sample, with a proper inter spacer distance. In certain embodiments, at least one of the spacers is inside the sample, at least two of the spacers inside the sample or the relevant volume of the sample, or at least of "n" spacers inside the sample or the relevant volume of the sample, where "n" may be determined by a sample thickness uniformity or a required sample flow property during a CROF.

Spacer Height.

In some embodiments, all spacers have the same pre-determined height. In some embodiments, spacers have different pre-determined height. In some embodiments, spacers can be divided into groups or regions, wherein each group or region has its own spacer height. And in certain embodiments, the predetermined height of the spacers is an average height of the spacers. In some embodiments, the spacers have approximately the same height. In some embodiments, a percentage of number of the spacers have the same height.

The height of the spacers is selected by a desired regulated final sample thickness and the residue sample thickness. The spacer height (the predetermined spacer height) and/or sample thickness is 3 nm or less, 10 nm or less, 50 nm or less, 100 nm or less, 200 nm or less, 500 nm or less, 800 nm or less, 1000 nm or less, 1 um or less, 2 um or less, 3 um or less, 5 um or less, 10 um or less, 20 um or less, 30 um or less, 50 um or less, 100 um or less, 150 um or less, 200 um or less, 300 um or less, 500 um or less, 800 um or less, 1 mm or less, 2 mm or less, 4 mm or less, or a range between any two of the values.

The spacer height and/or sample thickness is between 1 nm to 100 nm in one preferred embodiment, 100 nm to 500 nm in another preferred embodiment, 500 nm to 1000 nm in a separate preferred embodiment, 1 um (i.e. 1000 nm) to 2 um in another preferred embodiment, 2 um to 3 um in a separate preferred embodiment, 3 um to 5 um in another preferred embodiment, 5 um to 10 um in a separate preferred embodiment, and 10 um to 50 um in another preferred embodiment, 50 um to 100 um in a separate preferred embodiment.

In some embodiments, the spacer height and/or sample thickness (i) equal to or slightly larger than the minimum dimension of an analyte, or (ii) equal to or slightly larger than the maximum dimension of an analyte. The "slightly larger" means that it is about 1% to 5% larger and any number between the two values.

In some embodiments, the spacer height and/or sample thickness is larger than the minimum dimension of an analyte (e.g. an analyte has an anisotropic shape), but less than the maximum dimension of the analyte.

For example, the red blood cell has a disk shape with a minim dimension of 2 um (disk thickness) and a maximum dimension of 11 um (a disk diameter). In an embodiment of the present invention, the spacers is selected to make the inner surface spacing of the plates in a relevant area to be 2 um (equal to the minimum dimension) in one embodiment, 2.2 um in another embodiment, or 3 (50% larger than the minimum dimension) in other embodiment, but less than the maximum dimension of the red blood cell. Such embodiment has certain advantages in blood cell counting. In one embodiment, for red blood cell counting, by making the inner surface spacing at 2 or 3 um and any number between the two values, a undiluted whole blood sample is confined in the spacing, on average, each red blood cell (RBC) does not overlap with others, allowing an accurate counting of the red blood cells visually. (Too many overlaps between the RBC's can cause serious errors in counting).

In the present invention, in some embodiments, it uses the plates and the spacers to regulate not only a thickness of a sample, but also the orientation and/or surface density of the analytes/entity in the sample when the plates are at the closed configuration. When the plates are at a closed configuration, a thinner thickness of the sample gives a less the analytes/entity per surface area (i.e. less surface concentration).

Spacer Lateral Dimension.

For an open-spacer, the lateral dimensions can be characterized by its lateral dimension (sometime being called width) in the x and y—two orthogonal directions. The lateral dimension of a spacer in each direction is the same or different. In some embodiments, the lateral dimension for each direction (x or y) is . . . .

In some embodiments, the ratio of the lateral dimensions of x to y direction is 1, 1.5, 2, 5, 10, 100, 500, 1000, 10,000, or a range between any two of the value. In some embodiments, a different ratio is used to regulate the sample flow direction; the larger the ratio, the flow is along one direction (larger size direction).

In some embodiments, the different lateral dimensions of the spacers in x and y direction are used as (a) using the spacers as scale-markers to indicate the orientation of the plates, (b) using the spacers to create more sample flow in a preferred direction, or both.

In a preferred embodiment, the period, width, and height.

In some embodiments, all spacers have the same shape and dimensions. In some embodiments, each spacers have different lateral dimensions.

For enclosed-spacers, in some embodiments, the inner lateral shape and size are selected based on the total volume of a sample to be enclosed by the enclosed spacer(s), wherein the volume size has been described in the present disclosure; and in certain embodiments, the outer lateral shape and size are selected based on the needed strength to support the pressure of the liquid against the spacer and the compress pressure that presses the plates.

Aspect Ratio of Height to the Average Lateral Dimension of Pillar Spacer.

In certain embodiments, the aspect ratio of the height to the average lateral dimension of the pillar spacer is 100,000, 10,000, 1,000, 100, 10, 1, 0.1, 0.01, 0.001, 0.0001, 0, 00001, or a range between any two of the values.

Spacer Height Precisions.

The spacer height should be controlled precisely. The relative precision of the spacer (i.e. the ratio of the deviation to the desired spacer height) is 0.001% or less, 0.01% or less, 0.1% or less; 0.5% or less, 1% or less, 2% or less, 5% or less, 8% or less, 10% or less, 15% or less, 20% or less, 30% or less, 40% or less, 50% or less, 60% or less, 70% or less, 80% or less, 90% or less, 99.9% or less, or a range between any of the values.

Inter-Spacer Distance.

The spacers can be a single spacer or a plurality of spacers on the plate or in a relevant area of the sample. In some embodiments, the spacers on the plates are configured and/or arranged in an array form, and the array is a periodic, non-periodic array or periodic in some locations of the plate while non-periodic in other locations.

In some embodiments, the periodic array of the spacers has a lattice of square, rectangle, triangle, hexagon, polygon, or any combinations of thereof, where a combination means that different locations of a plate has different spacer lattices.

In some embodiments, the inter-spacer distance of a spacer array is periodic (i.e. uniform inter-spacer distance) in at least one direction of the array. In some embodiments, the inter-spacer distance is configured to improve the uniformity between the plate spacing at a closed configuration.

The distance between neighboring spacers (i.e. the inter-spacer distance) is 1 um or less, 5 um or less, 10 um or less, 20 um or less, 30 um or less, 40 um or less, 50 um or less, 60 um or less, 70 um or less, 80 um or less, 90 um or less, 100 um or less, 200 um or less, 300 um or less, 400 um or less, or a range between any two of the values.

In certain embodiments, the inter-spacer distance is at 400 or less, 500 or less, 1 mm or less, 2 mm or less, 3 mm or less, 5 mm or less, 7 mm or less, 10 mm or less, or any range between the values. In certain embodiments, the inter-spacer distance is a 10 mm or less, 20 mm or less, 30 mm or less, 50 mm or less, 70 mm or less, 100 mm or less, or any range between the values.

The distance between neighboring spacers (i.e. the inter-spacer distance) is selected so that for a given properties of the plates and a sample, at the closed-configuration of the plates, the sample thickness variation between two neighboring spacers is, in some embodiments, at most 0.5%, 1%, 5%, 10%, 20%, 30%, 50%, 80%, or any range between the values; or in certain embodiments, at most 80%, 100%, 200%, 400%, or a range between any two of the values.

Clearly, for maintaining a given sample thickness variation between two neighboring spacers, when a more flexible plate is used, a closer inter-spacer distance is needed.

Specify the Accuracy of the Inter Spacer Distance.

In a preferred embodiment, the spacer is a periodic square array, wherein the spacer is a pillar that has a height of 2 to 4 um, an average lateral dimension of from 5 to 20 um, and inter-spacer spacing of 1 um to 100 um.

In a preferred embodiment, the spacer is a periodic square array, wherein the spacer is a pillar that has a height of 2 to 4 um, an average lateral dimension of from 5 to 20 um, and inter-spacer spacing of 100 um to 250 um.

In a preferred embodiment, the spacer is a periodic square array, wherein the spacer is a pillar that has a height of 4 to 50 um, an average lateral dimension of from 5 to 20 um, and inter-spacer spacing of 1 um to 100 um.

In a preferred embodiment, the spacer is a periodic square array, wherein the spacer is a pillar that has a height of 4 to 50 um, an average lateral dimension of from 5 to 20 um, and inter-spacer spacing of 100 um to 250 um.

The period of spacer array is between 1 nm to 100 nm in one preferred embodiment, 100 nm to 500 nm in another preferred embodiment, 500 nm to 1000 nm in a separate preferred embodiment, 1 um (i.e. 1000 nm) to 2 um in another preferred embodiment, 2 um to 3 um in a separate preferred embodiment, 3 um to 5 um in another preferred embodiment, 5 um to 10 um in a separate preferred embodiment, and 10 um to 50 um in another preferred embodiment, 50 um to 100 um in a separate preferred embodiment, 100 um to 175 um in a separate preferred embodiment, and 175 um to 300 um in a separate preferred embodiment.

Spacer Density.

The spacers are arranged on the respective plates at a surface density of greater than one per $um^2$, greater than one per 10 $um^2$, greater than one per 100 $um^2$, greater than one per 500 $um^2$, greater than one per 1000 $um^2$, greater than one per 5000 $um^2$, greater than one per 0.01 $mm^2$, greater than one per 0.1 $mm^2$, greater than one per 1 $mm^2$, greater than one per 5 $mm^2$, greater than one per 10 $mm^2$, greater than one per 100 $mm^2$, greater than one per 1000 $mm^2$, greater than one per 10000 $mm^2$, or a range between any two of the values.

(3) the spacers are configured to not take significant surface area (volume) in a given sample area (volume);

Ratio of Spacer Volume to Sample Volume.

In many embodiments, the ratio of the spacer volume (i.e. the volume of the spacer) to sample volume (i.e. the volume of the sample), and/or the ratio of the volume of the spacers that are inside of the relevant volume of the sample to the relevant volume of the sample are controlled for achieving certain advantages. The advantages include, but not limited to, the uniformity of the sample thickness control, the uniformity of analytes, the sample flow properties (i.e. flow speed, flow direction, etc.).

In certain embodiments, the ratio of the spacer volume r) to sample volume, and/or the ratio of the volume of the spacers that are inside of the relevant volume of the sample to the relevant volume of the sample is less than 100%, at most 99%, at most 70%, at most 50%, at most 30%, at most 10%, at most 5%, at most 3% at most 1%, at most 0.1%, at most 0.01%, at most 0.001%, or a range between any of the values.

Spacers Fixed to Plates.

The inter spacer distance and the orientation of the spacers, which play a key role in the present invention, are preferably maintained during the process of bringing the plates from an open configuration to the closed configuration, and/or are preferably predetermined before the process from an open configuration to a closed configurations.

Some embodiments of the present invention is that the spacers are fixed on one of the plates before bring the plates to the closed configuration. The term "a spacer is fixed with its respective plate" means that the spacer is attached to a plate and the attachment is maintained during a use of the plate. An example of "a spacer is fixed with its respective plate" is that a spacer is monolithically made of one piece of material of the plate, and the position of the spacer relative to the plate surface does not change. An example of "a spacer is not fixed with its respective plate" is that a spacer is glued to a plate by an adhesive, but during a use of the plate, the adhesive cannot hold the spacer at its original location on the plate surface (i.e. the spacer moves away from its original position on the plate surface).

In some embodiments, at least one of the spacers are fixed to its respective plate. In certain embodiments, at two spacers are fixed to its respective plates. In certain embodiments, a majority of the spacers are fixed with their respective plates. In certain embodiments, all of the spacers are fixed with their respective plates.

In some embodiments, a spacer is fixed to a plate monolithically.

In some embodiments, the spacers are fixed to its respective plate by one or any combination of the following methods and/or configurations: attached to, bonded to, fused to, imprinted, and etched.

The term "imprinted" means that a spacer and a plate are fixed monolithically by imprinting (i.e. embossing) a piece of a material to form the spacer on the plate surface. The material can be single layer of a material or multiple layers of the material.

The term "etched" means that a spacer and a plate are fixed monolithically by etching a piece of a material to form the spacer on the plate surface. The material can be single layer of a material or multiple layers of the material.

The term "fused to" means that a spacer and a plate are fixed monolithically by attaching a spacer and a plate together, the original materials for the spacer and the plate fused into each other, and there is clear material boundary between the two materials after the fusion.

The term "bonded to" means that a spacer and a plate are fixed monolithically by binding a spacer and a plate by adhesion.

The term "attached to" means that a spacer and a plate are connected together.

In some embodiments, the spacers and the plate are made in the same materials. In other embodiment, the spacers and the plate are made from different materials. In other embodiment, the spacer and the plate are formed in one piece. In other embodiment, the spacer has one end fixed to its respective plate, while the end is open for accommodating different configurations of the two plates.

In other embodiment, each of the spacers independently is at least one of attached to, bonded to, fused to, imprinted in, and etched in the respective plate. The term "independently" means that one spacer is fixed with its respective plate by a same or a different method that is selected from the methods of attached to, bonded to, fused to, imprinted in, and etched in the respective plate.

In some embodiments, at least a distance between two spacers is predetermined ("predetermined inter-spacer distance" means that the distance is known when a user uses the plates).

In some embodiments of all methods and devices described herein, there are additional spacers besides to the fixed spacers.

Specific Sample Thickness.

In present invention, it was observed that a larger plate holding force (i.e. the force that holds the two plates together) can be achieved by using a smaller plate spacing (for a given sample area), or a larger sample area (for a given plate-spacing), or both.

In some embodiments, at least one of the plates is transparent in a region encompassing the relevant area, each plate has an inner surface configured to contact the sample in the closed configuration; the inner surfaces of the plates are substantially parallel with each other, in the closed configuration; the inner surfaces of the plates are substantially planar, except the locations that have the spacers; or any combination of thereof.

2.4 Final Sample Thickness and Uniformity

In some embodiments, significantly flat is determined relative to the final sample thickness, and has, depending upon on embodiments and applications, a ratio of to the sample thickness of less than 0.1%, less than 0.5%, less than 1%, less than 2%, less than 5%, or less than 10%, or a range between any two of these values.

In some embodiments, flatness relative to the sample thickness may be less than 0.1%, less than 0.5%, less than 1%, less than 2%, less than 5%, less than 10%, less than 20%, less than 50%, or less than 100%, or a range between any two of these values.

In some embodiments, significantly flat may mean that the surface flatness variation itself (measured from an average thickness) is less than 0.1%, less than 0.5%, less than 1%, less than 2%, less than 5%, or less than 10%, or a range between any two of these values. Generally, flatness relative to the plate thickness may be less than 0.1%, less than 0.5%, less than 1%, less than 2%, less than 5%, less than 10%, less than 20%, less than 50%, or less than 100%, or a range between any two of these values.

2.5 Spacer Fabrication Methods.

The spacers can be fabricated on a plate in a variety of ways, using lithography, etching, embossing (nanoimprint), depositions, lift-off, fusing, or a combination of thereof. In some embodiments, the spacers are directly embossed or imprinted on the plates. In some embodiments, the spacers imprinted into a material (e.g. plastics) that is deposited on the plates. In certain embodiments, the spacers are made by directly embossing a surface of a CROF plate. The nanoimprinting may be done by roll to roll technology using a roller imprinter, or roll to a planar nanoimprint. Such process has a great economic advantage and hence lowering the cost.

In some embodiments, the spacers are deposited on the plates. The deposition can be evaporation, pasting, or a lift-off. In the pasting, the spacer is fabricated first on a carrier, then the spacer is transferred from the carrier to the plate. In the lift-off, a removable material is first deposited on the plate and holes are created in the material; the hole bottom expose the plate surface and then a spacer material is deposited into the hole and afterwards the removable material is removed, leaving only the spacers on the plate surface. In some embodiments, the spacers deposited on the plate are fused with the plate. In some embodiments, the spacer and the plates are fabricated in a single process. The single process includes imprinting (i.e. embossing, molding) or synthesis.

In some embodiments, at least two of the spacers are fixed to the respective plate by different fabrication methods, and optionally wherein the different fabrication methods include at least one of being deposition, bonded, fuse, imprinted, and etched.

In some embodiments, one or more of the spacers are fixed to the respective plate(s) is by a fabrication method of being bonded, being fused, being imprinted, or being etched, or any combination of thereof.

In some embodiments, the fabrication methods for forming such monolithic spacers on the plate include a method of being bonded, being fused, being imprinted, or being etched, or any combination of thereof.

2.6 Scale-Markers

The term "scale-marker(s) refers to the scale-marker(s) that able to assist a quantification (i.e. dimension measurement) or a control of the relevant area and/or the relative volume of a sample. In some embodiments, the scale-markers are on the first plate or the second plate, on both on plates, on one surface of the plate, on both surfaces of the plate, between the plates, near the plates, or any combination of thereof. In some embodiments, the scale-markers are fixed on the first plate or the second plate, on both on plates, on one surface of the plate, on both surfaces of the plate, between the plates, near the plates, or any combination of thereof. In some embodiments, the scale-markers are deposited on the first plate or the second plate, on both on plates, on one surface of the plate, on both surfaces of the plate, between the plates, near the plates, or any combination of thereof. In some embodiments, some of spacers are fixed and some spacers are deposited.

In some embodiments, the scale-marks are etched scale-marks, deposited materials, or printed materials. In certain embodiments, the materials that absorbing the light, reflecting light, emitting light, or any combination of thereof.

In some embodiments, the scale-markers are a or a plurality of object(s) with known dimensions and/or known separation distances. Examples of the objects include, not limited to, rectangles, cylinders, or circles.

In some embodiments, the scale-markers have a dimension of in the range of nanometers (nm), microns (um) or millimeters (mm) or other sizes.

In some embodiments, the scale-markers are a ruler, which has scale scale-marks that are configured to measure a dimension of an object. In some embodiments, the scale-marks are in the scale of nanometer (nm), microns (um) or millimeter (mm) or other sizes. In some embodiments, the scale marks are etched scale-marks, deposited materials, or printed materials. In some embodiments, the materials for the scale-markers are the materials that absorbing the light, reflecting light, scattering light, interfering light, diffracting light, emitting light, or any combination of thereof.

In some embodiments, the makers are the spacers, which server dual functions of "regulating sample thickness" and "providing scale-marking and/or dimension scaling". For examples, a rectangle spacer with a known dimension or two spacers with a known separation distance can be used to measure a dimension related to the sample round the spacer(s). From the measured sample dimension, one can calculate the volume of the relevant volume of the sample.

In some embodiments, the scale-markers is configured to at least partially define a boundary of the relevant volume of the sample.

In some embodiments, at least one of the scale-markers is configured to have a known dimension that is parallel to a plane of the lateral area of the relevant volume of the sample.

In some embodiments, at least a pair of the scale-markers are separated by a known distance that is parallel to a plane of the lateral area.

In some embodiments, the scale-markers are configured for optical detection.

In some embodiments, each scale-marker independently is at least one of light absorbing, light reflecting, light scattering, light diffracting, and light emitting.

In some embodiments, the scale-markers are arranged in a regular array with a known lateral spacing.

In some embodiments, each scale-marker independently has a lateral profile that is at least one of square, rectangular, polygonal, and circular.

In some embodiments, at least one of the scale-markers is attached to, bonded to, fused to, imprinted in, and etched in one of the plates.

In some embodiments, at least one of the scale-markers is one of the spacers.

In some embodiments, some spacers also play a role of scale-marker to quantification of a relevant volume of the sample.

In certain embodiments, a binding site(s) (that immobilizes the analytes), storage sites, or alike, serves as a scale-marker(s). In one embodiment, the site with a known lateral dimension interacts with light generating a detectable signal, that reals the known lateral dimension of the site, hence serving a scale-marker(s).

In another embodiment, the dimension of the sites are predetermined before a CROF process and the thickness of the portion of the sample sitting on the site is, when the plates are at the closed configuration, significantly smaller than the lateral average dimension of the site, then by controlling the incubation time so that, after the incubation, (1) the majority of the analytes/entity that bind to the binding site come from the sample volume that sites on top of the binding site, or (2) the majority of the reagent that is mixed (diffused) into the sample volume that sites on top of the binding site come from the storage site. In these cases, the relevant volume of the sample to the binding or the reagent mixing is the volume that is approximately equal to the predetermined site area multiplies the sample thickness at the site. A key reason for this be possible is that, for the given incubation time, the analytes/entity in the sample volume outside the relevant volume do not have enough time to diffuse into the binding site, or the reagents on the storage site do not have enough time to diffuse into in the sample volume outside the relevant volume.

An example to illustrate the method of measuring and/or controlling the relevant area and volume by using a site with known dimension and by limiting the incubation time is that an assay has a binding site (i.e. the area with capture agents) of 1,000 um by 1000 um on a first plate of a CROF process (which has a surface large than the binding site); at the closed configuration of the plates, a sample with analytes is over the binding site, has a thickness of about 20 um (in the bind site area) and an area larger than the binding site and is incubated for a time equal to the target analyte/entity diffusion time across the sample thickness. In this case, the majority of the analytes/entity that bind to the binding site come from the sample volume that sites on top of the binding site, which is 1,000 um by 1000 um by 20 um=0.02 p, because the analytes in the sample portion that is 20 um away from the binding site do not have time to diffuse to the binding site (statistically). In this case, if the signal, due to the analytes/entity captured by the binding site, is measured after the incubation, one can determine the analyte/entity concentration in the relevant area and relevant volume of the sample from the information (provided by the binding site) of the relevant area and relevant volume. The analyte concentration is quantified by the number of analytes captured by the binding site divided the relevant volume.

In some embodiments, the relevant volume is approximately equal to the binding site area times the sample thickness, and the target analyte concentration in the sample is approximately equal to the number of analyte captured by the binding site divided by the relevant sample volume. This accuracy of the method of quantification of target analyte volume gets better as the ratio of the binding site dimension to the sample thickness gets larger (assuming the incubation time is about the target analyte diffusion time in the sample for a distance of the sample thickness).

Spreading Times in CROF.

In the present invention, in the methods and the devices of all paragraphs that spread the sample by two plates, the time for spreading the sample to the final thickness at a closed configuration is 0.001 sec or less, 0.01 sec, 0.1 sec, 1 sec, 5 sec, 10 sec, 20 sec, 30 sec, 60 sec, 90 sec, 100 sec, 150 sec, 200 sec, 300 sec, 500 sec, 1000 sec, or a range between any two of the values.

In the methods and the devices of all paragraphs that spread the sample by two plates, in a preferred embodiment, the time for spreading the sample to the final thickness at a closed configuration is 0.001 sec or less, 0.01 sec, 0.1 sec, 1 sec, 3 sec, 5 sec, 10 sec, 20 sec, 30 sec, 60 sec, 90 sec, 100 sec, 150 sec, or a range between any two of the values.

In the methods and the devices of all paragraphs that spread the sample by two plates, in a preferred embodiment, the time for spreading the sample to the final thickness at a closed configuration is 0.001 sec or less, 0.01 sec, 0.1 sec, 1 sec, 3 sec, 5 sec, 10 sec, 20 sec, 30 sec, 60 sec, 90 sec, or a range between any two of the values.

In the methods and the devices of all paragraphs that spread the sample by two plates, in a preferred embodiment, the time for spreading the sample to the final thickness at a closed configuration is 0.001 sec or less, 0.01 sec, 0.1 sec, 1 sec, 3 sec, 5 sec, 10 sec, 20 sec, 30 sec, or a range between any two of the values.

In the methods and the devices of all paragraphs that spread the sample by two plates, in a preferred embodiment, the time for spreading the sample to the final thickness at a closed configuration is 0.001 sec or less, 0.01 sec, 0.1 sec, 1 sec, 3 sec, 5 sec, 10 sec, or a range between any two of the values.

In the methods and the devices of all paragraphs that spread the sample by two plates, in a preferred embodiment, the time for spreading the sample to the final thickness at a closed configuration is 0.001 sec or less, 0.01 sec, 0.1 sec, 1 sec, 3 sec, or a range between any two of the values.

The embodiments and any of their combinations described in the Section 3 are applied to (i.e. are combined with) other embodiments in the entire description of the present invention.

In one preferred embodiment, the spacers are monolithically made on the X-Plate by embossing (e.g. nanoimprinting) a thin plastic film using a mold, and are made of the same materials.

In one preferred embodiment, the spacers are monolithically made on the X-Plate by embossing (e.g. nanoimprinting) a thin plastic film using a mold, and are made of the same materials, and the thickness of the X-Plate is from 50 um to 500 um.

In one preferred embodiment, the spacers are monolithically made on the X-Plate by embossing (e.g. nanoimprinting) a thin plastic film using a mold, and are made of the same materials, and the thickness of the X-Plate is from 50 um to 250 um.

In one preferred embodiment, the spacers are monolithically made on the X-Plate and are made of the same materials, and the thickness of the X-Plate is from 50 um to 500 um.

In one preferred embodiment, the spacers are monolithically made on the X-Plate a thin plastic film using a mold, and are made of the same materials, and the thickness of the X-Plate is from 50 um to 250 um.

In one preferred embodiment, the spacers are monolithically made on the X-Plate by embossing (e.g. nanoimprinting) a thin plastic film using a mold, and are made of the same materials, where the plastic film are either PMMA (polymethyl methacrylate) of PS (polystyrene).

In one preferred embodiment, the spacers are monolithically made on the X-Plate by embossing (e.g. nanoimprinting) a thin plastic film using a mold, and are made of the same materials, where the plastic film are either PMMA (polymethyl methacrylate) of PS (polystyrene) and the thickness of the X-Plate is from 50 um to 500 um.

In one preferred embodiment, the spacers are monolithically made on the X-Plate by embossing (e.g. nanoimprinting) a thin plastic film using a mold, and are made of the same materials, where the plastic film are either PMMA (polymethyl methacrylate) of PS (polystyrene) and the thickness of the X-Plate is from 50 um to 250 um.

In one preferred embodiment, the spacers are monolithically made on the X-Plate by embossing (e.g. nanoimprinting) a thin plastic film using a mold, and are made of the same materials, where the plastic film are either PMMA (polymethyl methacrylate) of PS (polystyrene), and the spacers have either a square or rectangle shape, and have the same spacer height.

In one preferred embodiment, the spacers have a square or rectangle shape (with or without round corners).

In one preferred embodiment, the spacers have square or rectangle pillars with the pillar width (spacer width in each lateral direction) between 1 um to 200 um; pillar period (i.e. spacer period) from 2 um-2000 um, and pillar height (i.e. spacer height) from 1 um-100 um.

In one preferred embodiment, the spacers made of PMMA or PS have square or rectangle pillars with the pillar width (spacer width in each lateral direction) between 1 um to 200 um; pillar period (i.e. spacer period) from 2 um-2000 um, and pillar height (i.e. spacer height) from 1 um-100 um.

In one preferred embodiment, the spacers are monolithically made on the X-Plate and are made of plastic materials, and the spacers have square or rectangle pillars with the pillar width (spacer width in each lateral direction) between 1 um to 200 um; pillar period (i.e. spacer period) from 2 um-2000 um, and pillar height (i.e. spacer height) from 1 um-100 um.

In one preferred embodiment, the spacers are monolithically made on the X-Plate and are made of the same materials, and the spacers have square or rectangle pillars with the pillar width (spacer width in each lateral direction) between 1 um to 200 um; pillar period (i.e. spacer period) from 2 um-2000 um, and pillar height (i.e. spacer height) from 1 um-10 um.

In one preferred embodiment, the spacers are monolithically made on the X-Plate and are made of the same materials selected from PS or PMMA or other plastics, and the spacers have square or rectangle pillars with the pillar width (spacer width in each lateral direction) between 1 um to 200 um; pillar period (i.e. spacer period) from 2 um-2000 um, and pillar height (i.e. spacer height) from 10 um-50 um.

In one preferred embodiment of a CROF device, one plate is X-Plate and the other plate is a planar thin film, wherein the thickness of at least one of the plates is in a range of from 10 um to 250 um; wherein the spacers are fixed on the X-Plate, and wherein the plates and the spacers can have the same materials or different materials and are made of PMMA (polymethyl methacrylate), PS (polystyrene), or a material of similar mechanical properties as PMMA or PS.

In one preferred embodiment of a CROF device, one plate is X-Plate and the other plate is a planar thin film, wherein the thickness of at least one of the plates is in a range of from 250 um to 500 um; wherein the spacers are fixed on the X-Plate, and wherein the plates and the spacers can have the same materials or different materials and are made of PMMA (polymethyl methacrylate), PS (polystyrene), or a material of similar mechanical properties as PMMA or PS.

In one preferred embodiment of a CROF device, one plate is X-Plate and the other plate is a planar thin film, wherein the thickness of at least one of the plates is in a range of from 10 um to 250 um; wherein the spacers are fixed on the X-Plate, and are an array of square or rectangle pillars with the pillar width (spacer width in each lateral direction) between 1 um to 200 um; pillar period (i.e. spacer period) from 2 um-2000 um, and pillar height (i.e. spacer height) from 1 um-100 um, and wherein the plates and the spacers can have the same materials or different materials and are made of PMMA (polymethyl methacrylate), PS (polystyrene), or a material of similar mechanical properties as PMMA or PS.

The "similar" in above paragraphs means that the difference in mechanical properties within 60%.

Guard Ring.

Some embodiments have a guard ring to prevent sample flow out of the plate surface. Some embodiments of the guard ring is an enclosed wall around the sample area. The wall has a height equal to the spacer height or different from the spacer height. The wall ca be a significant distance away from the sample measurement area.

The movable plates in a CROF process may include and/or may be coupled to a hinge, a stage, or some other positioning system that is configured to transition the plates between an open configuration and a closed configuration. Movable plates may be coupled together with one or more joints in a manner that leaves an opening to access the space between the plates (e.g., to insert and/or remove sample), provided that at least one of the joints and/or at least one of the plates is flexible enough to achieve the described open and closed configurations. A membrane pump is not considered to be a movable plate(s).

2. Uniform Plate Spacing and Sample Thickness (U)

In many applications of a CROF process, it is desirable to improve the uniformity of the plate spacing and hence the sample thickness at the closed configuration, particularly when the spacing is in the micron and/or nanoscale. A good uniformity can improve the uniformity of an assay. The present invention provides the means to improve the uniformity.

The factors that can degrade the uniformity of the plate spacing in CROF include (a) a local bending of a plate, (b) a non-flatness of the inner surface of a plate, and (c) dusts. The smaller the final plate spacing, the worse effects these factors become.

To improve the spacing (hence sample thickness) uniformity, the present invention uses certain design in the plates (mechanical strength, thickness, etc.), spacer size, number of spacers, layout of the spacers, inter spacer spacing, the precision of spacer height, among other things to overcome the factors that cause a non-uniformity.

Inner Surface Smoothness 3.1 Use of Inter Spacer Distance to Achieve Uniform Sample Thickness for a Flexible Plate It is desirable, in some applications, to have one or both of CROF plates flexible. However, as illustrated in FIG. 5a, for a flexible plate (e.g. a plastic thin film), if the inter-spacer distance is too large, during a CROF process, the flexibility of the plate(s) can lead a local bending (e.g. sag, namely bending inward) of the plate at the locations that are between the two neighboring spacers, leading to a poor sample thickness uniformity. A poor sample thickness uniformity has many disadvantages, such as large errors in determining the sample volume and/or analytes concentration, variation of the incubation time, etc.

Figure 5:
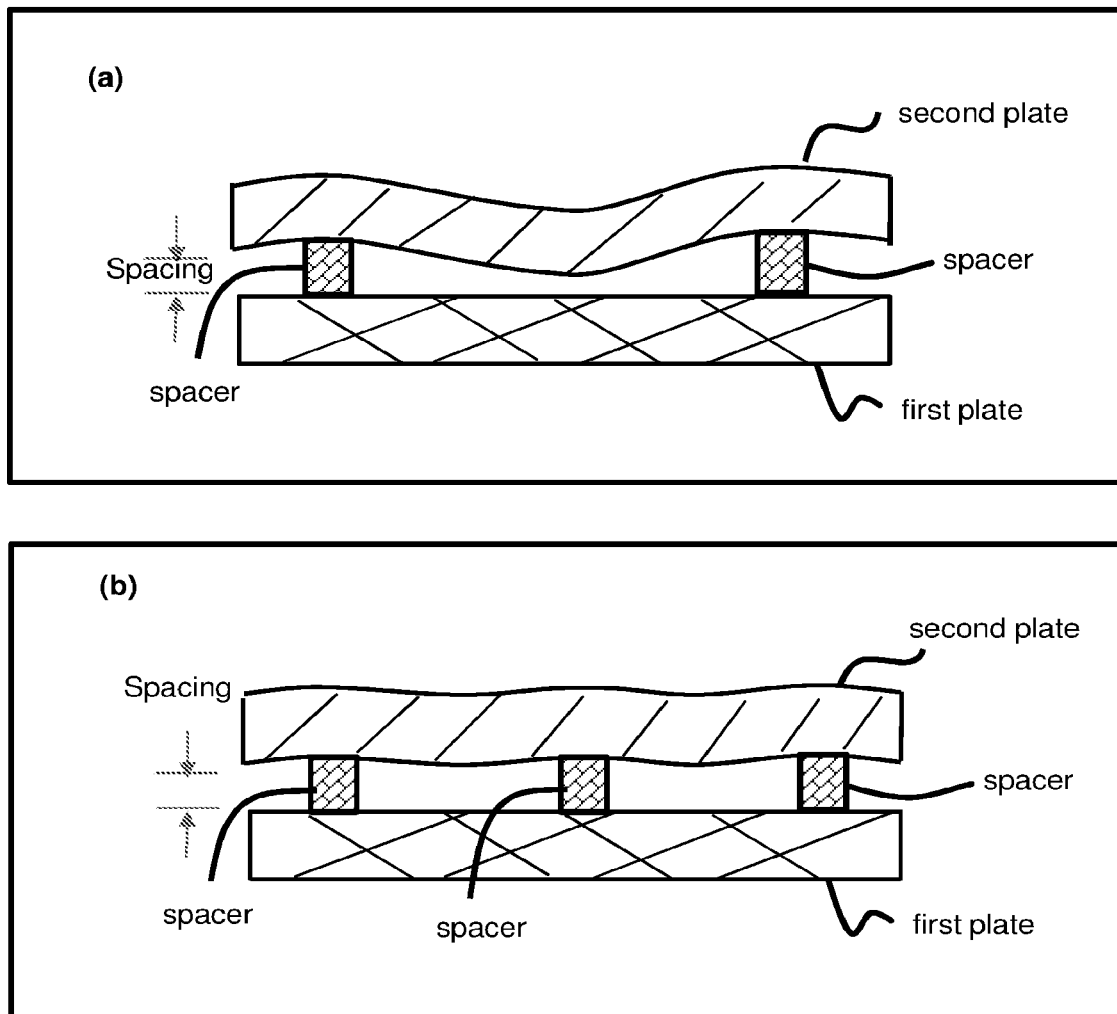
FIG. 5 shows how to avoid or reduce local bending in a flexible plate. Panel (a) illustrates if the inter-spacer distance is too large for a flexible plate (the second plate, e.g. a plastic film) under a given set of sample and compress conditions, the plate has, at the closed configuration, a local sag (i.e. bending inward) between the two neighboring pacers, assuming the first plate is rigid. The sample between the plates is not drawn. Panel (b) illustrates local bending (sag) in a flexible plate in panel (a) is reduced or virtually avoided by using a proper inter-spacer distance and a proper compression force. The sample between the plates is not drawn.

One embodiment of the present invention provides a solution that reduce a local bending and hence the final sample thickness variation by using a proper inter-spacer distance. As illustrated in FIG. 5, a CROF device has one rigid plate with a flat sample surface and one flexible plate that has local bending between two neighboring spacers, if the inter spacer distance is too large (FIG. 5a). To reduce the local bending, the inter spacer distance is set to be equal or smaller the critical bending span of the flexible plate (FIG. 5b). When both plates are flexible, the inter spacer distance should less than the smallest of the critical bending span of the two plates.

U1. A method for uniformly regulating a thickness of a relevant volume of a sample using two plates, comprising:
(a) obtaining a sample, wherein a thickness of a relevant volume of the sample is to be regulated;
(b) obtaining two plates that are movable relative to each other into different configurations; wherein one or both plates are flexible; and wherein one or both of the plates comprise spacers, the spacers have a predetermined inter-spacer distance and height, and each of the spacers is fixed with its respective plate;
(c) depositing, when the plates are configured in an open configuration, the sample on one or both of the plates; wherein the open configuration is a configuration in which the two plates are either partially or completely separated apart and the spacing between the plates is not regulated by the spacers;
(d) after (c), spreading the sample by bringing the plates into a closed configuration, wherein, in the closed configuration: the plates are facing each other, the spacers and the relevant volume of the sample are between the plates, the thickness of the relevant volume of the sample is regulated by the plates and the spacers;
wherein for the given plates, the spacers are configured to make the thickness of the relevant volume of the sample having a variation over a given area less than a predetermined value; and wherein the relevant volume is a portion or an entire volume of the sample.

In the method of paragraph U1, the configuration of the spacers comprises selecting a proper inter spacer distance. In some embodiments, the inter spacer distance is selected, so that for an allowed sample thickness variation, given two plate, and a compression method, the bending of the two plates, under the compression method, is equal to or less than the allowed sample thickness variation. The regulated sample thickness at the closed configuration can be thinner than the maximum thickness of the sample when the plates are in the open configuration U2. A device for regulating a thickness of a relevant volume of a sample, comprising:
a first plate and a second plate that are movable relative to each other into different configurations;
wherein one or both of the plates are flexible, and wherein one or both of the plates comprise spacers, the spacers have a predetermined inter-spacer distance and height, and each of the spacers is fixed with its respective plate;
wherein one of the configurations is an open configuration, in which: the two plates are either partially or completely separated apart, the spacing between the plates is not regulated by the spacers, and the sample is deposited on one or both of the plates;
wherein another of the configuration is a closed configuration, which is configured after the sample deposition in the open configuration; and in the closed configuration: the plates are facing each other, the spacers and the relevant volume of the sample are between the plates, the thickness of the relevant volume of the sample is regulated by the plates and the spacers;

wherein for the given plates, the spacers are configured to make the thickness of the relevant volume of the sample having a thickness variation over an area less than a predetermined value; and wherein the relevant volume is a portion or an entire volume of the sample.

In the device of paragraph U2, the configuration of the spacers and plates comprises selecting a proper inter spacer distance. In some embodiments, the inter spacer distance is selected, so that for an allowed sample thickness variation, given two plate, and a compression method, the bending of the two plates, under the compression method, is equal to or less than the allowed sample thickness variation. The regulated sample thickness at the closed configuration can be thinner than the maximum thickness of the sample when the plates are in the open configuration In some embodiments, small interspace spacing also allow to use flexible thin films (e.g. Plastic file of 100 um thick) by making the inter-spacer distance less than the bending f the plate between two spacers.

In some embodiments for having a uniform sample thickness over a large area at a closed configuration, for a given allowed maximum bending of the flexible plate, the ratio of inter spacer distance to the critical bending span of the plate is at most 0.001%, at most 0.001%, at most 0.001%, at most 0.01%, at most 0.1%, at most 1%, at most 10%, at most 20%, at most 50%, at most 70%, at most 100%, or a range between any two of the values.

Figure 6:
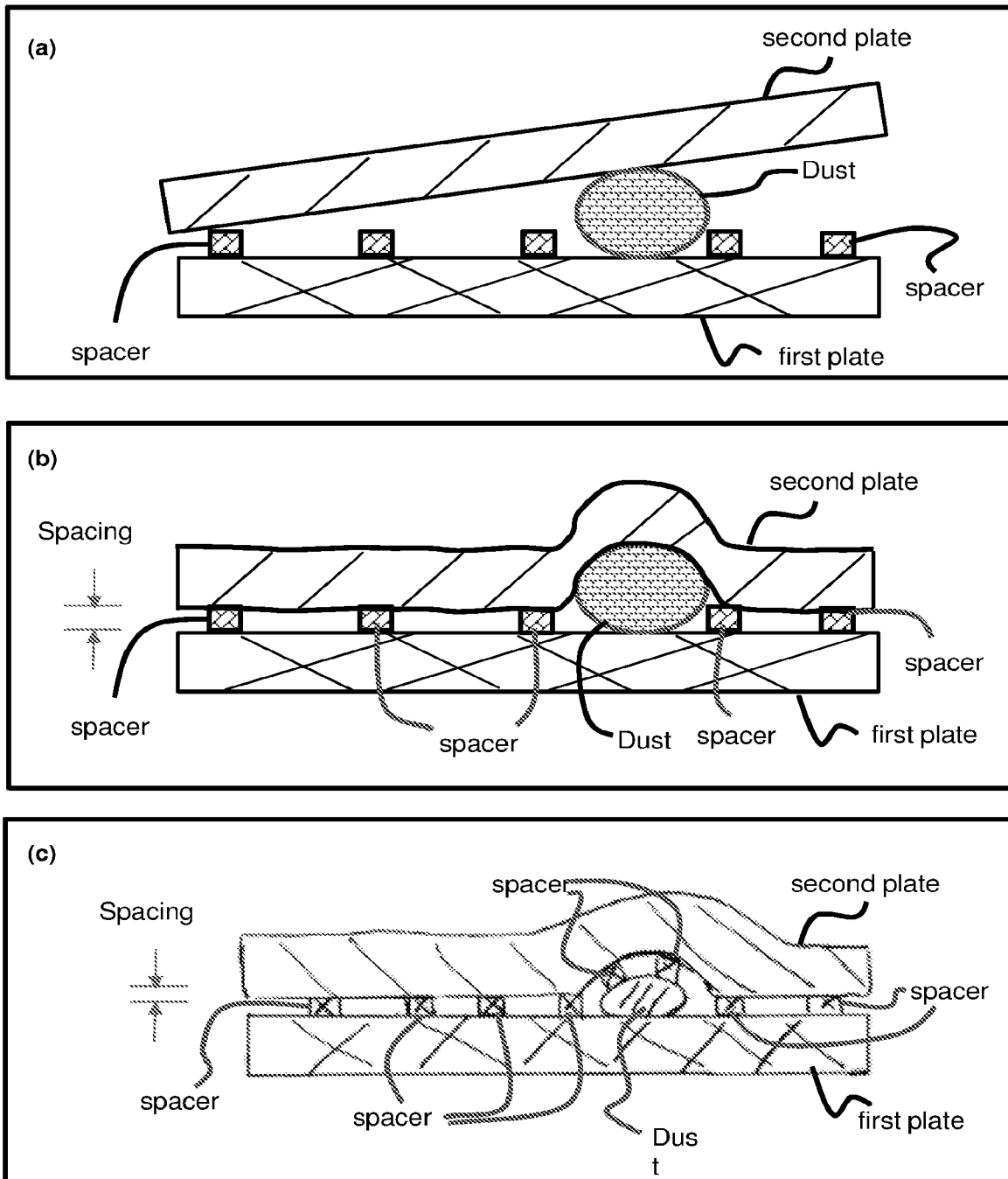
FIG. 6 illustrates reducing effect of large dust on the plate spacing (sample thickness) regulation. Panel (a) illustrates When using two rigid plates, a dust with a thickness larger than a spacer height can destroy an intended plate spacing regulation by the spacers (hence destroy the intended sample thickness regulation). The sample between the plates is not drawn. Panel (b) illustrates using a proper flexible plate and a proper inter-spacer distance, the effect of a dust is isolated to a small area around dust, while in other areas, the plate spacing (hence the sample thickness) is regulated by the spacers not the dust. This illustration has the first plate is rigid, the second plate is flexible, and the spacers are initially fixed on the first plate. Panel (c) illustrates an illustration of using a proper flexible plate and a proper inter-spacer distance, the effect of a dust is isolated to a small area around dust, while in other areas, the plate spacing (hence the sample thickness) is regulated by the spacers not the dust. This illustration has the first plate is rigid, the second plate is flexible, and the spacers are initially fixed on the second plate.

3.2 Use of Flexible Plate(s) and Spacers to Overcome the Effects of Dust in CROF One problem that needs to be overcome in a CROF process is that a dust with a thickness larger than a spacer height can destroy the regulation of the spacers to achieve an intended final plate spacing (hence the sample final thickness) (illustrated in FIG. 6a). When two rigid plates are used, one such dust would can destroy the spacer regulation over the entire plate area.

Certain embodiments of the present invention solve the problem by using a proper flexible plate(s) and inter spacer distance to limit the effect of the dust in a small area around the dust, while allowing the area outside the small area to have a final plate spacing and sample thickness set (regulated) by the spacers).

For example, FIG. 6b illustrates that, to overcome the effects of the dust, one flexible plate with a proper flexibility is used to limit the dust area, and it is used together with a rigid plate that has fixed spacers. FIG. 6c shows another embodiment of reducing the dust effect, where the spacers are fixed on the flexible plate. Clearly, another solution is to make both plate flexible.

The proper flexibility of the plates to minimize the effects of the dust in a CROF process can be selected from the thickness and the mechanical property of the plate. Based on the test illustrated in an Example preferred embodiments are following.

U3. A method for minimizing the effects of a dust on regulating a thickness of a relevant volume of a sample, comprising:

(a) obtaining a sample, wherein a thickness of a relevant volume of the sample is to be regulated;

(b) obtaining two plates that are movable relative to each other into different configurations; wherein one or both plates are flexible; and wherein one or both of the plates comprise spacers, the spacers have a predetermined inter-spacer distance and height, and each of the spacers is fixed with its respective plate;

(c) depositing, when the plates are configured in an open configuration, the sample on one or both of the plates; wherein the open configuration is a configuration in which the two plates are either partially or completely separated apart and the spacing between the plates is not regulated by the spacers;

(d) after (c), spreading the sample by bringing the plates into a closed configuration, wherein, in the closed configuration: the plates are facing each other, the spacers, the relevant volume of the sample, and one or a plurality of dusts of a thickness larger than the spacer height are between the plates, the thickness of the relevant volume of the sample is regulated by the plates and the spacers;

wherein the spacers and plates are configured to minimize the area between the two plates that is affected by the dust; wherein the area affected by the dust is the area where the dust prevents the spacers to regulate the final spacing between the plates in the area at a closed configuration of the plates in the same way as if there is no dust; and wherein the relevant volume is a portion or an entire volume of the sample.

In the method of paragraph U3, the configuration of the spacers and plates for minimizing the dust effect area comprises selecting a proper thickness and mechanical property of the flexible plate.

In some embodiments, the inter spacer distance is selected, so that for an allowed sample thickness variation, given two plate, and a compression method, the bending of the two plates, under the compression method, is equal to or less than the allowed sample thickness variation. The regulated sample thickness at the closed configuration can be thinner than the maximum thickness of the sample when the plates are in the open configuration.

Specify the flexibility of the plate.

U4. A device for minimizing the effects of a dust on regulating a thickness of a relevant volume of a sample, comprising:

a first plate and a second plate that are movable relative to each other into different configurations and that each plate has a sample contact surface that contact a sample, wherein one or both of the plates are flexible;

spacers on the sample contacting surface of one or both of the plates, wherein the spacers have a predetermined inter-spacer distance and height, and each of the spacers is fixed with its respective plate;

wherein one of the configurations is an open configuration, in which: the two plates are either partially or completely separated apart, the spacing between the plates is not regulated by the spacers, and the sample is deposited on one or both of the plates;

wherein another of the configuration is a closed configuration, which is configured after the sample deposition in the open configuration; and in the closed configuration: the plates are facing each other, the spacers, the relevant volume of the sample, and one or a plurality of dusts of a thickness larger than the spacer height are between the plates, the thickness of the relevant volume of the sample is regulated by the plates and the spacers; and wherein the spacers and plates are configured to minimize the area between the two plates that is affected by the dust; wherein the area affected by the dust is the area of the inner surface of the plates where the plates and the spacers no longer be able to regulate the sample thickness as the area that has no dust; and wherein the relevant volume is a portion or an entire volume of the sample.

3.3 Use of Spacers to Reducing the Effects of Surface Flatness Variation.

Figure 7:
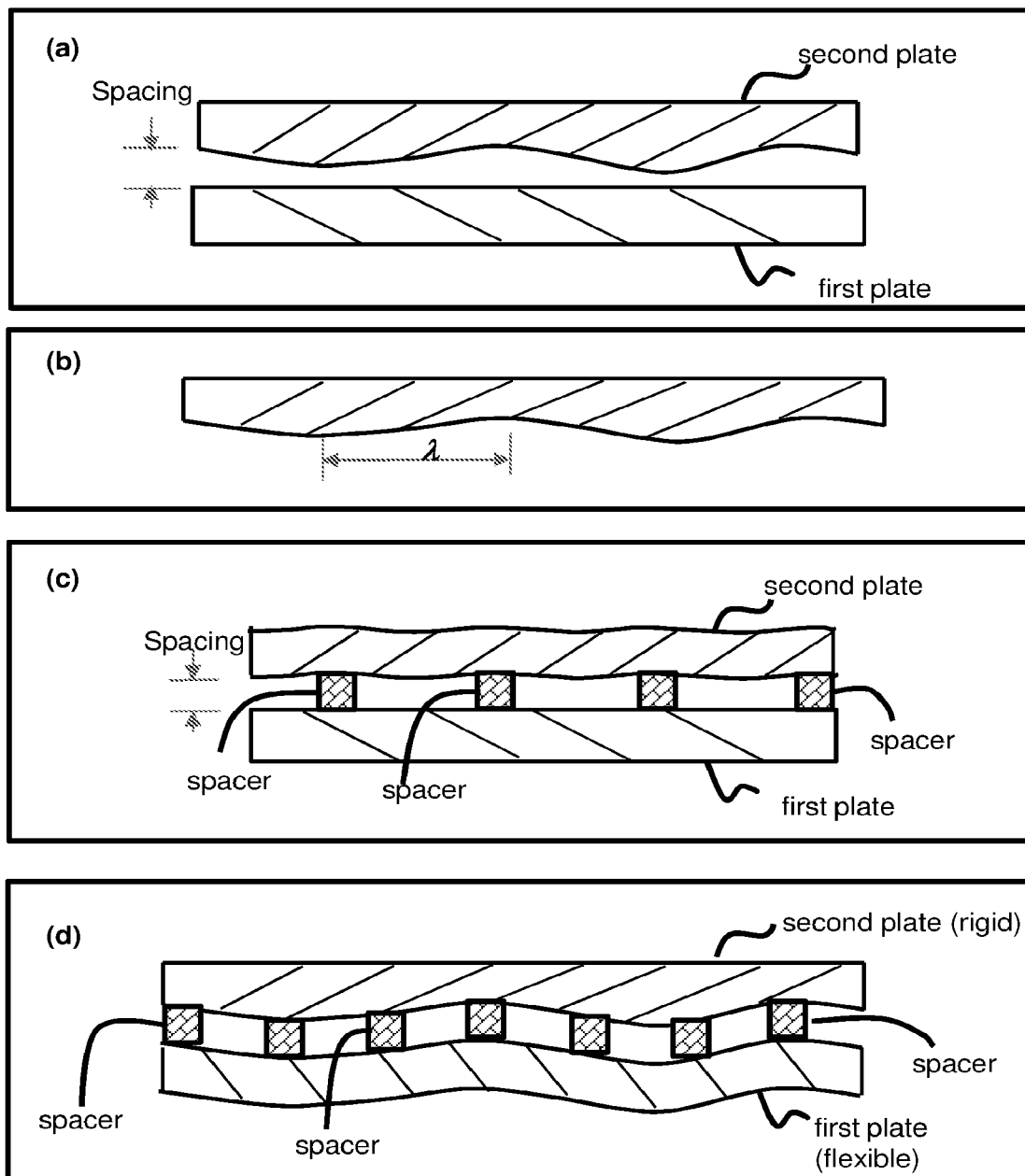
FIG. 7 illustrates reducing effects of surface flatness variation of plate by using proper spacer arrangement and flexible plate(s). Panel (a) shows that surface flatness variation can be significantly large compared with a desired sample thickness, causing errors in determining a sample thickness. In this illustration, only one plate has a large flatness variation (in reality, both plates may have large flatness variation). The sample between the plates is not drawn. Panel (b) illustrates a surface flatness variation distance of a plate, $\lambda$, is the distance from a local maximum to a neighboring local minimum of a surface height. Panel (c) illustrates how a small surface flatness variation can be achieved by making one or both plate flexible and using a proper inter-spacer distance and proper compressing force to correct, at the closed configuration, the original surface flatness variation of the plate when they are at open configuration. The sample between the plates is not drawn. Panel (d) illustrates making the sample thickness variation less than the initial surface flatness variation of the plate by using a flexible second plate and a proper inter spacer distance. The flexible plate follows the contour of the rigid plate. The sample between the plates is not drawn.

In reality, no surface of plate is perfectly flat. As illustrated in FIG. 7a, in CROF, a surface flatness variation can be significantly large compared with a desired sample thickness, which can causes large errors in determining a sample thickness. As the final sample thickness in CROF become very thin (e.g. in micro or nanometer arrange), a surface flatness variation can increasingly cause significant errors.

A surface flatness variation can be characterized by the surface flatness variation distance of a plate, λ, is the distance from a local maximum of a surface height to a neighboring local minimum (illustrated in FIG. 7b).

The present invention provides the means that make the variation of the final sample thickness at the closed configuration of a CROF process smaller than the surface flatness variation on the sample surface of the plates that was existed when the plates in an open configuration. A key approach in the present invention for achieving a uniform final sample thickness is to use a flexible plate, a proper inter-spacer distance, and proper compressing force (illustrated in FIGS. 7c and d).

Considering the case where one rigid plate and a flexible plate are used in a CROF process, at the open configuration of the plates, the sample surface of the rigid plate has a good flatness, but the sample surface of the flexible plate has a significant surface flatness variation (i.e. significant compared to the intended final sample thickness), as illustrated in FIGS. 7a and b. The present invention corrects the initial flatness variation of the sample surface at an open configuration (e.g. making the flatness variation smaller) by using (i) an inter spacer distance that is less than the initial surface flatness variation distance; (ii) a proper compression force and/or a proper capillary force between the sample and the plates at the closed configuration to deform the flexible plate; and (iii) a proper flexibility of the flexible plate, so that, at a final configuration of the plates, the sample surface of the flexible plate deforms and follows the contour of the flat surface of the rigid plate (FIG. 7c). Furthermore, to reduce the final sample thickness variation, the inter-spacer distance should also be smaller than the critical bending span of the flexible plate as well.

The above method of correcting surface flatness variation also works for the cases (a) the rigid plate has an initial significant sample surface flatness variation while the flexible plate has a smooth sample surface, (b) both the flexible plate and the rigid plate have significant flatness variation on their prospective sample surface, and (c) both plates are flexible and the sample surface(s) of one or both plate(s) has significant surface flatness variation (FIG. 7d).

U5. A method for reducing the effect of surface flatness variation of a plate on the uniformity of the final thickness of a relevant volume of a sample in a CROF process, comprising:

(a) obtaining a sample, wherein a thickness of a relevant volume of the sample is to be regulated;
(b) obtaining two plates that are movable relative to each other into different configurations; wherein one or both plates are flexible; wherein one or both plates have a surface flatness variation, and wherein one or both of the plates comprise spacers, the spacers have a predetermined height, and each of the spacers is fixed with its respective plate;
(c) depositing, when the plates are configured in an open configuration, the sample on one or both of the plates; wherein the open configuration is a configuration in which the two plates are either partially or completely separated apart and the spacing between the plates is not regulated by the spacers;
(d) after (c), spreading the sample by bringing the plates into a closed configuration, wherein, in the closed configuration: the plates are facing each other, the spacers and the relevant volume of the sample are between the plates, the thickness of the relevant volume of the sample is regulated by the plates and the spacers;

wherein the spacers and plates are configured to make the thickness variation of the relevant volume of the sample at the closed configuration is less than the surface flatness variation of the plate(s) at the open configuration, and wherein the relevant volume is a portion or an entire volume of the sample.

U6. A device for reducing the effect of surface flatness variation of a plate on the uniformity of regulating a thickness of a relevant volume of a sample, comprising:

a first plate and a second plate that are movable relative to each other into different configurations, wherein one or both of the plates are flexible, and one or both plates has a surface flatness variation;

spacers that are fixed on one or both of the plates and have a predetermined height;

wherein one of the configurations is an open configuration, in which: the two plates are either partially or completely separated apart, the spacing between the plates is not regulated by the spacers, and the sample is deposited on one or both of the plates;

wherein another of the configuration is a closed configuration, which is configured after the sample deposition in the open configuration; and in the closed configuration: the plates are facing each other, the spacers and the relevant volume of the sample are between the plates, the thickness of the relevant volume of the sample is regulated by the plates and the spacers;

wherein the spacers and plates are configured to make the thickness variation of the relevant volume of the sample at the closed configuration is less than the surface flatness variation of the plate(s) at the open configuration, and wherein the relevant volume is a portion or an entire volume of the sample, and the average dimension of the relevant volume is larger than that the surface flatness variation of the plate at the open configuration.

In the method of paragraph U5 and the device of paragraph U6, the configuration of the spacers and plates to reduce the effect of surface flatness variation of a plate on the uniformity of the final thickness of a relevant volume of a sample comprises using a proper inter spacer distance (IDS). One preferred embodiment is that the IDS is equal to or less than the initial surface flatness variation distance of a plate at an open configuration.

In the method and the device of paragraphs U5 and U6, in some embodiments, (1) the spacers are inside the sample at the closed configuration, (2) the spacers are fixed with respective plates, (3) Short inter-spacer distance, or (4) any combinations of thereof.

In the methods and the devices in the paragraphs of U1 to U8, the configuration of the spacers and plates that make the thickness of the relevant volume of the sample uniform has an embodiment described above. In some embodiments, the predetermined inter-spacer distance is configured to limit a local bending of the plates between two spacers, and wherein the relevant volume is a portion or an entire volume of the sample.

This include the cases that one or both of the plate are flexible and various different flexibility. (e.g. 100 um thick of PMMA or PS).

In one preferred embodiment, one plate is PMMA. In one preferred embodiment, one plate (first plate) is a glass of a thickness of 0.5 to 1.5 mm thick and does not have any spacer, and the other plate (second) plate is a PMMA film of 175 um thick and has a spacer array, wherein the spacer are pillars with a rectangle shape (a dimension of 40 um in x-direction and 30 um in y-direction) with round corners and a period of 120 um in x-direction and 110 um in y-direction (leading to the inter-spacer spacing of 80 um in both x and y directions).

In the methods and the devices of Section 3, some embodiments for the spacers inside of the sample at the closed configuration, the spacers' materials and the plates are the embodiments of Section 2.

In the methods and the devices of paragraphs U1-6, in some embodiments, the ratio of pillar width (or lateral average dimension) to pillar height is 0.01 or larger, 0.1 or larger, 1 or larger, 1.5 or larger, 2 or larger, 3 or larger, 5 or larger, 10 or larger, 50 or larger, 100 or larger, or a range between any two of the values.

In the methods and the devices of paragraphs U1-6, in a preferred embodiment, the ratio of pillar width (or lateral average dimension) to pillar height is 1, 1.5, 2, 10, 20, 30, 50, 100, or a range between any two of the values.

In the methods and the devices of paragraphs U1-6, in some embodiments, the ratio of pillar period to pillar width (or lateral average dimension) is 1.01, 1.1, 1.2, 1.5, 1.7, 2, 3, 5, 7, 10, 20, 50, 100, 500, 1000, 10,000, or a range between any two of the values.

In the methods and the devices of paragraphs U1-6, in a preferred embodiment, the ratio of pillar period to pillar width (or lateral average dimension) is 1.2, 1.5, 1.7, 2, 3, 5, 7, 10, 20, 30, or a range between any two of the values.

In the methods and the devices of paragraphs U1-6, in a preferred embodiment, the ratio of pillar period to pillar width (or lateral average dimension) is 1.2, 1.5, 1.7, 2, 3, 5, 7, 10, or a range between any two of the values.

c) For example, in blood cell counting application, preferred X-Plate pillar height is between 1 um to 5 um, pillar width is between 2 um to 30 um, pillar period is between 4 um to 300 um.

d) For example, in immunoassay application, preferred X-Plate pillar height is between 5 um to 50 um, pillar width is between 10 um to 250 um, pillar period is between 20 um to 2500 um.

The embodiments and any of their combinations described in the Section 3 are applied to (i.e. are combined with) other embodiments in the entire description of the present invention.

In some embodiments, other factors are also used to control the sample thickness uniformity, these factors include, but not limited to, the sample area, the plate mechanical properties, the final sample thickness at the closed configuration, and the plate surface wetting properties.

Below are some preferred embodiments for the methods and the devices in the Section 1 and the rest of the disclosures.

In a preferred embodiment, the spacer is a periodic square array, wherein the spacer is a pillar that has a height of 2 to 4 um, an average lateral dimension of from 5 to 20 um, and inter-spacer spacing of 1 um to 100 um.

In a preferred embodiment, the spacer is a periodic square array, wherein the spacer is a pillar that has a height of 2 to 4 um, an average lateral dimension of from 5 to 20 um, and inter-spacer spacing of 100 um to 250 um.

In a preferred embodiment, the spacer is a periodic square array, wherein the spacer is a pillar that has a height of 4 to 50 um, an average lateral dimension of from 5 to 20 um, and inter-spacer spacing of 1 um to 100 um.

In a preferred embodiment, the spacer is a periodic square array, wherein the spacer is a pillar that has a height of 4 to 50 um, an average lateral dimension of from 5 to 20 um, and inter-spacer spacing of 100 um to 250 um.

The period of spacer array is between 1 nm to 100 nm in one preferred embodiment, 100 nm to 500 nm in another preferred embodiment, 500 nm to 1000 nm in a separate preferred embodiment, 1 um (i.e. 1000 nm) to 2 um in another preferred embodiment, 2 um to 3 um in a separate preferred embodiment, 3 um to 5 um in another preferred embodiment, 5 um to 10 um in a separate preferred embodiment, and 10 um to 50 um in another preferred embodiment, 50 um to 100 um in a separate preferred embodiment, 100 um to 175 um in a separate preferred embodiment, and 175 um to 300 um in a separate preferred embodiment, and.

4 Sample and Deposition

In the present invention of the methods and devices that use a CROF process, the sample is deposited by several methods or a combination of the methods. In one embodiment of the deposition, the sample is deposited on only one plate. In certain embodiments, the sample is deposited on both plates (i.e. the first and the second plate).

The sample is deposited when the plates are at an open configuration. In some embodiments, the first plate and the second plate are well separated from each other during the sample deposition, so that the sample is easily deposited onto one plate without a hindrance of another plate. For example, the first plate and the second plate can be far away, so that the sample is directly dropped onto the first plate or the second plate, as if the other plate does not exist. In certain embodiments of the sample deposition, the first plate and the second plate are separated with a distance from each other at an opening configuration of the plates, then the sample is deposited on the plates (e.g. by lateral flow or other dropping methods). In certain embodiment the two plates have one side (e.g. edge) connected together during all operations of the plates (FIG. 30); and an opening and a closing of the two plates similar to opening and closing a book.

The deposition of the sample can be a single drop or multiple drops. The multiple drops can be at one location or multiple locations of either one plate or both plates. The droplets can be well separated from each other, connected, or a combination of thereof.

In some embodiments, a sample comprises more than one materials, and the materials are deposited together or separately. The materials are deposited separately either in parallel or sequence.

The deposition of the sample to the plates (i.e. the first plate and the second plate) can be performed using a device or directly from test subject to the plates. In some embodiments, a sample is deposited using a device. The device include, but not limited to, pipettes, needle, stick, swab, tube, jet, liquid dispenser, tips, stick, inkjets, printers, spraying devices, etc. In certain embodiments, a sample is deposited by a direct contacting between the sample at the sample source and a CROF plate without using any devices (i.e. bring the sample and the plate together to make a contact between the two). This is termed "direct sample deposition".

Examples of a direct sample deposition of a sample to a plate(s) are (a) a direct contact of between pricked finger (or other body parts) and a plate, (b) spitting saliva onto the plate(s), (c) taking a tear in human eyes by a direct contact between the tear and the plate(s), (d) a direct contact between the sweat and the plate(s), and (e) a direct breathing onto the plate(s) to deposit a breath, etc. Such direct deposition method can be used for both human and animals.

In some embodiments, both a direct and indirect (through a device) sample deposition are used.

In present invention, the volume of the sample that is deposited on the plate or the plates ("sample volume") is at most 0.001 pL (pico liter), at most 0.01 pL, at most 0.1 pL, at most 1 pL, at most 10 pL, at most 100 pL, at most 1 nL (nano liter), at most 10 nL, at most 100 nL, at most 1 uL (micro liter), at most 10 uL, at most 100 uL, at most 1 mL (milliliter), at most 10 mL, or a range of any two of these values.

In some embodiments, the depositing of a sample comprise the steps of (a) put a sample on one or both of the plates, and (b) spreading the sample using a means other than the second plate compression in a CROF process. The means of spreading the sample include using another device (e.g. stick, blade), air blow, or others.

Sample Deformation.

During a CROF process, in some embodiments, the samples behave approximately like an incompressible liquid (which refers a liquid that maintains a constant volume under a shape deformation), therefore a change in the sample thickness would lead to the change in the sample area. In some embodiments, the samples behave like a compressible liquid, yet their lateral area still expand when their thickness is reduced during a CROF process. In certain embodiments, the sample are liquid, gel, or soft-solids, as long as that, during a CROF process, their lateral area expands when their thickness is reduced.

In the of the present invention disclosed, "facing the first plate and the second plate" is a process that manipulates the position and orientation of the first plate or the second plate or both, so that the sample is between the inner surfaces of the first plate and the second plate. In some embodiments, the action of "facing the first plate and the second plate" is performed by human hands, human hands with certain devices, or automatic devices without human hands.

In some embodiments, the thickness is at most 1 mm, at most 100 μm, at most 20 μm, at most 10 μm, or at most 2 μm. In some embodiments, the thickness is at least 0.1 μm. In some embodiments, further comprising measuring the thickness.

In some embodiments, a variation of the thickness of the relevant volume of the sample is at most 300%, at most 100%, at most 30%, at most 10%, at most 3%, at most 1%, at most 0.3%, or at most 0.1% of an effective diameter of the relevant area In some embodiments, the thickness is at least partially determined by the predetermined height.

5. Analytes, Entity, Binding Site, Storage Site, and Transfer Media

In present invention, the entity include, but not limited to, one of a protein, an amino acid, a nucleic acid, a lipid, a carbohydrate, a metabolite, a cell, or a nanoparticle.

In some embodiments, the binding site includes a binding partner configured to bind to the respective entity.

In some embodiments, the binding site includes an entity bound to the binding site.

In some embodiments, the placing the sample includes placing the sample within the binding site.

In some embodiments, the reagent includes at least one of a protein, an amino acid, a nucleic acid, a lipid, a carbohydrate, and a metabolite.

In certain embodiments, the storage site includes dried reagent.

In some embodiments, the storage site includes reagent configured to be released from the storage site upon contact with the sample.

In some embodiments, the first storage site and the second storage site are in a common storage site.

In some embodiments, the transfer media is a sample. In some embodiments, the transfer media is a liquid, wherein the reagent or the entity can be dissolved and diffuse in the liquid.

In some embodiments, a plate has multiple storage sites. In another embodiment, one storage site has multiple reagent.

Different Release Time.

In some embodiments, a plate has multiple storage sites on different locations of the plate or one storage site stores multiple reagent, and upon in touch with the sample by the storage sites, the reagents are released but released at different time for different reagents on the same storage site or reagents on different storage sites.

In some embodiments, the first reagent is configured to be released from the first storage site upon contact with the sample in a first average release time and the second reagent is configured to be released from the second storage site upon contact with the sample in a second average release time, and wherein the first average release time is less than the second average release time.

In some embodiments, the first reagent is configured to be released from the first storage site upon contact with the sample and wherein the second reagent is a bound reagent.

In some embodiments, the depositing includes binding at least one of the reagents to the respective plate.

In some embodiments, the contacting includes releasing at least one of the reagents from the respective plate.

In some embodiments, the depositing includes depositing a first reagent and a second reagent, and wherein the contacting includes releasing the first reagent before the second reagent.

In some embodiments, at least one of the plates comprises a storage site that includes a reagent that is to be added to the relevant volume of the sample.

In some embodiments, wherein the reagent includes at least one of a protein, an amino acid, a nucleic acid, a lipid, a carbohydrate, and a metabolite.

In some embodiments, the storage site includes dried reagent.

In some embodiments, the storage site includes reagent configured to be released from the storage site upon contact with the sample.

In some embodiments, the storage site is a first storage site and the reagent is a first reagent, wherein the device includes a second storage site including a second reagent that is to be added into the relevant volume of the sample, wherein the second storage site is on one of the plates.

In some embodiments, the first storage site and the second storage site are in a common storage site.

In some embodiments, the first reagent is configured to be released from the first storage site upon contact with the sample in a first average release time and the second reagent is configured to be released from the second storage site upon contact with the sample in a second average release time, and wherein the first average release time is less than the second average release time.

In some embodiments, at least one of the reagents is dried on the respective plate.

In some embodiments of a kit, at least one of the reagents is bound to the respective plate.

In some embodiments of a kit, at least one of the reagents is configured to be released from the respective plate upon contact with the sample.

In some embodiments of a kit, a first reagent is on one or both of the plates and a second reagent is on one or both of the plates, wherein the first reagent is configured to be released from the respective plate upon contact with the sample in a first average release time and the second reagent is configured to be released from the respective plate upon contact with the sample in a second average release time, and wherein the first average release time is less than the second average release time.

In some embodiments of the devices, the storage site is a first storage site and the reagent is a first reagent, wherein the device includes a second storage site including a second reagent that is to be added into the relevant volume of the sample, wherein the second storage site is on one of the plates.

6. Locally Binding or Mixing in a Portion of a Sample (P)

In some applications, it is desirable to have a binding site to capture (i.e. bind) the analytes only in a portion of a sample, not in the entire sample. It is also desirable in some cases that a reagent is added (i.e. mixed) into a port of a sample, not the entire sample. It is often desirable that there is no fluidic separation between the portion of the sample and the rest of the sample. Such requirements are preferable or necessary in certain multiplexed detections.

The present invention offers a solution to the above requirements by using a CROF method and device to reshape a sample into a ultra-thin film of a thickness, that is smaller than the lateral dimension of the portion of the sample, wherein only an analyte inside that portion of the sample will be captured, or only the portion of the sample will be mixed with a reagent. The working principle for such approach is that when the thickness of the sample is smaller than the lateral dimension of the portion of the sample, a capture of an analyte by a surface or a mixing of reagent placed on a surface can be primarily limited by the diffusion of the analytes and the reagent in the thickness direction, where the diffusion in the lateral diffusion is relatively insignificant. For example, if a sample is reshaped in to a thin film of 5 um thick, if the portion of the sample that an analyte should be captured or a reagent should be mixed has a lateral dimension of 5 mm by 5 mm, and if the diffusion time of analyte or reagent across the 5 um is 10 sec, then the lateral diffusion of the analyte or the reagent across the 5 mm distance is 1,000,000 sec (since the diffusion time is proportional to the square of the diffusion distance). This means that by selecting a proper ratio of the lateral dimension of the interested portion of the sample to the sample thickness, in certain time interval, the analytes captured primarily come from the sample portion interested, or the regent is mixed primarily into the portion of the sample of interest.

6.1 Locally Binding of Entity in a Portion of a Sample to a Surface (P: Volume to Surface)

P1. A method for locally bind target entities in a relevant volume of a sample to a binding site on a surface, comprising:
  (i) perform the steps of (a) to (d) in the method of paragraph X1, wherein the sample thickness at the closed configuration is significantly less than the average linear dimension of the binding site; and wherein the relevant volume is the volume of the sample that sits on the binding site when the plates are in the closed configuration;
  (ii) after (i) and while the plates are in the closed configuration, either:
    (1) incubating the sample for a relevant time length and then stopping the incubation; or
    (2) incubating the sample for a time that is equal or longer than the minimum of a relevant time length, and then assessing, within a time period that is equal or less than the maximum of the relevant length of time, the binding of target entity to in the binding site;
  wherein the relevant time length is:
    i. equal to or longer than the time that it takes for the target entity to diffuse across the thickness of the uniform thickness layer at the closed configuration; and
    ii. significantly shorter than the time that it takes the target entity to laterally diffuse across the minimum lateral dimension of the binding site;
  wherein at the end of the incubation in (1) or during the assessing in (2), the majority of the target entity bound to the binding site is from a relevant volume of the sample;
  wherein the incubation allows the target entity to bind to the binding site, and wherein the relevant volume is a portion of the sample that is above the binding site at the closed configuration.

The method of paragraph P2, wherein the term "the thickness of a relevant volume of the sample is significantly less than the minimum average dimension of the binding site" means that the ratio of the minimum average dimension of the binding site to the sample thickness (termed "length to thickness ratio") is at least 3, at least 5, at least 10, at least 20, at least 50, at least 100, at least 500, at least 1,000, at least 10,000, at least 100,000, or any range between the values. In preferred embodiments, the length to thickness ratio is at least 3, at least 5, at least 10, at least 20, at least 50, at least 100, at least 500, or any range between the values.

The method of paragraph P2, wherein the term "significantly shorter than the time that it takes the target entity to laterally diffuse across the minimum lateral dimension of the binding site" means that the ratio of the time for diffusing across the minimum lateral dimension of the binding site to the time for diffusion across the sample thickness (termed "length to thickness diffusion time ratio") is at least 3, at least 10, at least 50, at least 10, at least 100, at least 1,000, at least 10,000, at least 100,000, at least 1,00,000, or any range between the values. In preferred embodiments, the length to thickness diffusion time ratio is at least 3, at least 10, at least 50, at least 10, at least 100, at least 1,000, at least 10,000, or any range between the values.

P2. A device for locally binding entity in a relevant volume of a sample to a binding site on surface, comprising:
  a first plate and a second plate, that are movable relative to each other into different configurations, wherein the first plate has, on its surface, a binding site that has an area smaller than that of the plate and is configured to bind target entity in a sample, wherein the target entity are capable of diffusing in the sample, and wherein one or both of the plates comprise spacers and each of the spacers is fixed with its respective plate and has a predetermined height;

wherein one of the configurations is an open configuration, in which: the two plates are either partially or completely separated apart, the spacing between the plates is not regulated by the spacers, and the sample is deposited on one or both of the plates, wherein another of the configuration is a closed configuration, which is configured after the sample deposition in the open configuration; and in the closed configuration: the plates are facing each other, the spacers, the binding site, and at least a portion of the sample are between the plates, the sample contacts at least a part of the binding site, the thickness of a relevant volume of the sample is regulated by the plates and the spacers, is thinner than the maximum thickness of the sample when the plates are in the open configuration, wherein the relevant volume is the volume of the sample that sits on the binding site;

wherein the spacer height is selected to regulate the thickness of the relevant volume at the closed configuration to be at least 3 times less than the average linear dimension of the binding site.

The regulation of the thickness of the relevant volume to 3 times less than the average linear dimension of the binding site makes the diffusion time of the entity across the sample thickness is 9 times less than that across a distance equal to the average linear dimension of the binding site. Such thickness regulation makes it possible to select an incubation time, such that the incubation results in (i) a significant number of target entity in the relevant volume are bound to the binding site and (ii) a significant number of the target entity bound to the binding site are from the relevant volume of the sample, and wherein the incubation is a process to allow the target entity to bind to the binding site.

For example, if the incubation time is set to be the time that equals to the diffusion time of the entity across the thickness of the relevant volume of the sample, then after the incubation, most of the entity inside the relevant volume are already reached the binding site and being bound according to the rate equation, while the entity originally (i.e. before the incubation) outside of the relevant volume can only diffuse into the peripheral of the relevant volume (relative small volume) and such volume becomes less significant, as the ratio of the average linear dimension of the binding site to the relevant volume thickness gets larger.

6.2 Locally Binding Entity Stored on a Plate Surface to a Binding-Site on Other Plate Surface (Surface to Surface)

P3. A method for locally binding entity stored on a storage site of one plate to a binding site on another plate, comprising:

(a) obtaining a first plate and a second plate that are movable relative to each other into different configurations, wherein a surface of first plate has a binding site; and a surface of the second plate has a storage site that comprises entity to be bound to the binding site; wherein the area of the binding site and the area of the reagent site is less than that of respective plates; and wherein one or both of the plates comprise spacers and each of the spacers is fixed with its respective plate and has a predetermined height;

(b) obtaining a transfer medium, wherein the entity are capable of being dissolving into the transfer medium and diffusing in the transfer medium;

(c) depositing, when the plates are configured in an open configuration, the transfer medium on one or both of the plates; wherein the open configuration is a configuration in which the two plates are partially or completely separated apart and the spacing between the plates is not regulated by the spacers;

(d) after (c), spreading the transfer medium by bringing the plates into a closed configuration, wherein, in the closed configuration: the plates are facing each other, the spacers, the binding site, the storage site and at least a portion of the transfer medium are between the plates; at least a portion of the storage site is directly facing the binding site with a portion of the transfer medium between them, and the thickness of a relevant volume of the transfer medium is regulated by the plates and the spacers, is thinner than the maximum thickness of the sample when the plates are in the open configuration, and is significantly less than the average linear dimension of the relevant volume in the plate surface direction; and (e) after (d) and while the plates are in the closed configuration, incubating for a time and stopping the incubation, wherein the incubation time is selected in such that results in a significant number of the entity bound to the binding site are from the storage site, wherein the relevant volume is the volume of the transfer medium that sits on the binding site and the incubation is a process to allow the entity to bind to the binding site.

The term of "at least a port of the storage site is directly facing the binding site" means that the shortest distance from a point in the portion to the binding site is the same as the thickness of the relevant volume at the closed configuration of the plates.

P4. A device for binding entity stored on a storage site of one plate to a relevant binding site on another plate, comprising:

a first plate and a second plate that are movable relative to each other into different configurations, wherein a surface of first plate has a binding site; and a surface of the second plate has a storage site that contains entity to be bound to the binding site; wherein the area of the binding site and the area of the storage site is less than that of respective plates; and wherein one or both of the plates comprise spacers and each of the spacers is fixed with its respective plate and has a predetermined height;

wherein one of the configurations is an open configuration, in which: the two plates are either partially or completely separated apart, the spacing between the plates is not regulated by the spacers, and a transfer medium is deposited on one or both of the plates, wherein the entity on the storage site are capable of being dissolving into the transfer medium and diffusing in the transfer medium, wherein another of the configuration is a closed configuration, which is configured after the transfer medium deposition in the open configuration; and in the closed configuration: the plates are facing each other, the spacers, the binding site, the storage site and at least a portion of the transfer medium are between the plates; at least a portion of the storage site is directly facing the binding site with a portion of the transfer medium between them, and the thickness of a relevant volume of the transfer medium is regulated by the plates and the spacers, and is thinner than the maximum thickness of the sample when the plates are in the open configuration;

wherein the relevant volume is the volume of the transfer medium that sits on the storage site when the plates are in closed configuration; and wherein the spacer height is selected to regulate the thickness of the relevant volume at the closed configuration to be at least 3 times less than the average linear dimension of the binding site.

wherein at least one of the spacers is inside the sample contact area;

and the spacers that have a predetermined inter-spacer distance and height.

6.3 A Method for Locally Binding Entity on Multiple Storage Sites of One Plate to Multiple Corresponding Binding Sites on Another Plate P5. A method for locally binding entity stored on multiple storage sites of one plate to multiple corresponding binding sites on another plate, comprising:

(a) obtaining a first plate and a second plate that are movable relative to each other into different configurations; wherein a surface of first plate has multiple binding sites, and a surface of the second plate has multiple corresponding storage sites; wherein each corresponding storage site is located in a location on the second plate that is corresponding to the location of a binding site, so that when the two plates are placed face-to-face, each binding site overlaps only one storage site; and wherein one or both of the plates comprise spacers and each of the spacers is fixed with its respective plate and has a predetermined height;

(b) obtaining a transfer medium, wherein the entity on the storage sites are capable of being dissolving into the transfer medium and diffusing in the transfer medium;

(c) depositing, when the plates are configured in an open configuration, the transfer medium on one or both of the plates; wherein the open configuration is a configuration in which the two plates are partially or completely separated apart and the spacing between the plates is not regulated by the spacers;

(d) after (c), spreading the transfer medium by bringing the plates into a closed configuration, wherein, in the closed configuration: the two plates are facing each other, the spacers, the binding sites, the storage sites and at least a portion of the transfer medium are between the plates, each binding site directly faces only one corresponding storage site, the transfer medium contacts at least a part of each of the binding sites and a part of each of the storage sites, the thickness of a relevant volume of the transfer medium is regulated by the plates and the spacers, is thinner than the maximum thickness of the transfer medium when the plates are in the open configuration, and is significantly less than the average linear dimension of the binding sites; and (e) after (d) and while the plates are in the closed configuration, incubating for a time and stopping the incubation, wherein the incubation time is selected in such that results in a significant number of the entity bound to each binding site are from a corresponding storage site, wherein the relevant volume is the volume of the transfer medium that sits on the binding sites, and the incubation is a process to allow the entity to be bound to the binding site.

In some embodiments the spacing is limited to the binding sample area.

In some embodiments of the method P5, the transfer medium is a sample with target analyte, the binding site comprises capture agent, and the entity in the storage site is detection agent, wherein the target analyte binds the capture agent and the detection agent to form a capture agent-analyte-detection agent sandwich. The method P5 simplify an assay steps and can reduce the assay time by using smaller spacer height to have a thinner sample thickness and shorter vertical diffusion time for both analytes and detection agents for a shorter saturation assay time.

P6. A device for locally binding entity stored on multiple storage sites of one plate to multiple corresponding binding sites on another plate, comprising:

a first plate and a second plate that are movable relative to each other into different configurations;

wherein a surface of first plate has multiple binding sites, and a surface of the second plate has multiple corresponding storage sites; wherein each corresponding storage site is located in a location on the second plate that is corresponding to the location of a binding site, so that when the two plates are placed face-to-face, each binding site overlaps only one storage site; and wherein one or both of the plates comprise spacers and each of the spacers is fixed with its respective plate and has a predetermined height;

wherein one of the configurations is an open configuration, in which: the two plates are either partially or completely separated apart, the spacing between the plates is not regulated by the spacers, and a transfer medium is deposited on one or both of the plates, wherein the entity on the storage site are capable of being dissolving into the transfer medium and diffusing in the transfer medium, wherein another of the configuration is a closed configuration, which is configured after the transfer medium deposition in the open configuration; and in the closed configuration: the two plates are facing each other, the spacers, the binding sites, the storage sites and at least a portion of the transfer medium are between the plates, each binding site directly faces only one corresponding storage site, the transfer medium contacts at least a part of each of the binding sites and a part of each of the storage sites, the thickness of a relevant volume of the transfer medium is regulated by the plates and the spacers, and is thinner than the maximum thickness of the transfer medium when the plates are in the open configuration;

wherein the relevant volume is the volume of the transfer medium that sits on the storage site when the plates are in closed configuration; and wherein the predetermined spacer height is selected to regulate the thickness of the relevant volume at the closed configuration to be significantly less than the average linear dimension of the binding sites.

6.4 Locally Adding Reagent Stored on a Surface to a Portion of a Sample (Surface to Volume)

P7. A method for locally adding a reagent into a relevant volume of a sample, comprising:

(a) obtaining a first plate and a second plate that are movable relative to each other into different configurations, wherein the first plate has, on its surface, a storage site that contains reagents to be added into a relevant volume of a sample, the reagents are capable of being dissolving into the sample and diffusing in the sample, and the area of the storage site is less than that of the plate; and wherein one or both of the plates comprise spacers and each of the spacers is fixed with its respective plate and has a predetermined height;

(b) obtaining the sample;

(c) depositing, when the plates are configured in an open configuration, the sample on one or both of the plates; wherein the open configuration is a configuration in which the two plates are partially or completely separated apart and the spacing between the plates is not regulated by the spacers;

(d) after (c), spreading the sample by bringing the plates into a closed configuration; wherein, in the closed configuration: the plates are facing each other; the spacers, the storage site, and at least a portion of the sample are between the plates; the sample contacts at least a portion of the storage site and contacts the plates over an area that is larger than that of the storage site; the thickness of a relevant volume of the sample is regulated by the plates and the spacers, is thinner than the maximum thickness of the sample when the plates are in the open configuration, and is significantly less than the average linear dimension of the relevant volume in the plate surface direction; and (e) after (d) and while the plates are in the closed configuration, incubating for a time and stopping the incubation, wherein the incubation time is selected in such that results in (i) a significant number of the reagents dissolved in the sample are contained in the relevant volume of the sample and (ii) the reagents are in the significant part of the relevant volume, and wherein the relevant volume is the volume of the sample that sits on the storage site when the plates are in closed configuration, and the incubation is a process to allow the reagent to dissolve and diffuse in the sample.

P8. A device for locally adding a reagent stored on a plate surface into a relevant volume of a sample, comprising:

a first plate and a second plate that are movable relative to each other into different configurations, wherein the first plate has, on its surface, a storage site that contains reagents to be added into a relevant volume of a sample, the reagents are capable of being dissolving into the sample and diffusing in the sample; and wherein one or both of the plates comprise spacers and each of the spacers is fixed with its respective plate and has a predetermined height;

wherein one of the configurations is an open configuration, in which: the two plates are either partially or completely separated apart, the spacing between the plates is not regulated by the spacers, and the sample is deposited on one or both of the plates;

wherein another of the configuration is a closed configuration, which is configured after the sample deposition in the open configuration; and in the closed configuration: the plates are facing each other, the spacers, the storage site, and at least a portion of the sample are between the plates, the sample contacts at least a portion of the storage site and at least a port of plate surface outside the storage site, the thickness of a relevant volume of the sample is regulated by the plates and the spacers, is thinner than the maximum thickness of the sample when the plates are in the open configuration, and wherein the relevant volume is the volume of the sample that sits on the storage site when the plates are in closed configuration;

wherein the spacer height is selected to regulate the thickness of the relevant volume at the closed configuration of the plates to be at least 3 times less than the average linear dimension of the relevant volume in the plate surface direction.

7 Formation of Capture-Analyte-Detection Sandwich on a Binding Site (W)

One aspect of the present invention is to form a capture-analyte-detection sandwich on a binding site on a solid surface in a single step by using a CROF process and by putting the binding site on one plate and a storage site which stores the detection agent on the corresponding location of the other plate.

7.1 Forming Capture-Analyte-Detection Sandwich on a Binding Site in a Single Step of Incubation (General) (W)

W1. A method for forming a capture-analyte-detection sandwich on a binding site of a plate, comprising:

(a) obtaining a sample that contains a target analyte, wherein the target analyte is capable of diffusion in the sample;

(b) obtaining capture agents and obtaining detection agents, wherein the capture agents and the detection agents (are capable to) bind to the target analyte to form a capture agent-target analyte-detection agent sandwich;

(c) obtaining a first plate and a second plate that are movable relative to each other into different configurations; wherein the first plates has a binding site that has the capture agents being immobilized on the site, and the second plate has a storage site that stores the detection agents; wherein when the storage site is in contact with the sample, the detection agents are capable to be dissolved into the sample and diffuse in the sample; and wherein one or both of the plates comprise spacers and each of the spacers is fixed with its respective plate and has a predetermined height;

(d) depositing, when the plates are configured in an open configuration, the sample on one or both of the plates; wherein the open configuration is a configuration in which the two plates are partially or completely separated apart and the spacing between the plates is not regulated by the spacers;

(e) after (d), spreading the sample by bringing the plates into a closed configuration, wherein, in the closed configuration: the plates are facing each other, the spacers and a relevant volume of the sample are between the plates, the thickness of the relevant volume of the sample is regulated by the plates and the spacers, and is thinner than the sample thickness when the plates are in the open configuration, and the sample is in contact with the binding site and the storage site; and (f) after (e), while the plates are in the closed configuration, incubating for a time to allow a formation of capture agent-target analyte-detection agent sandwich;

wherein the relevant volume is at least a portion or an entire volume of the sample.

W2. A device for forming a capture-analyte-detection sandwich on a binding site of a plate, comprising:

a first plate and a second plate that are movable relative to each other into different configurations;

wherein the first plates has a binding site that has capture agents being immobilized on the site, and the second plate has a storage site that stores detection agents; wherein the capture agents and the detection agents (are capable to) bind to a target analyte in a sample to form a capture agent-target analyte-detection agent sandwich; wherein when the storage site is in contact with the sample, the detection agents are capable to be dissolved into the sample and diffuse in the sample; and wherein one or both of the plates comprise spacers and each of the spacers is fixed with its respective plate and has a predetermined height;

wherein one of the configurations is an open configuration, in which: the two plates are either partially or completely separated apart, the spacing between the plates is not regulated by the spacers, and the sample is deposited on one or both of the plates;

wherein another of the configuration is a closed configuration, which is configured after the sample deposition in the open configuration; and in the closed configuration: the plates are facing each other, the spacers and a relevant volume of the sample are between the plates, the thickness of the relevant volume of the sample is regulated by the plates and the spacers and is thinner than the sample thickness when the plates are in the open configuration, and the sample is in contact with the binding site and the storage site; and wherein the relevant volume is at least a portion or an entire volume of the sample.

7.2 Forming Capture-Analyte-Detection Sandwich on a Binding Site in a Single Step Incubation Using the Analyte that is from a Portion of the Sample (i.e. Locally).

W3. A method for forming a capture-analyte-detection sandwich on a binding site of a plate using the analytes that are from a portion of the sample, comprising:

(a) obtaining a sample that contains a target analyte, wherein the target analyte is capable of diffusion in the sample;

(b) obtaining capture agents and obtaining detection agents, wherein the capture agents and the detection agents are capable to bind to the target analyte to form a capture agent-target analyte-detection agent sandwich;

(c) obtaining a first plate and a second plate that are movable relative to each other into different configurations; wherein the first plates has a binding site that has the capture agents being immobilized on the site, and the second plate has a storage site that stores the detection agents, which, when the reagent a storage site is in contact with the sample, are capable to be dissolved into the sample and diffuse in the sample; and wherein one or both of the plates comprise spacers and each of the spacers is fixed with its respective plate and has a predetermined height;

(d) depositing, when the plates are configured in an open configuration, the sample on one or both of the plates; wherein the open configuration is a configuration in which the two plates are partially or completely separated apart and the spacing between the plates is not regulated by the spacers;

(e) after (d), spreading the sample by bringing the plates into a closed configuration, wherein, in the closed configuration: the plates are facing each other, the spacers, the binding site, and the storage site are between the plates, the binding site and the storage site are in contact with a relevant volume of the sample, and the thickness of the relevant volume of the sample is regulated by the plates and the spacers and is thinner than the sample thickness when the plates are in the open configuration; and is significantly less than the average linear dimension of the binding site; and (f) after (e) and while the plates are in the closed configuration, incubating for a time and stopping the incubation, wherein the incubation time is selected in such that results in a significant number of the capture-analyte-detection sandwich formed at the binding site contain the analytes that come from the relevant volume of the sample, wherein the relevant volume is the volume of the sample that sits on the binding site, and the incubation is a process to allow a formation of a capture-analyte-detection sandwich.

In some embodiments the ratio of the spacing to the site dimension may be less than 1/5.

W4. A device for forming a capture-analyte-detection sandwich on a binding site of a plate with the analytes that are from a portion of the sample, comprising:

a first plate and a second plate that are movable relative to each other into different configurations;

wherein the first plates has a binding site that has capture agents being immobilized on the site, and the second plate has a storage site that stores detection agents; wherein the capture agents and the detection agents (are capable to) bind to a target analyte in a sample to form a capture agent-target analyte-detection agent sandwich; wherein when the storage site is in contact with the sample, the detection agents are capable to be dissolved into the sample and diffuse in the sample; and wherein one or both of the plates comprise spacers and each of the spacers is fixed with its respective plate and has a predetermined height;

wherein one of the configurations is an open configuration, in which: the two plates are either partially or completely separated apart, the spacing between the plates is not regulated by the spacers, and the sample is deposited on one or both of the plates;

wherein another of the configuration is a closed configuration, which is configured after the sample deposition in the open configuration; and in the closed configuration: the plates are facing each other, the spacers, the binding site, and the storage site are between the plates, the binding site and the storage site are in contact with a relevant volume of the sample, and the thickness of the relevant volume of the sample is regulated by the plates and the spacers and is thinner than the sample thickness when the plates are in the open configuration; and wherein the relevant volume is the volume of the sample that sits on the binding site; and wherein the spacer height is selected to regulate the thickness of the relevant volume at the closed configuration to be significantly less than the average linear dimension of the binding site.

7.3 A Method for Reducing the Time of Forming Capture-Analyte-Detection Sandwich on a Binding Site by Reducing the Diffusion Distance (W, X).

W5. A method for reducing the time of forming a capture-analyte-detection sandwich on a binding site of a plate, comprising:

(a) obtaining a sample that contains a target analyte, wherein the target analyte is capable of diffusion in the sample;

(b) obtaining capture agents and obtaining detection agents, wherein the capture agents and the detection agents are capable to bind to the target analyte to form a capture agent-target analyte-detection agent sandwich;

(c) obtaining a first plate and a second plate that are movable relative to each other into different configurations; wherein the first plates has a binding site that has the capture agents being immobilized on the site, and the second plate has a storage site that stores the detection agents, which, when the reagent a storage site is in contact with the sample, are capable to be dissolved into the sample and diffuse in the sample; and wherein one or both of the plates comprise spacers and each of the spacers is fixed with its respective plate and has a predetermined height;

(d) depositing, when the plates are configured in an open configuration, the sample on one or both of the plates; wherein the open configuration is a configuration in which the two plates are partially or completely separated apart and the spacing between the plates is not regulated by the spacers;

(e) after (d), spreading the sample by bringing the plates into a closed configuration, wherein, in the closed configuration: the plates are facing each other, the spacers, the binding site, and the storage site are between the plates, the binding site overlaps the storage site, the binding site and the storage site are in contact with a relevant volume of the sample, and the thickness of the relevant volume of the sample is regulated by the plates and the spacers and is thinner than the sample thickness when the plates are in the open configuration; and thereby the reduced thickness of the sample reduces the time for the analytes and the detection agents diffusing vertically across the thickness of the sample, wherein the relevant volume is at least a portion of an entire volume of the sample.

wherein the time period to allow the target entity in the relevant volume to bind to the binding site is shorter than that without the closed configuration.

the method may further comprise a wash step to remove the sample between the plates, and the wash step is performed when the plates are in either a closed configuration or an open configuration.

The methods further comprise a read step that reads the signal from the capture-analyte-detection sandwich immobilized on the binding site. The read is performed either after a wash or without any wash.

The method may further be multiplexed, as described above or below.

W6. A device for reducing the time of forming a capture-analyte-detection sandwich on a binding site of a plate, comprising:

a first plate and a second plate that are movable relative to each other into different configurations;

wherein the first plates has a binding site that has capture agents being immobilized on the site, and the second plate has a storage site that stores detection agents; wherein the capture agents and the detection agents (are capable to) bind to a target analyte in a sample to form a capture agent-target analyte-detection agent sandwich; wherein when the storage site is in contact with the sample, the detection agents are capable to be dissolved into the sample and diffuse in the sample; and wherein one or both of the plates comprise spacers and each of the spacers is fixed with its respective plate and has a predetermined height;

wherein one of the configurations is an open configuration, in which: the two plates are either partially or completely separated apart, the spacing between the plates is not regulated by the spacers, and the sample is deposited on one or both of the plates;

wherein another of the configuration is a closed configuration, which is configured after the sample deposition in the open configuration; and in the closed configuration: the plates are facing each other, the spacers, the binding site, and the storage site are between the plates, the binding site overlaps the storage site, the binding site and the storage site are in contact with a relevant volume of the sample, and the thickness of the relevant volume of the sample is regulated by the plates and the spacers and is thinner than the sample thickness when the plates are in the open configuration; and thereby the reduced thickness of the sample reduces the time for the analytes and the detection agents diffusing vertically across the thickness of the sample, wherein the relevant volume is at least a portion of an entire volume of the sample.

In these embodiments, the method may comprise attaching a capture agent a plate, wherein the attaching is done via a chemical reaction of the capture agent with a reactive group on the plate. The other plate may contain a patch of a dried detection reagent at a location such that, after the plates are closed, the affixed capture agent and the patch of detection reagent are facing each other. Next, the method may comprise contacting a sample containing a target-analyte with the device and closing the plates, as described above. The detection reagent dissolves and diffuses into the sample. Since the target analyte is in solution, the target analyte will be bound by the capture agent and immobilized to the surface of one of the plates. The detection agent can bind to the target analyte before or after it is bound to the capture agent. In some cases, the method may comprises removing any target-analytes that are not bound to the capture agent, or any unbound detection reagent (e.g., by washing the surface of a plate in binding buffer); The detection agent may be conjugated with an optical detectable label, thereby providing a way to detect the target analyte. After optionally removing the detection agent that are not bound to the target-analyte, the system can be read, e.g., using a reading system, to read a light signal (e.g., light at a wavelength that is in the range of 300 nm to 1200 nm) from detection agent that is bound to the plate. Further, as mentioned above, the detection agent may be labeled directly (in which case the detection agent may be strongly linked to a light-emitting label prior to deposition onto one of the plates), or labeled indirectly (i.e., by binding the detection agent to a second capture agent, e.g., a secondary antibody that is labeled or a labeled nucleic acid, that specifically binds to the detection agent and that is linked to a light-emitting label). In some embodiments, the method may comprise a blocking agent, thereby preventing non-specific binding of the capture agents to non-target analytes. Suitable conditions for the specific binding of target analytes to other agents, include proper temperature, time, solution pH level, ambient light level, humidity, chemical reagent concentration, antigen-antibody ratio, etc., are all well known or readily derivable from the present disclosure. General methods for methods for molecular interactions between capture agents and their binding partners (including analytes) are well known in the art (see, e.g., Harlow et al., *Antibodies: A Laboratory Manual*, First Edition (1988) Cold spring Harbor, N.Y.; Ausubel, et al, *Short Protocols in Molecular Biology*, 3rd ed., Wley & Sons, 1995). The methods described above and below are exemplary; the methods herein are not the only ways of performing an assay.

In certain embodiments, a nucleic acid capture agent can be used to capture a protein analyte (e.g., a DNA or RNA binding protein). In alternative embodiments, the protein capture agent (e.g., a DNA or RNA binding protein) can be used to capture a nucleic acid analyte.

The sample may be a clinical sample derived from cells, tissues, or bodily fluids. Bodily fluids of interest include but are not limited to, amniotic fluid, aqueous humour, vitreous humour, blood (e.g., whole blood, fractionated blood, plasma, serum, etc.), breast milk, cerebrospinal fluid (CSF), cerumen (earwax), chyle, chime, endolymph, perilymph, feces, gastric acid, gastric juice, lymph, mucus (including nasal drainage and phlegm), pericardial fluid, peritoneal fluid, pleural fluid, pus, rheum, saliva, sebum (skin oil), semen, sputum, sweat, synovial fluid, tears, vomit, urine and exhaled condensate.

In one embodiment of this assay, a plate is contacted with a sample containing a target analyte (e.g., a target protein) and the plates are closed. The sample contains, or is amended to contain, all necessary reagents (e.g., salts and the like) conditions suitable for specific binding. The capture agents (e.g., antibodies) and detection agent specifically bind to a target analyte in the sample, thereby leading to a patch of labeled analyte that can be detected.

As in any embodiment, the amount of target analyte in the sample can be measured to provide a qualitative or quantitative measure of the amount of target analyte in the sample. In some embodiments, the magnitude of the signal provides a quantitative determination of the amount of target analyte in the sample. In some cases, the evaluation may be compared to a standard curve (e.g., of a second analyte or a spiked-in analyte) that may in certain cases be at a known concentration. This comparison may be facilitated by depositing capture agents at different densities (e.g., different concentrations) and reading the signal from each patch of capture agent.

8 Binding and Adding Using Samples and Reagent with Small Volume (V)

It is highly desirable, in many applications, to use as small volume of a sample or reagent as possible. However, in microfluidic channel devices (the most popular approach today for using small samples), a significant volume of the sample is wasted in flowing from an inlet to a testing (detection) region of the device, resulting a need to a sample volume larger than the volume in the testing location. One aspect of the present invention is to significantly reduce the volume of the sample or reagent used in a testing, by depositing a tiny volume of a sample or a reagent on a plate and then reshaping the volume into a thin film with a smaller thickness but larger area than before. Such reshaping also allows faster reaction.

8-1 Binding Target Entity in a Small Volume Sample on a Surface Binding Site by Spreading the Sample.

V1. A method for binding target entity in a sample to a binding site, comprising:
(a) obtaining a first plate and a second plate that are movable relative to each other into different configurations, wherein the first plate has, on its surface, a binding site, and wherein one or both of the plates comprise spacers and each of the spacers is fixed with its respective plate and has a predetermined height;
(b) obtaining a sample that contains a target entity to be bound to the binding site;
(c) depositing, when the plates are configured in an open configuration, the sample on one or both of the plates; wherein, in the open configuration: the two plates are partially or completely separated apart, the spacing between the plates is not regulated by the spacers, and the sample, as deposited, covers either no area or a partial area of the binding site;
(d) after (c), spreading the sample by bringing the plates into a closed configuration; wherein, in the closed configuration: the plates are facing each other, the spacers and a relevant volume of the sample are between the plates, the sample contacts more area of the binding site than that when the plates are in the open configuration, and the thickness of the relevant volume of the sample on the binding site is regulated by the plates and the spacers, wherein the relevant volume is a portion or an entire volume of the sample.

V2. A device for binding target entity in a sample to a surface binding site, comprising:
a first plate and a second plate that are movable relative to each other into different configurations;
wherein the first plate has, on its surface, a binding site that binds target entity in a sample, and wherein the binding site has an area larger than the contact area of the sample when the sample is deposited on only one of the plates and without contacting the other plate;
wherein one or both of the plates comprise spacers and each of the spacers is fixed with its respective plate and has a predetermined height;
wherein one of the configurations is an open configuration, in which: the two plates are either partially or completely separated apart, the spacing between the plates is not regulated by the spacers, and the sample is deposited on one or both of the plates and covers, as deposited, either no area or a partial area of the binding site;
wherein another of the configuration is a closed configuration, which is configured after the sample deposition in the open configuration; and in the closed configuration: the plates are facing each other, the spacers and the sample are between the plates, the sample contacts more area of the binding site than that when the plates are in the open configuration, and the thickness of the sample on the binding site is regulated by the plates and the spacers.

8-2 Adding Reagents into a Small Volume Sample by Spreading the Sample

V3. A method for binding target entity in a sample to a binding site, comprising:
(a) obtaining a first plate and a second plate that are movable relative to each other into different configurations, wherein the first plate has, on its surface, a storage site that contains the reagents to be added into the sample, and wherein one or both of the plates comprise spacers and each of the spacers is fixed with its respective plate and has a predetermined height;
(b) depositing, when the plates are configured in an open configuration, the sample on one or both of the plates; wherein, in the open configuration: the two plates are partially or completely separated apart, the spacing between the plates is not regulated by the spacers, and the sample, as deposited, contacts either no area or a partial area of the storage site;
(c) after (b), spreading the sample by bringing the plates into a closed configuration; wherein, in the closed configuration: the plates are facing each other, the spacers and a relevant volume of the sample are between the plates, the sample contacts more area of the storage site than that when the plates are in the open configuration, and the thickness of the relevant volume of the sample is regulated by the spacer; and wherein the relevant volume is a portion of the sample that site on the storage site.

V4. A device for binding target entity in a sample to a binding site, comprising:
- a first plate and a second plate that are movable relative to each other into different configurations,
- wherein the first plate has, on its surface, a storage site that contains reagents and the reagents are to be added into the sample, and wherein one or both of the plates comprise spacers and each of the spacers is fixed with its respective plate and has a predetermined height;
- wherein one or both of the plates comprise spacers and each of the spacers is fixed with its respective plate and has a predetermined height;
- wherein one of the configurations is an open configuration, in which: the two plates are either partially or completely separated apart, the spacing between the plates is not regulated by the spacers, and the sample is deposited on one or both of the plates,
- wherein another of the configuration is a closed configuration, which is configured after the sample deposition in the open configuration; and in the closed configuration: the plates are facing each other, the spacers and a relevant volume of the sample are between the plates, the sample contacts more areas of the storage site than that when the plates are in the open configuration, and the thickness of the relevant volume of the sample is regulated by the spacer; and wherein the relevant volume is a portion of the sample that site on the storage site.

In the methods of paragraph V1 and V2 and the devices of V3 and V4, in some cases, even a sample is deposited in the binding site area or the storage area, due to the small volume of the sample and a wetting property of the surface, the contact area of as-deposited sample with a plate will be less than the area of the binding site or the storage site. Hence, a spreading, particular precisely spreading is needed.

Drops of a sample can be multiple drops, and in the closed configuration, the drops merged into a film with a thickness less than the maximum thickness.

In present invention, in the method in paragraph V1 to V7 and the devices in paragraph of V2 to V8, the volume of the sample that is deposited on the plate or the plates ("sample volume") is at most 0.001 pL (pico liter), at most 0.01 pL, at most 0.1 pL, at most 1 pL, at most 10 pL, at most 100 pL, at most 1 nL (nano liter), at most 10 nL, at most 100 nL, at most 1 uL (micro liter), at most 10 uL, at most 100 uL, at most 1 mL (milliliter), at most 10 mL, or a range of any two of these values.

9 Uniform Binding or Adding Reagents Using Uniform Sample Thickness (UAB)

For assays and chemical reactions, it is advantageous to make a thin sample thickness uniform over a significant area. The examples include binging of entity of sample to a surface binding site, adding reagents into a sample, quantification a relevant volume of the sample, quantification of analytes, and others. For the methods that use two plates to reduce and regulate a thickness of a relevant volume (a portion or an entire volume) of a sample, it is essential to be precise, uniform and easy-to-use.

One aspect of the present invention is to improve the precision, uniformity, or easy-to-use of the methods and/or devices that regulate a thickness of a relevant volume of a sample by compressing the sample with two plates.

9.1 A Method for Uniformly Binding an Entity in a Sample into a Binding Site of a Plate UAB1. A method for uniformly binding an entity in a sample into a binding site of a plate, comprising:
- (a) obtaining a sample that contains target entity which are capable of diffusing in the sample;
- (b) obtaining a first plate and a second plate that are movable relative to each other into different configurations, wherein the first plate has, on its surface, a binding site that is configured to bind the target entity, wherein one or both of the plates comprise spacers and each of the spacers is fixed with its respective plate and has a predetermined height;
- (c) depositing, when the plates are configured in an open configuration, the sample on one or both of the plates; wherein the open configuration is a configuration in which the two plates are either partially or completely separated apart and the spacing between the plates is not regulated by the spacers;
- (d) after (c), spreading the sample by bringing the plates into a closed configuration, wherein, in the closed configuration: the plates are facing each other, the spacers and the relevant volume of the sample are between the plates, the binding site is in contact with the relevant volume, the thickness of the relevant volume of the sample is regulated by the plates and the spacers and is, compared to the plates are in the open configuration, thinner than the maximum thickness of the sample and more uniform over the binding site;
- wherein the spacers and the plate are configured to make the regulated thickness of the relevant volume at the plate closed configuration more uniform than that in the plate open configuration; and wherein the relevant volume is a portion or an entire volume of the sample.
- It further has a storage site on the plate opposite to the binding site for forming a uniform sandwich.

UAB2. A device for uniformly binding an entity in a sample into a binding site on a plate, comprising:
- a first plate and a second plate that are movable relative to each other into different configurations;
- wherein the first plate has, on its surface, a binding site that is configured to bind the target entity, wherein one or both of the plates comprise spacers and each of the spacers is fixed with its respective plate and has a predetermined height;
- wherein one of the configurations is an open configuration, in which: the two plates are either partially or completely separated apart, the spacing between the plates is not regulated by the spacers, and the sample is deposited on one or both of the plates;
- wherein another of the configuration is a closed configuration, which is configured after the sample deposition in the open configuration; and in the closed configuration: the plates are facing each other, the spacers and the relevant volume of the sample are between the plates, the binding site is in contact with the relevant volume, the thickness of the relevant volume of the sample is regulated by the plates and the spacers and is, compared to the plates are in the open configuration, thinner than the maximum thickness of the sample and more uniform over the binding site;
- wherein the spacers and the plates are configured to make the regulated thickness of the relevant volume at the plate closed configuration more uniform than that in the plate open configuration; and wherein the relevant volume is a portion or an entire volume of the sample.

9.2 A Method for Uniformly Adding a Regent on a Plate into a Sample

UAB3. A method for uniformly adding a reagent into a relevant volume of a sample, comprising:
- (a) obtaining a first plate and a second plate that are movable relative to each other into different configurations, wherein the first plate has, on its surface, a storage site that contains reagents to be added into a relevant volume of a sample, the reagents are capable of being dissolving into the sample and diffusing in the sample; and wherein one or both of the plates comprise spacers and each of the spacers is fixed with its respective plate and has a predetermined height;
- (b) obtaining the sample;
- (c) depositing, when the plates are configured in an open configuration, the sample on one or both of the plates; wherein the open configuration is a configuration in which the two plates are partially or completely separated apart and the spacing between the plates is not regulated by the spacers;
- (d) after (c), spreading the sample by bringing the plates into a closed configuration, wherein, in the closed configuration: the plates are facing each other, the spacers and the relevant volume of the sample are between the plates, the storage site is in contact with the relevant volume, and the thickness of the relevant volume of the sample is regulated by the plates and the spacers and is thinner than the maximum thickness of the sample when the plates are in the open configuration;
  - wherein the spacers and plates are configured to make the thickness of the relevant volume of the sample more uniform over the area of the relevant volume at the plate closed configuration than that at the plate open configuration; and wherein the relevant volume is a portion or an entire volume of the sample.

UAB4. A device for uniformly adding a reagent into a relevant volume of a sample, comprising:
- a first plate and a second plate that are movable relative to each other into different configurations;
- wherein the first plate has, on its surface, a storage site that contains reagents to be added into a relevant volume of a sample, the reagents are capable of being dissolving into the sample and diffusing in the sample; and wherein one or both of the plates comprise spacers and each of the spacers is fixed with its respective plate and has a predetermined height;
- wherein one of the configurations is an open configuration, in which: the two plates are either partially or completely separated apart, the spacing between the plates is not regulated by the spacers, and the sample is deposited on one or both of the plates;
- wherein another of the configuration is a closed configuration, which is configured after the sample deposition in the open configuration; and in the closed configuration: the plates are facing each other, the spacers and the relevant volume of the sample are between the plates, the storage site is in contact with the relevant volume, and the thickness of the relevant volume of the sample is regulated by the plates and the spacers and is thinner than the maximum thickness of the sample when the plates are in the open configuration;
- wherein the spacers and plates are configured to make the thickness of the relevant volume of the sample more uniform over the area of the relevant volume at the plate closed configuration than that at the plate open configuration; and wherein the relevant volume is a portion or an entire volume of the sample.

9.3 A Method for Uniformly Forming a Capture-Analyte-Detection Sandwich

UAB5. A method for uniformly a capture-analyte-detection sandwich on a binding site of a plate, comprising:
- (a) obtaining a sample that contains a target analyte;
- (b) obtaining capture agents and obtaining detection agents, wherein the capture agents and the detection agents (are capable to) bind to the target analyte to form a capture agent-target analyte-detection agent sandwich;
- (c) obtaining a first plate and a second plate that are movable relative to each other into different configurations; wherein the first plates has a binding site that has the capture agents being immobilized on the site, and the second plate has a storage site that stores the detection agents, which, when the storage site is in contact with the sample, are capable to be dissolved into the sample and diffuse in the sample; and wherein one or both of the plates comprise spacers and each of the spacers is fixed with its respective plate and has a predetermined height;
- (d) depositing, when the plates are configured in an open configuration, the sample on one or both of the plates; wherein the open configuration is a configuration in which the two plates are partially or completely separated apart and the spacing between the plates is not regulated by the spacers;
- (e) after (d), spreading the sample by bringing the plates into a closed configuration, wherein, in the closed configuration: the plates are facing each other, the spacers and a relevant volume of the sample are between the plates, the thickness of the relevant volume of the sample is regulated by the plates and the spacers and is thinner than the sample thickness when the plates are in the open configuration, and the sample is in contact with the binding site and the storage site;
  - wherein the spacers and plates are configured to make the thickness of the relevant volume of the sample more uniform over the area of the relevant volume at the plate closed configuration than that at the plate open configuration; and wherein the relevant volume is a portion or an entire volume of the sample.

UAB6. A device for uniformly a capture-analyte-detection sandwich on a binding site of a plate, comprising:
- a first plate and a second plate that are movable relative to each other into different configurations;
  - wherein the first plates has a binding site that has capture agents being immobilized on the site, and the capture agents are capable of binding to a target analyte in a sample;
  - wherein the second plate has a storage site that stores the detection agents, which, are capable of (a) when the storage site is in contact with the sample, being dissolved into the sample and diffuse in the sample; and (b) binding to the target analyte and form a capture agent-target analyte-detection agent sandwich;
  - wherein one or both of the plates comprise spacers and each of the spacers is fixed with its respective plate and has a predetermined height;
  - wherein one of the configurations is an open configuration, in which: the two plates are either partially or completely separated apart, the spacing between the plates is not regulated by the spacers, and the sample is deposited on one or both of the plates;

wherein another of the configuration is a closed configuration, which is configured after the sample deposition in the open configuration; and in the closed configuration: the plates are facing each other, the spacers and a relevant volume of the sample are between the plates, the thickness of the relevant volume of the sample is regulated by the plates and the spacers and is thinner than the sample thickness when the plates are in the open configuration, and the sample is in contact with the binding site and the storage site;

wherein the spacers and plates are configured to make the thickness of the relevant volume of the sample more uniform over the area of the relevant volume at the plate closed configuration than that at the plate open configuration; and wherein the relevant volume is a portion or an entire volume of the sample.

9.4 Uniform Regulating a Thickness of a Relevant Volume of a Sample Between Two plates.

UAB7. A method for regulating a thickness of a relevant volume of a sample, comprising:
(a) obtaining a sample, wherein a thickness of a relevant volume of the sample is to be regulated;
(b) obtaining two plates that are movable relative to each other into different configurations, wherein one or both of the plates comprise spacers, the spacers have a predetermined inter-spacer distance and height, and each of the spacers is fixed with its respective plate;
(c) depositing, when the plates are configured in an open configuration, the sample on one or both of the plates; wherein the open configuration is a configuration in which the two plates are either partially or completely separated apart and the spacing between the plates is not regulated by the spacers;
(d) after (c), spreading the sample by bringing the plates into a closed configuration, wherein, in the closed configuration: the plates are facing each other, the spacers and the relevant volume of the sample are between the plates, the thickness of the relevant volume of the sample is regulated by the plates and the spacers and is thinner than the maximum thickness of the sample when the plates are in the open configuration;
wherein the spacers and plates are configured to make the thickness of the relevant volume of the sample more uniform over the area of the relevant volume at the plate closed configuration than that at the plate open configuration; and wherein the relevant volume is a portion or an entire volume of the sample.

UAB8. A device for regulating a thickness of a relevant volume of a sample, comprising:
a first plate and a second plate that are movable relative to each other into different configurations;
wherein one or both of the plates comprise spacers, the spacers have a predetermined inter-spacer distance and height, and each of the spacers is fixed with its respective plate;
wherein one of the configurations is an open configuration, in which: the two plates are either partially or completely separated apart, the spacing between the plates is not regulated by the spacers, and the sample is deposited on one or both of the plates;
wherein another of the configuration is a closed configuration, which is configured after the sample deposition in the open configuration; and in the closed configuration: the plates are facing each other, the spacers and the relevant volume of the sample are between the plates, the thickness of the relevant volume of the sample is regulated by the plates and the spacers and is thinner than the maximum thickness of the sample when the plates are in the open configuration;

wherein the spacers and plates are configured to make the thickness of the relevant volume of the sample more uniform over the area of the relevant volume at the plate closed configuration than that at the plate open configuration; and wherein the relevant volume is a portion or an entire volume of the sample In the methods and the devices in the paragraphs of U1 to U8, the configuration of the spacers and plates that make the thickness of the relevant volume of the sample uniform has an embodiment described in the disclosure.

Uniformity of Sample Thickness.

In the methods and the devices in the paragraphs of U1 to U8, the uniformity of the thickness of the relevant volume of the sample is such that the sample thickness at the closed configuration has a relative variation of at most 0.001%, at most 0.01%, at most 0.05%, at most 0.1%, at most 0.5%, at most 1%, at most 2%, at most 5%, at most 10%, at most 20%, at most 30%, at most 50%, at most 75%, at most 90%, less than 100%, or a range between any two of these values.

In a preferred embodiment of the methods and the devices in the paragraphs of U1 to U8, the uniformity of the thickness of the relevant volume of the sample is such that the sample thickness at the closed configuration has a relative variation of at most 0.1%, at most 0.5%, at most 1%, at most 2%, at most 5%, at most 10%, at most 20%, at most 30%, at most 50%, or a range between any two of these values.

Another parameter that can be important to reduce the saturation incubation time is the uniformity of the sample thickness. If the thickness has a large variation over the binding site, the saturation incubation time can vary from location to location in the binding site, forcing a longer saturation incubation time to ensure all locations in the binding site having reached the saturation.

10 Amplification Surface

One of current major obstacles for PoC diagnostics and for any assays which use a small sample volume is poor sensitivities. It is desirable to enhance the signal of an assay. One aspect of the present invention is related to the devices and methods that put the binding site on a signal amplification surface (SAS) to amplify the signal for achieving higher sensitivity. Signal amplification surfaces may also be referred to as signal amplification layers (SAL).

The general structures of SAL comprise nanoscale metal-dielectric/semiconductor-metal structures, which amplifies local surface electric field and gradient and light signals. The amplification are the high at the location where there are the sharp (i.e. large curvature) edges of a metal structure and the between a small gaps of the two metal structures. The highest enhancement regions are those having both the sharp edges and the small gaps. Furthermore, the dimensions for all metallic and non-metallic micro/nanostructures generally are less than the wavelength of the light the SAL amplifies (i.e., subwavelength).

In some embodiments, a SAL layer has as many of the metallic sharp edges and the small gaps as possible. This requires having a dense group of metallic nanostructures with small gaps between the nanostructures. SAL structures may include several different layers. Furthermore, the SAL layer itself can be further improved by a process that can further cover the portions of the metallic materials that do not have sharp edges and small gaps, as described in U.S.

provisional application Ser. No. 61/801,424, filed on Mar. 15, 2013, and PCT application WO2014197096, filed on Mar. 15, 2014, which are incorporated by reference for all purposes, as well as PCT/US2014/028417 (Chou et al, "Analyte Detection Enhancement By Targeted Immobilization, Surface Amplification, And Pixelated Reading And Analysis"), which is incorporated by reference herein for all purposes.

One particular embodiment of a signal amplification surface is the D2PA array (disk-coupled dots-on-pillar antenna arrays), which may also comprise a molecular adhesion layer that covers at least a part of said metallic dot structure, said metal disc, and/or said metallic back plane and, optionally, a capture agent that specifically binds to an analyte, wherein said capture agent is linked to the molecular adhesion layer of the D2PA array. The nanosensor can amplify a light signal from an analyte, when said analyte is bound to the capture agent. In some embodiments, the dimension of one, several or all critical metallic and dielectric components of SAL are less than the wavelength of the light in sensing. Details of the physical structure of disk-coupled dots-on-pillar antenna arrays, methods for their fabrication, methods for linking capture agents to disk-coupled dots-on-pillar antenna arrays and methods of using disk-coupled dots-on-pillar antenna arrays to detect analytes are described in a variety of publications including WO2012024006, WO2013154770, Li et al (Optics Express 2011 19, 3925-3936), Zhang et al (Nanotechnology 2012 23: 225-301); and Zhou et al (Anal. Chem. 2012 84: 4489) which are incorporated by reference for all purposes.

10.1 Amplifying Signal of Assaying a Target Entity in a Relevant Volume of a Sample M1. A method for amplifying the signal of assaying a target entity in a relevant volume of a sample, comprising:
(a) obtaining a sample that contains a target entity;
(b) obtaining two plates that are movable relative to each other into different configurations, wherein one of the plates comprises, on its surface, one binding site that comprises a signal amplification surface that is configured to bind the target entity and to amplify an optical signal which is on or near the signal amplification surface; and wherein one or both of the plates comprise spacers and each of the spacers is on its respective plate and has a predetermined height;
(c) depositing, when the plates are configured in an open configuration, the sample on one or both of the plates; wherein the open configuration is a configuration in which the two plates are separated apart and the spacing between the plates is not regulated by the spacers;
(d) after (c), spreading the sample by bringing the plates into a closed configuration, wherein, in the closed configuration: the plates are facing each other, the spacers and the relevant volume of the sample are between the plates, the thickness of the relevant volume of the sample is regulated by the plates and the spacers and is thinner than that when the plates are in the open configuration, and the relevant volume of the sample is in contact with the binding site; and
(e) after (e), incubating, while the plates are in the closed configuration, for a time period to allow the target entity in the relevant volume of the sample to bind to the binding site;
wherein the relevant volume is a portion of the sample that contact to the binding site when the plates are in the closed configuration.

M2. A device for amplifying the signal in assaying a target entity in a relevant volume of a sample, comprising:
a first plate and a second plate that are movable relative to each other into different configurations,
wherein the first plate comprises, on its surface, one binding site, and the binding site comprises a signal amplification surface that is configured to (i) bind a target entity in a sample and (ii) amplify an optical signal which is on or near the signal amplification surface;
wherein one or both of the plates comprise spacers and each of the spacers is on its respective plate and has a predetermined height;
wherein one of the configurations is an open configuration, in which: the two plates are either partially or completely separated apart, the spacing between the plates is not regulated by the spacers, and the sample is deposited on one or both of the plates,
wherein another of the configuration is a closed configuration, which is configured after the sample deposition in the open configuration; and in the closed configuration: the plates are facing each other, the spacers and the relevant volume of the sample are between the plates, the thickness of the relevant volume of the sample is regulated by the plates and the spacers and is thinner than that when the plates are in the open configuration;
wherein the relevant volume is a portion of the sample that contact to the binding site when the plates are in the closed configuration.

In some embodiments, the signal amplification surface includes at least one of a metal-dielectric nanostructure, a metal-semiconductor nanostructure, and a disk-coupled dots-on-pillar antenna array.

In some embodiments, the signal amplification surface includes a metal layer.

11 Saving Reagent Volume in Assaying in Fast Binding (S)

In the situation for binding entity in a reagent to a binding site on a surface (e.g. coating a plate with capture agent or stain a bio sample surface), it is desirable to have a short incubation time. One approach for a short incubation time is to increases the entity concentration in a reagent significantly. However, such approach is wasteful of the entity and hence costly, since in a short incubation time, only small portion of the entity in the reagent that are near the binding site can reach the binding site for binding, and the rest are too far away to diffuse to the binding site for binding and are useless and wasted. For a typical diffusion constant of common reagents in a common solutions, the typical diffusion length is about 10 um, 33 um, and 100 um, respectively, for an incubation time of 1 s (second), 10 s and 100 s. A typical thickness of a liquid drop on a typical surface is 2.5 mm, which is at least 25 time thicker than the above diffusion lengths, leading significant waste (costly) if the incubation time is 100 s or less. One aspect of the present invention is to spread a drop(s) of reagent into a large area but very thin thickness (thinner than a natural dropping) to save the reagents and hence reduce the cost.

11-1 A Method for Saving Reagent that Contains Target Entity in Reagents that Bind to a Surface Binding Site by Spreading the Reagent. (the Volume has a Natural Contacting Area Less than the Binding Site)

S1. A method for saving a reagent that contains target entity that bind to a surface binding site, comprising:
(a) obtaining a first plate and a second plate that are movable relative to each other into different configurations, wherein the first plate has, on its surface, a binding site, and wherein one or both of the plates comprise spacers and each of the spacers is fixed with its respective plate and has a predetermined height;

(b) obtaining a reagent that (i) contains target entity capable to bind the binding site, and (ii) has a volume and a wetting property such that the contact area of the reagent deposited on the binding site, without contacting the other plate, is less than the area of the binding site;

(c) depositing, when the plates are configured in an open configuration, the sample on one or both of the plates; wherein, in the open configuration: the two plates are partially or completely separated apart, and the spacing between the plates is not regulated by the spacers;

(d) after (c), spreading the sample by bringing the plates into a closed configuration; wherein, in the closed configuration: the plates are facing each other, the spacers and the sample are between the plates, the sample contacts more area of the binding site than that when the plates are in the open configuration, and the thickness of the sample on the binding site is regulated by the plates and the spacers, and is thinner than that when the plates are in the open configuration.

In the method of Paragraph S1, it further comprised a step that after (d) and while the plates are in the closed configuration, incubating for a time and stopping the incubation, wherein the incubation time is approximately equal to the time for the target entity diffusing across the maximum sample thickness when the plates are in the closed configuration, and wherein the incubation is a process to allow the entity to bind to the binding site.

S2. A device for saving a reagent that contain target entity that bind to a surface binding site, comprising:

a first plate and a second plate that are movable relative to each other into different configurations, wherein the first plate has, on its surface, a binding site that binds target entity in a reagent, and wherein the binding site has an area larger than the contact area of the reagent if the reagent is deposited on only one of the plates, without contacting the other plate;

wherein one or both of the plates comprise spacers and each of the spacers is fixed with its respective plate and has a predetermined height;

wherein one of the configurations is an open configuration, in which: the two plates are either partially or completely separated apart, the spacing between the plates is not regulated by the spacers, and the reagent is deposited on one or both of the plates;

wherein another of the configuration is a closed configuration, which is configured after the reagent deposition in the open configuration; and in the closed configuration: the plates are facing each other, the spacers and the reagent are between the plates, the reagent contacts more area of the binding site than that when the plates are in the open configuration, and the thickness of the reagent on the binding site is regulated by the plates and the spacers, and is thinner than that when the plates are in the open configuration.

12 Detection and/or Quantification of Volume and/or Concentration (Q)

Quantification and/or control of a relevant volume of a sample is useful for quantification and/or control of the concentration of chemical compounds (including analytes, entity, reagents, etc.) in the sample.

Common methods for a sample volume quantification include a use of a metered pipette (e.g., Eppendorf's "Research plus pipette, adjustable, 0.5-10 µL", SKU #3120000020), or a geometry. For PoC (point of care) or home uses, such metering devices are inconvenient to use and/or expensive. There are needs for simpler and cheaper methods and devices for the quantification and/or control of the sample volume and/or the concentration.

One aspect of the present invention is related to the methods, devices, and systems that quantify and/or control a relevant volume of a sample that deposited on a plate, without using a metered pipette and/or a fixed microfluidic channel. The relevant volume, which can be a portion or the entire volume of the sample, is relevant to the quantification and/or control of the concentration of target analyte and/or entity in the sample. The methods, devices and systems in the present invention are easy to use and low cost.

12.1 A Method for Quantifying a Relevant Volume of a Sample

Q1. A method for quantifying a relevant volume of a sample, comprising:

(a) obtaining a sample, wherein a relevant volume of the sample is to be quantified;

(b) obtaining two plates that are movable relative to each other into different configurations, wherein one or both of the plates comprise spacers and the spacers have a predetermined inter-spacer distance and height, and each of the spacers is fixed with its respective plate;

(c) depositing, when the plates are configured in an open configuration, the sample on one or both of the plates; wherein the open configuration is a configuration in which the two plates are either partially or completely separated apart and the spacing between the plates is not regulated by the spacers;

(d) after (c), spread the sample by bringing the plates into a closed configuration, wherein, in the closed configuration: the plates are facing each other, the spacers and the relevant volume of the sample are between the plates, the thickness of the relevant volume of the sample is regulated by the plates and the spacers and is thinner than the maximum thickness of the sample when the plates are in the open configuration, and at least one of the spacers is inside the sample;

(e) quantifying the relevant volume of the sample while the plates are in the closed configuration;

wherein the relevant volume is at least a portion of an entire volume of the sample.

Q2. In some embodiments, a method for quantifying a relevant volume in a sample, comprises:

(a) obtaining a first plate and a second plate;

(b) making a sample to quantified between the two plates;

(c) deforming the shape of the sample by compressing the two plate that reduces the sample thickness and spreading the sample between the plates laterally; and (d) quantifying the relevant volume of the sample while the plates are in the closed configuration;

wherein the relevant volume is at least a portion of an entire volume of the sample.

12.2 A Plate for Use in Quantifying a Relevant Volume in a Sample

Q3. A plate for use in quantifying a relevant volume in a sample, comprising:

a plate that comprises, on its surface, (i) spacers that have a predetermined inter-spacer distance and height and are fixed on the surface, and (ii) a sample contact area for contacting a sample with a relevant volume to be quantified, wherein at least one of the spacers is inside the sample contact area.

12.3 A Device for Use in Quantifying a Relevant Volume in a Sample

Q4. A device for quantifying a relevant volume in a sample, comprising:

a first plate and a second plate that (a) are movable relative to each other into different configurations and (b) each has a sample contact area for contacting a sample with a relevant volume to be quantified, wherein one or both of the plates comprise, on its surface(s), spacers that have a predetermined inter-spacer distance and height, and the spacers are fixed with respective plates;

wherein one of the configurations is an open configuration, in which: the two plates are separated apart, the spacing between the plates is not regulated by the spacers, and the sample is deposited on one or both of the plates, wherein another of the configuration is a closed configuration, which is configured after the sample deposition in the open configuration; and in the closed configuration: the plates are facing each other, the spacers and the relevant volume of the sample are between the plates, the thickness of the relevant volume of the sample is regulated by the plates and the spacers and is thinner than that when the plates are in the open configuration, and at least one of the spacers is inside the sample; and wherein the relevant volume of the sample is quantified in the closed configuration, and the relevant volume is at least a portion of an entire volume of the sample.

12-5. Measuring a Relevant Volume of a Sample

MS1. In the present invention, the quantifying of a relevant volume of the sample while the plates are at a closed configuration includes, but not limited to, each of the following five embodiments:

(a) measuring the relevant volume of the sample by a method of mechanical, optical, electrical, or any combination of thereof;

(b) measuring one or several parameter(s) related to the relevant volume of the sample independently using a method selected from a method that is mechanical, optical, electrical, or any combination of thereof;

(c) using predetermined one or several parameter(s) related to the relevant volume of the sample (i.e. the parameter(s) of the sample determined prior to the plates are at the closed configuration);

(d) determining the relevant volume of the sample by (i) measuring one or several parameters related to the revelvent volume when the plates are at a closed configuration and (ii) predetermining other parameters related to the relevant volume before the plates are at the closed configuration;

(e) determining none-sample volume (f) any combinations of the above (i.e. a, b and c).

In the method of paragraph MS1, the mechanical methods include, but not limited to, a use of the spacers (i.e. the mechanical device that regulate the spacing between the inner surfaces of the substrate and the cover-plate to a predetermined value), mechanical probe or rulers, sound waves (e.g. reflection and/or interference of ultrasound wave to measure the spacing), or any combination of thereof.

In the method of paragraph MS1, the optical methods include, but not limited to, a use of light interference, or optical imaging (e.g. taking a 2D (two-dimensional)/3D (three-dimensional) image of the sample, optical imaging of multiple times (with different viewing angles, different wavelength, different phase, and/or different polarization), image processing, or any combination of thereof.

The electrical methods include, but not limited to, capacitive, or resistive or impedance measurements, or any combination of thereof.

In the method of paragraph MS1, in some embodiments, the measurement of the sample thickness is to measure the spacing between the inner surfaces of the two plate.

In the method of paragraph MS1, in some embodiments, the use of predetermined one or several parameter(s) related to the relevant volume of the sample, wherein the predetermined parameter is the predetermined sample thickness that is regulated by the spacers when the plates are in a closed configuration.

In the method of paragraph MS1, in some embodiments, the use of predetermined one or several parameter(s) related to the relevant volume of the sample, wherein the predetermined parameter is the predetermined the spacer height.

In the method of paragraph of MS1, in some embodiments, the parameters related to the relevant volume of the sample are the parameters at a closed configuration, that include, but not limited to, (i) the spacing between the inner surfaces of the first plate and the second plate (in CROF), (ii) the sample thickness, (iii) the entire or a relevant portion of the sample area, (iv) the entire or a relevant portion of the sample volume, or (v) any combination of thereof.

In the method of paragraph MS1, in some embodiments, the quantification of the sample volume or a relevant sample volume, comprising steps of (i) multiplying the sample thickness by the entire sample area to get the entire sample volume, (ii) multiplying the sample thickness by the relevant sample area to get the relevant sample volume, or (iii) multiplying the relevant sample thickness by the entire or relevant sample area to get the relevant sample volume.

In the method of paragraph MS1, in some embodiments, the measurement is to take 3D (three-dimensional) image of the relevant volume.

In the method of paragraph MS1, in some embodiments, the quantification of the relevant volume of the sample by measuring the lateral area of the relevant volume of the sample, then using it with the thickness of the relevant volume to determine the volume of the relevant volume of the sample, wherein the thickness of the relevant volume is determined from the information of the spacer, and the information of the spacer include the spacer height;

In the method of paragraph MS1, in some embodiments, the quantification of the relevant volume of the sample by measuring the lateral area of the relevant volume of the sample and the spacer together, then using it with the thickness of the relevant volume and the volume of the spacers to determine the volume of the relevant volume of the sample, wherein the thickness of the relevant volume is determined from the inform of the spacer;

In the method of paragraph MS1, in some embodiments, the quantification of the relevant volume of the sample by measuring the lateral area and the thickness of the relevant volume of the sample;

In the method of paragraph MS1, in some embodiments, the quantification of the relevant volume of the sample by measuring the volume of the relevant volume of the sample optically.

In the method of paragraph MS1, in some embodiments, scale marks are used to assist the quantification of a relevant volume of the sample while the plates are at a closed configuration, wherein some embodiments of the scale markers, their use and measurements, etc. are described in Section 2.

In the method of paragraph MS1, in some embodiments, the quantification of the relevant volume of the sample comprises a step of subtracting the none-sample volume, wherein the none-sample volume is determined, in some embodiments, by the embodiments described in the disclosures 12-4. A Method for Quantifying Analytes Concentration in a Relevant Volume of a Sample Q5. A method for quantifying analytes in a relevant volume of a sample, comprising:
  (a) perform the steps in the method of paragraph Q1; and
  (b) measuring, after step (a), a signal related to the analytes from the relevant volume, wherein the relevant volume is at least a portion of an entire volume of the sample.

Q6. A method for quantifying analytes in a relevant volume of a sample, comprising:
  (a) perform the steps in the method of paragraph Q2; and
  (b) measuring, after step (a), a signal related to the analytes from the relevant volume, wherein the relevant volume is at least a portion of an entire volume of the sample.

In the method of any of paragraphs Q5-6, in some embodiments, it further comprises a step of calculating the analytes concentration by dividing the signal related to the analytes from the relevant volume of the sample by the volume of the relevant volume.

In the method of any of paragraphs Q5-6, one or both plates further comprise a binding site, a storage site, or both.

In the method of any of paragraphs Q5-6, in some embodiments, the signal related to the analyte is a signal directly from the analytes or a label attached to the analyte.

Q7. A method for quantifying analytes in a relevant volume of a sample, comprising:
  (a) perform the steps in the method of paragraph Q1, wherein one or both plates further comprise a binding site; and
  (b) measuring, after step (a), a signal related to the analytes from the relevant volume,
wherein the relevant volume is at least a portion of an entire volume of the sample.

Q8. A method for quantifying analytes in a relevant volume of a sample, comprising:
  (a) perform the steps in the method of paragraph Q2, wherein one or both plates further comprise a binding site; and
  (b) measuring, after step (a), a signal related to the analytes from the relevant volume,
wherein the relevant volume is at least a portion of an entire volume of the sample.

In the method of any of paragraphs Q7-8, in some embodiments, the signal related to the analyte is a signal directly from the analytes that binds to the binding site or a label attached to the analyte that binds to the binding site.

12.5 A Plate for Use in Quantifying Analyte Concentration in a Relevant Volume in a Sample Q9. A plate for use in quantifying analyte concentration in a relevant volume in a sample, comprising:
  a plate that comprises, on its surface, (i) spacers that have a predetermined inter-spacer distance and height, and (ii) a sample contact area for contacting a sample with analyte concentration in a relevant volume to be quantified, wherein at least one of the spacers is inside the sample contact area.

12.6 A Device for Use in Quantifying Analyte Concentration in a Relevant Volume in a Sample The concentration of target analytes and/or entity in a sample can be quantified or controlled, if the number of target analytes and/or entity in the sample are quantified, as well as the relevant volume of the sample is quantified.

Q10. A device for quantifying analyte concentration in a relevant volume in a sample, comprising:
  a first plate and a second plate that (a) are movable relative to each other into different configurations and (b) each has a sample contact area for contacting a sample with analyte concentration in a relevant volume to be quantified, wherein one or both of the plates comprise, on its surface(s), spacers that have a predetermined inter-spacer distance and height, and each of the spacers are fixed with respective plates;
  wherein one of the configurations is an open configuration, in which: the two plates are separated apart, the spacing between the plates is not regulated by the spacers, and the sample is deposited on one or both of the plates,
  wherein another of the configuration is a closed configuration, which is configured after the sample deposition in the open configuration; and in the closed configuration: the plates are facing each other, the spacers and the relevant volume of the sample are between the plates, the thickness of the relevant volume of the sample is regulated by the plates and the spacers and is thinner than that when the plates are in the open configuration, and at least one of the spacers is inside the sample; and
  wherein analyte concentration in the relevant volume of the sample is quantified in the closed configuration, and the relevant volume is at least a portion of an entire volume of the sample.

In the device of any of paragraphs Q9 and Q10, the plate further comprises a binding site, or a storage site, or both. One embodiment of the binding site is a binding site that bind the analytes in the sample.

In the device of any of paragraphs Q9 and Q10, the plate further comprises a or a plurality of scale-markers, wherein some embodiments of the scale-markers described in Section 2.

In the method or the device of any of paragraphs of Q1-10, in some embodiments, the measuring device includes at least one of an imager and a camera.

In the method or the device of any of paragraphs of Q1-10, in some embodiments, the measuring device is configured to image the lateral area of the relevant volume of the sample.

In the method or the device of any of paragraphs of Q1-10, in some embodiments, the measuring device includes a light source to illuminate the lateral area of the relevant volume of the sample.

In the method or the device of any of paragraphs of Q1-10, in some embodiments, the step of calculating the concentration is to divide the total target analytes or the entity by the relevant sample volume.

In the method or the device of any of paragraphs of Q1-10, in some embodiments, measuring signal is to use an optical imager to count the number of target analytes or entity. For example, the measurement can be a use of optical microscope to measure blood cells (red cell, white cells, platelets) in a blood sample.

In the method or the device of any of paragraphs of Q1-10, in some embodiments, measuring the number of target analytes or entity in a sample can be an embodiment of surface-immobilization assay that catch the target analytes or the entity on the surface.

In some embodiments, an apparatus for quantifying a volume of a sample or detecting/quantifying an analyte in a sample comprises any of the devices in paragraphs Q1-10, plus (1) optical imagers, and/or (2) a light source and optical imagers, etc. The optical imager includes a photosensor, optical lenses, filters, polarizers, waveplates, beam splitters, mechanical mounts, or any combination of thereof.

In some embodiments, the measuring of the relevant sample area or volume comprises (i) having a marker on the first plate, the cover plate, between them, or any combination of thereof, (ii) taking optical imaging (e.g. taking a 2D (two-dimensional)/3D (three-dimensional) image of the sample and the image taking can be multiple times with different viewing angles, different wavelength, different phase, and/or different polarization) and (iii) image processing based on the maker and the sample images. The relevant means to be related to the determination of target analyte concentration.

Scanning.

In some embodiments, the reading of a signal from a sample uses a scanning method, where a reader (e.g. photodetectors or camera) reads a portion of the sample (or plate) and then moves to another portion of the sample (or plate), and such process continues until certain pre-specified port of the sample (or plate) being read. The scan reading of a sample covers all part of the sample (or the plate) or a fraction of the sample (or the plate). In some embodiments, the scan reading are assisted by the location markers that indicate a location of the sample (or the plate). One example of the location markers is the periodic spacers, which has a fixed period and location, or the markers for the relevant area which also has predetermined location and size for indicating a location of the sample or plate.

13 Detection and Quantification of Analytes and Others (D)

In certain embodiments, an analyte is detected and/or quantified (i.e. assayed) by measuring a signal related to the analyte, wherein the signal is an optical signal, electrical signal, mechanical signal, chemi-physical signal, or any combination of thereof. In some embodiments, the analyte assaying are performed when the two plates in a CROF device are close to each other. In some embodiments, the analyte assaying are performed when the two plates in a CROF device are separated from each other.

The optical signal includes, but not limited to, light reflection, scattering, transmission, absorption, spectrum, color, emission, intensity, wavelength, location, polarization, luminescence, fluorescence, electroluminescence, chemoluminescence, eletrochemoluminescence, or any combination of thereof. The optical signal is in the form of optical image (i.e. light signal vs location of the sample or device) or a lump sum of all photons coming from a given area or volume. A preferred wavelength of the light is in a range of 400 nm to 1100 nm, a range of 50 nm to 400 nm, a range of 1 nm to 50 nm, or a range of 1100 to 30,000 nm. Another preferred wavelength is in terahertz.

The electrical signal includes, but not limited to, charge, current, impedance, capacitance, resistance, or any combination of thereof. The mechanical signal includes, but not limited to, mechanical wave, sound wave, shock wave, or vibration. The chemi-physical signal includes, but not limited to, PH value, ions, heat, gas bubbles, color change, that are generated in an reaction.

For example, the label is a bead and the label is attached to the label through an analyte specific binding process (e.g. use detection agent to bind the bead to the analyte, use capture agent to capture the analyte with bead, use a capture agent to bind the analyte and then use detection agent to attach the bead, or other approaches. Note the capture and detection agents bind the analyte specifically), then a measurement is used to identify each of the beads that are attached to the analytes, and count them.

In some embodiments, each of the analyte or the beads are sensed and counted by optical means (such as (i) optical labels and reading of the labels, (ii) surface plasmon resonance, (iii) optical interferences, (iv) electrical methods (e.g. capacitance, resistance, impedance, etc.), or others. The sensors can be on the surface of the first plate and/or the second plate.

Certain embodiments may include determining the analyte concentration in (a) surface immobilization assay, (b) bulk assay (e.g., blood cell counting), and (c) others. In some embodiments, the methods of the sample volume, the relevant volume of the sample, or the concentration uses a smart-phone.

In the method or the device of any of paragraphs of Q1-10, in some embodiments, the measuring a signal is to measure the number of the analytes in the sample, or measure the number of a label being attached to the analytes in the sample. In another embodiment of paragraph Q5, the "measuring signal" is to (a) identify each of the analyte or the label attached to each analyte, and (b) count their number.

In some embodiments, the analytes detection is an electrical method when electrodes are put on one or both of the first and second plates (this applies to any of the methods and devices that uses CROF). The electrodes measure the charge, current, capacitance, impedance, or resistance of a sample, or any combination of thereof. The electrodes measure an electrolyte in a sample. The electrodes have a thickness equal or less than the thickness spacer. In some embodiments, the electrode serve as a part of the spacers. The electrodes are made of various conducting materials. A preferred electrode material is gold, silver, aluminum, copper, platinum, carbon nanotubes, or any combination of thereof.

In the method or the device of any of paragraphs of Q1-10, in some embodiments, the measuring uses the devices that is a camera or photodetector plus an optional processor configured to make the measurement.

In the method or the device of any of paragraphs of Q1-10, in some embodiments, the concentration determining devices comprises a processor configured to determine the concentration from the measurements (volume, area, thickness, number of analytes, intensity)

In the method or the device of any of paragraphs of Q1-10, in some embodiments, it further comprising a concentration determining device is configured to determine the concentration of the target analytes in the relevant volume from the measured lateral area, the thickness, and the measured amount of the target molecules.

More on Signal Detection Using Pixelated Reading and Analysis

In present invention, in some embodiments, the signals from the sample, analytes, and entity, binding sites, reagents, CROF plates, or any combinations of thereof are detected and analytes. Some embodiments of the signal detection using pixelated reading and analysis are described in the disclosure, while some other embodiments are described in Publication Number: WO2014144133 A and Application Number: PCT/US2014/028417 (Chou et al, "Analyte Detection Enhancement By Targeted Immobilization, Surface Amplification, And Pixelated Reading And Analysis"), which is incorporated by reference herein for all purposes.

In some embodiments, the signal is electromagnetic signal, including electrical and optical signals with different frequencies, light intensity, fluorescence, chromaticity, luminescence (electrical and chemo-luminescence), Raman scattering, time resolved signal (including blinking). The signals also can be the forces due to local electrical, local mechanical, local biological, or local optical interaction between the plate and the reading device. The signal also includes the spatial (i.e. position), temporal and spectral distribution of the signal. The detection signal also can be absorption.

The analyte include proteins, peptides, DNA, RNA, nucleic acid, small molecules, cells, nanoparticles with different shapes. The targeted analyte can be either in a solution or in air or gas phase. The sensing includes the detection of the existence, quantification of the concentration, and determination of the states of the targeted analyte.

In some embodiments, electric field is used to assist molecular selectivity, or bonding, and detection.

Detection/Reading Methods

In some embodiments of optical detection (i.e. detection by electromagnetic radiation), the methods include, but not limited to, far-field optical methods, near-field optical methods, epi-fluorescence spectroscopy, confocal microscopy, two-photon microscopy, and total internal reflection microscopy, where the target analytes are labelled with an electro-magnetic radiation emitter, and the signal in these microscopies can be amplified by the amplification surface of a CROF plate.

In some embodiments, the signal comprises the information of the position, local intensity, local spectrum, local polarization, local phase, local Raman signature of said signals, or any combination of thereof.

In some embodiments, the detection of a signal is to measure a lump-sum signal from an area (i.e. the signal from the area, regardless which location in the area).

In certain embodiments, the detection of signal is to measure an signal image of an area (i.e. signal vs location); namely, the area is divided into pixels and the signal from each pixel of the area is individually measured, which is also termed "PIX" or "pixelated imaging detection". The individual measurement of each pixel can be in parallel or sequential or a mix.

In some embodiments, the reading uses appropriate detecting systems for the signal to be detected in sequence or in parallel or their combination. In a sequential detection, one or several pixels are detected a time, and scanner will be used to move the detection into other areas of the SAL. In a parallel detection, a multipixel detector array, such as imaging camera (e.g. CCD's), will be used to take detect the signals from different pixels at the same time. The scan can be single path or multi-path with a different pixel size for each path. FIG. 2C of PCT/US2014/028417 schematically illustrates pixelated reading on an x, y, z stage.

The pixel size for the reading/detection will be adjusted to for the balance of optical resolution and total reading time. A smaller pixel size will take a longer time for reading/scanning the entire or fraction of the SAL. A typical pixel size is 1 um to 10 um in size. The pixel has different shapes: round, square and rectangle. The lower limit of the pixel size is determined by the optical resolution of the microscope system, and the higher limit of the pixel size is determined in order to avoid reading error from the uneven optical response of the imager (optical aberration, illumination uniformity, etc.).

Reading System

Referred to the Figures in of PCT/US2014/028417, an embodiment of a reading system comprises (a) a plate or plates used for CROF; (b) a reading device 205 for producing an image of signals emanating from a surface of said plate, wherein signals represent individual targeted analyte binding events; (c) a device assembly 300 that holds the plate and the imager; (d) an electronics and a data storage 301 for storing said image; and (e) a computer comprising programming for identifying and counting individual binding events in an area of the image.

The device assembly 300 controls or changes the relative position between the plate and the reading device, in at least one of the three (x, y, z) orthogonal directions, for reading the signal. An embodiment of the device assembly comprises a scanner 301. In some embodiments, the scanner 301 scans in at least one of the three (x, y, z) orthogonal directions.

In some embodiments, the reading device 302 is a CCD camera. In some embodiments, the reading device 302 is a photodetector comprising one or more other optical devices that are selected from optical filters 303, spectrometer, lenses 304, apertures, beam splitter 305, mirrors 306, polarizers 307, waveplates, and shutters. In some embodiments, the reading device 302 is a smartphone or mobile phone, which have the capability of local and remote communications. The reading device collects the position, local intensity, local spectrum, local Raman signature of said signals, or any combination of thereof.

In some embodiments, optical filters 303, light beam splitters 305, optical fibers, a photodetector (e.g. pn junction, a diode, PMT (photomultiplier tube), or APD (Avalanch Photo Diode), imaging camera (e.g. CCD's, or cellphone camera) and spectrometer together with a scanner provided by the device assembly 301 are coupled to a microscope system which uses a far-field confocal setting or a wide-field view setting.

Figure 9:
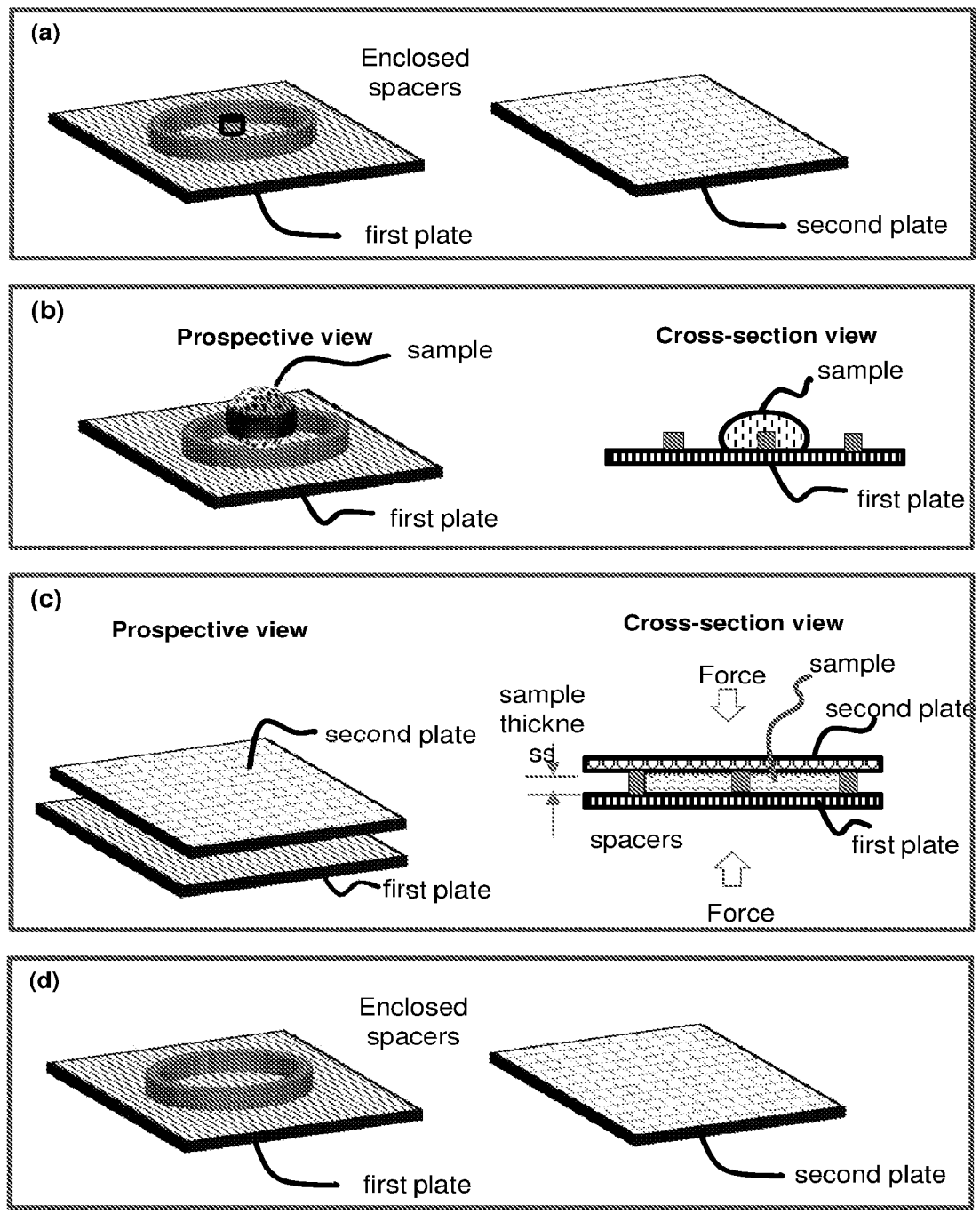
FIG. 9 illustrates another embodiment that uses enclosed-spacers (well) for sample thickness regulation. Panel (a) illustrates a first plate and a second plate, wherein the first plate has an enclosed-spacer (well) and at least one spacer inside the well. Panel (b) illustrates depositing a sample on the first plate (shown), or the second plate (not shown), or both (not shown) at an open configuration. Panel (c) illustrates (i) using the two plates to spread the sample (the sample flow between the plates) and reduce the sample thickness, and (ii) using the spacers and the plate to regulate the sample thickness at the closed configuration. Panel (d)

In some embodiments, in confocal setting, the reading is performed by recording the brightness, temporal change and spectral change of one or a few pixels a time and raster scanning the entire interested area of the SAL. In some embodiments, in wide-field view setting, a camera is used to record the brightness and temporal change of the entire or a fraction of SAL area a time. In some embodiments, proper optical filters and light beam manipulators (polarizer, beam splitters, optical fibers, etc.) is need to ensure only the desired signal is collected and detected. FIG. 9 of PCT/US2014/028417 schematically illustrates one arrangement of components for this system. In some embodiments, the analysis comprises of an imaging processing methods, including, not limited to, the methods in Open-CV or Image-J.

Pixelated Analysis (PIX).

In some embodiments of PIX, the signals detected in a pixelated manner are analyzed to determine the number and/or types of the particular molecules at a particular pixel or several pixels, which, in turn is used to quantify the type and/or concentration of the targeted analytes. The term "signal detected in a pixelated manner" refers to the method where the area that has signal(s) is divided into pixels and the signal from each pixel of the area is individually measured, which is also termed "PIX" or "pixelated imaging detection". The individual measurement of each pixel can be in parallel or sequential or a mix.

In some embodiments, the analysis comprises to analyze the spatial, tempo, spectral information of the signal. In some embodiments, the analysis include, but not limited to, statistical analysis, comparison, integration, and others. FIG. 5 of PCT/US2014/028417 shows a flow chart for one embodiment of this method.

14 Labels

One or any combinations of the embodiments of the optical labels described in the entire disclosure applies to all the methods and devices described in the entire description of the present invention.

In some embodiments, a label(s) is attached to a detection agent(s), an analyte(s) or an entity (ties). In certain embodiments, the label is an optical label, an electric label, enzymes that can be used to generate an optical or electrical signal, or any combination of thereof. In certain embodiments, a detection agent(s), an analyte(s) or an entity (ties) are attached a connection molecule (e.g. protein, nucleic acid, or other compounds) which later is attached to a label. In certain embodiments, cells (e.g. blood cells, bacteria, etc.) or nanoparticles are stained by a labels. In some embodiments, an optical label is an object that can generate an optical signal, wherein the generation of the optical signal includes, but not limited to, light (i.e. photon's) reflection, scattering, transmission, absorption, spectrum, color, emission, intensity, wavelength, location, polarization, luminescence, fluorescence, electroluminescence, photoluminescence (fluorescence), chemoluminescence, electrochemiluminescence, or any combination of thereof. In some embodiments, the optical signal is in the form of optical image (i.e. light signal vs location of the sample or device) or a lump sum of all photons coming from a given area or volume. A preferred wavelength of the light is in a range of 400 nm to 1100 nm, a range of 50 nm to 400 nm, a range of 1 nm to 50 nm, or a range of 1100 to 30,000 nm. Another preferred wavelength is in terahertz.

Beads, Nanoparticles, and Quantum Dots.

In some embodiments, the optical label is beads, nanoparticles, quantum dots, or any combination of thereof.

In some embodiments, the diameter of the bead, nanoparticles, or quantum dots is 1 nm or less, 2 nm or less, 5 nm or less, 10 nm or less, 20 nm or less, 30 nm or less, 40 nm or less, 50 nm or less, 60 nm or less, 70 nm or less, 80 nm or less, 100 nm or less, 120 nm or less, 200 nm or less, 300 nm or less, 500 nm or less, 800 nm or less, 1000 nm or less, 1500 nm or less, 2000 nm or less, 3000 nm or less, 5000 nm or less, or a range between any two of the values.

In some embodiments, the beads or quantum dots are used as labels and they are precoated on the plates of CROF and the inner spacing between the two plates are 1 um or less, 10 um or less, 50 um or less, or a range between any two of the values.

In some embodiment, the separation between the beads in a solution

Diffusion time. (The thickness of the relevant volume of the transfer medium leads to the diffusion time of an optical label across the thickness, to be less than 1 ms, The dissolving time can controlled. The control can use photon, heat or other exications and their combinations. The dissolving will not start until an excitation energy is applied.

In some embodiments of the label are nanoparticles that has a diameter of 10 nm or larger. The nanoparticles of such large diameter has less diffusion constant than small molecules (mass <1000 Da) and large molecules (mass=1,000 to 1,000,000 Dalton (da), leading to a longer diffusion time for a given solution and distance. To reduce the diffusion time, is to reduce the diffusion distance.

They have particular advantages over the prior art, when the optical labels are beads or other nanoparticles that have a diameter large than a few nanometers. This is because that the diffusion constant of an object in a liquid is, for the first order approximation, inversely proportional to the diameter of the object (according to Einstein-Stokes equation).

For example, a bead optical label with a diameter of 20 nm, 200, and 2000 nm respectively has a diffusion constant and hence a diffusion time 10, 100, and 1000 times larger and longer than that for a bead of 2 nm. For a typical diffusion distance used in current assays, this would lead to a long saturation incubation time that is in practical for PoC (Point of Care) applications.

However, the present invention has solved the long incubation time for optical labels with a diameter larger than a few nanometers. The present invention has the optical label stored on a plate surface, and then places the storage surface next to binding site with a separate distance (between the two) in sub-millimeter, microns or even nanometer scale and fill the separation gap by a transfer medium (where the stored optical label dissolved into the transfer medium and diffuse to the binding site). The present invention also able to control such small distance uniformly over large binding site area and easily by using spacer technologies.

Labeling the analyte may include using, for example, a labeling agent, such as an analyte specific binding member that includes a detectable label. Detectable labels include, but are not limited to, fluorescent labels, colorimetric labels, chemiluminescent labels, enzyme-linked reagents, multi-color reagents, avidin-streptavidin associated detection reagents, and the like. In certain embodiments, the detectable label is a fluorescent label. Fluorescent labels are labeling moieties that are detectable by a fluorescence detector. For example, binding of a fluorescent label to an analyte of interest may allow the analyte of interest to be detected by a fluorescence detector. Examples of fluorescent labels include, but are not limited to, fluorescent molecules that fluoresce upon contact with a reagent, fluorescent molecules that fluoresce when irradiated with electromagnetic radiation (e.g., UV, visible light, x-rays, etc.), and the like.

In certain embodiments, suitable fluorescent molecules (fluorophores) for labeling include, but are not limited to, IRDye800CW, Alexa 790, Dylight 800, fluorescein, fluorescein isothiocyanate, succinimidyl esters of carboxyfluorescein, succinimidyl esters of fluorescein, 5-isomer of fluorescein dichlorotriazine, caged carboxyfluorescein-alanine-carboxamide, Oregon Green 488, Oregon Green 514; Lucifer Yellow, acridine Orange, rhodamine, tetramethyl-rhodamine, Texas Red, propidium iodide, JC-1 (5,5',6,6'-tetrachloro-1,1',3,3'-tetraethylbenzimidazoylcarbocyanine iodide), tetrabromorhodamine 123, rhodamine 6G, TMRM (tetramethyl rhodamine methyl ester), TMRE (tetramethyl rhodamine ethyl ester), tetramethylrosamine, rhodamine B and 4-dimethylaminotetramethylrosamine, green fluorescent protein, blue-shifted green fluorescent protein, cyan-shifted green fluorescent protein, red-shifted green fluorescent protein, yellow-shifted green fluorescent protein, 4-acetamido-4'-isothiocyanatostilbene-2,2'disulfonic acid; acridine and derivatives, such as acridine, acridine isothiocyanate; 5-(2'-aminoethyl)aminonaphthalene-1-sulfonic acid (EDANS); 4-amino-N-[3-vinylsulfonyl)phenyl]naphthalimide-3,5 disulfonate; N-(4-anilino-1-naphthyl)maleimide; anthranilamide; 4,4-difluoro-5-(2-thienyl)-4-bora-3a,4a diaza-5-indacene-3-propionic acid BODIPY; cascade blue; Brilliant Yellow; coumarin and derivatives: coumarin, 7-amino-4-methylcoumarin (AMC, Coumarin 120), 7-amino-4-trifluoromethylcoumarin (Coumarin 151); cyanine dyes; cyanosine; 4',6-diaminidino-2-phenylindole (DAPI); 5',5"-dibromopyrogallol-sulfonaphthalein (Bromopyrogallol Red); 7-diethylamino-3-(4'-isothiocyanatophenyl)-4-methylcoumarin; diethylenetriaamine pentaacetate; 4,4'-diisothiocyanatodihydro-stilbene-2-,2'-disulfonic acid; 4,4'-diisothiocyanatostilbene-2,2'-disulfonic acid; 5-(dimethylamino]naphthalene-1-sulfonyl chloride (DNS, dansylchloride); 4-dimethylaminophenylazophenyl-4'-isothiocyanate (DABITC); eosin and derivatives: eosin, eosin isothiocyanate, erythrosin and derivatives: erythrosin B, erythrosin, isothiocyanate; ethidium; fluorescein and derivatives: 5-carboxyfluorescein (FAM), 5-(4,6-dichlorotriazin-2-yl)amino-fluorescein (DTAF), 2',7'dimethoxy-4'5'-dichloro-6-carboxyfluorescein (JOE), fluorescein, fluorescein isothiocyanate, QFITC, (XRITC); fluorescamine; IR144; IR1446; Malachite Green isothiocyanate; 4-methylumbelliferoneortho cresolphthalein; nitrotyrosine; pararosaniline; Phenol Red; B-phycoerythrin; o-phthaldialdehyde; pyrene and derivatives: pyrene, pyrene butyrate, succinimidyl 1-pyrene; butyrate quantum dots; Reactive Red 4 (Cibacron™ Brilliant Red 3B-A) rhodamine and derivatives: 6-carboxy-X-rhodamine (ROX), 6-carboxyrhodamine (R6G), lissamine rhodamine B sulfonyl chloride rhodamine (Rhod), rhodamine B, rhodamine 123, rhodamine X isothiocyanate, sulforhodamine B, sulforhodamine 101, sulfonyl chloride derivative of sulforhodamine 101 (Texas Red); N,N,N',N'-tetramethyl-6-carboxyrhodamine (TAMRA); tetramethyl rhodamine; tetramethyl rhodamine isothiocyanate (TRITC); riboflavin; 5-(2'-aminoethyl) aminonaphthalene-1-sulfonic acid (EDANS), 4-(4'-dimethylaminophenylazo)benzoic acid (DABCYL), rosolic acid; CAL Fluor Orange 560; terbium chelate derivatives; Cy 3; Cy 5; Cy 5.5; Cy 7; IRD 700; IRD 800; La Jolla Blue; phthalo cyanine; and naphthalo cyanine, coumarins and related dyes, xanthene dyes such as rhodols, resorufins, bimanes, acridines, isoindoles, dansyl dyes, aminophthalic hydrazides such as luminol, and isoluminol derivatives, aminophthalimides, aminonaphthalimides, aminobenzofurans, aminoquinolines, dicyanohydroquinones, fluorescent europium and terbium complexes; combinations thereof, and the like. Suitable fluorescent proteins and chromogenic proteins include, but are not limited to, a green fluorescent protein (GFP), including, but not limited to, a GFP derived from *Aequoria victoria* or a derivative thereof, e.g., a "humanized" derivative such as Enhanced GFP; a GFP from another species such as *Renilla reniformis, Renilla mulleri,* or *Ptilosarcus guernyi*; "humanized" recombinant GFP (hrGFP); any of a variety of fluorescent and colored proteins from *Anthozoan* species; combinations thereof; and the like.

In certain embodiments, the dyes can be used to stain the blood cells comprise Wright's stain (Eosin, methylene blue), Giemsa stain (Eosin, methylene blue, and Azure B), May-Grünwald stain, Leishman's stain ("Polychromed" methylene blue (i.e. demethylated into various azures) and eosin), Erythrosine B stain (Erythrosin B), and other fluorescence stain including but not limit to Acridine orange dye, 3,3-dihexyloxacarbocyanine (DiOC6), Propidium Iodide (PI), Fluorescein Isothiocyanate (FITC) and Basic Orange 21 (BO21) dye, Ethidium Bromide, Brilliant Sulfaflavine and a Stilbene Disulfonic Acid derivative, Erythrosine B or trypan blue, Hoechst 33342, Trihydrochloride, Trihydrate, and DAPI (4',6-Diamidino-2-Phenylindole, Dihydrochloride).

In certain embodiments, the labeling agent is configured to bind specifically to the analyte of interest. In certain embodiments, a labeling agent may be present in the CROF device before the sample is applied to the CROF device. In other embodiments, the labeling agent may be applied to the CROF device after the sample is applied to the CROF device. In certain embodiments, after the sample is applied to the CROF device, the CROF device may be washed to remove any unbound components, e.g. un bound analyte and other non-analyte components in the sample, and the labeling agent may be applied to the CROF device after the washing to label the bound analyte. In some embodiments, the CROF device may be washed after the labeling agent is bound to the analyte-capture agent complex to remove from the CROF device any excess labeling agent that is not bound to an analyte-capture agent complex.

In certain embodiments, the analyte is labeled after the analyte is bound to the CROF device, e.g., using a labeled binding agent that can bind to the analyte simultaneously as the capture agent to which the analyte is bound in the CROF device, i.e., in a sandwich-type assay. In some embodiments, a nucleic acid analyte may be captured on the CROF device, and a labeled nucleic acid that can hybridize to the analyte simultaneously as the capture agent to which the nucleic acid analyte is bound in the CROF device.

In certain aspects, a CROF device enhances the light signal, e.g., fluorescence or luminescence, that is produced by the detectable label bound directly or indirectly to an analyte, which is in turn bound to the CROF device. In certain embodiments, the signal is enhanced by a physical process of signal amplification. In some embodiments, the light signal is enhanced by a nanoplasmonic effect (e.g., surface-enhanced Raman scattering). Examples of signal enhancement by nanoplasmonic effects is described, e.g., in Li et al, Optics Express 2011 19: 3925-3936 and WO2012/024006, which are incorporated herein by reference. In certain embodiments, signal enhancement is achieved without the use of biological/chemical amplification of the signal. Biological/chemical amplification of the signal may include enzymatic amplification of the signal (e.g., used in enzyme-linked immunosorbent assays (ELISAs)) and polymerase chain reaction (PCR) amplification of the signal. In other embodiments, the signal enhancement may be achieved by a physical process and biological/chemical amplification.

Sensitivity.

In certain embodiments, the CROF device is configured to have a detection sensitivity of 0.1 nM or less, such as 10 pM or less, or 1 pM or less, or 100 fM or less, such as 10 fM or less, including 1 fM or less, or 0.5 fM or less, or 100 aM or less, or 50 aM or less, or 20 aM or less. In certain embodiments, the CROF device is configured to have a detection sensitivity in the range of 10 aM to 0.1 nM, such as 20 aM to 10 pM, 50 aM to 1 pM, including 100 aM to 100 fM. In some instances, the CROF device is configured to be able to detect analytes at a concentration of 1 ng/mL or less, such as 100 pg/mL or less, including 10 pg/mL or less, 1 pg/mL or less, 100 fg/mL or less, 10 fg/mL or less, or 5 fg/mL or less. In some instances, the CROF device is configured to be able to detect analytes at a concentration in the range of 1 fg/mL to 1 ng/mL, such as 5 fg/mL to 100 pg/mL, including 10 fg/mL to 10 pg/mL. In certain embodiments, the CROF device is configured to have a dynamic range of 5 orders of magnitude or more, such as 6 orders of magnitude or more, including 7 orders of magnitude or more.

Reading.

In certain instances, the period of time from applying the sample to the CROF device to reading the CROF device may range from 1 second to 30 minutes, such as 10 seconds to 20 minutes, 30 seconds to 10 minutes, including 1 minute to 5 minutes. In some instances, the period of time from applying the sample to the signal enhancing detector to generating an output that can be received by the device may be 1 hour or less, 30 minutes or less, 15 minutes or less, 10 minutes or less, 5 minutes or less, 3 minutes or less, 1 minute or less, 50 seconds or less, 40 seconds or less, 30 seconds or less, 20 seconds or less, 10 seconds or less, 5 seconds or less, 2 seconds or less, 1 second or less, or even shorter. In some instances, the period of time from applying the sample to the signal enhancing detector to generating an output that can be received by the device may be 100 milliseconds or more, including 200 milliseconds or more, such as 500 milliseconds or more, 1 second or more, 10 seconds or more, 30 seconds or more, 1 minute or more, 5 minutes or more, or longer.

Any suitable method may be used to read the CROF device to obtain a measurement of the amount of analyte in the sample. In some embodiments, reading the CROF device includes obtaining an electromagnetic signal from the detectable label bound to the analyte in the CROF device. In certain embodiments the electromagnetic signal is a light signal. The light signal obtained may include the intensity of light, the wavelength of light, the location of the source of light, and the like. In particular embodiments, the light signal produced by the label has a wavelength that is in the range of 300 nm to 900 nm. In certain embodiments, the light signal is read in the form of a visual image of the CROF device.

In certain embodiments, reading the CROF device includes providing a source of electromagnetic radiation, e.g., light source, as an excitation source for the detectable label bound to the biomarker in the CROF device. The light source may be any suitable light source to excite the detectable label. Exemplary light sources include, but are not limited to, sun light, ambient light, UV lamps, fluorescent lamps, light-emitting diodes (LEDs), photodiodes, incandescent lamps, halogen lamps, and the like.

Reading the CROF device may be achieved by any suitable method to measure the amount of analyte that is present in the sample and bound to the CROF device. In certain embodiments, the CROF device is read with a device configured to acquire the light signal from the detectable label bound to the analyte in the CROF device. In some cases, the device is a handheld device, such as a mobile phone or a smart phone. Any suitable handheld device configured to read the CROF device may be used in the devices, systems and methods in the present invention. Certain device embodiments configured to read the CROF device are described in, e.g., U.S. Provisional Application Ser. No. 62/066,777, filed on Oct. 21, 2014, which is incorporated herein by reference.

In some embodiments, the device includes an optical recording apparatus that is configured to acquire a light signal from the CROF device, e.g., acquire an image of the CROF device. In certain instances, the optical recording apparatus is a camera, such as a digital camera. The term "digital camera" denotes any camera that includes as its main component an image-taking apparatus provided with an image-taking lens system for forming an optical image, an image sensor for converting the optical image into an electrical signal, and other components, examples of such cameras including digital still cameras, digital movie cameras, and Web cameras (i.e., cameras that are connected, either publicly or privately, to an apparatus connected to a network to permit exchange of images, including both those connected directly to a network and those connected to a network by way of an apparatus, such as a personal computer, having an information processing capability). In one example, reading the CROF device may include video imaging that may capture changes over time. For example, a video may be acquired to provide evaluation on dynamic changes in the sample applied to the CROF device.

In certain embodiments, the optical recording apparatus has a sensitivity that is lower than the sensitivity of a high-sensitivity optical recording apparatus used in research/clinical laboratory settings. In certain cases, the optical recording apparatus used in the subject method has a sensitivity that is lower by 10 times or more, such as 100 times or more, including 200 times or more, 500 times or more, or 1,000 times or more than the sensitivity of a high-sensitivity optical recording apparatus used in research/clinical laboratory settings.

In certain embodiments, the device may have a video display. Video displays may include components upon which a display page may be displayed in a manner perceptible to a user, such as, for example, a computer monitor, cathode ray tube, liquid crystal display, light emitting diode display, touchpad or touchscreen display, and/or other means known in the art for emitting a visually perceptible output. In certain embodiments, the device is equipped with a touch screen for displaying information, such as the image acquired from the detector and/or a report generated from the processed data, and allowing information to be entered by the subject.

15 Multiplexing

In any embodiment described herein, the system may be designed for performing a multiplex assay and, as such, may contain multiple storage sites, multiple binding sites, or multiple storage sites and multiple binding sites such that different assays can be performed on different areas on the surface of one of the plates. For example, in one embodiment, in one embodiment, one of the plates may contain multiple binding site that each contain a different capture agent, thereby allowing the detection of multiple analytes in the sample in the same assay. The sites may be spatially separated from, although proximal to, one another.

FIG. 10 schematically illustrates an exemplary embodiment of the present invention, a multiplexed detection in a single CROF device using one binding site one plate and a plurality of storage sites on the other plate. Panel (a) and (b) is a perspective and a cross-sectional view of an exemplary device, respectively. In the exemplary case, the multiplexed CROF device comprises a first plate and a second plate, wherein one surface of the first plate has one binding site; wherein one surface of the second plate has a plurality of storage sites; and wherein different storage sites can have the same detection agent but of different concentrations or can have different detection agents of the same or different concentrations. In some embodiments, the area of the binding site is larger that of each storage site. In some embodiments, the binding site area is larger than the total area of all storage sites, and/or the binding site area is aligned with the storage sites (i.e. they are top each other, namely, the shortest distance between the binding site and a point on the storages are the same or nearly the same).

FIG. 11 schematically illustrates a further exemplary embodiment of the present invention, a multiplexed detection in a single CROF device using one storage site on one plate and multiple binding sites on the other plate. Panel (a) and (b) is a perspective and a cross-sectional view of an exemplary device, respectively. In the exemplary case, the multiplexed CROF device comprises a first plate and a second plate, wherein one surface of the first plate has multiple binding sites; wherein one surface of the second plate has one storage site; and wherein different binding sites can have the same capture agent but of different concentrations or can have different capture agents of the same or different concentrations. In some embodiments, the area of the storage site is larger that of each storage site. In some embodiments, the storage site area is larger than the total area of all binding sites, and/or is aligned with the binding sites (i.e. they are top each other).

FIG. 12 schematically illustrates a further exemplary embodiment of the present invention, a multiplexed detection in a single CROF device with multiple binding sites on one plate and multiple corresponding storage sites on another plate. Panel (a) and (b) is a perspective and a cross-sectional view of an exemplary device, respectively. In the exemplary case, a multiplexed CROF device comprises a first plate and a second plate, wherein one surface of the first plate has a plurality of binding sites; wherein one surface of the second plate has a plurality of corresponding storage sites; wherein each corresponding storage site is located in a location on the second plate that is corresponding to the location of a binding site on the first plate, so that when the plates are placed face-to-face, each binding site overlaps with only one storage site and each storage site overlaps with only one storage site; wherein different storage sites can have the same detection agent but of different concentrations or can have different detection agents of the same or different concentrations; and wherein different storage sites can have the same capture agent but of different concentrations or can have different capture agents of the same or different concentrations.

In certain embodiments, the device of any of FIGS. 10, 11, and 12, wherein the first plate further comprises, on its surface, a first predetermined assay site and a second predetermined assay site, wherein the distance between the edges of the neighboring multiple assay sites is substantially larger than the thickness of the uniform thickness layer when the plates are in the closed position, wherein at least a part of the uniform thickness layer of the sample is over the predetermined assay sites, and wherein the sample has one or a plurality of analytes that are capable of diffusing in the sample. By making the distance between the edges of the neighboring multiple assay sites large than the sample thickness, it makes it possible to have multiple binding sites without fluidically isolated the different portion of a sample, since an saturation incubation of the assay can complete between a significant inter-diffusion between the two neighboring sites. By properly choosing the ratio of the neighboring distance to the sample thickness and properly selecting the measurement time between a time longer than the assay saturation incubation time but less than a time for a significant inter-diffusion between two neighboring sites, one can do multiplexing by CROF without isolating different part of a sample. In some embodiments, the ratio of the neighbor distance to the sample thickness at the closed configuration is 1.5 or larger, 3 or larger, 5 or larger, 10 or larger, 20 or larger, 30 or larger, 50 or larger, 100 or larger, 200 or larger, 1000 or larger, 10,000 or larger, or a range between any two of the values. The ratio is 3 or larger for a preferred embodiment, 5 or larger for another preferred embodiment, 10 or larger for a certain preferred embodiment, 30 or larger for another preferred embodiment, and 100 or larger for another preferred embodiment.

In certain embodiments, the device of any of FIGS. 10, 11, and 12, wherein the first plate has, on its surface, at least three analyte assay sites, and the distance between the edges of any two neighboring assay sites is substantially larger than the thickness of the uniform thickness layer when the plates are in the closed position, wherein at least a part of the uniform thickness layer is over the assay sites, and wherein the sample has one or a plurality of analytes that are capable of diffusing in the sample.

In certain embodiments, the device of any of FIGS. 10, 11, and 12, wherein the first plate has, on its surface, at least two neighboring analyte assay sites that are not separated by a distance that is substantially larger than the thickness of the uniform thickness layer when the plates are in the closed position, wherein at least a part of the uniform thickness layer is over the assay sites, and wherein the sample has one or a plurality of analytes that are capable of diffusing in the sample.

The method or the devices of any of paragraph of U1-6, X-6, P1-8, W1-6, V1-4, UAB1-8, M1-2, S1-2, Q110, and H1 as well as their any combination, wherein the first and second plate further comprise the binding site(s) and the storage site, as described in FIG. 10, FIG. 11, or FIG. 12 for multiplexed detection.

In these embodiments the device may for parallel, multiplex, assaying of a liquid sample without fluidic isolation (i.e., without their being a physical barrier between the assay regions). This device may comprise a first plate and a second plate, wherein: i. the plates are movable relative to each other into different configurations; one or both plates are flexible; ii. one or both of the plates comprise spacers that are fixed with a respective plate; and the spacers have a predetermined substantially uniform height and a predetermined constant inter-spacer distance; iii. each of the plates has, on its respective surface, a sample contact area for contacting a sample that contains a sample that contains one or more target analytes which is capable of diffusing in the sample, iii. the first plate has, on its surface, one or a plurality of binding sites that each has a predetermined area comprising a capture agent that binds and immobilizes a corresponding target analyte of the sample; and iv the second plate has, on its surface, one or a plurality of corresponding storage sites that each has a predetermined area and comprises a detection agent of a concentration that, upon contacting the sample, dissolves into the sample and diffuses in the sample, wherein each capture agent, target analyte and corresponding detection agent is capable of forming a capture agent-target analyte-detection agent sandwich in a binding site of the first plate; wherein one of the configurations is an open configuration, in which: the two plates are either partially or completely separated apart, the spacing between the plates is not regulated by the spacers, and the sample is deposited on one or both of the plates, and wherein another of the configurations is a closed configuration which is configured after the sample deposition in the open configuration; and in the closed configuration: i. at least part of the sample is compressed into a layer of uniform thickness that is in contact with and confined by the inner surfaces of the two plates and that covers the one or a plurality of binding sites and the one or a plurality of storage sites, ii the one or a plurality of corresponding storage sites are over the one or a plurality of binding sites, and iii. the uniform thickness of the layer is regulated by the spacers and the plates, is less than 250 um, and is substantially less than the linear dimension of the predetermined area of each storage site; and iv. there is no fluidic isolation between the binding site and/or the storage sites, wherein the separation between the edges of the neighboring storage sites and the separation between the edges of the neighboring binding sites are larger than the distance that a target analyte or detection agent can diffuse in the relevant time, and wherein there is no fluidic isolation between the binding site sites and/or the storage sites.

In some embodiments, the first plate has, on its surface, a plurality of (at least 2, at least 4 or at least 16 or more) of the binding sites.

In some embodiments, each of said plurality of binding sites binds to a different target analyte.

In some embodiments, the second plate has, on its surface, a plurality (at least 2, at least 4 or at least 16 or more) of the corresponding storage sites.

In some embodiments, each of the plurality of corresponding storage sites binds to a different target analyte.

In some embodiments, the first plate has, on its surface, a plurality of said binding sites and the second plate has, on its surface, a plurality of said corresponding storage sites, wherein each binding site faces a corresponding storage site when the plates are in the closed configuration.

In some embodiments, the first plate has, on its surface, a plurality of said binding sites and the second plate has, on its surface, a storage site, wherein at least some of the binding sites face an area in the storage site when the plates are in the closed configuration.

In some embodiments the first plate has, on its surface, a binding site and the second plate has, on its surface, a plurality of storage sites, wherein at least some of the storage sites face an area in the binding site when the plates are in the closed configuration.

In some embodiments the first plate has, on its surface, a plurality of binding sites, wherein the binding sites contain different capture agents that bind and immobilize the same target analyte.

In some embodiments the first plate has, on its surface, a plurality of binding sites, wherein the binding sites contain the same capture agent.

In some embodiments, the capture agent is at different densities in the different binding sites. These embodiments may be used to provide a way to quantify the amount of analyte in a sample.

In some embodiments, there is a separation between two neighboring binding sites or two neighboring storage sites, and the ratio of the separation to the sample thickness in the closed configuration is at least 3, e.g., at least 5, at least 10, at least 20 or at least 50.

In some embodiments, the inter-spacer distance is in the range of 1 um to 120 um.

In some embodiments, the flexible plates have a thickness in the range of 20 um to 250 um (e.g., in the range of 50 um to 150 um) and Young's modulus in the range 0.1 to 5 GPa (e.g., in the range of 0.5-2 GPa).

In some embodiments, the thickness of the flexible plate times the Young's modulus of the flexible plate is in the range 60 to 750 GPa-um.

In some embodiments, this method may comprise (a) obtaining a sample that contains one or more target analytes, which are capable of diffusing in the sample; (b) obtaining a first and second plates that are movable relative to each other into different configurations, wherein: i. one or both of the plates comprise spacers that are fixed with a respective plate and one or both plates are flexible, ii. the spacers have a predetermined substantially uniform height and a predetermined constant inter-spacer distance, iii. the first plate has, on its surface, one or a plurality of binding sites that each has a predetermined area comprising a capture agent that binds and immobilizes a corresponding target analyte of (a); and iv. the second plate has, on its surface, one or a plurality of corresponding storage sites that each has a predetermined area and comprises a detection agent of a concentration that, upon contacting the sample, dissolves into the sample and diffuses in the sample, wherein each capture agent, target analyte and corresponding detection agent is capable of forming a capture agent-target analyte-detection agent sandwich in a binding site of the first plate; (c) depositing the sample on one or both of the plates when the plates are configured in an open configuration, wherein the open configuration is a configuration in which the two plates are either partially or completely separated apart and the spacing between the plates is not regulated by the spacers; (d) after (c), compressing the sample by bringing the two plates into a closed configuration, wherein the closed configuration is a configuration in which: i. at least part of the sample is compressed into a layer of uniform thickness that is in contact with and confined by the inner surfaces of the two plates and that is in contact with the one or a plurality of binding sites and the one or a plurality of storage sites, ii the one or a plurality of corresponding storage sites are over the one or a plurality of binding sites, and iii. the uniform thickness of the layer is regulated by the spacers and the plates, is less than 250 um, and is substantially less than the linear dimension of the predetermined area of each storage site; (e) after (d) and while the plates are in the closed configuration, either: (1) incubating the sample for a relevant time length and then stopping the incubation; or (2) incubating the sample for a time that is equal or longer than the minimum of a relevant time length and then assessing, within a time period that is equal or less than the maximum of the relevant length of time, the binding of each target analyte to a binding site; wherein the relevant time length is: i. equal to or longer than the time that it takes for a target analyte of (a) to diffuse across the thickness of the uniform thickness layer at the closed configuration; and ii.

significantly shorter than the time that it takes a target analyte of (a) to laterally diffuse across the smallest linear dimension of the predetermined area of a storage site or binding site; thereby producing a reaction in which, at the end of the incubation in (1) or during the assessing in (2), the majority of the capture agent-target analyte-detection agent sandwich bound to each binding site is from a corresponding relevant volume of the sample; wherein the incubation allows each target analyte to bind to a binding site and a detection agent, wherein the corresponding relevant volume is a portion of the sample that is above the corresponding storage site at the closed configuration, wherein the separation between the edges of the neighboring storage sites and the separation between the edges of the neighboring binding sites are larger than the distance that a target analyte or detection agent can diffuse in the relevant time, and wherein there is no fluidic isolation between the binding site sites and/or the storage sites.

Any embodiment of the multiplex assay device described above may be used in this method.

16 Small Volume Samples or Reagent in Wide Well (E)

Figure 8:
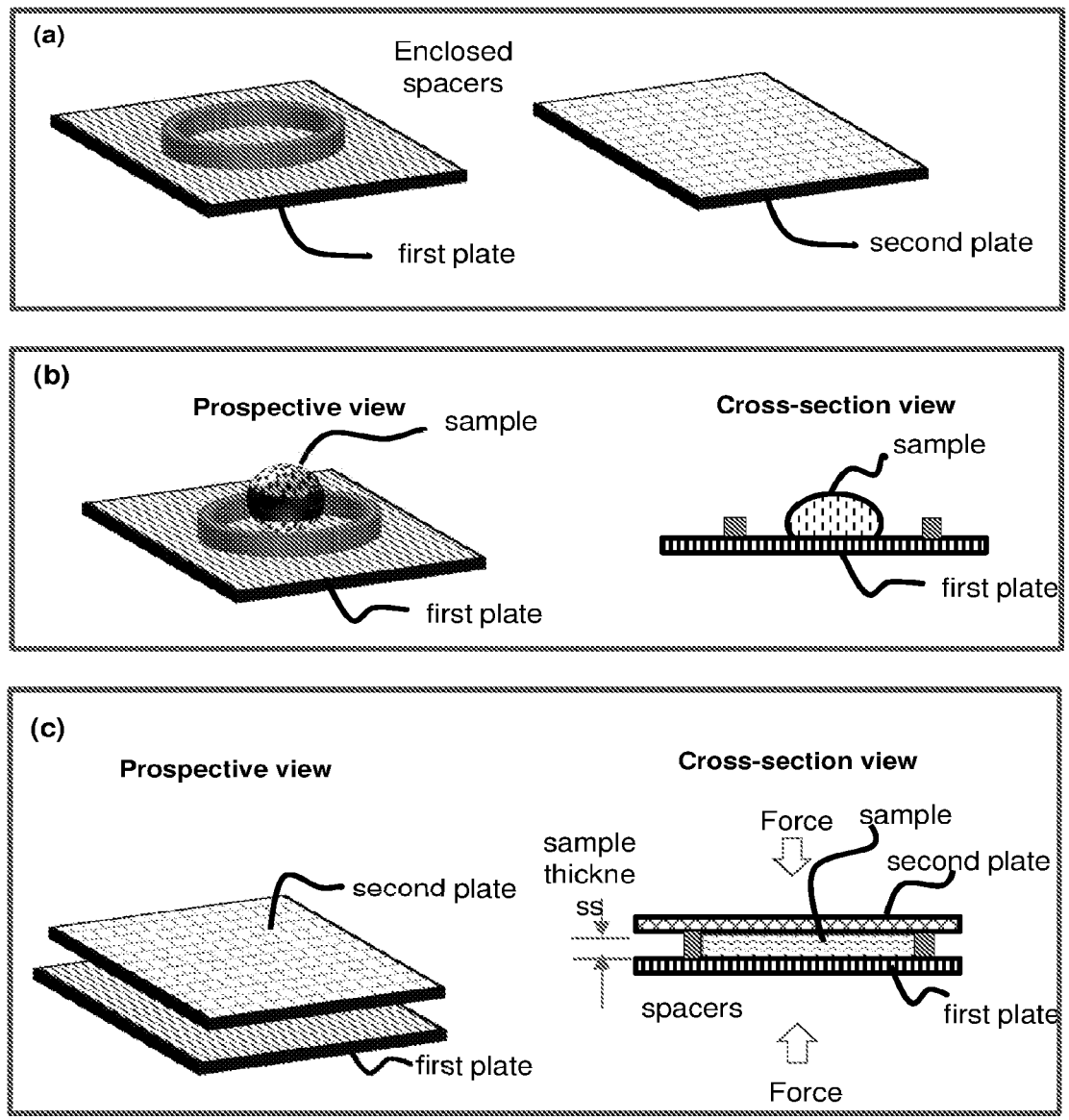
FIG. 8 illustrates plates and enclosed-spacers (well) for sample thickness regulation. Panel (a) illustrates a first plate and a second plate, wherein the first plate has an enclosed-spacer (well). Panel (b) illustrates depositing a sample on the first plate (shown), or the second plate (not shown), or both (not shown) at an open configuration. Panel (c) illustrates (i) using the two plates to spread the sample (the sample flow between the plates) and reduce the sample thickness, and (ii) using the spacers and the plate to regulate the sample thickness at the closed configuration.

In some applications, a well on a plate will be used for testing a sample with a sample volume small relative to the area of the well that sample must cover. One aspect of the present invention is the methods and devices that allow assaying and other chemical reactions of a small volume of sample or reagent in a wide well. The term "well" refers to a hollow compartment, recessed area, or a depression on a surface, which prevents a liquid deposited inside the well from flowing outside of the well by the well solid bottom and the enclosed sidewall (FIG. 8). The area of the well is the area enclosed by the sidewall. The term "a small volume of a sample" and "a wide well" mean that when the sample is dropped onto the well bottom and without any device to spread the sample, the volume of the sample on the well bottom has a contact area with the well bottom is less than the well area (i.e. the small and wide is a comparison of the sample natural contact area and the well bottom area). The well plays a role of enclosed spacer (E).

FIGS. 8 and 9 illustrate certain embodiments of plates and enclosed-spacers (well) for sample thickness regulation. Two exemplary embodiments are shown: (a) the first plate has an enclosed-spacer (well) and at least one spacer inside the well (FIG. 9), and (b) the first plate does not have a spacer inside the well (FIG. 8). Another embodiments is that before the first and second plates are in the closed configuration, the enclosed spacer is on one of the plate and the isolated spacer(s) are on another plate; and at the closed configuration of the plates, the isolated spacer(s) are inside of the well.

In one embodiment, the volume of the sample deposited on a well of the plate can have a predetermined volume (i.e. meter the volume to a specific volume) that is about equal to the inner volume of the well (i.e. inner well area times the well height), so that when the plates are in a closed configuration, the sample is nearly completely fill up the well, with no or nearly no sample flow out of the well.

In another embodiment, the volume of the sample deposited in a well of the plate are not metered, and at a closed configuration of the plate, a part of the sample fills up the well nearly completely, while the other part of the sample flow out of the well.

In another embodiments, a plurality of the wells are one plate. In some embodiments, there are trenches (dumping spaces) between wells for the samples that overflow from the wells. The dumping spaces prevent the sample overflow from one well flows into other well(s).

E1. As illustrated in FIG. 8, a method for assaying and/or chemical reactions with a small volume sample in a wide well, comprising:
(a) obtaining a first plate and a second plate that are movable relative to each other into different configurations, wherein the first plate has, on its surface, a well that has a predetermined dimension (including well bottom, depth, and rim) and a binding site at the bottom of the well;
(b) obtaining a sample that (i) contains target entity capable of binding to the binding site and diffusing in the sample, and (ii) has a volume and a wetting property such that the contact area of the sample deposited on only the bottom of the well, without contacting the second plate, is less than the area of the well bottom;
(c) depositing, when the plates are configured in an open configuration, the sample inside the well or on a corresponding area on the second plate, or both; wherein, in the open configuration: the two plates are partially or completely separated apart, and the spacing between the second plate and the bottom of the well is not regulated by the rim of the well (i.e. the depth of the well);
(d) after (c), spreading the sample by bringing the plates into a closed configuration;
wherein, in the closed configuration: the second plate covers over the well, the thickness of the sample on the binding site is regulated by the well and the second plate, and the sample has a larger contact area to the well bottom than that when the plates are in the open configuration;
wherein the corresponding area of the second plate is the area that is on top of the well and inside the rime of the well at the closed configuration.

In the method of paragraph E1, the plate further comprises at least an isolated spacer inside the well (i.e. well spacer).

In the method of paragraph E1, in some embodiments, the volume of the sample is metered (e.g. to have a selected volume). The metered volume is approximately equal to, less than, or larger than the volume of the well.

In the method of paragraph E1, in some embodiments, a compression force from outside of the plates is configured to hold the plates in the closed configuration.

In the method of a paragraph E1, in some embodiments, a capillary force is configured to hold the plates in the closed configuration.

As illustrated in FIG. 8*d*, in the method of paragraph E1, in some embodiments, the bottom of the well, the corresponding area of the second, or both are attached with spacers of predetermined heights, wherein at the closed configuration the sample thickness is regulated by the spacers, the rim, or both.

In some embodiments, the spacer height is equal to, less than, or larger than the depth of the well. The well bottom is planer (i.e. flat) or curved. In some embodiments, the spacers (1) have a predetermined inter spacer spacing, (2) inside a sample, (3) fixed to respective plates, or any combination of thereof.

In some embodiments, the volume of the sample is approximately equal to the volume of the well minus the volume of the spacers. In some embodiments, the second plate is configured to seal off the well.

In some embodiments, the ratio of the well area to the well depth square is 3 or larger, 5 or larger, 10 or larger, 20 or larger, 30 or larger, 50 or larger, 100 or larger, 200 or larger, 1000 or larger, 10,000 or larger, or a range between any two of the values.

The ratio of the well area to the well depth square is between 3 and 20 in a preferred embodiment, 20 and 100 in another preferred embodiment, and 100 and 1000 in another preferred embodiment, and 1000 and 10,000 in another preferred embodiment.

17 Quantification by Correcting Effects Generated by None-Sample Volume (C)

In a CROF process, often a sample is mixed with a none-sample-volume(s) which is due to objects that are not the sample, that include, but not limited to, spacers, air bubbles, dusts, or any combinations of thereof. The air bubbles or dust can be introduced using the sample deposition or other process in the CROF process. These none-sample objects occupy volume and inside the sample, which should be corrected in determine a relevant volume (a volume of interest) of a sample. One aspect of the present invention is to correct the effects generated by the none-sample volume inside a relevant volume of the sample between two plates, where the thickness of the relevant volume is regulated by spacers.

C1. A method for correcting the effects generated by a none-sample material in determining a relevant volume of a sample between two plates, comprising:
(a) obtaining a sample, wherein a relevant volume of the sample is to be quantified;
(b) obtaining two plates that are movable relative to each other into different configurations, wherein one or both of the plates comprise spacers and the spacers have a predetermined inter-spacer distance and height, and each of the spacers is fixed with its respective plate;
(c) depositing, when the plates are configured in an open configuration, the sample on one or both of the plates; wherein the open configuration is a configuration in which the two plates are partially or completely separated apart and the spacing between the plates is not regulated by the spacers;
(d) after (c), bringing the plates into a closed configuration, wherein, in the closed configuration: the plates are facing each other, the spacers and the relevant volume of the sample are between the plates, the thickness of the relevant volume of the sample is regulated by the plates and the spacers and is thinner than the maximum thickness of the sample when the plates are in the open configuration, and the relevant volume may contain a volume of a none-sample material;
(e) measuring, while the plates are in the closed configuration, (i) the lateral area of the relevant volume of the sample and (ii) the volume of the none-sample material; and
(f) calculating the relevant volume of the sample by using the thickness of the relevant volume regulated by the spacers and correcting the effects of a none-sample material;
wherein the relevant volume is at least a portion of an entire volume of the sample, and the none-sample materials are the materials that are not from the sample.
the measuring of the none-sample volume is by imaging of the sample between the two plates.

18 Precision Quantification by Double Checking the Spacing

In a CROF, for a given set of conditions, even the spacers and the plates can give a predetermining sample thickness at a closed configuration, the actual set of conditions during a particular CROF may be different from the expected, which lead to errors in the predetermined final sample thickness. To reduce such errors, one aspect of the present invention is to double check the final sample thickness at a closed configuration.

C2. A method for determining and checking a thickness of a relevant volume of a sample between two plates, comprising:
(a) obtaining a sample, wherein a relevant volume of the sample is to be quantified;
(b) obtaining two plates that are movable relative to each other into different configurations, wherein one or both of the plates comprise spacers and the spacers have a predetermined inter-spacer distance and height, and each of the spacers is fixed with its respective plate;
(c) depositing, when the plates are configured in an open configuration, the sample on one or both of the plates; wherein the open configuration is a configuration in which the two plates are partially or completely separated apart and the spacing between the plates is not regulated by the spacers;
(d) after (c), bringing the plates into a closed configuration, wherein, in the closed configuration: the plates are facing each other, the spacers and the relevant volume of the sample are between the plates, the thickness of the relevant volume of the sample is regulated by the plates and the spacers and is thinner than the maximum thickness of the sample when the plates are in the open configuration, and the relevant volume may contain a volume of a none-sample material;
(e) measuring, while the plates are in the closed configuration, (i) the lateral area of the relevant volume of the sample and (ii) the volume of the none-sample material; and
(f) calculating the relevant volume of the sample by correcting the effects of a none-sample material;
wherein the relevant volume is at least a portion of an entire volume of the sample, and the none-sample materials are the materials that are not from the sample.

19 Wash (WS)

In the present invention, one or any combinations of the embodiments of the plate pressing and holding described herein are used in all the methods and devices described in the entire description of the present invention.
A method for a wash step in assaying, comprising:
(a) Performing the steps in one or any combination of the methods described in above and
(b) washing away the sample or the transfer media between the plates.
In the method that uses CROF, the wash is performed by keep the plates in the closed-configuration.
In the method that uses CROF, the wash is performed by separating the plates from the closed-configuration.

20 Assays with Multiple Steps (MA)

In the present invention, the embodiments descripted by the disclosures (i.e. all sections) can be used in a combined (a) by combining one embodiment with other embodiment (s), by using the same embodiment(s) more than one times, and (c) any combination of (a) and (b).
MA1. A method for assaying an analyte in a sample, comprising:
(a) obtaining a sample with an analyte;
(b) performing the method that uses CROF; and
(c) separating the plates and performing the method that uses CROF.
In the method of paragraph MA1, in some embodiments, it further comprises, after the step (c) of MA1, a step of repeating the same steps of all the steps in the method of MA1 at least once.
MA2. A method for assaying an analyte in a sample, comprising:
(a) obtaining a sample with an analyte;
(b) performing the method that uses CROF;
(c) separating the plates and performing the method (washing) that uses CROF; and
(d) performing the method that uses CROF.
In the method of paragraph MA2, in some embodiments, it further comprises, after the step (d) in MA2, a step of repeating the same steps of all the steps in the method of MA2 at least once.
In the method of paragraph MA2, in some embodiments, it further comprises, after the step (c) in MA2, a step of repeating the same steps of all the steps in the method of MA1 at least once.
MA3. A kit for assaying an analyte in a sample, comprising:
a first CROF device that uses CROF; and
a third plate that, when the plates of the first CROF device are separated, combines with one of the plates of the first CROF device to form a second CROF device.
MA4. A kit for assaying an analyte in a sample, comprising:
a first CROF device that uses CROF;
at least one binding site or storage site that is on the sample contact area of the plate of a CROF device; and a third plate that, when the plates of the first CROF device are separated, combines with one of the plates of the first CROF device to form a second CROF device;

wherein the binding site binds a target analyte to the plate surface, and the storage site has a reagent that, upon in touch with the sample, can be dissolved into the sample and diffuse in the sample.

The imaging may comprise a use of a smart phone. The methods of this section may further comprise a step of illumination by a light source. The light source may be a laser, LED, a lamp, or a camera flash light.

A Kit (MQXA) for Performing Assay for Detecting a Target Entity in a Sample

A kit for assaying a target entity in a sample, may comprise:

a. a first plate, wherein one surface of the first plate has one or a plurality of binding site(s) that can immobilize a target entity and the binding site has binding partner that binds the target entity;

b. a cover plate;

c. a sample in the inner space between the cover plate and the first plate, wherein the sample contains said target entity that is mobile in the sample, the shape of sample is deformable, the first plate and the second plate are movable relative to each other, the shape of the sample is substantially conformal to the inner surfaces, at least a part of the sample is in contact to the binding site, and the inner spacing is, during incubation, less than certain distance. the sample is in contact with said binding sites;

d. an imaging device that can image the first plate surface and/or the cover plate surface; and e. a measuring device that can measure the spacing of the inner space.

The methods of this section may include use of a smart phone. The methods of this section may include use of an illuminating device. The illuminating device may comprise a laser, LED, a lamp, or a camera flash light.

21 Plate Pressing and Holding (H)

Compressing Forces.

In a CROF process, forces are used to compress the two plates to bring the plates from an open configuration to a closed configuration. The compressing forces reduce the spacing between the inner surfaces of the plates and hence a thickness of the sample that is between the plates. In the present invention, the compressing forces include, but not limited to, mechanical force, capillary forces (due to surface tensions), electrostatic force, electromagnetic force (including the light), and any combination of thereof.

In some embodiments of bring the plates from an open configuration to a closed configuration, an external force is applied to push the first plate and the second plate to toward each other.

In some embodiments of bring the plates from an open configuration to a closed configuration, an external pressure is applied to outside the first plate and the second plate to push the plates toward each other, and the pressure is higher than the pressure inside of the plate. A device is used to make the pressure of outside the plates higher than that inside the plate. The device include, in limited to, a sealing device.

In some embodiments, the compress force is at least partially provided by the capillary force, which is due to a liquid between the first plate and the second plate and the corresponding surface tensions and interactions with the plates. In some embodiments, the liquid is the sample itself, or the sample mixed with liquid. In certain embodiments, capillary force is used together with other forces. In many cases, a sample is often in liquid and the surface tensions are suited for inserting a capillary force. In some embodiments, the sample deformation by the plates can automatically stop when the capillary force equals to the force needed to deform the sample.

In certain embodiments, the compressing force (hence the sample deformation) is created by isolating the pressure between the first plate and the second plate (inside pressure) from that outside of the plates (outside pressure), and then make the inside pressure lower than the outside pressure. The isolation can be done using a vacuum seal or other devices.

In some embodiments, it is a combination of the methods described above.

Gradual Pressing.

In certain embodiments, the compressing force to bring the plates to a closed configuration is applied in a process, termed "gradual pressing", which comprises: pressing (i.e. applying the compressing the force) is applied at one location of the plate(s) first, then is applied gradually to other locations of the sample. In some embodiments of the gradual pressing, the compressing force (except the capillary forces by the sample itself) at one location is, after deformed the sample to a desired thickness at that location, (i) maintained during the entire process of the pressing and the sample deformation, (ii) removed while other locations being pressed, or (iii) a use of (i) for certain part of the plates and a use of (ii) for other part of the sample.

In one embodiment of the gradual pressing, a roller is being used to press the first plate and the second plate (the sample is between the plates, and the plates are slightly flexible) against another roller or a flat surface.

In another embodiment, the human fingers are the tool of the pressing the plates (hence the sample). The pressing is one part of human hand against another part of human body (including another part of human hand) or a human hand against an object (e.g. a table surface). In one embodiment, the pressing starts at one location of the sample and gradual moved to other locations of the sample.

In one embodiment of the gradual pressing, a pressed air jet is first directed to a location (e.g. the center) of the plate pair (which is between the first plate and the second plate, one of the plates is slightly flexible) and the pressure is gradually extended to other part of the plate pair.

In another embodiment, one or both of the first plate and the second plate is flexible and is in contact with one location of the sample, then a capillary force in that location pulls the plate pair together (toward to each other) to deform the sample.

Advantage of the gradual pressing include: it allows one to use less force to deform the sample (because for the same force, the smaller press area, the larger the pressure); it helps motion (deformation) of the sample, and/or it reduces air bubble in the sample. The larger pressure is, the more sample deformation will be. A gradual pressing can improve the thickness uniformity of the deformed sample.

Pressing Devices.

The devices for asserting the compressing force(s) for the sample deformation in CROF have several implementations. Some embodiments are to use human hand to press, for example, to press by human fingers. Certain embodiments are to use a press device, where the press device includes, but not limited to, a human hand(s), a mechanical clip, a mechanical press, mechanical clamp, a mechanical slider, a mechanical device, ab electromagnetic device, roller that rolls on a surface, two rollers against each other, fluidic press, a hydraulic device, or any combination of thereof. Certain embodiments are use pressured liquid (including pressed air) to press the first plate and/or the second plate directly or indirectly. "Directly" means the pressured liquid is applied directly on the first plate and/or the second plate; and the "indirectly" means it is applied through a third object. Certain embodiments in pressing use a combination of the above embodiments of pressing devices and methods.

Furthermore, in some embodiments of the sample deformation, the pressing and the sample deformation are monitored. The monitoring can be used to control the pressing and the sample deformation. The monitoring of the deformation include, but not limited to, a mechanical method, electrical, optical, chemical, magnetic, and any combination of thereof. The mechanical methods include, but not limited to, mechanical gauges, spacer (mechanical stoppers, more discussed below), and sound waves.

In CROF, the spacing control device comprises mechanical press, mechanical translation stages, human fingers, liquid that provide capillary forces that pulls the plates toward each other, liquid (including air) that applies a pressure on the plates, or a combination of thereof.

In certain embodiments, the mechanical stages (translational and/or rotational) are used for the sample deformation and sample thickness control and work together with the monitoring systems.

In some embodiments, the compressing force is at least partly supplied by a press (which is a device that bring the plates to a closed configuration) configured to press the plates together into the closed configuration.

In some embodiments, the plate pressing is to use a human hand. The human can be the person being tested or a person who perform the test, or a person who collecting the sample.

In some embodiments, the plate pressing is to hold the two plates together is to use a capillary force. The capillary force is generated by making at least a portion of the inner surface of one plate or both hydrophilic. With a proper capillary force, the two plates is able to maintain the same plate-spacing and the same thickness of the relevant volume of the sample as that when the plates initially in the closed configuration, even a part or all of the forces (except the capillary force) that were used to compress the plate to the close configuration is removed.

In some embodiments, the device that applies a compressing force on the outer surface of the plates to reducing the plate inner surface spacing comprise a contacting surface that is comfortable to the outer surfaces of the plate, wherein the contacting surface of the device is the surface of the device that contacts the outer surface of the plates, and the "conformable to the outer surface of the plate" means that the device surface can deform, during the compressing, it shape to conform the shape of the plate outer surface. In one exemplary embodiment, the compressing device is human figures. In another exemplary embodiment, the compressing device has a contacting surface made of soft plastics or rubbers.

Self-Holding (Maintaining the Final Sample Thickness after Removing Compressing Forces).

In some embodiments of pressing in CROF, after the sample deformation at a closed configuration, some of the compressing forces are removed and the sample maintains the same final sample thickness as the compression forces still exist. Such situation is termed "self-holding". One reason for self-holding is that after removing the compressing forces that were inserted from outside of the plate pair, there are still other forces exist between the inner surfaces of the plates, such as a capillary force, which hold the plate pair together. The capillary force is the due to the wetting properties of the sample on the plates.

To have self-holding, one needs to control the plate surface wetting properties, the total contact area of the sample to the plates, the final sample thickness at a closed configuration, or a combination of thereof.

In some embodiments to achieve self-holding, one or both inner surfaces of the plates is hydrophilic. Namely, it is either one of plates have an inner surface that is hydrophilic or both of the plates have an inner surface that is hydrophilic.

The capillary force depends on the radius curvature of the liquid surface, smaller the curvature and higher the capillary force. A smaller curvature can be achieved by using smaller spacing between the two plates (i.e. plate pair) and hence a smaller sample thickness. In some embodiments, a final sample thickness for achieving self-holding is 10 nm or less, 100 nm or less, 100 nm or less, 500 nm or less, 1 um (micrometer) or less, 2 um or less, 3 um or less, 5 um or less, 10 um or less, 20 um or less, 50 um or less, 70 um or less, 100 um or less, 150 um or less, 300 um or less, 500 um or less, 700 um or less, 1000 um or less, 1200 um or less, or a range between any two of the values.

In some embodiments, the area of the sample in contract with the plates for self-holding is at most 10 um$^2$, at most 100 um$^2$, at most 200 um$^2$, at most 500 um$^2$, at most 1000 um$^2$, at most 2000 um$^2$, at most 5000 um$^2$, at most 8,000 um$^2$, at most 0.01 mm$^2$, at most 0.05 mm$^2$, at most 0.1 mm$^2$, at most 0.5 mm$^2$, at most 1 mm$^2$, at most 5 mm$^2$, at most 10 mm$^2$, at most 50 mm$^2$, at most 100 mm$^2$, at most 500 mm$^2$, at most 1,000 mm$^2$, at most 2,000 mm$^2$, at most 5,000 mm$^2$, at most 10,000 mm$^2$, at most 100,000 mm$^2$, or a range between any two of the values.

In some embodiments, one or both of the plate inner surface's wetting properties is modified for better self-holding.

HS.1 In some embodiments, in a CROF process, a device is used to insert a compressing force to bring the plates into a closed configuration, and after the closed configuration is reached, the compressing force by the device is removed and the sample thickness and the inner surface spacing of the plates are remained approximately the same as that before removing the compressing force by the device. In some embodiments, in the methods of previous paragraph, it further comprises a step of reading a signal from the plates or between the plates, wherein the signal includes, but not limited to, a signal related to analytes, entity, labels, sample volume, concentration of a matter (i.e. chemicals), or any combination of thereof.

In the method of paragraph SH.1, the device is a human hand(s), a mechanical clip, a mechanical press, mechanical clamp, a mechanical slider, a mechanical device, ab electromagnetic device, roller that rolls on a surface, two rollers against each other, fluidic press, a hydraulic device, or any combination of thereof.

In the method of paragraph SH.1, in some embodiments, "the sample thickness and the inner surface spacing of the plates are remained approximately the same as that before removing the compressing force by the device" means that the relative difference of the sample thickness and the plate inner surface spacing before and after removing the compressing force is 0.001% or less, 0.01% or less, 0.1% or less; 0.5% or less, 1% or less, 2% or less, 5% or less, 8% or less, 10% or less, 15% or less, 20% or less, 30% or less, 40% or less, 50% or less, 60% or less, 70% or less, 80% or less, 90% or less, 99.9% or less, or a range between any of the values.

In the method of paragraph SH.1, in some embodiments, the sample thickness and the inner surface spacing of the plates after removing the compressing force by the device care predetermined, wherein predetermined means that the thickness and the spacing after removing the compressing force is known before applying the compressing force for a given compressing conditions.

H1. A method for reducing the thickness of a relevant volume of a sample and maintain the reduced thickness, comprising:

(a) obtaining a sample, wherein a thickness of a relevant volume of the sample is to be reduced;

(b) obtaining two plates that are movable relative to each other into different configurations, wherein one or both of the plates comprise spacers and the spacers have a predetermined inter-spacer distance and height, and each of the spacers is fixed with its respective plate;

(c) depositing, when the plates are configured in an open configuration, the sample on one or both of the plates; wherein the open configuration is a configuration in which the two plates are either partially or completely separated apart and the spacing between the plates is not regulated by the spacers;

(d) after (c), spreading the sample by using a pressing device that brings the plates into a closed configuration, wherein, in the closed configuration: the plates are facing each other, the spacers and the relevant volume of the sample are between the plates, the thickness of the relevant volume of the sample is regulated by the plates and the spacers and is thinner than the maximum thickness of the sample when the plates are in the open configuration, and at least one of the spacers is inside the sample; and (e) after (d), releasing the device, wherein after releasing the pressing device, the spacing between the plates remains the same as or approximately same as that when the device is applied.

wherein the relevant volume is at least a portion of an entire volume of the sample.

In the method of paragraph H1, the approximately same as the spacing between the plates is at most 1%, at most 2%, at most 5%, at most 10%, at most 20%, at most 50%, at most 60%, at most 70%, at most 80%, at most 90%, or a range between any two of the values.

For example, in CROF, a human hand or hands are used to compressed two plate to a closed position, then the hand(s) and hence the compressing force by hand(s) are removed, but the final sample thickness is still the same as that when the compressing force by hands exist.

22 Other Combinations

In the present invention, each of the embodiments in the disclosures (i.e. all sections) can be used (a) alone, (b) combined with other embodiment(s), (c) multiple times, and (d) any combination of (a) to (c).

The methods and devices in the present invention disclosed can be used alone or any combination of thereof. The term a "QMAX" method or device refers to a method or device of the embodiments described here.

In some embodiments, the methods and devices in the present invention disclosed can be used in the form of Q, X, A, M, QX, QA, QM, XA, XM, AM, QXA, QAM, XAM, and QXAM.

Some embodiments of application of the Q, X, A, and M to surface immobilization assay, comprising a. having a first plate, wherein the first plate surface has at least one well of a known depth and volume, and bottom surface of the well has one or a plurality of binding site(s) that can immobilize a target entity in a sample;

b. depositing, into the well, the sample of a volume approximately the same as the well volume, wherein the sample contains the targeted entity, the targeted entity is mobile in the sample, the shape of sample is deformable, and the sample covers only a part of the well (hence have a simple thickness higher than the well depth);

c. having a cover plate;

d. facing the first plate and the cover plate to each other, wherein the sample is between the inner surfaces of the first plate and the second plate;

e. reducing the sample thickness by reducing the spacing between the inner surfaces of the first plate and the second plate; and f. Incubating the sample at the reduced sample thickness for a period of time;

One variation of these methods is to apply one or more of the above steps to 96 well plates or other well plates.

The methods and devices in the present invention disclosed in Section 1, 2, 3, and 5, can be used alone or any combination of thereof. Specifically, we use Q for the inventions disclosed in Section 1 and 2, A for the inventions disclosed in Section 3 and 5, X for the inventions disclosed in Section 4 and 5, and M for the inventions disclosed in Section 6. Hence the methods and devices in the present invention disclosed in Section 1, 2, 3, and 5, can be used in the form of Q, X, A, M, QX, QA, QM, XA, XM, AM, QXA, QAM, XAM, and QXAM.

Some embodiments of application of the Q, X, A, and M to surface immobilization assay, comprising a. having a first plate, wherein the first plate surface has at least one well of a known depth and volume, and bottom surface of the well has one or a plurality of binding site(s) that can immobilize a target entity in a sample;

b. depositing, into the well, the sample of a volume approximately the same as the well volume, wherein the sample contains the targeted entity, the targeted entity is mobile in the sample, the shape of sample is deformable, and the sample covers only a part of the well (hence have a simple thickness higher than the well depth);

c. having a cover plate;

d. facing the first plate and the cover plate to each other, wherein the sample is between the inner surfaces of the first plate and the second plate;

e. reducing the sample thickness by reducing the spacing between the inner surfaces of the first plate and the second plate; and f. Incubating the sample at the reduced sample thickness for a period of time.

One variation of these methods is to apply one or more of the above steps to 96 well plates or other well plates.

Several embodiments of the methods, devices, and systems combine one or more of the features of sample volume quantification (Q), reagents addition (A), and/or assay acceleration (X) (and may be referred to as the corresponding acronyms QA, QX, AX, and QAX). Some experimental demonstrations of Q, A, X, QA, QX, AX, and QAX methods and devices are described below.

23 Reagents

The term "reagents" refers to, unless stated otherwise, one or more of biological agents, biochemical agents, and/or chemical agents. For example, reagents may include capture agents, detection agents, chemical compounds, optical labels, radioactive labels, enzymes, antibodies, proteins, nucleic acids, DNA, RNA, lipids, carbohydrates, salts, metals, surfactants, solvents, or any combination of thereof.

In some embodiments, the reagents on a plate in the form of liquid, solid, molecular vapor, or a combination of thereof. The deposition of reagent, include, but are not limited to, depositing, placing, printing, stamping, liquid dispensing, evaporation (thermal evaporation, vapor evaporation, human breathing), chemical vapor deposition, and/or sputtering. Different reagents can be in different locations. Reagents may be printed and/or deposited as small dots of reagents.

In some embodiments, the reagents are deposited on a plate in a liquid or vapor form first, then are dried to become dry reagents on the plate before a CROF process.

Controlling Reagents Releasing Time.

A-methods may further comprise a step of controlling the reagent release time (i.e. the time measures how fast a reagent can be dissolved in a sample. Some embodiments in controlling the reagent release time of a reagent comprises a step of mixing or coating on top of the reagent a or several "releasing control material(s)" that affect the release (into the sample) of the reagent. In some embodiments, the releasing control material can be another reagent. For example, there are two reagents A and B, the reagent A is coated on top of the reagent B, under certain conditions, the reagent A will be dissolved into the sample before the reagent B.

Furthermore, the surface properties of the first plate and the second plate may be used to control the reagent release. One example is to control the surface wetting properties. For many reagents, a hydrophobic surface binds the reagent well, hence leading to slow release or no release of the reagent into the sample (depending upon how thick is the reagent layer), while a hydrophilic surface binds the reagent poorly hence leading a fast release into the sample.

Drying of Reagents.

In some embodiments, after the reagent deposition step (c) but before the sample deposition step (d), A-methods further comprise a step of drying some or all of the reagents deposited in the step (c).

Location of Reagents.

Reagents may be applied and/or arranged on one or both of the plates. Reagents may be in storage sites (locations) on the plate(s), with each storage site including one or more reagents. Different storage sites may include different reagents, the same reagents, or one or more common reagents.

Control Concentration of Added Reagents. In some embodiments, the methods may further comprise a step of controlling the concentration of the added reagents by controlling the samples thickness over the storage sites (i.e., the surface with reagents).

The reagent used in the present invention may be any suitable reagent required for an assay, e.g., a labeled or unlabeled antibody, a labeled or unlabeled nucleic acid, an enzyme that may or may not contain an affinity moiety, etc. In some embodiments and as noted above, the stored reagent may be a component of an assay designed to test a blood or other liquid sample for the presence of an analyte. For example, chloride ions can be measured by any of the following protocols, and components of these assays may be present in a storage site: Colorimetric methods: chloride ions displace thiocyanate from mercuric thiocyanate. Free thiocyanate reacts with ferric ions to form a colored complex-ferric thiocyanate, which is measured photometrically. Coulometric methods: passage of a constant direct current between silver electrodes produces silver ions, which react with chloride, forming silver chloride. After all the chloride combines with silver ions, free silver ions accumulate, causing an increase in current across the electrodes and indicating the end point to the reaction. Mercurimetric methods: chloride is titrated with a standard solution of mercuric ions and forms HgCl2 soluble complex. The end point for the reaction is detected colorimetrically when excess mercury ions combine with an indicator dye, diphenylcarbazon, to form a blue color. Likewise, magnesium can be measured colorimetrically using calmagite, which turns a red-violet color upon reaction with magnesium; by a formazan dye test; emits at 600 nm upon reaction with magnesium or using methylthymol blue, which binds with magnesium to form a blue colored complex. Likewise, calcium can be detected by a colorimetric technique using O-Cresolphtalein, which turns a violet color upon reaction of O-Cresolphtalein complexone with calcium. Likewise, Bicarbonate cab ne tested bichromatically because bicarbonate ($HCO3^-$) and phosphoenolpyruvate (PEP) are converted to oxaloacetate and phosphate in the reaction catalyzed by phosphoenolpyruvate carboxylase (PEPC). Malate dehydrogenase (MD) catalyzes the reduction of oxaloacetate to malate with the concomitant oxidation of reduced nicotinamide adenine dinucleotide (NADH). This oxidation of NADH results in a decrease in absorbance of the reaction mixture measured bichromatically at 380/410 nm proportional to the Bicarbonate content of the sample. Blood urea nitrogen can be detected in a colorimetric test in which diacetyl, or fearon develops a yellow chromogen with urea and can be quantified by photometry, or multiusing the enzyme urease, which converts urea to ammonia and carbonic acid, which can be assayed by, e.g., i) decrease in absorbance at 340 nm when the ammonia reacts with alpha-ketoglutaric acid, ii) measuring the rate of increase in conductivity of the solution in which urea is hydrolyzed. Likewise, creatinine can be measured colorimetrically, by treated the sample with alkaline picrate solution to yield a red complex. In addition, creatine can be measured using a non-Jaffe reaction that measures ammonia generated when creatinine is hydrolyzed by creatinine iminohydrolase. Glucose can be measured in an assay in which blood is exposed to a fixed quantity of glucose oxidase for a finite period of time to estimate concentration. After the specified time, excess blood is removed and the color is allowed to develop, which is used to estimate glucose concentration. For example, glucose oxidase reaction with glucose forms nascent oxygen, which converts potassium iodide (in the filter paper) to iodine, forming a brown color. The concentration of glycosylated hemoglobin as an indirect read of the level of glucose in the blood. When hemolysates of red cells are chromatographed, three or more small peaks named hemoglobin A1a, A1b, and A1c are eluted before the main hemoglobin A peak. These "fast" hemoglobins are formed by the irreversible attachment of glucose to the hemoglobin in a two-step reaction. Hexokinase can be measured in an assay in which glucose is phosphorylated by hexokinase (HK) in the presence of adenosine triphosphate (ATP) and magnesium ions to produce glucose-6-phosphate and adenosine diphosphate (ADP). Glucose-6-phosphate dehydrogenase (G6P-DH) specifically oxidises glucose-6-phosphate to gluconate-6-phosphate with the concurrent reduction of NAD+ to NADH. The increase in absorbance at 340 nm is proportional to the glucose concentration in the sample. HDL, LDL, triglycerides can be measured using the Abell-Kendall protocol that involves color development with Liebermann-Burchard reagent (mixed reagent of acetic anhydride, glacial acetic acid, and concentrated sulfuric acid) at 620 nm after hydrolysis and extraction of cholesterol. A fluorometric analysis may be used utilized to determine triglyceride reference values. Plasma high-density lipoprotein cholesterol (HDL-C) determination is measured by the same procedures used for plasma total cholesterol, after precipitation of apoprotein B-containing lipoproteins in whole plasma (LDL and VLDL) by heparin-manganese chloride. These compounds can also be detected colorimetrically in an assay that is based on the enzyme driven reaction that quantifies both cholesterol esters and free cholesterol. Cholesterol esters are hydrolyzed via cholesterol esterase into cholesterol, which is then oxidized by cholesterol oxidase into the ketone cholest-4-en-3-one plus hydrogen peroxide. The hydrogen peroxide is then detected with a highly specific colorimetric probe. Horseradish peroxidase catalyzes the reaction between the probe and hydrogen peroxide, which bind in a 1:1 ratio. Samples may be compared to a known concentration of cholesterol standard.

24 Applications, Samples, and More Bio/Chemical Biomarkers

The applications of the present invention include, but not limited to, (a) the detection, purification and quantification of chemical compounds or biomolecules that correlates with the stage of certain diseases, e.g., infectious and parasitic disease, injuries, cardiovascular disease, cancer, mental disorders, neuropsychiatric disorders and organic diseases, e.g., pulmonary diseases, renal diseases, (b) the detection, purification and quantification of microorganism, e.g., virus, fungus and bacteria from environment, e.g., water, soil, or biological samples, e.g., tissues, bodily fluids, (c) the detection, quantification of chemical compounds or biological samples that pose hazard to food safety or national security, e.g. toxic waste, anthrax, (d) quantification of vital parameters in medical or physiological monitor, e.g., glucose, blood oxygen level, total blood count, (e) the detection and quantification of specific DNA or RNA from biosamples, e.g., cells, viruses, bodily fluids, (f) the sequencing and comparing of genetic sequences in DNA in the chromosomes and mitochondria for genome analysis or (g) to detect reaction products, e.g., during synthesis or purification of pharmaceuticals. The present invention also can be used in the various fields include, but not limited to, human, veterinary, agriculture, foods, environments, drug testing, and others.

The detection can be carried out in various sample matrix, such as cells, tissues, bodily fluids, and stool. Bodily fluids of interest include but are not limited to, amniotic fluid, aqueous humour, vitreous humour, blood (e.g., whole blood, fractionated blood, plasma, serum, etc.), breast milk, cerebrospinal fluid (CSF), cerumen (earwax), chyle, chime, endolymph, perilymph, feces, gastric acid, gastric juice, lymph, mucus (including nasal drainage and phlegm), pericardial fluid, peritoneal fluid, pleural fluid, pus, rheum, saliva, sebum (skin oil), semen, sputum, sweat, synovial fluid, tears, vomit, urine and exhaled condensate. In some embodiments, the sample comprises a human body fluid. In some embodiments, the sample comprises at least one of cells, tissues, bodily fluids, stool, amniotic fluid, aqueous humour, vitreous humour, blood, whole blood, fractionated blood, plasma, serum, breast milk, cerebrospinal fluid, cerumen, chyle, chime, endolymph, perilymph, feces, gastric acid, gastric juice, lymph, mucus, nasal drainage, phlegm, pericardial fluid, peritoneal fluid, pleural fluid, pus, rheum, saliva, sebum, semen, sputum, sweat, synovial fluid, tears, vomit, urine, and exhaled condensate.

In embodiments, the sample is at least one of a biological sample, an environmental sample, and a biochemical sample.

In some embodiments, the sample is at least one of a biological sample, an environmental sample, and a biochemical sample.

In any embodiment, the CROF device may be placed in a microfluidic device and the applying step b) may include applying a sample to a microfluidic device comprising the CROF device.

In any embodiment, the reading step d) may include detecting a fluorescence or luminescence signal from the CROF device.

In any embodiment, the reading step d) may include reading the CROF device with a handheld device configured to read the CROF device. The handheld device may be a mobile phone, e.g., a smart phone.

In any embodiment, the CROF device may include a labeling agent that can bind to an analyte-capture agent complex on the CROF device.

In any embodiment, the devices, systems and methods in the present invention may further include, between steps c) and d), the steps of applying to the CROF device a labeling agent that binds to an analyte-capture agent complex on the CROF device, and washing the CROF device.

In any embodiment, the reading step d) may include reading an identifier for the CROF device. The identifier may be an optical barcode, a radio frequency ID tag, or combinations thereof.

In any embodiment, the devices, systems and methods in the present invention may further include applying a control sample to a control CROF device containing a capture agent that binds to the analyte, wherein the control sample includes a known detectable amount of the analyte, and reading the control CROF device, thereby obtaining a control measurement for the known detectable amount of the analyte in a sample.

In any embodiment, the sample may be a diagnostic sample obtained from a subject, the analyte may be a biomarker, and the measured amount of the analyte in the sample may be diagnostic of a disease or a condition.

The amount of sample may be about a drop of a sample. The amount of sample may be the amount collected from a pricked finger or fingerstick. The amount of sample may be the amount collected from a microneedle or a venous draw.

A sample may be used without further processing after obtaining it from the source, or may be processed, e.g., to enrich for an analyte of interest, remove large particulate matter, dissolve or resuspend a solid sample, etc.

Any suitable method of applying a sample to the CROF device may be employed. Suitable methods may include using a pipet, dropper, syringe, etc. In certain embodiments, when the CROF device is located on a support in a dipstick format, as described below, the sample may be applied to the CROF device by dipping a sample-receiving area of the dipstick into the sample.

A sample may be collected at one time, or at a plurality of times. Samples collected over time may be aggregated and/or processed (by applying to a CROF device and obtaining a measurement of the amount of analyte in the sample, as described herein) individually. In some instances, measurements obtained over time may be aggregated and may be useful for longitudinal analysis over time to facilitate screening, diagnosis, treatment, and/or disease prevention.

Washing the CROF device to remove unbound sample components may be done in any convenient manner, as described above. In certain embodiments, the surface of the CROF device is washed using binding buffer to remove unbound sample components.

Detectable labeling of the analyte may be done by any convenient method. The analyte may be labeled directly or indirectly. In direct labeling, the analyte in the sample is labeled before the sample is applied to the CROF device. In indirect labeling, an unlabeled analyte in a sample is labeled after the sample is applied to the CROF device to capture the unlabeled analyte, as described below.

Data Processing.

In certain embodiments, the subject device is configured to process data derived from reading the CROF device. The device may be configured in any suitable way to process the data for use in the subject methods. In certain embodiments, the device has a memory location to store the data and/or store instructions for processing the data and/or store a database. The data may be stored in memory in any suitable format.

In certain embodiments, the device has a processor to process the data. In certain embodiments, the instructions for processing the data may be stored in the processor, or may be stored in a separate memory location. In some embodiments, the device may contain a software to implement the processing.

In certain embodiments, a device configured to process data acquired from the CROF device contains software implemented methods to perform the processing. Software implemented methods may include one or more of: image acquisition algorithms; image processing algorithms; user interface methods that facilitate interaction between user and computational device and serves as means for data collection, transmission and analysis, communication protocols; and data processing algorithms. In certain embodiments, image processing algorithms include one or more of: a particle count, a LUT (look up table) filter, a particle filter, a pattern recognition, a morphological determination, a histogram, a line profile, a topographical representation, a binary conversion, or a color matching profile.

In certain embodiments, the device is configured to display information on a video display or touchscreen display when a display page is interpreted by software residing in memory of the device. The display pages described herein may be created using any suitable software language such as, for example, the hypertext markup language ("HTML"), the dynamic hypertext markup language ("DHTML"), the extensible hypertext markup language ("XHTML"), the extensible markup language ("XML"), or another software language that may be used to create a computer file displayable on a video or other display in a manner perceivable by a user. Any computer readable media with logic, code, data, instructions, may be used to implement any software or steps or methodology. Where a network comprises the Internet, a display page may comprise a webpage of a suitable type.

A display page according to the invention may include embedded functions comprising software programs stored on a memory device, such as, for example, VBScript routines, JScript routines, JavaScript routines, Java applets, ActiveX components, ASP.NET, AJAX, Flash applets, Silverlight applets, or AIR routines.

A display page may comprise well known features of graphical user interface technology, such as, for example, frames, windows, scroll bars, buttons, icons, and hyperlinks, and well known features such as a "point and click" interface or a touchscreen interface. Pointing to and clicking on a graphical user interface button, icon, menu option, or hyperlink also is known as "selecting" the button, option, or hyperlink. A display page according to the invention also may incorporate multimedia features, multi-touch, pixel sense, IR LED based surfaces, vision-based interactions with or without cameras.

A user interface may be displayed on a video display and/or display page. The user interface may display a report generated based on analyzed data relating to the sample, as described further below.

The processor may be configured to process the data in any suitable way for use in the subject methods. The data is processed, for example, into binned data, transformed data (e.g., time domain data transformed by Fourier Transform to frequency domain), or may be combined with other data. The processing may put the data into a desired form, and may involve modifying the format of data. Processing may include detection of a signal from a sample, correcting raw data based on mathematical manipulation or correction and/or calibrations specific for the device or reagents used to examine the sample; calculation of a value, e.g., a concentration value, comparison (e.g., with a baseline, threshold, standard curve, historical data, or data from other sensors), a determination of whether or not a test is accurate, highlighting values or results that are outliers or may be a cause for concern (e.g., above or below a normal or acceptable range, or indicative of an abnormal condition), or combinations of results which, together, may indicate the presence of an abnormal condition, curve-fitting, use of data as the basis of mathematical or other analytical reasoning (including deductive, inductive, Bayesian, or other reasoning), and other suitable forms of processing. In certain embodiments, processing may involve comparing the processed data with a database stored in the device to retrieve instructions for a course of action to be performed by the subject.

In certain embodiments, the device may be configured to process the input data by comparing the input data with a database stored in a memory to retrieve instructions for a course of action to be performed by the subject. In some embodiments, the database may contain stored information that includes a threshold value for the analyte of interest. The threshold value may be useful for determining the presence or concentration of the one or more analytes. The threshold value may be useful for detecting situations where an alert may be useful. The data storage unit may include records or other information that may be useful for generating a report relating to the sample.

In certain embodiments, the device may be configured to receive data that is derived from the CROF device. Thus in certain cases, the device may be configured to receive data that is not related to the sample provided by the subject but may still be relevant to the diagnosis. Such data include, but are not limited to the age, sex, height, weight, individual and/or family medical history, etc. In certain embodiments, the device is configured to process data derived from or independently from a sample applied to the CROF device.

Network.

In certain embodiments the device may be configured to communicate over a network such as a local area network (LAN), wide area network (WAN) such as the Internet, personal area network, a telecommunications network such as a telephone network, cell phone network, mobile network, a wireless network, a data-providing network, or any other type of network. In certain embodiments the device may be configured to utilize wireless technology, such as Bluetooth or RTM technology. In some embodiments, the device may be configured to utilize various communication methods, such as a dial-up wired connection with a modem, a direct link such as TI, integrated services digital network (ISDN), or cable line. In some embodiments, a wireless connection may be using exemplary wireless networks such as cellular, satellite, or pager networks, general packet radio service (GPRS), or a local data transport system such as Ethernet or token ring over a LAN. In some embodiments, the device may communicate wirelessly using infrared communication components.

In certain embodiments, the device is configured to receive a computer file, which can be stored in memory, transmitted from a server over a network. The device may receive tangible computer readable media, which may contain instructions, logic, data, or code that may be stored in persistent or temporary memory of the device, or may affect or initiate action by the device. One or more devices may communicate computer files or links that may provide access to other computer files.

In some embodiments, the device is a personal computer, server, laptop computer, mobile device, tablet, mobile phone, cell phone, satellite phone, smartphone (e.g., iPhone, Android, Blackberry, Palm, Symbian, Windows), personal digital assistant, Bluetooth device, pager, land-line phone, or other network device. Such devices may be communication-enabled devices. The term "mobile phone" as used herein refers to a telephone handset that can operate on a cellular network, a Voice-Over IP (VoIP) network such as Session Initiated Protocol (SIP), or a Wireless Local Area Network (WLAN) using an 802.11x protocol, or any combination thereof. In certain embodiments, the device can be hand-held and compact so that it can fit into a consumer's wallet and/or pocket (e.g., pocket-sized).

Environmental Testing.

As summarized above, the devices, systems and methods in the present invention may find use in analyzing an environmental sample, e.g., a sample from water, soil, industrial waste, etc., for the presence of environmental markers. An environmental marker may be any suitable marker, that can be captured by a capturing agent that specifically binds the environmental marker in a CROF device configured with the capturing agent. The environmental sample may be obtained from any suitable source, such as a river, ocean, lake, rain, snow, sewage, sewage processing runoff, agricultural runoff, industrial runoff, tap water or drinking water, etc. In some embodiments, the devices and systems in the present invention detect the concentration of lead or toxins in water. In some embodiments, the presence or absence, or the quantitative level of the environmental marker in the sample may be indicative of the state of the environment from which the sample was obtained. In some cases, the environmental marker may be a substance that is toxic or harmful to an organism, e.g., human, companion animal, plant, etc., that is exposed to the environment. In some cases, the environmental marker may be an allergen that may cause allergic reactions in some individuals who are exposed to the environment. In some instances, the presence or absence, or the quantitative level of the environmental marker in the sample may be correlated with a general health of the environment. In such cases, the general health of the environment may be measured over a period of time, such as week, months, years, or decades.

In some embodiments, the devices, systems and methods in the present invention further includes receiving or providing a report that indicates the safety or harmfulness for a subject to be exposed to the environment from which the sample was obtained based on information including the measured amount of the environmental marker. The information used to assess the safety risk or health of the environment may include data other than the type and measured amount of the environmental marker. These other data may include the location, altitude, temperature, time of day/month/year, pressure, humidity, wind direction and speed, weather, etc. The data may represent an average value or trend over a certain period (minutes, hours, days, weeks, months, years, etc.), or an instantaneous value over a shorter period (milliseconds, seconds, minutes, etc.).

The report may be generated by the device configured to read the CROF device, or may be generated at a remote location upon sending the data including the measured amount of the environmental marker. In some cases, an expert may be at the remote location or have access to the data sent to the remote location, and may analyze or review the data to generate the report. The expert may be a scientist or administrator at a governmental agency, such as the US Centers for Disease Control (CDC) or the US Environmental Protection Agency (EPA), a research institution, such as a university, or a private company. In certain embodiments, the expert may send to the user instructions or recommendations based on the data transmitted by the device and/or analyzed at the remote location.

Foodstuff Testing.

As summarized above, the devices, systems and methods in the present invention may find use in analyzing a foodstuff sample, e.g., a sample from raw food, processed food, cooked food, drinking water, etc., for the presence of foodstuff markers. A foodstuff marker may be any suitable marker, such as those shown in Table B9, below, that can be captured by a capturing agent that specifically binds the foodstuff marker in a CROF device configured with the capturing agent. The environmental sample may be obtained from any suitable source, such as tap water, drinking water, prepared food, processed food or raw food, etc. In some embodiments, the presence or absence, or the quantitative level of the foodstuff marker in the sample may be indicative of the safety or harmfulness to a subject if the food stuff is consumed. In some embodiments, the foodstuff marker is a substance derived from a pathogenic or microbial organism that is indicative of the presence of the organism in the foodstuff from which the sample was obtained. In some embodiments, the foodstuff marker is a toxic or harmful substance if consumed by a subject. In some embodiments, the foodstuff marker is a bioactive compound that may unintentionally or unexpectedly alter the physiology if consumed by the subject. In some embodiments, the foodstuff marker is indicative of the manner in which the foodstuff was obtained (grown, procured, caught, harvested, processed, cooked, etc.). In some embodiments, the foodstuff marker is indicative of the nutritional content of the foodstuff. In some embodiments, the foodstuff marker is an allergen that may induce an allergic reaction if the foodstuff from which the sample is obtained is consumed by a subject.

In some embodiments, the devices, systems and methods in the present invention further includes receiving or providing a report that indicates the safety or harmfulness for a subject to consume the food stuff from which the sample was obtained based on information including the measured level of the foodstuff marker. The information used to assess the safety of the foodstuff for consumption may include data other than the type and measured amount of the foodstuff marker. These other data may include any health condition associated with the consumer (allergies, pregnancy, chronic or acute diseases, current prescription medications, etc.).

The report may be generated by the device configured to read the CROF device, or may be generated at a remote location upon sending the data including the measured amount of the foodstuff marker. In some cases, a food safety expert may be at the remote location or have access to the data sent to the remote location, and may analyze or review the data to generate the report. The food safety expert may be a scientist or administrator at a governmental agency, such as the US Food and Drug Administration (FDA) or the CDC, a research institution, such as a university, or a private company. In certain embodiments, the food safety expert may send to the user instructions or recommendations based on the data transmitted by the device and/or analyzed at the remote location.

25 Blood Testing

Some exemplary embodiments of the application of the present invention are in simple, rapid blood cell counting using a smartphone.

In some embodiments, the first plate and the second plate are selected from a thin glass slide (e.g. 0.2 mm thick) or a thin plastic film (e.g. 15 mm thick) of a relative flat surface, and each have an areas with a length and width in about 0.5 cm to 10 cm. The spacers are made of glass, plastics, or other materials that would not deform significantly under a pressing. Before the sample deposition, the spacer are placed on the first plate, the second plate or both; and the first plate, the second plate or both are optionally coated with reagent that facilitate the blood counting (staining dyes and/or anticoagulant). The first plate and the second plate can be optionally sealed in a bag for easy transport and longer shelf life-time.

In blood cell count testing, only about 1 uL (microliter) (or about 0.1 uL to 3 uL) of blood is needed for the sample, which can be taken from a finger or other human body location. The blood sample can be directly deposited from human body (e.g. finger) onto the first plate and the second plate, without any dilution. Then the first plate and the second plate are made facing each other, so that blood sample is between the inner surfaces of the first plate and the second plate. If the optional reagents are pre-deposited (staining dyes or anticoagulant), they are deposited on the inner surface for mixing with the sample. Then the first plate and the second plate are pressed by fingers or a simple mechanical device (e.g. a clip that presses using a spring). Under the press, the inner spacing is reduced, the reduction will be eventually stopped at the value set by the spacers' height and the final sample thickness is reached, which generally is equal to the final inner spacing. Since the final inner spacing is known, the final sample thickness become known, namely being quantified (measured) by this method.

If the blood sample is not diluted, after pressing (sample deformation) the spacers and hence the final sample thickness may be thin, e.g., less 1 um, less 2 um, less 3 um, less 4 um, less 5 um, less 7 um, less 10 um, less 15 um, less 20 um, less 30 um, less 40 um, less 50 um, less 60 um, less 80 um, less 100 um, less 150 um, or any ranges between any of the two numbers. A thin final sample may be useful because if the final sample thickness is thick, then many red cells may overlap during the imaging, which can make the cell counting inaccurate. For example, about 4 um thick of whole blood without dilution will give about one layer of blood red cells.

After the pressing, the sample may be imaged by a smartphone either directly or through an additional optical elements (e.g. lenses, filters, or light sources as needed). The image of the sample will be processed to identify the types of the cells as well as the cell number. The image processing can be done locally at the same smartphone that takes the image or remotely but the final result transmitted back to the smartphone (where the image is transmitted to a remote location and is processed there.) The smart phone will display the cell number for a particular cell. In some cases, certain advices will be displayed. The advices can stored on the smartphone before the test or come from a remote machines or professionals.

In certain embodiments, reagents will be put on the inner surfaces of the first plate and/or the second plate using the methods and devices described in Section 5 (Reagent mixing).

A device or a method for the blood testing comprises (a) a device or a method in paragraph described herein and (b) a plate spacing (i.e. the distance between the inner surfaces of the two plates) at the closed configuration or a use of such spacing, wherein a undiluted whole blood in the plate-spacing has an average inter-cell distance in the lateral direction for the red blood cells (RBC) larger than the average diameter of the disk shape of the RBC.

A device or a method to arrange the orientation of a non-spherical cell comprises (a) a device or a method in as described herein and (b) a plate spacing (i.e. the distance between the inner surfaces of the two plates) at the closed configuration or a use of such spacing, wherein the spacing less than the average size of the cell in its long direction (the long direction is the maximum dimension direction of a cell). Such arrangement can improve the measurements of the sample volume (e.g. red blood cell volume).

In the present invention, the analytes in the blood tests include protein markers, a list of which may be found at the website of the American Association for Clinical Chemistry).

26 Packages

Another aspect of the present invention is related to packaging, which would prolong the lifetime of the reagent used and facilitate the easy of the use.

In some embodiments, the plates in CROF with or without reagents are put inside a package, either one plate per package or more than one plates per package. In one embodiment, the first plate and second plate are packaged in a different package before a use. In some embodiments, different assays share a common first plate or a common second plate.

In some embodiments, each of the packages is sealed. In some embodiments, the seal is for preventing the air, chemicals, moisture, contamination, or any combination of them from outside of the package from entering inside the package. In some embodiments, the package is vacuum sealed or fill with nitrogen gas, or inner gases. In some embodiments, a material that can prolong a shelf-life-time of the plate and/or the reagents (including the capture agents, detection agents, etc.) is packaged inside the package with a plate.

In some embodiments, the package materials are a thin layer form, so that the package can be easily torn apart by a human hand.

27 PoC, SmartPhone, and Network

An aspect of the invention is directed to a method for monitoring the health status of a subject, the method including: applying a sample provided from a subject to a CROF based detector configured to indicate an output that is representative of the sample; processing the detector output with a device configured to acquire the detector output as input data and to analyze the input data to generate a report; and receiving the report. The signal enhancing detector offers the advantages of fast detection, simplified reader (e.g. replace large conventional reader by smarphone), and lost cost.

Body Fluid.

In certain embodiments, a sample may include various fluid or solid samples. In some instances, the sample can be a bodily fluid sample from the subject. In some instances, solid or semi-solid samples can be provided. The sample can include tissues and/or cells collected from the subject. The sample can be a biological sample. Examples of biological samples can include but are not limited to, blood, serum, plasma, a nasal swab, a nasopharyngeal wash, saliva, urine, gastric fluid, spinal fluid, tears, stool, mucus, sweat, earwax, oil, a glandular secretion, cerebral spinal fluid, tissue, semen, vaginal fluid, interstitial fluids derived from tumorous tissue, ocular fluids, spinal fluid, a throat swab, breath, hair, finger nails, skin, biopsy, placental fluid, amniotic fluid, cord blood, lymphatic fluids, cavity fluids, sputum, pus, microbiota, meconium, breast milk and/or other excretions. The samples may include nasopharyngeal wash. Nasal swabs, throat swabs, stool samples, hair, finger nail, ear wax, breath, and other solid, semi-solid, or gaseous samples may be processed in an extraction buffer, e.g., for a fixed or variable amount of time, prior to their analysis. The extraction buffer or an aliquot thereof may then be processed similarly to other fluid samples if desired. Examples of tissue samples of the subject may include but are not limited to, connective tissue, muscle tissue, nervous tissue, epithelial tissue, cartilage, cancerous sample, or bone.

In certain embodiments, the subject may be a human or a non-human animal. The subject may be a mammal, vertebrate, such as murines, simians, humans, farm animals, sport animals, or pets. In some embodiments, the subject may be a patient. In other embodiments, the subject may be diagnosed with a disease, or the subject may not be diagnosed with a disease. In some embodiments, the subject may be a healthy subject.

Device Reading

As summarized above, aspects of the method include processing the signal enhancing detector output with a device configured to acquire the detector output as input data and process the input data to generate a report. Any device suitable for acquiring the detector output as input data and processing the input data to generate a report may be used. In some embodiments, the device includes an optical recording apparatus that is configured to acquire an optical detector output as input data. In certain instances, the optical recording apparatus is a camera, such as a digital camera. The term "digital camera" denotes any camera that includes as its main component an image-taking apparatus provided with an image-taking lens system for forming an optical image, an image sensor for converting the optical image into an electrical signal, and other components, examples of such cameras including digital still cameras, digital movie cameras, and Web cameras (i.e., cameras that are connected, either publicly or privately, to an apparatus connected to a network to permit exchange of images, including both those connected directly to a network and those connected to a network by way of an apparatus, such as a personal computer, having an information processing capability). In one example, the input data may include video imaging that may capture changes over time. For example, a video may be acquired to provide evaluation on dynamic changes in the sample.

In certain embodiments, the device acquires the detector output by means of an adaptor that forms an interface between the device and the detector. In certain embodiments, the interface is universal to be compatible with any device suitable for performing the subject method. Interfaces of interest include, but are not limited to, USB, firewire, Ethernet, etc. In certain embodiments, the device acquires the detector output by wireless communication, including cellular, Bluetooth, WiFi, etc.

In certain embodiments, the device may have a video display. Video displays may include components upon which a display page may be displayed in a manner perceptible to a user, such as, for example, a computer monitor, cathode ray tube, liquid crystal display, light emitting diode display, touchpad or touchscreen display, and/or other means known in the art for emitting a visually perceptible output. In certain embodiments, the device is equipped with a touch screen for displaying information, such as the input data acquired from the detector and/or the report generated from the processed data, and allowing information to be entered by the subject.

In certain embodiments, the device is equipped with vibration capabilities as a way to alert the subject, for example, of a report generated upon processing the detector output or in preparation for acquiring an output from the detector.

In certain embodiments, the device is configured to display information on a video display or touchscreen display when a display page is interpreted by software residing in memory of the device. The display pages described herein may be created using any suitable software language such as, for example, the hypertext mark up language ("HTML"), the dynamic hypertext mark up language ("DHTML"), the extensible hypertext mark up language ("XHTML"), the extensible mark up language ("XML"), or another software language that may be used to create a computer file displayable on a video or other display in a manner perceivable by a user. Any computer readable media with logic, code, data, instructions, may be used to implement any software or steps or methodology. Where a network comprises the Internet, a display page may comprise a webpage of a suitable type.

A display page according to the invention may include embedded functions comprising software programs stored on a memory device, such as, for example, VBScript routines, JScript routines, JavaScript routines, Java applets, ActiveX components, ASP.NET, AJAX, Flash applets, Silverlight applets, or AIR routines.

A display page may comprise well known features of graphical user interface technology, such as, for example, frames, windows, scroll bars, buttons, icons, and hyperlinks, and well known features such as a "point and click" interface or a touchscreen interface. Pointing to and clicking on a graphical user interface button, icon, menu option, or hyperlink also is known as "selecting" the button, option, or hyperlink A display page according to the invention also may incorporate multimedia features, multi-touch, pixel sense, IR LED based surfaces, vision-based interactions with or without cameras.

In certain embodiments, the device may be configured to acquire data that is not an output from the signal enhancing detector. Thus in certain cases, the device may be configured to acquire data that is not representative of the sample provided by the subject but may still be representative of the subject. Such data include, but are not limited to the age, sex, height, weight, individual and family medical history, etc. In certain embodiments, the device is configured to process the input data acquired from the detector output combined with data that was acquired independently of the detector output.

In certain embodiments the device may be configured to communicate over a network such as a local area network (LAN), wide area network (WAN) such as the Internet, personal area network, a telecommunications network such as a telephone network, cell phone network, mobile network, a wireless network, a data-providing network, or any other type of network. In certain embodiments the device may be configured to utilize wireless technology, such as Bluetooth or RTM technology. In some embodiments, the device may be configured to utilize various communication methods, such as a dial-up wired connection with a modem, a direct link such as TI, ISDN, or cable line. In some embodiments, a wireless connection may be using exemplary wireless networks such as cellular, satellite, or pager networks, GPRS, or a local data transport system such as Ethernet or token ring over a LAN. In some embodiments, the device may communicate wirelessly using infrared communication components.

In certain embodiments, the device is configured to receive a computer file, which can be stored in memory, transmitted from a server over a network. The device may receive tangible computer readable media, which may contain instructions, logic, data, or code that may be stored in persistent or temporary memory of the device, or may somehow affect or initiate action by the device. One or more devices may communicate computer files or links that may provide access to other computer files.

In some embodiments, the device is a personal computer, server, laptop computer, mobile device, tablet, mobile phone, cell phone, satellite phone, smartphone (e.g., iPhone, Android, Blackberry, Palm, Symbian, Windows), personal digital assistant, Bluetooth device, pager, land-line phone, or other network device. Such devices may be communication-enabled devices. The term "mobile phone" as used herein refers to a telephone handset that can operate on a cellular network, a Voice-Over IP (VoIP) network such as Session Initiated Protocol (SIP), or a Wireless Local Area Network (WLAN) using an 802.11x protocol, or any combination thereof. In certain embodiments, the device can be hand-held and compact so that it can fit into a consumer's wallet and/or pocket (e.g., pocket-sized).

In certain embodiments, the method includes transmitting the sample-derived data to a remote location where the transmitted data is analyzed. The remote location may be a location that is different from the location where the device is located. The remote location may include, but is not limited to, a hospital, doctor's office or other medical facility, or a research laboratory. In some instances, the remote location may have a computer, e.g., a server, that is configured to communicate with (i.e. receive information from and transmit information to) the device over a network. In some embodiments, the device may transmit data to a cloud computing infrastructure. The device may access the cloud computing infrastructure. In some embodiments, on-demand provision of computational resources (data, software) may occur via a computer network, rather than from a local computer. The device may contain very little software or data (perhaps a minimal operating system and web browser only), serving as a basic display terminal connected to the Internet. Since the cloud may be the underlying delivery mechanism, cloud-based applications and services may support any type of software application or service. Information provided by the device and/or accessed by the devices may be distributed over various computational resources. Alternatively, information may be stored in one or more fixed data storage unit or database.

In certain embodiments, the remote location includes a central database stored in a data storage unit that receives and analyzes the data transmitted from the device. The data storage units may be capable of storing computer readable media which may include code, logic, or instructions for the processor to perform one or more step. In some embodiments, the received data is analyzed in a comparative fashion with data contained in the central database and the result sent back to the subject. Analyzing may include correcting raw data based on mathematical manipulation or correction and/or calibrations specific for the device or reagents used to examine the sample; calculation of a value, e.g., a concentration value, comparison (e.g., with a baseline, threshold, standard curve, historical data, or data from other sensors), a determination of whether or not a test is accurate, highlighting values or results that are outliers or may be a cause for concern (e.g., above or below a normal or acceptable range, or indicative of an abnormal condition), or combinations of results which, together, may indicate the presence of an abnormal condition, curve-fitting, use of data as the basis of mathematical or other analytical reasoning (including deductive, inductive, Bayesian, or other reasoning), and other suitable forms of processing.

In certain embodiments, analyzing may involve comparing the analyzed data with a database stored in a data storage unit at the remote location to retrieve instructions for a course of action to be performed by the subject. In some embodiments, the database may contain stored information that includes a threshold value for the analyte of interest. The threshold value may be useful for determining the presence or concentration of the one or more analyte. The threshold value may be useful for detecting situations where an alert may be useful. The data storage unit may include any other information relating to sample preparation or clinical tests that may be run on a sample. The data storage unit may include records or other information that may be useful for generating a report relating to the analyzed data.

In certain embodiments, a health care professional is at the remote location. In other embodiments, a health care professional has access to the data transmitted by the device at a third location that is different from the remote location or the location of the device. A health care professional may include a person or entity that is associated with the health care system. A health care professional may be a medical health care provider. A health care professional may be a doctor. A health care professional may be an individual or an institution that provides preventive, curative, promotional or rehabilitative health care services in a systematic way to individuals, families and/or communities. Examples of health care professionals may include physicians (including general practitioners and specialists), dentists, physician assistants, nurses, midwives, pharmaconomists/pharmacists, dietitians, therapists, psychologists, chiropractors, clinical officers, physical therapists, phlebotomists, occupational therapists, optometrists, emergency medical technicians, paramedics, medical laboratory technicians, medical prosthetic technicians, radiographers, social workers, and a wide variety of other human resources trained to provide some type of health care service. A health care professional may or may not be certified to write prescriptions. A health care professional may work in or be affiliated with hospitals, health care centers and other service delivery points, or also in academic training, research and administration. Some health care professionals may provide care and treatment services for patients in private homes. Community health workers may work outside of formal health care institutions. Managers of health care services, medical records and health information technicians and other support workers may also be health care professionals or affiliated with a health care provider.

In some embodiments, the health care professional may already be familiar with the subject or have communicated with the subject. The subject may be a patient of the health care professional. In some instances, the health care professional may have prescribed the subject to undergo a clinical test. In one example, the health care professional may be the subject's primary care physician. The health care professional may be any type of physician for the subject (including general practitioners, and specialists).

Thus, a health care professional may analyze or review the data transmitted from the device and/or the results of an analysis performed at a remote location. In certain embodiments, the health care professional may send to the subject instructions or recommendations based on the data transmitted by the device and/or analyzed at the remote location.

28 Control and Measure the Sample Thickness without Using Spacers

In some embodiments of the present invention, the spacers that are used to regulate the sample or a relevant volume of the sample are replaced by (a) positioning sensors that can measure the plate inner spacing, and (b) the devices that can control the plate positions and move the plates into a desired plate inner spacing based on the information provided the sensors. In some embodiment, all the spacers are replaced by translation stage, monitoring sensors and feedback system. Measuring of Spacing and/or Sample Thickness Using Optical Method.

In some embodiments, the measuring (f) of the spacing between the inner surfaces comprises the use of optical interference. The optical interference can use multiple wavelength. For example, the light signal due to the interference of a light reflected at the inner surface of the first plate and the second plate oscillate with the wavelength of the light. From the oscillation, one can determine the spacing between the inner surfaces. To enhance the interference signal, one of the inner surfaces or both can be coated with light reflection material.

In some embodiments, the measuring (f) of the spacing between the inner surfaces comprises taking optical imaging (e.g. taking a 2D (two-dimensional)/3D (three-dimensional) image of the sample and the image taking can be multiple times with different viewing angles, different wavelength, different phase, and/or different polarization) and image processing.
Measuring of Entire Sample Area or Volume Using Optical Methods.

In some embodiments, the measuring (f) of the entire sample area or volume comprises taking optical imaging (e.g. taking a 2D (two-dimensional)/3D (three-dimensional) image of the sample and the image taking can be multiple times with different viewing angles, different wavelength, different phase, and/or different polarization) and image processing. The sample area means the area in the direction approximately parallel to the first plate and the second plate. The 3D imaging can use the method of fringe projection profilometry (FPP), which is one of the most prevalent methods for acquiring three-dimensional (3D) images of objects.

In some embodiments, the measuring of the sample area or volume by imaging comprises (a) calibration of the image scale by using a sample of the known area or volume (e.g., The imager is a smartphone and the dimensions of the image taken by the phone can be calibrated by comparing an image of the a sample of known dimension taken the same phone); (b) comparison of the image with the scale markers (rulers) placed on or near the first plate and second plate (discussed further herein), and (c) a combination of thereof.

As used herein, light may include visible light, ultraviolet light, infrared light, and/or near infrared light. Light may include wavelengths in the range from 20 nm to 20,000 nm.

29 Other Descriptions of Embodiments

The following methods, devices and systems are provided. These embodiments may be implemented using any of the components, materials, parameters or steps described above or below. The following embodiments use a CROF plate.

Embodiment 1

A method for analyzing a liquid sample, comprising:
(a) obtaining a sample that contains an analyte;
(b) obtaining a first and second plates that are movable relative to each other into different configurations, wherein each plate has a sample contact surface that is substantially planar, one or both plates are flexible, and one or both of the plates comprise spacers that are fixed with a respective sample contacting surface, and wherein the spacers have a predetermined substantially uniform height and a predetermined constant inter-spacer distance that is at least about 2 times larger than the size of the analyte, up to 200 um (micrometer);
(c) depositing the sample on one or both of the plates when the plates are configured in an open configuration, wherein the open configuration is a configuration in which the two plates are either partially or completely separated apart and the spacing between the plates is not regulated by the spacers;
(d), after (c), using the two plates to compress at least part of the sample into a layer of substantially uniform thickness that is confined by the sample contact surfaces of the plates, wherein the uniform thickness of the layer is regulated by the spacers and the plates, wherein the compressing comprises:
bringing the two plates together; and
conformable pressing, either in parallel or sequentially, an area of at least one of the plates to press the plates together to a closed configuration, wherein the conformable pressing generates a substantially uniform pressure on the plates over the at least part of the sample, and the pressing spreads the at least part of the sample laterally between the sample contact surfaces of the plates, and wherein the closed configuration is a configuration in which the spacing between the plates in the layer of uniform thickness region is regulated by the spacers; and
(e) analyzing the analyte in the layer of uniform thickness while the plates are the closed configuration;
wherein a conformable pressing is a method that makes the pressure applied over an area is substantially constant regardless the shape variation of the outer surfaces of the plates; and
wherein the parallel pressing applies the pressures on the intended area at the same time, and a sequential pressing applies the pressure on a part of the intended area and gradually move to other area.

Embodiment 2

A device for analyzing a liquid sample, comprising:
a first plate and a second plate, wherein:
i. the plates are movable relative to each other into different configurations;
ii. one or both plates are flexible;
iii. each of the plates has, on its respective surface, a sample contact area for contacting a sample that contains an analyte,
iv. one or both of the plates comprise spacers that are fixed with a respective sample contact area, wherein the spacers have a predetermined substantially uniform height and a predetermined constant inter-spacer distance that is at least about 2 times larger than the size of the analyte, up to 200 um, and wherein at least one of the spacers is inside the sample contact area;
wherein one of the configurations is an open configuration, in which: the two plates are separated apart, the spacing between the plates is not regulated by the spacers, and the sample is deposited on one or both of the plates; and
wherein another of the configurations is a closed configuration which is configured after the sample deposition in the open configuration; and in the closed configuration: at least part of the sample is compressed by the two plates into a layer of highly uniform thickness, wherein the uniform thickness of the layer is confined by the sample contact surfaces of the plates and is regulated by the plates and the spacers.

Embodiment 3

A method for analyzing a blood sample, comprising:
(a) obtaining a blood sample;
(b) obtaining a first and second plates that are movable relative to each other into different configurations, wherein each plate has a sample contact surface that is substantially planar, one or both plates are flexible, and one or both of the plates comprise spacers that are fixed with a respective sample contacting surface, and wherein the spacers have:
 i. a predetermined substantially uniform height,
 ii. a shape of pillar with substantially uniform cross-section and a flat top surface;
 iii. a ratio of the width to the height equal or larger than one;
 iv. a predetermined constant inter-spacer distance that is in the range of 10 $\square$m to 200 $\square$m;
 v. a filling factor of equal to 1% or larger; and
 vi. a product of the filling factor and the Young's modulus of the spacer is 2 MPa or larger; and
  (c) depositing the blood sample on one or both of the plates when the plates are configured in an open configuration, wherein the open configuration is a configuration in which the two plates are either partially or completely separated apart and the spacing between the plates is not regulated by the spacers;
  (d), after (c), using the two plates to compress at least part of the blood sample into a layer of substantially uniform thickness that is confined by the sample contact surfaces of the plates, wherein the uniform thickness of the layer is regulated by the spacers and the plates, and has an average value in the range of 1.8 $\square$m to 3 $\square$m with a variation of less than 10%, wherein the compressing comprises:
bringing the two plates together; and
conformable pressing, either in parallel or sequentially, an area of at least one of the plates to press the plates together to a closed configuration, wherein the conformable pressing generates a substantially uniform pressure on the plates over the at least part of the sample, and the pressing spreads the at least part of the sample laterally between the sample contact surfaces of the plates, and wherein the closed configuration is a configuration in which the spacing between the plates in the layer of uniform thickness region is regulated by the spacers; and
  (e) analyzing the blood in the layer of uniform thickness while the plates are the closed configuration;
wherein the filling factor is the ratio of the spacer contact area to the total plate area;
wherein a conformable pressing is a method that makes the pressure applied over an area is substantially constant regardless the shape variation of the outer surfaces of the plates; and
wherein the parallel pressing applies the pressures on the intended area at the same time, and a sequential pressing applies the pressure on a part of the intended area and gradually move to other area.

Embodiment 4

A device for analyzing a liquid sample, comprising:
a first plate and a second plate, wherein:
v. the plates are movable relative to each other into different configurations;
vi. one or both plates are flexible;
vii. each of the plates has, on its respective surface, a sample contact area for contacting a blood sample;
viii. one or both of the plates comprise spacers that are fixed with a respective plate, wherein the spacers have a predetermined substantially uniform height and a predetermined constant inter-spacer distance that is in the range of 7 $\square$m to 200 $\square$m and wherein at least one of the spacers is inside the sample contact area;
wherein one of the configurations is an open configuration, in which: the two plates are separated apart, the spacing between the plates is not regulated by the spacers, and the sample is deposited on one or both of the plates; and
wherein another of the configurations is a closed configuration which is configured after the sample deposition in the open configuration; and in the closed configuration: at least part of the sample is compressed by the two plates into a layer of highly uniform thickness, wherein the uniform thickness of the layer is confined by the inner surfaces of the two plates and is regulated by the plates and the spacers, and has an average value in the range of 1.8 $\square$m to 3 $\square$m with a small variation.

Embodiment 5

A method for locally binding a target entity in a portion of a liquid sample, comprising:
  (a) obtaining a sample that contains a target entity that is capable of diffusing in the sample;
  (b) obtaining a first and second plates that are movable relative to each other into different configurations, wherein one or both of the plates comprise spacers that are fixed on a respective plate, wherein the spacers have a predetermined substantially uniform height, and wherein the first plate comprises, on its surface, a binding site that has a predetermined area and binds to and immobilizes the target entity;

(c) depositing the sample on one or both of the plates when the plates are configured in an open configuration, wherein the open configuration is a configuration in which the two plates are either partially or completely separated apart and the spacing between the plates is not regulated by the spacers;

(d) after (c), compressing the sample by bringing the two plates into a closed configuration, wherein the closed configuration is a configuration in which at least part of the sample is compressed into a layer of uniform thickness that is in touch to and confined by the inner surfaces of the two plates and that in touch to the binding site, wherein the uniform thickness of the layer is regulated by the spacers and the plates, is less than 250 um, and is substantially less than the linear dimension of the predetermined area of the binding site;

(e) after (d) and while the plates are in the closed configuration, either:

(1) incubating the sample for a relevant time length and then stopping the incubation; or (2) incubating the sample for a time that is equal or longer than the minimum of a relevant time length, and then assessing, within a time period that is equal or less than the maximum of the relevant length of time, the binding of target entity to in the binding site;

wherein the relevant time length is:

i. equal to or longer than the time that it takes for the target entity to diffuse across the thickness of the uniform thickness layer at the closed configuration; and ii. significantly shorter than the time that it takes the target entity to laterally diffuse across the minimum lateral dimension of the binding site;

wherein at the end of the incubation in (1) or during the assessing in (2), the majority of the target entity bound to the binding site is from a relevant volume of the sample;

wherein the incubation allows the target entity to bind to the binding site, and wherein the relevant volume is a portion of the sample that is above the binding site at the closed configuration.

Embodiment 6

A device for locally binding target entity in a portion of a liquid sample, comprising:

a first plate and a second plate, wherein:

i. the plates are movable relative to each other into different configurations; one or both plates are flexible;

iii. each of the plates has, on its respective surface, a sample contact area for contacting a sample that contains an entity which is capable of diffusing in the sample, iv. one of the plates has, on its sample contact area, a binding site that has a predetermined area and binds and immobilize the target entity;

v. one or both of the plates comprise spacers that are fixed with a respective plate, wherein the spacers have a predetermined substantially uniform height and a predetermined constant inter-spacer distance, and wherein at least one of the spacers is inside the sample contact area;

wherein one of the configurations is an open configuration, in which: the two plates are either partially or completely separated apart, the spacing between the plates is not regulated by the spacers, and the sample is deposited on one or both of the plates, and wherein another of the configurations is a closed configuration which is configured after the sample deposition in the open configuration; and in the closed configuration: at least part of the sample is compressed by the two plates into a layer of uniform thickness, wherein at least a part of the uniform thickness layer is over the binding site, and wherein the uniform thickness of the layer is confined by the inner surfaces of the two plates, is regulated by the plates and the spacers, is less than 250 um, and is substantially less than the average linear dimension of the predetermined area of the binding site.

Embodiment 7

A method for locally releasing a reagent into a portion of a liquid sample, comprising:

(a) obtaining a sample;

(b) obtaining a first and second plates that are movable relative to each other into different configurations, wherein:

(i) one or both of the plates comprise spacers that are fixed with a respective plate, (ii) the spacers have a predetermined uniform height, and (iii) the first plate comprises, on its surface, a storage site that has a predetermined area and that comprises a reagent that, upon contacting the sample, dissolves into the sample and diffuses in the sample;

(c) depositing the sample on one or both of the plates when the plates are configured in an open configuration, wherein the open configuration is a configuration in which the two plates are either partially or completely separated apart and the spacing between the plates is not regulated by the spacers;

(d) after (c), compressing the sample by bringing the two plates into a closed configuration, wherein the closed configuration is a configuration in which at least part of the sample is compressed into a layer of uniform thickness that is confined by the inner surfaces of the two plates and that covers the storage site, wherein the uniform thickness of the layer is regulated by the spacers and the plates, is less than 250 um, and is substantially less than the linear dimension of the predetermined area of the storage site;

(e) after (d) and while the plates are in the closed configuration, incubating the sample for a relevant time length and then stopping the incubation, wherein the relevant time length is:

i. about equal to or longer than the time that it takes for the target entity to diffuse across the thickness of the uniform thickness layer at the closed configuration; and ii. shorter than the time that it takes the target entity to laterally diffuse across the linear dimension of the predetermined area of the binding site;

thereby, after the incubation, the majority of the reagent that initially are on storage site are in the relevant volume of the sample, wherein the incubation is a process to allow the reagent to bind or mix with the sample, and wherein the relevant volume is a portion of the sample that is above the binding site at the closed configuration.

Embodiment 8

A device for locally releasing a reagent into a portion of a liquid sample, comprising:

a first plate and a second plate, wherein:

i. the plates are movable relative to each other into different configurations; ii. one or both plates are flexible;

vi. each of the plates has, on its respective surface, a sample contact area for contacting a sample;

vii. one of the plates comprises, on its sample contact area, a storage site that has a predetermined area and comprises an reagent that, upon contacting the sample, dissolves into the sample, diffuses in the sample, and bind to the target entity;

viii. one or both of the plates comprise spacers that are fixed with a respective plate, wherein the spacers have (a) a predetermined substantially uniform height that is 250 □m or less and is substantially less than the average linear dimension of the predetermined area of the reagent site, and (b) a predetermined constant inter-spacer distance that is 200 □m or less, and wherein at least one of the spacers is inside the sample contact area;

wherein one of the configurations is an open configuration, in which: the two plates are either partially or completely separated apart, the spacing between the plates is not regulated by the spacers, and the sample is deposited on one or both of the plates, and wherein another of the configurations is a closed configuration which is configured after the sample deposition in the open configuration; and in the closed configuration: at least part of the sample is compressed by the two plates into a layer of uniform thickness, wherein at least a part of the uniform thickness layer is over the binding site, and wherein the uniform thickness of the layer is confined by the inner surfaces of the two plates, is regulated by the plates and the spacers.

Embodiment 9

A method for reducing the time for binding a target entity in a relevant volume of a sample on a binding site on a plate surface, comprising:

(a) obtaining a sample that contains a target entity that is capable of diffusing in the sample;

(b) obtaining a first and second plates that are movable relative to each other into different configurations, wherein one or both of the plates comprise spacers that are fixed on a respective plate and one or both plates are flexible, wherein the spacers have a substantially predetermined uniform height and a predetermined constant inter-spacer distance, and wherein the first plate comprises, on its surface, a binding site that has a predetermined area and binds to and immobilizes the target entity;

(c) depositing the sample on one or both of the plates when the plates are configured in an open configuration, wherein the open configuration is a configuration in which the two plates are either partially or completely separated apart and the spacing between the plates is not regulated by the spacers;

(d) after (c), compressing the sample by bringing the two plates into a closed configuration, wherein the closed configuration is a configuration in which the thickness of a relevant volume of the sample is reduced, compared to that in the open configuration of the plates, into a layer of substantially uniform thickness having a lateral area of at least 1 mm2 that is confined by the inner surfaces of the two plates and that covers the binding site, wherein the uniform thickness of the layer is regulated by the spacers and the plates, is less than 250 um, and is substantially less than the linear dimension of the predetermined area of the binding site; wherein the relevant volume is a portion or an entire volume of the sample;

wherein reducing the thickness of the relevant volume of the sample reduces the time for binding between the binding site and the target entity in the relevant volume to reach equilibrium.

Embodiment 10

A device for locally binding target entity in a portion of a liquid sample, comprising:

a first plate and a second plate, wherein:

i. the plates are movable relative to each other into different configurations; one or both plates are flexible;

iii. each of the plates has, on its respective surface, a sample contact area for contacting a sample that contains an entity which is capable of diffusing in the sample, iv. one of the plates has, on its sample contact area, a binding site that has a predetermined area and binds and immobilize the target entity;

v. one or both of the plates comprise spacers that are fixed with a respective plate, wherein the spacers have a predetermined substantially uniform height and a predetermined constant inter-spacer distance, and wherein at least one of the spacers is inside the sample contact area;

wherein one of the configurations is an open configuration, in which: the two plates are either partially or completely separated apart, the spacing between the plates is not regulated by the spacers, and the sample is deposited on one or both of the plates, and wherein another of the configurations is a closed configuration which is configured after the sample deposition in the open configuration; and in the closed configuration: at least part of the sample is compressed by the two plates into a layer of uniform thickness, wherein at least a part of the uniform thickness layer is over the binding site, and wherein the uniform thickness of the layer is confined by the inner surfaces of the two plates, is regulated by the plates and the spacers, is less than 250 um, and is substantially less than the average linear dimension of the predetermined area of the binding site; and wherein reducing the thickness of the relevant volume of the sample reduces the time for binding between the binding site and the target entity in the relevant volume to reach equilibrium.

Embodiment 11

A method for parallel, multiplex, assaying of a liquid sample without fluidic isolation, comprising:

(a) obtaining a sample that contains one or more target analytes, which are capable of diffusing in the sample;

(b) obtaining a first and second plates that are movable relative to each other into different configurations, wherein:

i. one or both of the plates comprise spacers that are fixed with a respective plate and one or both plates are flexible, ii. the spacers have a predetermined substantially uniform height and a predetermined constant inter-spacer distance, iii. the first plate has, on its surface, one or a plurality of binding sites that each has a predetermined area comprising a capture agent that binds and immobilizes a corresponding target analyte of (a); and iv. the second plate has, on its surface, one or a plurality of corresponding storage sites that each has a predetermined area and comprises a detection agent of a concentration that, upon contacting the sample, dissolves into the sample and diffuses in the sample, wherein each capture agent, target analyte and corresponding detection agent is capable of forming a capture agent-target analyte-detection agent sandwich in a binding site of the first plate;

(c) depositing the sample on one or both of the plates when the plates are configured in an open configuration, wherein the open configuration is a configuration in which the two plates are either partially or completely separated apart and the spacing between the plates is not regulated by the spacers;

(d) after (c), compressing the sample by bringing the two plates into a closed configuration, wherein the closed configuration is a configuration in which:

i. at least part of the sample is compressed into a layer of uniform thickness that is in contact with and confined by the inner surfaces of the two plates and that is in contact with the one or a plurality of binding sites and the one or a plurality of storage sites, ii the one or a plurality of corresponding storage sites are over the one or a plurality of binding sites, and iii. the uniform thickness of the layer is regulated by the spacers and the plates, is less than 250 um, and is substantially less than the linear dimension of the predetermined area of each storage site;

(e) after (d) and while the plates are in the closed configuration, either:

(1) incubating the sample for a relevant time length and then stopping the incubation; or (2) incubating the sample for a time that is equal or longer than the minimum of a relevant time length and then assessing, within a time period that is equal or less than the maximum of the relevant length of time, the binding of each target analyte to a binding site;

wherein the relevant time length is:

i. equal to or longer than the time that it takes for a target analyte of (a) to diffuse across the thickness of the uniform thickness layer at the closed configuration; and ii. significantly shorter than the time that it takes a target analyte of (a) to laterally diffuse across the smallest linear dimension of the predetermined area of a storage site or binding site;

thereby producing a reaction in which, at the end of the incubation in (1) or during the assessing in (2), the majority of the capture agent-target analyte-detection agent sandwich bound to each binding site is from a corresponding relevant volume of the sample;

wherein the incubation allows each target analyte to bind to a binding site and a detection agent, wherein the corresponding relevant volume is a portion of the sample that is above the corresponding storage site at the closed configuration, wherein the separation between the edges of the neighboring storage sites and the separation between the edges of the neighboring binding sites are larger than the distance that a target analyte or detection agent can diffuse in the relevant time, and wherein there is no fluidic isolation between the binding site sites and/or the storage sites.

Embodiment 12

A device for parallel, multiplex, assaying of a liquid sample without fluidic isolation, comprising a first plate and a second plate, wherein:

i. the plates are movable relative to each other into different configurations; one or both plates are flexible;

ii. one or both of the plates comprise spacers that are fixed with a respective plate; and the spacers have a predetermined substantially uniform height and a predetermined constant inter-spacer distance;

iii. each of the plates has, on its respective surface, a sample contact area for contacting a sample that contains a sample that contains one or more target analytes which is capable of diffusing in the sample, iv. the first plate has, on its surface, one or a plurality of binding sites that each has a predetermined area comprising a capture agent that binds and immobilizes a corresponding target analyte of the sample; and v. the second plate has, on its surface, one or a plurality of corresponding storage sites that each has a predetermined area and comprises a detection agent of a concentration that, upon contacting the sample, dissolves into the sample and diffuses in the sample, wherein each capture agent, target analyte and corresponding detection agent is capable of forming a capture agent-target analyte-detection agent sandwich in a binding site of the first plate;

wherein one of the configurations is an open configuration, in which: the two plates are either partially or completely separated apart, the spacing between the plates is not regulated by the spacers, and the sample is deposited on one or both of the plates, and wherein another of the configurations is a closed configuration which is configured after the sample deposition in the open configuration; and in the closed configuration:

i. at least part of the sample is compressed into a layer of uniform thickness that is in contact with and confined by the inner surfaces of the two plates and that covers the one or a plurality of binding sites and the one or a plurality of storage sites, ii the one or a plurality of corresponding storage sites are over the one or a plurality of binding sites, and iii. the uniform thickness of the layer is regulated by the spacers and the plates, is less than 250 um, and is substantially less than the linear dimension of the predetermined area of each storage site; and iv. there is no fluidic isolation between the binding site and/or the storage sites.

wherein the separation between the edges of the neighboring storage sites and the separation between the edges of the neighboring binding sites are larger than the distance that a target analyte or detection agent can diffuse in the relevant time, and wherein there is no fluidic isolation between the binding site sites and/or the storage sites.

Embodiment 13A

A system for rapidly analyzing a sample using a mobile phone comprising:

(a) a CROF device, wherein one or both plates of the CROF device are movable relative to each other into different configurations; wherein:

i. one of the configurations is an open configuration, in which: the two plates are either partially or completely separated apart, the spacing between the plates is not regulated by the spacers, and the sample is deposited on one or both of the plates, and ii. another of the configurations is a closed configuration which is configured after the sample deposition in the open configuration; and in the closed configuration: at least part of the sample is compressed by the two plates into a layer of uniform thickness, and wherein the uniform thickness of the layer is in touch with and confined by the inner surfaces of the two plates, is regulated by the plates and the spacers;

(b) a mobile communication device comprising:

i. one or a plurality of cameras for the detecting and/or imaging the sample;

ii. electronics, signal processors, hardware and software for receiving and/or processing the detected signal and/or the image of the sample and for remote communication; and (c) a light source from either the mobile communication device or an external source.

Embodiment 13B

A method for rapidly analyzing a sample using a mobile phone, comprising:

(a) depositing a sample on the CROF device of a system of Embodiment 13A;

(b) assaying the sample deposited on the CROF device to generate a result; and (c) communicating the result from the mobile communication device to a location remote from the mobile communication device.

Embodiment 14

A method for analyzing a liquid sample, comprising:

(a) obtaining a sample that contains an analyte that is capable of diffusing in the sample;

(b) obtaining a first and second plates that are movable relative to each other into different configurations, wherein one or both of the plates comprise spacers that are fixed with a respective plate, wherein the spacers have a predetermined uniform height, and wherein the first plate comprises, on its surface, an analyte assay area that has a predetermined area;

(c) depositing the sample on one or both of the plates when the plates are configured in an open configuration, wherein the open configuration is a configuration in which the two plates are either partially or completely separated apart and the spacing between the plates is not regulated by the spacers;

(d), after (c), using the two plates to compress at least part of the sample into a layer of uniform thickness that is confined by the inner surfaces of the two plates, wherein at least a part of the layer is over the analyte assay area, wherein the uniform thickness of the layer is regulated by the spacers and the plates, and is substantially less than the linear dimension of the predetermined lateral area of the analyte assay area, wherein the compressing comprises:

bringing the two plates together; and applying an external force on the outer surfaces of the plates to press the plates together to a closed configuration, wherein the force generates pressure on the plates over the at least part of the sample, and the pressing spreads the at least part of the sample laterally between the inner surfaces of the plates, and wherein the closed configuration is a configuration in which the spacing between the plates in the layer of uniform thickness region is regulated by the spacers;

(e) incubating the sample while the plates are in the closed configuration, for a time that is: (i) about equal or longer then the time that it takes the analyte to diffuse across the thickness of the uniform thickness layer, and (i) significantly shorter than the time that it takes the analyte to diffuse across the area of the analyte assay area; and (f) immediately after (e) either stopping the incubation and measuring the analyte in the assay area, or continuing the incubation while the plates are the closed configuration and measuring the analyte in the assay area in a time that is significantly shorter than the time that it takes the analyte to diffuse across the area of the analyte assay area.

The following descriptions may be applied to embodiments 1-14, as set forth above.

In any embodiment that uses CROF, the spacers can be inside of the sample area and inside the relevant area of the sample for good uniformity of the sample thickness control.

In any embodiment that uses CROF, at least one of two plate can be plastic film of a thickness from 1 um to 50 um.

In any embodiment that uses CROF, at least one of two plate can be plastic film of a thickness from 50 um to 100 um.

In any embodiment that uses CROF, at least one of two plate can be plastic film of a thickness from 100 um to 150 um.

In any embodiment that uses CROF, at least one of two plate can be plastic film of a thickness from 150 um to 250 um.

In any embodiment that uses CROF, both two plates can be a plastic film of a thickness that each of them is independently selected from 10 um to 300 um.

In any embodiment that uses CROF, both two plates can be a plastic film of a thickness that each of them is independently selected from 100 um to 200 um.

In any embodiment that uses CROF, both two plates can be a plastic film of a thickness that each of them is independently selected from 10 um to 100 um.

In any embodiment that uses CROF, the height of the spacer on the plate can be in the range of 5 nm to 100 nm.

In any embodiment that uses CROF, the height of the spacer on the plate can be in the range of 100 nm to 500 nm In any embodiment that uses CROF, the height of the spacer on the plate can be in the range of 500 nm to 1 um In any embodiment that uses CROF, the height of the spacer on the plate can be in the range of 1 to 2 um In any embodiment that uses CROF, the height of the spacer on the plate can be in the range of 2 to 5 um.

In any embodiment that uses CROF, the height of the spacer on the plate can be in the range of 5 to 10 um.

In any embodiment that uses CROF, the height of the spacer on the plate can be in the range of 10 to 30 um.

In any embodiment that uses CROF, the height of the spacer on the plate can be in the range of 30 to 50 um.

In any embodiment that uses CROF, the height of the spacer on the plate can be in the range of 50 to 100 um.

In any embodiment that uses CROF, the inter spacer distance (IDS) is no greater than 200 um.

In any embodiment that uses CROF, the inter spacer distance (IDS) is no greater than 150 um.

In any embodiment that uses CROF, the inter spacer distance (IDS) is no greater than 100 um.

In any embodiment that uses CROF, the inter spacer distance (IDS) is no greater than 80 um, e.g., no greater than 60 um, no greater than 40 um, or no greater than 20 um.

In any embodiment that uses CROF, the width to height ratio of the spacers is at least 1.5 (e.g., at least 2, at least 3, at least 4 or at least 5).

In any embodiment that uses CROF, the ratio of pillar width to pillar height can be at least 1, at least 2, at least 5, or at least 10.

In any embodiment that uses CROF, the distance between the plates may be in the range of 2-50 um and any assay may have a saturation time of less then 1 minute.

In any embodiment that uses CROF, the method includes a wash.

In any embodiment that uses CROF, the method does not include a wash.

In any embodiment that uses CROF, the method has a sensitivity of less than 1 nM, e.g., 0.1 nmol, 10 pmol, 1 pmol, 0.1 pmol, 10 fmole, 1 fmole or 0.1 fmol, after an incubation of less then 1 minute.

In any embodiment that uses CROF, the ratio of the period to the spacer width may be less than about 7.0 (e.g., about 7.0 to 1.0), particularly when the pillar height is less than about 100 um.

In any embodiment that uses CROF, a plate may have a thickness of 20-200 um, e.g., 10-50 or 50-200 um.

In any embodiment that uses CROF, the sample volume may be less than 0.5 um, e.g., less than 0.5 um, less than 0.4 um, less than 0.3 um, less than 0.2 um, or less than 0.1 um.

In any embodiment that uses CROF, the interspacing distance may be less than 200 um, e.g., 20-200 um, 20-50 um or 50-200 um.

Other embodiments. In a preferred embodiment for reducing a saturation incubation time of a binding process, a regent mixing process, a combination of two, or other process, the final sample thickness at a closed configuration is less than 0.5 um (micron). In another preferred embodiment, the final sample thickness is in a range of 0.5 um to 1 um. In another preferred embodiment, the final sample thickness is in a range of 1 um to 4 um. In another preferred embodiment, the final sample thickness is in a range of 4 um to 10 um. In another preferred embodiment, the final sample thickness is in a range of 10 um to 30 um. In another preferred embodiment, the final sample thickness is in a range of 30 um to 100 um.

In a preferred embodiment for reducing a saturation incubation time of a binding process, a regent mixing process, a combination of two, or other process, the final sample thickness is selected to make the saturation incubation time less than 2 sec. In another preferred embodiments, the final sample thickness is selected to make the saturation incubation time in a range of less than 4 sec, less than 8 sec, less than 12 sec, less than 20 sec, less than 30 sec, less than 40 sec, less than 60 sec, less than 120 sec, less than 300 sec, less than 420 sec, or a range between any two of the values.

In any embodiment that uses CROF, the device may be compressed by hand for a period of less than 1 minute, e.g., less than 10 sec.

In certain embodiments, the CROF device is integrated a microfluidic platform or device. The microfluidic device may be configured to have different areas for receiving a sample, detecting analytes in the sample with a CROF device, collecting waste material in a reservoir, etc. Thus, in certain embodiments, the microfluidic channel platform may include fluid handling components to direct a sample applied to a sample receiving area of the microfluidic device to a CROF device configured to detect an analyte, as described above. The fluid handling components may be configured to direct one or more fluids through the microfluidic device. In some instances, the fluid handling components are configured to direct fluids, such as, but not limited to, a sample solution, buffers and the like. Liquid handling components may include, but are not limited to, passive pumps and microfluidic channels. In some cases, the passive pumps are configured for capillary action-driven microfluidic handling and routing of fluids through the microfluidic device disclosed herein. In certain instances, the microfluidic fluid handling components are configured to deliver small volumes of fluid, such as 1 mL or less, such as 500 µL or less, including 100 µL or less, for example 50 µL or less, or 25 µL or less, or 10 µL or less, or 5 µL or less, or 1 µL or less. Thus, in certain embodiments, no external source of power is required to operate the microfluidic device and perform the devices, systems and methods in the present invention.

In certain embodiments, the microfluidic device has dimensions in the range of 5 mm×5 mm to 100 mm×100 mm, including dimensions of 50 mm×50 mm or less, for instance 25 mm×25 mm or less, or 10 mm×10 mm or less. In certain embodiments, the microfluidic device has a thickness in the range of 5 mm to 0.1 mm, such as 3 mm to 0.2 mm, including 2 mm to 0.3 mm, or 1 mm to 0.4 mm.

In certain embodiments, the CROF device is disposed within a container, e.g., a well of a multi-well plate. The CROF device also can be integrated into the bottom or the wall of a well of a multi-well plate.

In some embodiments, a support containing a CROF device, such as a microfluidic device or multi-well plate, may have an identifier for the CROF device that is contained in the support. An identifier may be a physical object formed on the support, such as a microfluidic device. For example, the identifier may be read by a handheld device, such as a mobile phone or a smart phone, as described above.

In some embodiments, a camera may capture an image of the identifier and the image may be analyzed to identify the CROF device contained in the microfluidic device. In one example, the identifier may be a barcode. A barcode may be a 1D or 2D barcode. In some embodiments, the identifier may emit one or more signal that may identify the signal enhancing detector. For example, the identifier may provide an infrared, ultrasonic, optical, audio, electrical, or other signal that may indicate the identity of the CROF device. The identifier may utilize a radiofrequency identification (RFID) tag.

The identifier may contain information that allows determination of the specific type of CROF device present in a microfluidic device or multi-well plate. In certain embodiments, the identifier provides a key to a database that associates each identifier key to information specific to the type of CROF device present in a microfluidic device or multi-well plate. The information specific to the type of CROF device may include, but are not limited to, the identity of the analytes which the CROF device configured to detect, the coordinates of the position where a specific analyte may bind on the CROF device, the sensitivity of detection for each analyte, etc. The database may contain other information relevant to a specific CROF device, including an expiration date, lot number, etc. The database may be present on a handheld device, provided on a computer-readable medium, or may be on a remote server accessible by a handheld device.

In certain embodiments, when the CROF card (e.g. CROF plate) in the closed configure ration, the total thickness of the CROF card is the range of 10 um to 3 mm (e.g. in the range of 10 um to 100 um, 100 to 500 um, 500 um to 1 mm, 1 mm to 2 mm or 2 mm to 3 mm); and the lateral dimension of CROF card is in the range of 2 mm to 50 mm (e.g. 2 mm to 5 mm, 5 mm to 10 mm, 10 mm to 20 mm, 20 mm to 30 mm, 30 mm to 40 mm or 40 mm to 50 mm), wherein the x and y direction takes respectively a value in the range.

In certain embodiments, the CROF plate slide in and out the optical adaptor for a testing.

In certain embodiment, the optical adaptor has a thickness in the range of 2 mm to 40 mm (e.g. 2 to 5 mm, 5 to 10 mm, 10 to 20 mm, 20 to 30 mm, or 30 to 40 mm) and a lateral dimension in the range of 10 mm to 100 mm (e.g. 10 to 20 mm, 20 to 30 mm, 30 to 40 mm, 40 to 50 mm, 50 to 60 mm, 50 to 60 mm, 60 to 70 mm, 70 to 80 mm, or 80 to 100 mm), wherein a particular thickness, x-lateral dimension and y lateral dimension takes one of the value in the range, respectively In certain embodiments, the spacers for testing white blood cells is the range of 2 um to 40 um (e.g. 2 to 10 um, 10 to 20 um, 20 to 30 um, or 30 um to 40 um).

30. Homogenous Assay Using a Signal Amplification Surface

In many applications of an assay, particularly in PoC or other fast assays, it is desirable to avoid washing steps. One aspect of the present invention is related to the devices, systems, and methods that can avoid washing of the assay.

By incorporating and/or using a signal amplification surface, the disclosed devices, systems, and methods may facilitate performing assays without washing. The surface amplification surface may only amplify the light emitted in a small distance from the surface (e.g. 20 nm, or 50 nm, or 100 nm). One example of the surface amplification layer is D2PA.

31. An Example of Assay Acceleration Using CROF with a Ring (Enclosure) Spacer An experiment has been performed for assay acceleration that uses a polystyrene thin film as one of the CROF plate, a thin glass as the other plate, and a wax ring was the spacer, and was fixed on the polystyrene plate. During a CROF process, 2 uL (microliter) of sample was dropped inside the ring spacer (and at the center, forming a small droplet as dropped) and was compressed by the two plates into a thinner film with the spacing between the plates was regulated by the ring spacer (i.e. a closed configuration of two CROF plate). The plates were compressed by hands. The sample thickness was found uniform at the closed configuration of the plates. One main reason for the uniformity is that the volume of the sample is the same as the volume between the ring spacers and two plates. Both immunoassay and DNA hybridization assay were tested.

In the immunoassay testing (wax ring spacer of ~40 um height and 0.8 cm diameter), the Protein A was used as the capture agent and was coated on the polystyrene surface, a labeled IgG was used as an analyte. After incubation for a binding between Protein A and the labeled IgG, the unbound IgG was washed away and the label of captured IgG was measured. Different incubation time were tested. Our experiment found that the binding saturates in less than 1 min incubation time (i.e. after 1 min or less the signal of captured IgG will not change with the incubation time). Such short saturation incubation time is expected for a 40 um spacing (hence sample thickness), since the diffusion time for IgG in a solution over a 40 um distance is about a few seconds.

We also tested the incubation of such direct assay in a normal 96 wellplate with 3 mm thick sample thickness, and found that a typical saturation incubation time is about 120 min. If the incubation process is limited by diffusion of the labeled IgG, by reducing the sample thickness from 3 mm to 40 um reduced the incubation time from ~120 min to 1.28 sec, which is consistent with our observation of sub-1 min saturation incubation time.

In the DNA hybridization testing (wax ring spacer of ~52 um height and 0.7 cm diameter), the streptavidin-BSA was the molecular linking layer on the polystyrene substrate and was linked to biotinylated capture strand, the capture strand captures labeled target strand through hybridization. After an incubation, the un-hybridized target strand was wash away, and the label signal was tested. Different incubation time were tested. Our experiment found that the hybridization saturates in within 30 sec incubation time (i.e. after 1 min or less the signal of captured IgG will not change with the incubation time). Such short saturation incubation time is expected for a 52 um spacing (hence sample thickness), since the diffusion time for the target probe in a solution over a 52 um distance is about a few seconds. (More details of the experiments were disclosed in, e.g., provisional application Ser. No. 62/202,989

As a references, the same assays with a thicker sample thickness were tested, we found that for 1 mm thick sample, it would require about 20 mins to reach saturation incubation.

(More details of the experiments were disclosed in, e.g., provisional application Ser. no. 62/202,989

32. Example of Assay Acceleration (QAX and QMAX) by CROF with Pillar Spacers E-1.1 QAX Assay with a CROFF Device of a Pillar Spacer Array of 30 Um Spacer Height, to Achieving an Saturation Incubation Time Less than 30 Sec.

The QAX by CROF was tested and ~30 sec saturation time was achieved. The experiment is illustrated in FIGS. 13.a and b. In the experiment, the capture agent and the labeled detection agent was predeposited and dried on one of the pair CROF plate before a CROF process, then the sample was dropped on a plate and closed with another plate using a CROF process. The dropping the sample took a few seconds, the CROF process took less than 10 secs. Our experiment found that for 30 um spacer height, the saturation incubation time is within 30 secs.

Plates, Samples, Reagents.

(1) the CROF used the self-holding CROF device comprises (i) a 2.5 cm by 2.5 cm area X-Plate made of 175 um thick PMMA film with a spacer array in the sample contact area, where the spacer array has a rectangle lattice with a constant period of 120 um/110 um (in x and y lateral direction respectively), all spacers are pillars and have the same of rectangle shape of the same spacer height 30 um height and 40 um width in x and 30 um in y, and the spacers are made of the sample material (PMMA) as the plate and are fabricated by nanoimprint the PMMA film with a mold (hence the spacers are fixed on the plate with predetermined spacer height and inter spacer spacing of 80 um); and (ii) a glass plate of planar surface (1 mm thick, 3 cm by 5 cm). The surfaces of the X-Plate and glass plate are untreated and are hydrophilic for the sample. (2) The dry capture agent (cAb) of anti-IgG were pre-coated on the glass plate before sample dropping and a CROF process; (3) The dry detection agent (dAb) of anti-IgG were pre-coated on the X-Plate before sample dropping an da CROF process; and (4) The sample is Human-IgG in BSA buffer with different convention concentration.

Experimental Steps and Results

A small volume of the sample with the analytes (Human IgG) was dropped onto the surface of one of the plates of CROF devices described in E2-1. Initially the sample on the plate forms puddle, but by placing the other plate of the CROF device on the paddle and compressing the two plates together, the original blood puddle spreads into a large-area sample film but ultra-thin (~30 um) regulated by the spacer array, which are inside of the spread sample. Then, human hands uniformly pressed the X-Plate onto droplet (center to center) against the glass plate for 5-10 s, release the hand, wait 30 s, and the plates stay in their closed configuration.

Then different samples (with different CROF devices) were incubated in different times and washed and measured (optical signal). The results are in FIG. 13.b, which shows that the saturation incubation time of less than 30 secs for a QAX assay described in FIG. 13.a.

E.1.2 QMAX Assay and Homogeneous Assay

QMAX has been tested experimentally using M-Plate (i.e. D2PA) for the magnification of the signal. Furthermore the QMAX assay was compared with QAX assay where is no M0Pate to magnify the signal. Both heterogeneous (with wash) and homogenous (without wash) were tested. The test assay is human IgG fluorescence immunoassay using QAX & QMAX.

Materials and methods: X-Plate (30 um pillar height, 30 um×40 um pillar size, 80 um ISD) 25 mm×25 mm; M-Plate, size 25 mm×25 mm; and the assay reagents (in coating order) were (a) DSU, Protein-A, anti-human IgG (coated and dry on the substrate plate), (b) human IgG (analyte), and (c) anti-human IgG-IR800 reagents (coated and dry on the storage site of the x-plate)

Results (also shown in FIG. 14): Our experiments showed that for a CROF device with 30 um spacing at a closed configuration, the saturation incubation is within 1 min, and the sensitivity for lumpsum reading is LoD=2 pM for QMAX with wash, LoD=10 pM for QMAX without wash (homogenous); LoD=200 pM for QAX with wash, and QAX without wash (homogenous) LoD=(cannot read, no difference for different analyte concentration).

33. Additional Exemplary Experimental Testing and Preferred Embodiments

In this section, additional exemplary experimental testing and observations, and additional preferred embodiments of the present invention are given, which were performed using the following conditions and sharing the following common observations.

Volume of Deposited Sample.

Unless specified otherwise, all the samples deposited on the plate of CROF have a unknown volume, namely, the exact volume is not known at time of deposition.

Plates.

In the CROF devices used this section, unless specified otherwise, one of the two plates, termed "X-Plate" is the only plate that has the spacers. The other plate, termed "the substrate plate", has a planar surface and does not have any spacers. Different materials (including glass, PMMA (polymethacrylate), and PS (polystyrene)) for the plate and the spacers, different plate thicknesses and spacer geometries (shapes and sizes) have been tested. The sample contact surface of each plate is a planar surface (except the protruding spacers) with a surface smoothness variation typically less than 30 nm, but many of the planar surfaces had surface flatness variation, which was caused by a flexibility of the plates, intrinsic surface flatness (not related to the plate flexibility), or both. Some of the plates have an inner surface smoothness variation larger than 30 nm. The typical dimensions of the plates used in the examples are, unless specified otherwise, at least 25 mm wide and at least 25 mm long.

Spacers.

Unless specified otherwise, all the spacers in the Section: (i) were fixed on the sample surface of the X-plate and fabricated by embossing the surface (hence the material of the spacers are the same as the X-plate); (ii) were array of pillars that have a nearly uniform cross-section of a shape of rectangle or square with round corners, a nearly straight sidewall with a tilt angle from the normal less than 5 degree, a flat top surface, and uniform spacer height; and (iii) had a fixed inner spacer distance (ISD) in each X and Y direction (note the spacing in X may be different from the spacing in Y) (See FIG. 17.b). Furthermore, the lateral shape of the pillar spacers are either square and rectangles with round corners; different spacer height, size, inter-spacer distance, shape, and materials were tested.

Fabrication of Spacers.

The spacers embossed on the X-Plate surface were fabricated by nanoimprint, where a mold was pressed directly into the plate and embossed an originally completely flat surface into a flat surface but having the pillar spacers protruding from the surface. The embossing used a temperature higher than the glass transition temperature of the plastic material, where the plastic material can flow under the embossing. The mold was fabricated by lithography and etching, and in some cases, by electroplating over a master mold. The mold was made in Si, silicon dioxide, or nickel.

FIG. 17 shows examples of the spacers fabricated on the plate. The spacers were fabricated by direct imprinting of the plastic plate surface using a mold. FIGS. 17(a) and (b) is the top view of optical micrograph of a square spacer lattice. Top view of photograph of (a) 46 um×46 um pillar spacer size and 54 um inter pillar distance, and (b) 10 um×70 um pillar spacer size and 10 um pillar distance; and prospect view SEM of (c) 30 um×40 um pillar spacer size of 2 um spacer height, and (d) 30 um×40 um pillar spacer size of 30 um spacer height. The micrographs show that (1) the top of the pillar spacer is very flat, (2) the spacer has nearly uniform cross-section, and (3) the corners of the pillar spacer are round with a radius curvature about 1 um. A large radius curvature (e.g. less sharp edge) is preferred, since a sharp edge can lyse a cell or affect fluidic flow more than a rounded edge.

Using a surface profilometer, we measured the pillar height over 2 cm by 2 cm area of the X-Plate. We found that the typical uniformity of the pillar spacer height of the X-Plate fabricated using the methods described above has an average variation of 4 nm, 10 nm, and 100 nm, and a relative average variation of 0.2%, 0.2% and 0.33%, respectively for the spacer height of 2 um, 5 um, and 30 um.

Typical Experiment Procedure.

As illustrate in FIG. 15, first, a small volume (a few uL or less) of sample was deposited on either the substrate or the x-plate, which forms form a small paddle(s). Second the plates were brought together with overlaps of the sample surface of the plate. Third, hand is used to press the plates into a closed configuration, where the sample become a thin film with an area much larger than the original paddle.

Fourth, the hand(s) was related. And fifth, various measurements were performed at the closed configuration. Certain details of the steps are given below.

Sample Deposition Methods.

Two sample deposition methods were used. One method deposited a sample on the plates by a pipette. In another method, the blood samples were directly deposited from a subject finger (picked by a tool) by making the blood on the subject and the plate in contact. There were not dilutions to the blood that were directly deposited from the finger to the plate. In our experiments, we found that the final experimental results is, unless specified, independent of the sample deposition methods.

The samples depositions were performed inside a room and under a standard room conditions without any special temperature control or dust filters. We found that under such conditions, the dusts fall on the samples do not affect the final measurements results, because (1) the flexible plate used conformable to the dust, allowing the sample thickness in other areas still being regulated by the spacers and not affecting the sample thickness self-holding, and (2) the area of having dusts were only very small portion of the total available sample area and the measurements were done the areas that were not affected by the dust. The selection of the non-dust area were done by optical imaging.

In some situations, the two plates have surface protection covers to reduce the number of dusts fall on the plates. In some situations, the two plates are placed together with sample surfaces inside to prevent dusts and other contaminations.

Plate's Surface Wetting Properties.

We have measured the wetting properties of different plate surfaces used in our exemplary experiments. The table below gives the measured contact angle of a sample of 5 uL on a untreated or treated surfaces of different plate materials (glass, PMMA, and PS) and different surface geometry (flat surface and X-plate sample surface) for different sample types (water, PBS buffer (Phosphate-Buffered Saline), and blood), where the X-plate is 175 um thick PMMA, and its sample surface has an array of pillar (i.e. spacer) of 2 um height, 30 um×40 um lateral size, and 110 um/120 um period (i.e. 80 inter spacer distance).

| Plate Material & Surface | Water | PBS | Blood |
|---|---|---|---|
| Untreated flat Glass | 45° | 46° | 46° |
| Untreated flat PMMA | 60° | 57° | 59° |
| Untreated flat PS | 61° | 59° | 58° |
| Untreated X-Plate (PMMA) | 62° | 60° | 58° |

The experiments showed that (1) all untreated surfaces of glass, PMMA, and PS have a hydrophilic surface (i.e. the contact angle is less than 90 degree); (2) the untreated glass surface has a smaller wetting angle (more hydrophilic) than untreated PMMA and PS; (3) the contact angles are similar for water PBS and blood, and blood has slightly better wetting than the water and PBS; (4) the untreated PMMA X-plate has nearly the sample contact angle as the untreated PMMA plate; and (5) the surface wetting properties can be, as expected, significantly altered by surface treatment to become more hydrophilic or more hydrophobic.

Surface hydrophobicity of a plate can be changed by a surface treatment. For example, for PMMA X-plate, we made it more hydrophilic by exposed a surface in an oxygen plasma, and more hydrophobic treatment by treating the surface with tridecafluoro-1,1,2,2-tetrahydrooctyltrichlorosilane. The contact angles was 25, 27, 28 degree for hydrophobic treated X-Plate, and 105, 104, and 103 degree for hydrophilic treated X-Plate, respectively for the samples of water, PBS buffer, and blood.

In the discussion below, unless particularly specified, all the sample surface (i.e. the inner surface that contacts a sample) of the plates are untreated.

Area and Height of Deposited Sample.

We measured the sample area and height on the plate when a water sample was deposited using a pipette on the plates that were at an open configuration.

| Liquid Volume | Substrate: | Untreated Glass | Untreated PMMA |
|---|---|---|---|
| 1 uL | Diameter (mm): | 2.4 | 2 |
|  | Estimated Height (mm): | 0.5 | 0.6 |
| 2 uL | Diameter (mm): | 3.0 | 2.5 |
|  | Estimated Height (mm): | 0.6 | 0.8 |
| 5 uL | Diameter (mm): | 4.1 | 3.5 |
|  | Estimated Height (mm): | 0.9 | 1.0 |

The experiments showed that a typical sample deposited on the plate at the open configuration has a thickness much larger than that at the closed configuration.

We observed that at a closed configuration of the plates, (1) the total sample area expands from a few millimeter diameters to a few centimeter (depending upon the spacer height), and (2) if the spacer array has a square lattice, then the area of the sample at the closed configuration of the plates is also nearly a square shape with the edge of the sample square aligned to the direction of the spacer square lattice. Therefore, it demonstrated that the final sample area at the closed configuration can be controlled by using different spatial arrangements of the spacers. If the spacer has a rectangle lattice, then the final sample area at the closed configuration should be rectangle. If the spacer is a radial circular pattern, then the final sample area at the closed configuration can be circular.

Hand-Press.

In all the experiments in the Section 30, the plates in a CROF process were brought together and compressed into a closed configuration of the plates by human hand(s). In a final pressing for uniform sample thickness over a large area of the CROF plates, often a thumb presses one area and rub into different areas of the CROF plates. A process that uses hand(s) to press a CROF device (plates) into a closed configuration is referred as "hand-pressing".

Self-Holding.

We observed, unless stated otherwise, that after pressing the CROF plates into the final configuration and releasing the compressing force (e.g. the pressing hand), the thickness of the sample between the two plates was still regulated by the spacer height and was kept in a constant thickness for a long period time (until the sample eventually dry). The observation is termed "self-holding". The self-holding is the capillary forces between the plates, the liquid sample, and the environment (e.g. air), caused by the surface tensions. We observed that the hand-pressing and self-holding of the CROF-device gave excellent sample thickness, as illustrated in E-1.

Measurements for Plate Spacing and Sample Thickness.

In all the experiments below, the spacing between the inner surfaces (i.e. the sample surfaces) of the two plates at a closed configuration were measured by the Fabry-Pérot cavity resonance (FP resonance) caused by the inner surfaces of the plates. Due to the optical index differences between a sample (and air) and the inner surface, each inner surface of the plates acts as an optical reflector and the two inner surfaces form an optical cavity. The FP resonance spectra is periodic, and the inner surface spacing, h, (hence the sample thickness) at the optical measurement point can be calculated from:

$$h = \frac{c}{2n\Delta v}$$

where c is the speed of light, $\Delta v$ is the period in frequency domain, and n is the refractive index of the sample between the plates.

In our FP resonance testing, the light source had an area of about around 2 um by 2 urn. Typically, we measured the plate inner surface spacing at 25 different points over 1.6 cm by 1.6 cm area round center of the CROF-device, where the 25 points is 5×5 square lattice with a period (i.e. the distance between the two neighbor points) of 4 mm. The measurements stayed away from the regions that occupied by the spacers (i.e. pillars).

Since the inner surfaces and the sample are in contact at a closed configuration of the plates, the measured inner surface spacing is the same as the sample thickness at the measurement point.

Average Sample Thickness, H.

The average sample thickness, H, is calculated using the plate spacing measured at the 25 points and the formula:

$$H = \frac{\sum_{i=1}^{25} h_i}{25}.$$

Sample thickness deviation refers to the deviation of the sample average thickness, H, over a given area from a predetermined spacer height, $H_0$: $(H-H_0)$. And the relative sample thickness deviation is the deviation divided by the predetermined spacer height: $[(H-H_0)/H_0]$. A positive thickness deviation means that the sample is in average thicker than the spacer height, and a negative thickness deviation means that the sample is in average thinner than the spacer height.

Sample Thickness Uniformity.

The uniformity of a sample thickness, □, over a given area is defined as the standard deviation of the sample thickness over the given area.

$$\Delta = \sqrt{\frac{\sum_{i=1}^{25}(h_i - H)^2}{25}}$$

32.1 Sample Thickness Deviation and Uniformity in Hand-Pressing Self-Holding CROF Experimentally, we studied the parameters in the CROF devices and process that can affect the sample thickness deviation and uniformity at a closed configuration of the plates after releasing the hands. We found that the parameters include, but not limited to, the inter-spacer distance (IDS), spacer's shape and dimensions (e.g. spacer lateral dimension, spacer height, the ratio of the spacer width to the height, spacer area filling factors (the ratio of spacer area to the total area or the ratio of spacer period to the width), the material mechanical strength (Young's modulus) of the spacers and the plate, plate thickness, and surface flatness of each plate. Certain findings and preferred embodiments obtained from the experiments are given below. The definition of spacer height, the IDS, period, and lateral size of spacers are given in FIG. 16.

E-1.1 Effects of IDS (Inter-Spacer Distance) and Plate Thickness and Materials on Sample Thickness.

Experimentally, we observed that the inter-spacer distance (ISD) of a periodic spacer array can significantly affect the sample thickness deviation (from the spacer height) and uniformity that a closed configuration of a CROF process.

FIG. 18 shows the effects of IDS and plate thickness and materials on sample thickness. The measured sample thickness deviation and uniformity vs. inter-spacer distance (IDS) for different plate and spacer materials, different plate thickness, and different samples. The spacers are a periodic array, and have 5 um spacer height, flat top, and a square shape (10×10 um pillar lateral size, nearly uniform cross-section, and round corners). The IDS was 20 um, 50 um, 100 um, 200 um, and 500 um respectively. The substrate was non-treated 250 um thick PMMA plate of flat surface (1 in×1 in area). The X-Plates, where the spacers were directly fabricated on, was, respectively, non-treated PMMA plate of 175 um and 50 um thick, and non-treated PS of 125 um and 25 um thick. The sample was, respectively, 2 uL blood (dropped by direct contact with finger), saliva, or PBS (dropped by pipette). The CROF devices were pressed by hand pressing and rubbed over the 1 in by 1 in area, and were self-hold after the press. The sample thickness were measured at the closed configuration of the CROF devices.

FIG. 18 shows that for the given experimental conditions and for the spacer of a square shape (10×10 um pillar lateral size, nearly uniform cross-section, and round corners):

(1) When ISD are 20 um, 50 um, 100 um, the average final sample thickness is 5.1 um to 5.2 um, which is very close to the predetermined spacer height of 5 um, and has a thickness deviation and uniformity both less than 4% (namely, if the ISD is equal or less than about 120 um, the deviation and uniformity can be less than 4%).

(2) But when the ISD is 200 um and 500 um, the average final sample thickness becomes 4.3 um and 3.5 um, respectively, which significantly less than the predetermined spacer height (5 um), and has a thickness deviation of −13.9% and −30.9% and uniformity of 10.9% and 27.7%, respectively. This means that when the ISD is larger than about 200 um, not only the average of the thickness is significantly reduced, but also the uniformity becomes very poor.

For a 40 um by 40 um lateral dimension pillar spacer array (FIG. 18), when ISD are 60 um and 150 um, 100 um, the average final sample thickness is 5.1 um to 5.2 um, which is very close to the predetermined spacer height of 5 um, and has a thickness deviation and uniformity both less than 4% (namely, if the ISD is equal or less than about 100 um, the deviation and uniformity can be less than 4%).

E-1.2 Effects of IDS/(Eb^3) on Sample Thickness

Our experiments show (e.g. FIG. 19) that to achieve small sample thickness deviation and good uniformty, the SD$^4$/(h×E) (x=1 in the plot) value of X-Plates, should be less than 10^6 um^3/GPa, where ISD is inter spacing distance, h is the height (thickness) of the material, and E is the Young's modulus of the material.

In all methods and devices that uses CROF, in certain embodiments, SD4/(h×E) (x=1 in the plot) value is less than 10^6 um^3/GPa, less than 5×10^5, less than 1×10^6, less than 5×10^6 less etc.

In any embodiment, a flexible plates may have a thickness in the range of 20 um to 250 um (e.g., in the range of 50 um to 150 um) and Young's modulus in the range 0.1 to 5 GPa (e.g., in the range of 0.5-2 GPa).

In any embodiment, the thickness of the flexible plate times the Young's modulus of the flexible plate may be in the range 60 to 750 GPa-um.

E-1.3 Effects Pf Spacer's Size and Height on Sample Thickness

Our experiments show (e.g. FIG. 20) that to achieve small sample thickness deviation and for the given plate thickness, the sample, and the pressing, the IDS should be about 150 um or less.

E-1.4 Effects Pf Spacer's Width-to-Height Ratio on Sample Thickness

Our experiments show (e.g. FIG. 21) that, to achieve small sample thickness deviation, for the given plate thickness, the sample, and the pressing, and for ISD between 20 um to 150 um, the pillar width to height ratio (WRH) should larger than 1, and in certain embodiments, preferably equal larger than 2.

This indicates that when the WHR of ~1 or larger, the spacers are strong enough to sustain the pressing and rubbing in the hand pressing, otherwise the deviation and uniformity will all be poor and large for all of ISD.

E-1.5 Effects Pf Spacer's Filling Factors on Sample Thickness

Our experiments show (e.g. FIG. 22) that, to achieve small sample thickness deviation and good thickness uniformity, for the given plate thickness, the sample, the spacer filling factor should be about 2.3 or larger.

For example, the less than 4% deviation and uniformity in achieved in FIG. 22 imply that for the given pillar area and IDS, and for the given spacer area filling factor (i.e. ratio of pillar lateral area to the total area), the PS pillars are strong enough to sustain the pressing and rubbing of the hand pressing. The PS pillar deformation can be estimated by the following: the pressure from the thumb is about 1 to 10 kg/cm2 ($10^5$ Pa), the Young's modulus for PS is ~3 GPa, and the filling factor for 20 um width pillar spacer and ISD of 100 um is ~4%, leading the pillar's relative deformation (strain) under the press of the thumb is 1% to 0.1%, which is consistent to our experimental observation.

E-1.6 Effects of Plate Thickness on Sample Thickness

Our experiments show (e.g. FIG. 23) that (i) to achieve small sample thickness deviation (equal or less than 5%) and good thickness uniformity, for the given plate thickness, the sample, at least one of the plates should have a plate thickness less than 200 um; and (ii) If both the X-Plate and substrate are thicker than 200 um, they are too rigid, which cannot overcome the dusts, leading to worse spacing uniformity/deviation.

E-1.7. Effects of Substrate Plate on Sample Thickness

Our experiments found (e.g. FIG. 25) that if a thicker (1 mm) glass substrate plate is used, the maximum IDS for smaller sample thickness deviation and good sample thickness uniformity, can extended from 150 um for PMMA substrate to 200 um.

E-1.8 Plate Surface Wetting Property Modification and Effects on Self-Holding

Our experiments found (e.g. FIG. 24) that: (1) Good self-holding for CROF device requires at least one of the two inner surfaces of the CROF device be hydrophilic. (2) If the both inner surfaces of the CROF device are hydrophilic, it offers the best self-holding and sample thickness regulation and uniformity. (3) If one inner surface of the CROF device is hydrophilic and the other inner surface is hydrophobic, sample area needs to larger than 0.5 cm2 to get a good self-holding. (4) If both of the inner surfaces are hydrophobic, the self-hold either poor or fails (unstable). (Lines in figures are for eye-guiding purpose.)

E-1.9 Effects of Hand Pressing Time on Sample Thickness

Our experiments found that the CROF device can self-holding with pressing time 1 s to 60 s, and have similar good performances. CROF device have bad performances and cannot self-hold if no press (press 0 s).

E-1.10. Comparison of Effects of Periodic Pillar Spacers to Random Ball Spacers on Sample Thickness The measurements in FIG. 27 show that for the given experimental conditions, the CROF device with periodic pillar spacer have much smaller sample thickness deviation and better uniformity (both less than 5%) that the random ball (i.e. beads) spacer. Specifically, for 20 um, 50 um and 100 um ISD, the average thickness deviation and uniformity with periodic, uniform-cross-section pillar spacer are 2.3% and ~3.4%. However, when using random ball spacer with average ISD of 20 um, 50 um and 100 um, the average thickness deviation and uniformity area 11.2% and 12.5% using the 220 um thick glass cover plate, and 10.8% and 20% using the 175 um thick PMMA cover plate, which are about 5 times larger sample thickness deviation and poorer uniformity.

E1.12. Other Findings

FIG. 28 shows the Effects of Different X-Plate Thickness and Substrate Thickness on Sample Thickness.

Our experiments found that the liquid dropped by pipette and direct from finger have a similar performance in the final sample thickness and uniformity.

Our experiments also found that the liquid dropped on Substrate or on X-Plate have similar performances in measured sample thickness and uniformity.

32.2 Complete Blood Count in Undiluted Whole Blood Using Self-Holding CROF

E2.1 CROF Devices Used

The CROF devices, used in all tests in Example 32.2, comprised an X-plate and a flat glass plate. The X-Plate was a 175 um thick PMMA film of 2.5 cm by 2.5 cm area and having a periodic spacer array in the sample contact area. The glass plate is 1 mm thick and has planar surface and 3 cm by 5 cm area. The spacers on the X-plate were directly embossed onto the initially flat PMMA film, hence they were made of PMMA (the same material as the X-plate) and were attached to the X-plate.

Each spacer is a pillar that has nearly uniform lateral cross-section, flat top, and a rectangle shape of 40 um and 30 um width in x and y lateral direction, respectively. All the spacers on a given X-plate have the same spacer height. The periodic spacer array had a rectangle lattice with a constant period of 120 um and 110 um (in x and y, respectively), giving a constant inter spacer spacing (IDS) of 80 um.

The surfaces of the X-Plate and the glass plate are untreated and are hydrophilic for human blood dropped on the surfaces with a contact angle about 40 to 50 degrees. Both plates are transparent to visible light.

E2.2 Sample, Preparation, Deposition, CROF Process, Self-Holding

Unless specified otherwise, all blood samples were from healthy subjects, that freshly and directly deposited on a CROF plate, no dilution, and no anti-coagulant added.

In all experiments in Example 3, unless specifically described otherwise, the blood came from picking human finger, and the blood was deposited on a plate of CROF by a direct touching between the blood and the plate. Typically, the direct touch deposited about 0.1 to 1 uL volume blood on the surface of the plate. Within about 60 sec after the blood deposition, the CROF process were applied to compressed the blood sample into a thin film and then perform of the measurements. Unless specifically stated, neither anti-conglutination agents nor any liquid-diluent were added into the blood sample.

In certain experiments where the WBC's need to be stained, prior to a blood testing, the reagent, a dry acridine orange dye layer, was precoated on an inner surface (sample contact surface) of one of the plates of the CROF devices. The coating of the dry dye layer comprised the steps in sequence: (a) dropping 30 uL acridine orange dye in water of a 20 ug/mL concentration onto the glass plate, (b) spreading it into an area of ~1 cm$^2$, and (c) drying for about 1 hour.

Regardless the methods of depositing about 1 uL or less volume blood on one of the CROF plates, the as-deposited blood on the plate formed puddle of a few millimeter or less diameter. Then the two plates of a CROF device were put into a closed configuration by hand and were pressed by hand for a few seconds, where the original blood puddle was compressed by the two plates into a large-area thin blood film (about 1-3 cm in lateral size). We found that in all of Example 3, unless described otherwise, the CROF devices pressed by hands had uniform sample thickness regulated by the spacer and were able to self-hold the uniform sample thickness after the hands were released. The samples were deposited in ordinary room conditions. We found that the dust did not affect to achieve the predetermined final sample thickness over a large sample area. We also found the that final blood sample spread into a rectangle shape with round corners, which we believe, is caused by the rectangle lattice of the periodic spacers. This step is illustrated in FIG. 15.

For the sample using that used the dry dye on the plate, the sample were waited for 30 sec before any measurements.

The blood sample directly deposited on the plate did not have any dilution by liquid (i.e. no liquid dilution), were only mixed the dry reagent coated the plate.

all spacers have the same of rectangle shape of the same spacer height 2 um height The 2 um spacer height is selected to make the final blood sample spacing at the closed configuration of CROF device to about 2 um, which is about equal to the thickness of the red blood cells (RBCs) (2-2.5 μm) but much less than the diameter of RBC (6.2-8.2 μm). Such final sample thickness makes that at the closed configuration of CROF, each RBC is well separated from others and there is not overlap or rouleaux between the different RBC, allowing accurate accounting of RBC by taking an image of the sample area.

E2.3 Imaging of Blood Cells

The imaging of the blood samples in Example 3 were performed, unless stated otherwise, with the samples between two CROF plates which were in a closed configuration, and by using commercial DSLR camera (Nikon) and iPhone respectively. The results from each type of cameras are similar. Unless stated otherwise, the images are the top view of the samples through one of the plates which is transparent (i.e. two dimensional images in the sample in a plane that is parallel to the surface of the plates).

Nikon Camera.

The samples are observed by normal commercial DSLR camera (Nikon) with two filters (a 470±20 nm band pass filter as the excitation filter and a 500 nm long pass filter as the emission filter), one light source (a Xenon lamp) and a magnification/focus lens set. In bright field mode, a broadband white light source without using any of the filters. In fluorescence mode, the 470±20 nm filter was placed in front of the Xenon lamp to create a narrow band excitation source round 470 nm wavelength, and the 500 nm long pass filter was placed in front of the camera to block the light with wavelength less than 500 nm entering the camera.

Mobile-Phone.

iPhone-6 was used for our experiments.

E2.4 Spacer Height (Sample Thickness) Effects on Blood Cells and RBC Counting

In our experiments, the sample thicknesses were controlled to be the same as the spacer height. We experimentally investigated the effects of the spacer height (hence the sample thickness) in a CROF process on the blood cells as well as their imaging and counting. The CROF devices and process used and the blood deposition were those described in beginning of this section of Example 2. The blood samples were from the same healthy subject. Four different spacer heights (1 um, 2 um, 3 um and 5 um) were tested in one of our experiment.

FIG. 29 shows the top view optical micrographs (bright field optical microscope) of a blood sample that was CROFed inside four different CROF devices, where each CROF device has a rectangle lattice of periodic spacers and a different constant spacer height: 1 um (a), 2 um (b), 3 um (c), and 5 um (d). The blood sample were directly deposited by a subject finger to a plate of the CROF device, and neither anti-congluent nor liquid diluent were added into the blood.

In a bright field optical microscopy, the RBC cells can be seen much easier than the WBCs. The red blood cells (RBCs), also termed erythrocytes, has a disk diameter of approximately 6.2-8.2 μm and a thickness at the thickest point of 2-2.5 μm (near the rim of the disk) and a minimum thickness in the center of 0.8-1 μm.

Our optical microscope observation showed that for 1 um spacer height, ~99% of the RBCS are lysed. For example, FIG. 29(a) showed only RBC left in the observation field. The 1 um spacer height is significantly less than the average RBC thickness. This experiment demonstrated that CROF devices and process can be used to lyse a cell, by making the final plate spacer (through a control of the spacer height) less than a minimum dimension of the cell.

Our optical microscope observation (e.g. FIG. 29) showed that for the 2 um spacer height (sample thickness), the RBCs are all separated from each other, have virtually no overlaps between them, and have a shape of nearly round and symmetrical. The separation between each RBC are clearly seen by a complete-circular dark boundary line of each RBC (i.e. the boundary line completely circulates each (and only one) cell) in the 2D microscope image Furthermore, the microscope observation also shown that the center of the RBCs are darker in the center of cells than that of the rim, indicating that at 2 um spacer height (sample thickness), the center of the RBCs is still thinner than that at the rim.

Our optical microscope observation showed that (e.g. FIG. 29) that when the spacer height (hence the sample thickness) was 3 um, the image of the blood sample was drastically different from that at 2 um spacer height in several ways, including, but not limited to: (1) RBCs became significantly overlap, and most of RBC did not have the complete-circular dark boundary line that separates each cell as they existed in 2 um spacer height, but rather several RBCs shared a single dark bound line which no long be circular shape; and (2) some of RBCs did not appear in as nearly as round shape as in 2 um spacer height, rather more elliptical shape, and the center dark disk of each RBC, which was clear in 2 um spacer height, become hard to see. As the spacer height became 5 um, the RBC had more overlaps and more RBCs had non-circular shape and nearly invisible dark center (e.g. FIG. 29).

It is well known that in a blood without a confinement in space, the RBCs would like to overlap with each other, (e.g. including rouleaux). By confining a blood sample between two planar plate with a spacing of 2 um using the spacer height and the plates, the blood thickness is about equal to the thickest point of a RBC (which is 2-2.5 µm), thus at a given location on the plate surface, the confinement forces only one RBC can exit between the two plates and forces the RBC oriented with its disk parallel to the plate surface, leading to well separation between RBCS, the complete-circular dark boundary line, and the nearly round shape, when viewed using a top view optical microscopy.

As the spacer height and hence the sample thickness becomes larger, such as in 3 um and 5 um spacer height, the sample thickness allows more than one RBCs between the two plates in a location of the plates, leading RBC overlaps and disappearance of well-defined boundary of each RBC; and allows a RBC rotating between the two plate and rotating away from the disk parallel to the plate surface position, leading to un-circular shape in RBC top view image.

For counting RBC number (e.g. used for RBC concentration measurement), our experimentally clearly shown that making a sample thickness to 2 um thick (e.g. using 2 um spacer height) can be easier and more accurate than that in that the sample thickness of 3 um and 5 um.

By making a spacer height (hence the spacing between two plates and the blood sample thickness) to be about 2 um, which is about equal to the thickness of the red blood cells (RBCs) (2-2.5 µm) but much less than the diameter of RBC (6.2-8.2 µm), the blood cell count is much easily and more accurate than a larger sample thickness.

At a final sample thickness of (2-2.5 µm), or a preferred 1.9 to 2.2 um, makes that at the closed configuration of CROF, each RBC is well separated from others and there is not overlap or rouleaux between the different RBC, allowing accurate accounting of RBC by taking an image of the sample area.

On the other hand, we observed the CROF device of 1 um spacer height, most of the RBCs are lysed, but not the WBCs or platellets. In our experiments, the optical imaging from the top of the CROF (i.e. the CROF plates are nearly parallel to the imaging plane of the imager of microscope or camera) determined (a) the number of cells in an area and (b) the exact lateral size of the area. A lateral size of CROF device can be determined by pre-calibration. Or the lateral size of an area of a CROF device can be determined during an imaging, using the lateral size of the spacer as a marker. In our experiments, we used both.

In the experiment of Example 2, for the given CROF plates, the spacing between the two CROF plates (hence the blood sample thickness) were the same as the spacer height within 5% or better. Using this sample thickness information, together with the lateral sizes of a given area determined from optical imaging, the sample volume associated with the given area was determined, which is equal to the sample lateral area times the sample thickness. Knowing the sample volume and the number of cells inside the volume (determined by imaging), we were able to determine the concentration of cells in that sample volume.

FIG. 29b shows (b) the ratio of the red blood cell area (measured from 2D top view image) to the total lateral area of CROF plate. The maximum at 2 um plate spacing (i.e. sample thickness), because below 2 um some RBC are lysed and higher than 2 um the RBCs are overlapped and rotated, all of them gives smaller RBC area in the 2D image.

One conclusion from the following experiments is that the CROF-device optimized spacing size for blood cell count (RBC and WBC) is 1.9 um-2.2 um, or 2 um to 2.2 um, or 2 um to 2.1 um.

Another Our Experimental Finding is that CROF Device with 1 Um Spacing Between the Two Plates Lyses Most of RBCs, but not Lyses WBCs: CROF-Device We found that when CROF-device gap spacing is much smaller than the thickness of RBC (e.g. 1 um plate-spacing), the RBC are lysed. WBC is more elastic, most of them can still be observed, and might be not lysed.

E3.5 Counting RBCs (Red Blood Cells).

In one embodiment, the RBC were counted with bright field mode without any filter. A 4×, 10×, 20× or 40× magnification factor were used to take the pictures. Since both the gap spacing of the X-Plate (t) and the field of view (A) for each magnification are known (the spacers and their periods were used as scale-markers (i.e. rulers), the RBC concentration in the blood sample are calculated. Fox example, for the count of N RBC in one field of view, the RBC concentration (C) in blood is C=N/t/A. This calculation approach is also same for WBC, PLT concentration measurements.

E2.6. Counting WBC and Platelets

Each white blood cell (WBC), also called leukocyte or leucocyte, has a typical disk diameter of approximately 10-15 µm. A typical platelet (PLT) has a typical size of 1-2 um. Since WBCs and PLT do not have visible pigment on their own, they are hard to be observable in an ordinary microscopy than RBC. To make the WBC and PTL be more visible in counting, in one embodiment, they are stained in acridine orange (AO) dye.

Acridine orange is a stable dye that has a natural affinity for nucleic acids. When binding to DNA, AO intercalates with DNA as a monomer and yields intense green fluorescence under blue excitation (470 nm excitation, 525 nm green emission for WBC). When binding to RNA and proteins it forms an electrostatic complex in a polymeric form that yields red fluorescence under blue excitation (470 nm excitation, 685 nm red emission for WBC, PLTs). RBCs have no nucleic acids, thus the cannot be stained. WBCs have nuclei, both DNA and RNA, thus strongly stained. PLTs have the slight amount of RNA, thus weakly stained. See FIG. 33.

The WBC were counted under fluorescence mode with a 470±20 nm excitation filter, and the emission filter is a 500 nm long pass filter, and choose 4×, 10×, 20× or 40× magnification factors for taking picture. Using these embodiments, the WBC and the PLT were proper counted.

E2.7 Measurements of Different WBCs

WBCs can be classified into five main sub-classes: neutrophils, eosinophils, basophils, lymphocytes, and monocytes; or, sometimes three main classes: Granulocytes, lymphocytes, and monocytes. The concentration of each class in a subject blood may have clinic significance, since different infection by virus, bacteria, or fungus, or allergy may change the concentration of certain WBC sub-class concentration.

The WBC are nucleated, which distinguishes them from the anucleated red blood cells and platelet. Furthermore, different sub-class of WBC has different ratio of DNA vs. RNA and proteins, they can be differentiated accordingly by using a proper dye to stain DNA and RNA separately.

For example, AO dye intercalates with DNA as a monomer and yields intense green fluorescence under blue excitation (470 nm excitation, 525 nm green emission for WBC).

When binding to RNA and proteins it forms an electrostatic complex in a polymeric form that yields red fluorescence under blue excitation (470 nm excitation, 685 nm red emission for WBC, PLTs). Thus different WBC will have different R/G color ratio (green emission vs. red emission) after stained by AO dye.

AO dye can potentially differentiate 3 kinds of WBC: Granulocytes (including Neutrophil, Eosinophil, Basophil), Lymphocytes, Monocytes. Furthermore, we can directly use camera (or iPphone)'s building-in RGB filter set to distinguish the green and red emission from G channel and R channel from one photo taken. Thus we have no need to use 2 separate filter sets (as 525 nm and 685 nm band-pass filter).

As shown in FIG. 34, there are total 594 WBC counted and plotted. We can clearly see that the cells cluster into three distinct regions (shaded areas provided as guides for the eye), corresponding to the three main white cell subpopulations. The percentage of each subpopulations is given in the table, matches well with the normal human blood value.

E2.8. Hematocrit Measurements

The hematocrit (Ht or HCT), also known as packed cell volume (PCV) or erythrocyte volume fraction (EVF), is the volume percentage (%) of red blood cells in blood. In X-CBC setup, we use 2 um gap spacing, which will pack every RBC tightly by substrate and X-Plate. Thus the HCT in this case is equal to the RBC volume over overall blood volume.

E2.10. Dried AO Dye Staining WBC Speed

WBCs were stained dried AO dye after 30 s, 10 min, 30 min, 90 min. In a CROF process with the dried AO dye on the plate surface, AO dye can stain WBCs fully less than 1 min and will not influence others or over-stain other area after long time. Also, because bound AO fluoresces more intensely than the unbound dye, no washing step was required.

E2.11. Other Non-Fluorescence Dye to Stain WBC

Non-fluorescence dye to stain WBC can simplify the WBC counting setup. Crystal violet or gentian violet (also known as methyl violet 10B or hexamethyl pararosaniline chloride) is a triarylmethane dye can be used to stain the nucleus of WBC. Similar to AO dye, we dried 1 mg/mL, 30 uL acridine orange dye in water onto the glass slide with area 1 $cm^2$ for 1 hour. Then, repeat the X-CBC experiment process. WBC will be stained to violet color. One drawback of this method is hard to differentiate the WBC subpopulations.

E2.12. No Anti-Coagulant Needed Blood Test by CROP

One advantage of the present invention is that no need to use anti-coagulant reagents to help counting, as being observed experimentally. In our experiments, X-Plates with 2 um, 3 um and 10 um spacing, and 1 cm×1 cm blood area were tested in a CROF device for a blood sample. In a time duration from 0 min to 80 min, in every 10 min, the pictures at 5 typical points from center to edge of the sample were taken. All the samples tested are without anti-coagulant reagents. It was observed that for the given experimental conditions, there were no conglutination of the blood sample at the closed configuration during the observation period. This is because that (1) the CROF with ~2 um spacing (sample thickness at the closed configuration) separate the blood cells from each other, and (2) the plates of the CROF protect the most of the blood cells from the oxygen.

E2.13. Further Experiments in Blood Cell Count Using CROF and iPhone.

In other experiments, we have tested and validated of a technology and a compact easy-to-use device that allow a person to perform blood cell counting completely by her/himself in under 20 seconds using a smartphone with less than a drop of blood (<1 uL). All a person needs to do is to let a tiny amount (an arbitrary unknown volume) of blood from a pricked finger touch a card, close the card, and take a picture with a smartphone.

One aspect of the present invention is the observation that by precisely reshaping a blood droplet into a uniform blood layer that is only one red-blood-cell thick (~2 um) and is confined between two plates, it offers unprecedented advantages in blood cell counting. The advantages include (i) for fresh undiluted whole blood without adding any anti-coagulant, the blood cells will be well-separated from each other, not coagulated, and hence easily identifiable by imaging; and (ii) the sample has nearly zero evaporation (in the testing area), keeping the blood cell concentration constant over a long period of time. A second key technology we developed is termed "compressed regulated open flow" (CROF), that uses a CROF-Card (a foldable, disposable, stamp-sized (1 in-wide, paper-thin) plastic film operated by hand) to perform the blood reshaping, measure the reshaped blood sample thickness (hence volume), and mix (if needed) pre-coated dry reagents into the blood (and complete all functions in one stroke and in under 5 sec). The last two technologies reported here are a small-match-box-sized optical adapter for smartphone imaging, and software for controlling the smartphone and analyzing images. The method ("blood-cell-counting using CROF and imaging" or BCI) by a smartphone was validated by comparison with a standard commercial machine, a commercial manual hamocytometer, and microscope imaging (in place of smartphone). Over 42 tests using two types of blood (stored and fresh from a subject) were run for each method, and red blood cells (RBCs), white blood cells (WBCs), platelets, three WBC differentials, hematocrit (HCT), and mean corpuscular volume (MCV) were measured. The validation shows that the BCI by smartphone has the accuracy the same as, or even better, than that a commercial manual hemocytometer (can be further improved), and the same day-to-day stability as commercial instruments. Clearly, the BCI technology has broad and significant applications in cell imaging, immunoassays, nucleic-acid assays, personal health monitoring, and other bio-chemical detections.

The BCI device comprises three hardware components: a disposable stamp-size plastic CROF-Card (1 in by 1 in area, paper-thin), a smartphone, and a match-box-sized optical adapter (1.5×1.5 in×0.7 in (L×W×H)); and software that controls the smartphone, creates user interface, and analyzes blood cells. All of them (except smartphone) were designed, and developed by the authors. The optical adapter ("Adapter"), which comprises lenses, mirrors, and filters; and is amounted on the smartphone, makes the smartphone's flash and camera become the light source and the imager for the testing, respectively. The optical adapter also has a slot for sliding a CROF-Card in a proper position in the front of the camera (FIG. 30). An iPhone-6 was used in our current tests.

In a blood test using the BCI (FIG. 30), a person first pricks her/his finger, then deposits a small amount (arbitrary unknown volume) of the blood (e.g. less than one drop (<1 uL) directly from the finger onto the CROF-Card by touching the card, closes the card, inserts the card into the optical adapter, and finally takes a picture of the card using the smartphone. From the pictures taken, the software does analysis and gives blood cell counts and other parameters.

The total time from depositing the blood onto the CROF-Card to the display of the blood cell count results on the smartphone is ~12 to 19 seconds, where 1-2 s for depositing the blood on the CROF-card, 3-5 s for closing the card, ~2-4 s for inserting the card into the Adapter, ~3-5 s for taking images, and 3 s for finishing analysis to show blood cell count results.

One key innovation of the BCI is the CROF-Card technology developed at us [Ref]. The CROF-Card comprises two pieces of thin plastics, each about 1 in.×1 in. in area, a paper thick in thickness, hinged with another piece at one edge (FIG. 30) (note the hinge is not necessary but convenient). The CROF-Card offers the following key functions in handling the blood sample: (i) spreading quickly (e.g. 1 sec) the blood sample from the as-deposited shape (e.g. a puddle of 2 mm diameter and 0.4 mm height) into a uniform film of 2 um thick (~1/200 of the original thickness) over a significant area (~500 mm2) and confined by the two plates of the CROF; (ii) stopping any further reduction of the sample thickness once the 2 um thickness is reached; (iii) keeping the uniform 2 um thickness even when the hands are released from the compression (i.e. self-holding, which is due to the capillary forces between the blood and the plates); and (iv) preventing sample evaporation at such thin thickness (i.e. with the confinement by the two plates, the evaporation occurs only the blood film edge, and the testing area of the sample has a zero evaporation over a very long time). Experimentally, using optical interferences (i.e. Fabry-Perot cavity effect from the two inner surfaces of the CROF-Card), we found that the CROF-Card by Essenlix can keep the uniform thickness at 2 um with 5% (i.e. 100 nm) uniformity at least over a 20 mm by 20 mm area.

The CROF-Card offers several key and unprecedented advantages for the blood cell counting over the existing methods. The most significant one is our observation that when a blood drop is reshaped into a uniform blood layer that is only one red-blood-cell thick (~2 um) and is confined between two plates, (i) the blood cells in fresh undiluted whole blood without any anti-coagulant, are well-separated from each other, have zero coagulation, have much less blood cell motion, and are easily identifiable by imaging; and (ii) the blood sample has nearly zero evaporation in the testing area, hence keeping the blood cell concentration in that area constant over a long period of time.

The second key advantage of the CROF-Card is an "automatic" measurement of the blood sample volume (since the sample thickness is determined). A third advantage is that it uses least amount of blood sample (since there are no fluidic inlet or outlet, or any sample transfer channels and/or devices). Other advantages are (i) it can mix a dry reagent on the CROF-Card surface with the sample in a few seconds; (ii) it is simple and fast, and operated by hands, and (iii) it is convenient and low cost.

Although the method of a blood cells counting by imaging a blood sample confined between two plates has over 150 years history and is the foundation of a commercial manual hemocytometer; to our best knowledge, no one has performed blood cell counting using a plate-confined blood layer of a uniform thickness that is just one red-blood cell thick, and no one has examined the behavior of blood cells in a uniform confined blood sample that is at, or around, one red-blood cell thickness. In previous imaging-based approaches, because the confinement spacing of the blood sample is larger than a red-cell thickness, the blood sample must be diluted (often uses anti-coagulant) to avoid the overlaps (hence miscounting) of the red cells.

Our study has observed intriguing behavior of the blood cells in a whole blood sample that is confined between two plates and has a uniform sample thickness of just one red-blood cell thick or slightly larger or smaller than that thickness. The blood cell behavior is drastically different, depending upon the confinement gap of the CROF-Card (i.e. the sample thickness).

Let us first look at a whole blood that is undiluted, freshly from a pricked finger onto the CROF-card, and without adding any anti-coagulant (FIG. 31.a). For a confinement gap of 2 um, the optical microscopy image shows that all blood cells (RBCs, WBCs, PLTs) are separated from each other in the sample plane (i.e. no overlap), and that each RBC has a well-defined boundary surrounding each cell with a shadowed center, and each boundary does not cross-over into other RBC's boundary. Furthermore, during the imaging, there were almost no observable cell movements. One explanation for such behavior is that since 2 um confinement spacing is slightly smaller than the average thickness of a red cell, each RBC is pinched slightly by the confinement plates, leaving no space for other cells to overlap and unable to move. Clearly, the behavior of the cells with 2 um gap gives an optimum condition to count the cells by imaging.

However, at 2.2 um gap, some RBCs start to overlap with another RBCs, but there is no observable platelet overlap. A possible reason is that there is not enough space for platelets to overlap with PLT. For 2.6 um and 3 um gaps, more RBC's overlap, triple RBCs overlaps become visible, and the platelets overlap with RBCs. These overlaps increase with the gap. Counting blood cells by imaging is possible at the gap of 2.2, 2.6 and 3 um, but accuracy is getting poorer with the increasing gap. At 5 um and 10 um gap, massive numbers of cells overlap (e.g. coagulated), rouleaux of RBCs are visible, and many RBCs have a narrow elliptical shape, which is due to the rotation of the RBCs relative to the imaging plane (the large gap makes the rotation possible). Clearly, it is extremely difficult, if not impossible, to accurately count the blood cells at these gaps.

Now let us look at stored undiluted whole blood with anticoagulant (collected subjects by a commercial service (Bioreclamation Inc.)) Our study showed that (FIG. 31.b) it has a different response to the CROF-Card confinement gap, compared with fresh undiluted blood without anticoagulant. For a 2 um gap, the blood cells in stored blood behave similar to those for fresh blood without anti-coagulant. But for larger gaps, the stored blood with anti-coagulant has different 2D image behavior from that of fresh blood without anticoagulant. With the anticoagulant and at larger than 2 um confinement gap, although the RBCs do not coagulate together, they can (a) overlap on top of each other and (b) rotate into a narrow elliptical shape in 2D top view imaging, all of which greatly degrade cell counting accuracy.

In the blood cell counting by the smartphone BCI, presented here, the confinement gap of the CROF-Card (hence the sample thickness) was preset at 2 um with an accuracy better than 5%. The sample volume was determined by the sample thickness preset by the CROF-Card and the images of a relevant area taken by smartphone. The blood cell concentrations (RBCs, WBCs, PLTs) were determined by counting the cells in a relevant area from the image taken by smartphone, and then dividing by the relevant volume. The mean corpuscular volume (MCV) of RBCs was determined by measuring the area of each RBC in a 2D top view image and the average total volume associated with each RBC, while using the pre-set sample thickness of 2 um. The hematocrit was determined from the product of MCV and RBC concentration.

For counting the three WBCs differentials (granulocytes, lymphocytes, monocytes), we stained the blood sample by putting a dried acridine orange (AO) dye layer on one of the CROF-Card surfaces. Since the AO stains the nucleic acids and stain DNA and RNA differently, only WBCs and PLT are stained, and are stained differently according to the amount and ratio of the DNA and RNA in each cell, while RBCs are not stained. The difference in staining gives different fluorescence wavelengths (e.g. 525 nm green emission for stained DNA and 685 nm red emission for stained RNA) and intensity, allowing an identification of each of the three WBCs differential and PLTs. We found that using the CROF-Card, the WBCs were stained by the precoated AO dye layer in less than 5 sec, due to the small sample thickness and hence a short dye diffusion time. The dye staining of the WBC and their fluorescence offer, in addition to the bright-field microscopy, another way to measure the WBCs and was used in the validation below.

The optical adapter allows an effective field of view of 0.84 mm×0.63 mm for RBCs, 2.8 mm×2.1 mm for WBC, and 0.2 mm radius in circle for PLT. Currently, the optical adapter needs to move in a slider to for taking the RBCs and WBCs separately, adding an additional ~5 secs operation time. In the next generation, a combined optical adapter without the need for a slider will be developed. All software for image analysis, user interface, and iPhone control were built by writing our own codes and using certain open source codes. Currently, all blood cell analysis presented here were done by our software in less 2 sec from the image to the blood counts, except the PLT analysis, which will be less than 5 sec in our next generation.

To validate the smartphone BCI, we compared it with the following four different reference methods (RMs). RM-1 used a high resolution microscope (Nikon Diaphot Inverted Microscope) and DSLR camera (Nikon D5100) rather than the iPhone and the optical adapter to read the CROF-Card for the same reading area as the current iPhone BCI. RM-2 is the same as RM-1, except that the reading area on the CROF-Card is extended to 3×3 array with a 8 mm period (total 9 reading areas), equally distributed in 16 mm by 16 mm CROF-Card area. RM-3 uses a commercial manual hemocytometer (purchased from Sigma-Aldrich, Z359629) plus imaging by the same microscope and camera as the RM 1 and 2, but 3 mm by 3 mm imaging area. The manual hemocytometer has two chambers, each 3 mm by 3 mm in the measurements area and 100 um gap). It requires a dilution of blood by 100 times and lysing RBCs for measuring PLTs. RM-4 uses a commercial PoC blood cell counting machine (made by one of the largest blood testing instrument companies); which uses a flow cytometer, and is ~1 cubic-foot in size and weights ~20 lb, and costs ~$20,000. The PoC machine requires at least 10 uL volume of blood (over 10 drops), blood dilutions, three liquid reagents (lysing, dilution, and cleaning), 5 min operation time and 30 minutes of calibration daily. The comparisons allow us to examine each individual function as well as combined effects of the CROF-Card, imaging by optical adapter and smartphone, and the imaging by microscope on their performances in blood cell counting.

In the validation, two types of blood were used: (i) stored blood, purchased from a commercial vendor (Boreclamation.inc), that was mixed with an anti-coagulant (EDTA); and (ii) fresh blood, which was the finger-picked blood from two volunteers (During each test, the freshly finger-pricked blood was immediately and directly deposited from the finger to (a) the CROF-Card for the CROF-Card testing and (b) a EDTA coated tube for the commercial PoC and manual hemocytometer. A total 42 samples were tested for each method, over a period of several days.

A total 24 samples were tested in 4 different days (3, 3, 3, and 15 samples), and the blood samples were from the same lot for the tests in first three days, but different lot for the last day. In the fresh blood samples, total of 18 samples were tested on 3 different days (6, 6, and 6 samples).

The test results showed a number of significant facts. (1) For a given blood sample, the daily average value of the blood cell counts for the smartphone BCI (p-BCI) and the all four reference methods are in agreement with each other within its perspective daily CV (coefficient of variation, ratio of the standard deviation to the average).

(2) The comparison of p-BCI with the RM-1 showed that for a given CROF-Card sample, the blood cell counting using the iPhone and the optical adapter we developed has the same accuracy (CV) as using the high-resolution microscope and DSLR camera (e.g. both have a CV of ~12% for RBCs) (FIG. 32).

(3) The comparison of RM-1 and RM-2 showed that an imaging of the multiple fields of CROF-Card offers better accuracy than the current imaging of a single field. CV was improved from ~12% to ~6% for RBCs. The multiple field viewing capability will be implemented in our next generation of smartphone BCI for a higher accuracy.

(4) The comparison of RM-2 and RM-3 showed that (i) the CROF-Card is not only much simpler to use, but also gives a cell counting accuracy that is the same as or better than the commercial manual hemocytometer in blood cell counting, and (ii) considering the fact in (i) and the comparison of RM1 and RM2, it lead to the conclusion that a multi-field smartphone BCI should have the same as, or even better, accuracy than the commercial manual hemocytometer in blood cell counting. We would like also point out that the variation, although the same for the current CROF-Card and the manual hemocytometer, comes from different reasons. For the hemocytometer, the variation comes from the dilution, lysing, and manual counting, But for the CROF-Card, the current variation (~7% for RBCs) is mainly due to the sample thickness variation (~5%), which can be improved further.

(5) The smartphone BCI can identify each of three WBC differentials by staining and measure the ratio of the intensity of each WBC cell as a function of the ratio of the fluorescent intensity of green color to red color. The standard deviation is similar to that for other blood cell measurements. This is because that each sub-type of white blood cells has a special ratio in fluorescence color (depending their relative amount and ratio of RNA (red fluorescence) and DNA (green fluorescence); granulocyte has large amounts of RNA and granules (thus high red fluorescence and low green fluorescence); lymphocyte has low amounts of RNA and high amounts of DNA (thus low red, but high green fluorescence); and monocyte has a red to green ratio between granulocyte and lymphocyte.

(6) Within the statistical significance, the inter-day (i.e. day-to-day) variations for all five methods tested are essentially the same, indicating that the smart-BCI is very stable over the multiple day period that the tests were conducted.

And finally, (7) with our current optical imaging hardware and software, the blood cell counting by imaging is not yet as accurate as the commercial flow cytometer PoC machine (e.g. ~7% vs. 1% for RBCs). However, one must recognize two important facts: (i) just with the current accuracy, the p-BCI demonstrated here already has significant value in monitoring health and clinical value in the remote area or the developing countries, and (ii) the accuracy of the p-BCI can be further improved to have better accuracy. Undoubtedly, the BCI technology has broad and significant applications in cell imaging, immunoassays, nucleic-acid assays, personal health monitoring, and other bio-chemical detections.

Certain aspects of the present invention have been described in the following documents and all of these documents are incorporated by reference for all purposes:

U.S. application Ser. No. 13/838,600, filed Mar. 15, 2013 (NSNR-003), which application claims the benefit of U.S. provisional application Ser. No. 61/622,226 filed on Apr. 10, 2012, and is a continuation-in-part of U.S. patent application Ser. No. 13/699,270, filed on Jun. 13, 2013, which application is a § 371 filing of US2011/037455, filed on May 20, 2011, and claims the benefit of U.S. provisional application Ser. No. 61/347,178, filed on May 21, 2010;

U.S. application Ser. No. 13/699,270, filed Jun. 13, 2013 (NSNR-001), which application is a § 371 filing of international application serial no. US2011/037455, filed on May 20, 2011, which application claims the benefit of U.S. Provisional Patent Application Ser. No. 61/347,178 filed on May 21, 2010; and U.S. provisional application Ser. No. 61/801,424, filed Mar. 15, 2013 (NSNR-004PRV), provisional application Ser. No. 61/801,096, filed Mar. 15, 2013 (NSNR-005PRV), provisional application Ser. No. 61/800,915, filed Mar. 15, 2013 (NSNR-006PRV), provisional application Ser. No. 61/793,092, filed Mar. 15, 2013 (NSNR-008PRV), provisional Application Ser. No. 61/801,933, filed Mar. 15, 2013 (NSNR-009PRV), provisional Application Ser. No. 61/794,317, filed Mar. 15, 2013 (NSNR-010PRV), provisional application Ser. No. 61/802,020, filed Mar. 15, 2013 (NSNR-011PRV) and provisional application Ser. No. 61/802,223, filed Mar. 15, 2013 (NSNR-012PRV).

Further examples of inventive subject matter according to the present disclosure are described in the following enumerated paragraphs.

As used herein, the terms "adapted" and "configured" mean that the element, component, or other subject matter is designed and/or intended to perform a given function. Thus, the use of the terms "adapted" and "configured" should not be construed to mean that a given element, component, or other subject matter is simply "capable of" performing a given function but that the element, component, and/or other subject matter is specifically selected, created, implemented, utilized, programmed, and/or designed for the purpose of performing the function. It is also within the scope of the present disclosure that elements, components, and/or other recited subject matter that is recited as being adapted to perform a particular function may additionally or alternatively be described as being configured to perform that function, and vice versa. Similarly, subject matter that is recited as being configured to perform a particular function may additionally or alternatively be described as being operative to perform that function.

As used herein, the phrase, "for example," the phrase, "as an example," and/or simply the terms "example" and "exemplary" when used with reference to one or more components, features, details, structures, embodiments, and/or methods according to the present disclosure, are intended to convey that the described component, feature, detail, structure, embodiment, and/or method is an illustrative, non-exclusive example of components, features, details, structures, embodiments, and/or methods according to the present disclosure. Thus, the described component, feature, detail, structure, embodiment, and/or method is not intended to be limiting, required, or exclusive/exhaustive; and other components, features, details, structures, embodiments, and/or methods, including structurally and/or functionally similar and/or equivalent components, features, details, structures, embodiments, and/or methods, are also within the scope of the present disclosure.

As used herein, the phrases "at least one of" and "one or more of," in reference to a list of more than one entity, means any one or more of the entity in the list of entity, and is not limited to at least one of each and every entity specifically listed within the list of entity. For example, "at least one of A and B" (or, equivalently, "at least one of A or B," or, equivalently, "at least one of A and/or B") may refer to A alone, B alone, or the combination of A and B.

As used herein, the term "and/or" placed between a first entity and a second entity means one of (1) the first entity, (2) the second entity, and (3) the first entity and the second entity. Multiple entity listed with "and/or" should be construed in the same manner, i.e., "one or more" of the entity so conjoined. Other entity may optionally be present other than the entity specifically identified by the "and/or" clause, whether related or unrelated to those entity specifically identified. Thus, as a non-limiting example, a reference to "A and/or B," when used in conjunction with open-ended language such as "comprising" may refer, in some embodiments, to A only (optionally including entity other than B); in certain embodiments, to B only (optionally including entity other than A); in yet certain embodiments, to both A and B (optionally including other entity). These entity may refer to elements, actions, structures, steps, operations, values, and the like.

In the event that any patents, patent applications, or other references are incorporated by reference herein and (1) define a term in a manner that is inconsistent with and/or (2) are otherwise inconsistent with, either the non-incorporated portion of the present disclosure or any of the other incorporated references, the non-incorporated portion of the present disclosure shall control, and the term or incorporated disclosure therein shall only control with respect to the reference in which the term is defined and/or the incorporated disclosure was present originally.

It is believed that the following claims particularly point out certain combinations and subcombinations that are directed to one of the disclosed inventions and are novel and non-obvious. Inventions embodied in other combinations and subcombinations of features, functions, elements and/or properties may be claimed through amendment of the present claims or presentation of new claims in this or a related application. Such amended or new claims, whether they are directed to a different invention or directed to the same invention, whether different, broader, narrower, or equal in scope to the original claims, are also regarded as included within the subject matter of the inventions of the present disclosure.

The invention claimed is:

1. A device for staining and analyzing a tissue, comprising:
   a first plate, a second plate, and spacers, wherein:
   (i) the first and second plates are movable relative to each other into different configurations, including an open configuration and a closed configuration;
   (ii) one or both plates are flexible;
   (iii) each of the plates has, on its respective surface, a contact area for contacting the tissue and/or a staining solution that stains the tissue; and
   (iv) one or both of the plates comprise the spacers that are fixed with a respective plate, wherein the spacers have pillar shape, a predetermined substantially uniform height of 250 um or less, and wherein at least one of the spacers is inside the contact area;

wherein in the open configuration, the two plates are separated apart, the spacing between the plates is not regulated by the spacers, and the tissue is deposited on one or both of the plates; and wherein in the closed configuration, which is configured after the tissue deposition in the open configuration, at least a part of the tissue and the staining solution is sandwiched between the two plates forming a layer of uniform thickness, wherein the uniform thickness of the layer is confined by the contact areas of the two plates and is regulated by the plates and the spacers.

2. A kit for staining a tissue, comprising:
(i) the device of claim 1; and
(ii) a staining solution.

3. An apparatus for staining a tissue sample contains or is suspected to contain an analyte, comprising:
(i) the device of claim 1, and
(ii) an imager that images the tissue sample and the analyte.

4. A system for staining and analyzing a tissue, comprising:
(i) the device of claim 1; and
(ii) an imager that images the tissue.

5. A system for staining and analyzing a tissue sample using a mobile phone comprising:
(i) a sample;
(ii) the device of claim 1; and
(iii) a mobile communication device comprising:
  a. one or a plurality of cameras for the detecting and/or imaging the sample;
  b. electronics, signal processors, hardware and software for receiving and/or processing the detected signal and/or the image of the sample and for remote communication; and
(iv) a light source from either the mobile communication device or an external source.

6. A method for rapidly staining and analyzing a tissue sample using a mobile communication device, comprising:
(a) depositing a tissue sample and a staining liquid on the device of the system claim 5, and placing the two plate into a closed configuration;
(b) obtaining a mobile phone that has hardware and software of imaging, data processing, and communication;
(c) assaying by the tissue sample deposited on the device by the mobile communication device to generate a result; and
(d) communicating the result from the mobile phone to a location remote from the mobile communication device.

7. A method for analyzing a tissue, comprising:
(a) obtaining the device of claim 1;
(b) having the tissue onto one or both pates of the device;
(c) having the plates in a closed configuration by applying an external force over at least part of the plates; and
(d) analyzing the sample in the layer of uniform thickness while the plates are in the closed configuration.

8. The device of claim 1, wherein the staining solution is for IHC (immunohistochemistry) staining.

9. The device of claim 1, wherein the staining solution is for detection of a nucleic acid.

10. The device of claim 1, wherein the tissue contains or is suspected of containing an analyte that is a protein, a nucleic acid, DNA, RNA, or a cell.

11. The device of claim 1, further comprising a dry staining reagent coated on one or both plates, wherein the staining solution is a transfer solution that transfer the dry staining reagent onto the tissue.

12. The device of claim 1, wherein the highly uniform thickness has a value of 50 um or less.

13. The device of claim 1, wherein the uniform thickness has a value in the range of 0.5 um to 10 um.

14. The device of claim 1, wherein the materials of the plate and the spacers are selected from polystyrene, PMMA, PC, COC, COP, and another plastic.

15. The device of claim 1, wherein the inter-spacer distance is in the range of 1 um to 200 um.

16. The device of claim 1, wherein the inter-spacer distance is in the range of 200 um to 1000 um.

17. The device of claim 1, wherein the spacers regulating the layer of uniform thickness have a filling factor of at least 1%, wherein a ratio of the spacer contact area to the total plate area.

18. The device of claim 1, wherein for spacers regulating the layer of uniform thickness, the Young's modulus of the spacers times the filling factor of the spacers is equal to or larger than 20 MPa, wherein the filling factor is a ratio of the spacer contact area to the total plate area.

19. The device of claim 1, wherein:
(i) the thickness of the flexible plate times the Young's modulus of the flexible plate is in the range 60 to 750 GPa-um;
(ii) the fourth power of the inter-spacer distance (ISD) divided by the thickness of the flexible plate (h) and the Young's modulus (E) of the flexible plate, $ISD^4/(hE)$, is equal to or less than $5\times10^6$ $um^3/GPa$;
(iii) the inter-spacer distance is in the range of 1 um to 200 um;
(iv) for each spacer, the ratio of the lateral dimension of the spacer to its height is at least 1;
(v) at least a part of the spacers are arranged periodically; and
(vi) the Young's modulus of the spacers times the filling factor of the spacers is equal to or larger than 2 MPa, wherein the filling factor is a ratio of the spacer contact area to the total plate area.

20. The device of claim 1, wherein for a flexible plate, the fourth power of the inter-spacer distance (ISD) divided by the thickness of the flexible plate (h) and the Young's modulus (E) of the flexible plate, $ISD^4/(hE)$, is equal to or less than $5\times10^6$ $um^3/GPa$.

21. The device of claim 1, wherein one or both plates comprises a location marker, either on a surface of or inside the one or both plates, that provides information of a location of the plate.

22. The device of claim 1, wherein one or both plates comprises a scale marker, either on a surface of or inside the one or both plates, that provides information of a lateral dimension of a structure of the sample and/or the plate.

23. The device of claim 1, wherein one or both plates comprises an imaging marker, either on a surface of or inside the one or both plates, that assists an imaging of the sample.

24. The device of claim 1, wherein the spacers function as a location marker, a scale marker, an imaging marker, or any combination thereof.

25. The device of claim 1, wherein the spacers are pillars with a cross-sectional shape selected from round, polygonal, circular, square, rectangular, oval, elliptical, or any combination of the same.

26. The device of claim 1, wherein the tissue is from a nasal swab, mucus, earwax, a glandular secretion, tumorous tissue, a throat swab, skin, biopsy, sputum, pus, microbiota, meconium, breast milk, throat swab, stool samples, connective tissue, muscle tissue, nervous tissue, epithelial tissue, and cartilage.

27. The device of claim 1, wherein a dye for a stain is selected from the group consisting of Acid fuchsin, Alcian blue 8 GX, Alizarin red S, Aniline blue WS, Auramine O, Azocarmine B, Azocarmine G, Azure A, Azure B, Azure C, Basic fuchsine, Bismarck brown Y, Brilliant cresyl blue, Brilliant green, Carmine, Chlorazol black E, Congo red, C.I. Cresyl violet, Crystal violet, Darrow red, Eosin B, Eosin Y, Erythrosin, Ethyl eosin, Ethyl green, Fast green F C F, Fluorescein Isothiocyanate, Giemsa Stain, Hematoxylin, Hematoxylin & Eosin, Indigo carmine, Janus green B, Jenner stain 1899, Light green SF, Malachite green, Martius yellow, Methyl orange, Methyl violet 2B, Methylene blue, Methylene blue, Methylene violet, (Bernthsen), Neutral red, Nigrosin, Nile blue A, Nuclear fast red, Oil Red, Orange G, Orange II, Orcein, Pararosaniline, Phloxin B, Protargol S, Pyronine B, Pyronine, Resazurin, Rose Bengal, Safranine O, Sudan black B, Sudan III, Sudan IV, Tetrachrome stain (MacNeal), Thionine, Toluidine blue, Weigert, Wright stain, and any combination thereof.

28. The device of claim 1, wherein the staining is by a cell viability dye selected from the group consisting of: Propidium Iodide, 7-AAD, Trypan blue, Calcein Violet AM, Calcein AM, Fixable Viability Dyes, SYTO9 and other nucleic acid dyes, Resazurin and Formazan (MTT/XTT) and other mitochondrial dyes, and any combination thereof.

29. The device of claim 1, wherein the staining solution comprises antibodies configured to specifically bind to a protein analyte in the sample.

30. The device of claim 1, wherein the staining solution comprises oligonucleotide probes configured to specifically bind to DNA and/or RNA in the sample.

31. The method of claim 1, wherein each of the spacers function as a location marker, a scale marker, an imaging marker, or any combination thereof.

32. The device of claim 1, wherein the spacers have a pillar shape and have a substantially flat top surface, wherein, for each spacer, the ratio of the lateral dimension of the spacer to its height is at least 2.

33. The device of claim 1, wherein the thickness of the flexible plate times the Young's modulus of the flexible plate is in the range 60 to 750 GPa-um.

34. The device of claim 1, wherein the ratio of the width to the height of the spacer is equal or larger than 2, and a product of the filling factor and the Young's modulus of the spacer is 20 MPa or larger, wherein the filling factor is the filling factor is the ratio of the spacer contact area to the total plate area.

35. The device of claim 1, wherein the fourth power of the inter-spacer-distance (IDS) divided by the thickness (h) and the Young's modulus (E) of the flexible plate ($ISD^4/(hE)$) is $5 \times 10^6$ um$^3$/GPa or less.

36. The device of claim 1, wherein the spacers are substantially periodic.

37. The device of claim 1, wherein a plate has multiple stain reagent sites, wherein the ratio of the distance between two neighbor sites to the sample thickness in the closed configuration is 5 or larger.

38. The device of claim 1, further comprising, on one or both of the plates, a dry stain reagent or a release time control material or both.

39. The device of claim 1, wherein the spacers regulating the layer of uniform thickness is periodic and have a filling factor of at least 2%, wherein the filling factor is the ratio of the spacer contact area to the total plate area.

40. The device of claim 1, wherein one or both plates comprises a scale maker.

41. The device of claim 1, wherein the flexible plate has a thickness in the range of 10 um to 200 um.

42. The device of claim 1, further comprising electrodes on one or both of the first and second plates, and the electrodes measure the charge, current, capacitance, impedance, or resistance of the sample, or any combination thereof.

43. The device of claim 1, further comprising an amplification surface that is a surface enhancing the fluorescence or luminescence produced by a detection agent.

44. The device of claim 1, wherein the first and second plates are connected by a hinge.

45. The device of claim 1, further comprising, on one or both of the plates, a dry binding site comprising a capture agent, an antibody, nucleic acid, a labeled reagent or a cell stain.

46. The device of claim 1, wherein the spacers are fixed on a plate by directly embossing the plate or injection molding of the plate, and wherein the materials of the plate and the spacers are selected from polystyrene, PMMA, PC, COC, COP, or another plastic.

* * * * *